US009334263B2

(12) United States Patent
Hodous et al.

(10) Patent No.: US 9,334,263 B2
(45) Date of Patent: May 10, 2016

(54) COMPOSITIONS USEFUL FOR TREATING DISORDERS RELATED TO KIT

(71) Applicants: Brian L. Hodous, Cambridge, MA (US); Joseph L. Kim, Wayland, MA (US); Chandrasekhar V. Miduturu, Cambridge, MA (US); Douglas Wilson, Ayer, MA (US); Yulian Zhang, Acton, MA (US)

(72) Inventors: Brian L. Hodous, Cambridge, MA (US); Joseph L. Kim, Wayland, MA (US); Chandrasekhar V. Miduturu, Cambridge, MA (US); Douglas Wilson, Ayer, MA (US); Yulian Zhang, Acton, MA (US)

(73) Assignee: BLUEPRINT MEDICINES CORPORATION, Cambridge, MA (US)

( * ) Notice: Subject to any disclaimer, the term of this patent is extended or adjusted under 35 U.S.C. 154(b) by 0 days.

(21) Appl. No.: 14/517,480

(22) Filed: Oct. 17, 2014

(65) Prior Publication Data
US 2015/0111857 A1    Apr. 23, 2015

Related U.S. Application Data

(60) Provisional application No. 61/892,077, filed on Oct. 17, 2013.

(51) Int. Cl.
| | |
|---|---|
| C07D 403/14 | (2006.01) |
| C07D 401/14 | (2006.01) |
| C07D 413/14 | (2006.01) |
| A61K 31/53 | (2006.01) |
| A61K 31/517 | (2006.01) |
| A61P 35/00 | (2006.01) |
| A61P 35/02 | (2006.01) |
| A61P 17/00 | (2006.01) |
| A61K 31/5377 | (2006.01) |
| A61K 31/5415 | (2006.01) |
| A61K 31/55 | (2006.01) |
| A61K 31/553 | (2006.01) |
| A61K 31/635 | (2006.01) |
| A61K 31/675 | (2006.01) |
| A61K 45/06 | (2006.01) |
| C07D 403/12 | (2006.01) |
| C07D 405/14 | (2006.01) |
| C07D 417/14 | (2006.01) |
| C07D 471/04 | (2006.01) |
| C07F 9/6521 | (2006.01) |

(52) U.S. Cl.
CPC .............. *C07D 413/14* (2013.01); *A61K 31/53* (2013.01); *A61K 31/5377* (2013.01); *A61K 31/5415* (2013.01); *A61K 31/55* (2013.01); *A61K 31/553* (2013.01); *A61K 31/635* (2013.01); *A61K 31/675* (2013.01); *A61K 45/06* (2013.01); *C07D 401/14* (2013.01); *C07D 403/12* (2013.01); *C07D 403/14* (2013.01); *C07D 405/14* (2013.01); *C07D 417/14* (2013.01); *C07D 471/04* (2013.01); *C07F 9/65217* (2013.01)

(58) Field of Classification Search
CPC ... C07D 403/14; A61K 31/53; A61K 31/495; A61K 31/506
USPC .................. 544/179, 182, 209; 514/242, 245
See application file for complete search history.

(56) References Cited

U.S. PATENT DOCUMENTS 6,982,265 B1    1/2006  Hunt et al.

FOREIGN PATENT DOCUMENTS

| WO | 0071129 A1 | 11/2000 |
|---|---|---|
| WO | 01/25220 A1 | 4/2001 |
| WO | 2005117909 A2 | 12/2005 |
| WO | 2007085188 A1 | 8/2007 |
| WO | 2008005956 A2 | 1/2008 |
| WO | 2009015254 A1 | 1/2009 |
| WO | 2009117157 A1 | 9/2009 |
| WO | 2010022055 A2 | 2/2010 |
| WO | WO 2010022055 A2 * | 2/2010 |
| WO | 2010144345 A1 | 12/2010 |
| WO | 2011005119 A1 | 1/2011 |
| WO | 2011103196 A1 | 8/2011 |
| WO | WO 2011103196 A1 * | 8/2011 |
| WO | 2012027495 A1 | 3/2012 |
| WO | 2014160521 A1 | 10/2014 |
| WO | 2015057873 A1 | 4/2015 |
| WO | 2015058129 A1 | 4/2015 |

OTHER PUBLICATIONS

Antonescu, C. J Pathol. Jan. 2011; 223(2): 251-261.*
Lee et al., J Gastrointestin Liver Dis, Dec. 2013 vol. 22 No. 4: 413-418.*
Cecil Textbook of Medicine, edited by Bennet, J.C., and Plum F., 20th edition, vol. 1, 1004-101 O, 1996.*
Cohen et al., Current Opinion in Chemical Biology, 3,459-465, 1999.*
Freshney et al., Culture of Animal Cells, A Manual of Basic Technique, Alan R. Liss, Inc., 1983, New York, p4.*
Dermer et al., Bio/Technology, 1994, 12:320.*
International Search Report and Written Opinion for International Application No. PCT/US2014/027008 dated Jul. 17, 2014.
International Search Report and Written Opinion for International Application No. PCT/US2014/060746 dated Dec. 17, 2014.

(Continued)

*Primary Examiner* — Venkataraman Balasubramanian
(74) *Attorney, Agent, or Firm* — Lando & Anastasi, LLP

(57) ABSTRACT

Compounds and compositions useful for treating disorders related to KIT and PDFGR are described herein.

21 Claims, 1 Drawing Sheet

(56) References Cited

OTHER PUBLICATIONS

International Search Report and Written Opinion for International Application No. PCT/US2014/061211 dated Oct. 12, 2014.
Antonescu, "What lessons can be learned from the GIST paradigm that can be applied to other kinase-driven cancers" J. Pathol. (2011) vol. 223, No. 2, pp. 251-261.
Cairoli et al. "Prognostic impact of c-KIT mutations in core binding factor leukemias: an Italian retrospective study" Blood (2006) vol. 107, pp. 3463-3468.
Cecil Textbook of Medicine, Edited by Bennet and Plum (1996) 20th edition, vol. 1, pp. 1004-1010.
Cohen et al., "The development and therapeutic potential of protein kinase inhibitors" Current Opinion in Chemical Biology (1999) vol. 3, pp. 459-465.
Fresheny et al., "Culture of Animal Cells, A Manual of Basic Technique" Alan R. Liss, Inc. (1983) pp. 1-6.
International Search Report for International Application No. PCT/US2015/043624 dated Oct. 6, 2015.
Lee et al. "Correlation of Imatinib Resistance with the Mutational Status of KIT and ODGFRA Genes in Gastrointestinal Stromal Tumors: a Meta-analysis" J. Gastrointestin Liver Dis. (2013) vol. 22, No. 4, pp. 413-418.
Paschka et al. "Adverse Prognostic Significance of KIT Mutations in Adult Acute Myeloid Leukemia with inv(16) and t (8;21):A Cancer and Leukemia Group Study" Journal of Clinical Oncology (2006) vol. 24, No. 24, pp. 3904-3911.
Quintela et al, "A Ready One-pot Preparation for Pyrrolo[2,1-f]-[1,2,4]triazine and Pyrazolo[5,1-c]pyrimido[4,5-e]-[1,2,4]triazine Derivatives" Tetrahedron (1996) vol. 52, No. 8, pp. 3037-3048.
Schnittger et al. "KIT-D816 mutations in AML1-ETO-positive AML are associated with impaired event-free and overal survival" Blood (2006) vol. 107, pp. 1791-1799.

* cited by examiner

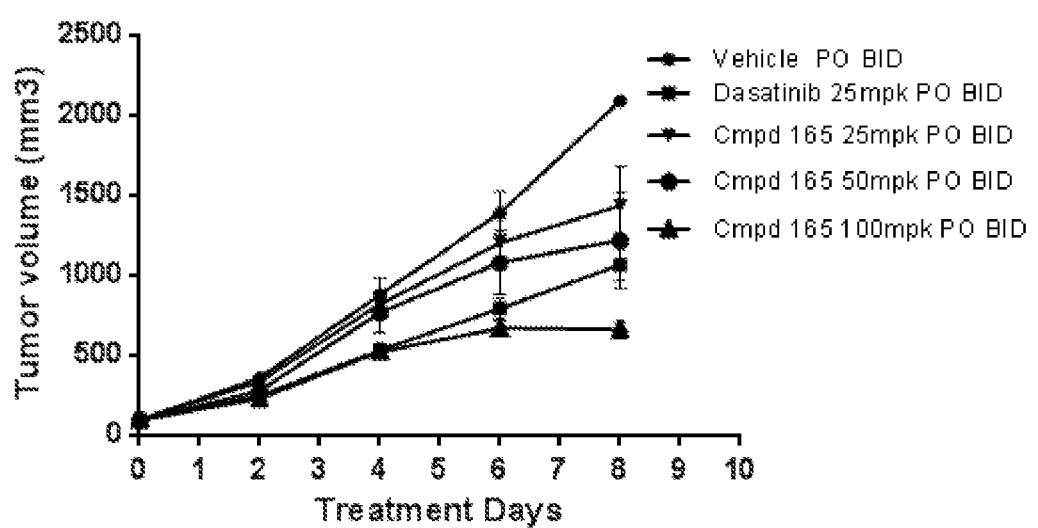

COMPOSITIONS USEFUL FOR TREATING DISORDERS RELATED TO KIT

CLAIM OF PRIORITY

This application claims priority to U.S. Ser. No. 61/892,077 filed Oct. 17, 2013, which is incorporated herein in its entirety.

BACKGROUND

The invention relates to compounds and compositions useful for treating disorders related to KIT and PDGFR.

The enzyme KIT (also called CD117) is a receptor tyrosine kinase expressed on a wide variety of cell types. The KIT molecule contains a long extracellular domain, a transmembrane segment, and an intracellular portion. The ligand for KIT is stem cell factor (SCF), whose binding to the extracellular domain of KIT induces receptor dimerization and activation of downstream signaling pathways. KIT mutations generally occur in the DNA encoding the juxtumembrane domain (exon 11). They also occur, with less frequency, in exons 7, 8, 9, 13, 14, 17, and 18. Mutations make KIT function independent of activation by SCF, leading to a high cell division rate and possibly genomic instability. Mutant KIT has been implicated in the pathogenesis of several disorders and conditions including systemic mastocytosis, GIST (gastrointestinal stromal tumors), AML (acute myeloid leukemia), melanoma, and seminoma. As such, there is a need for therapeutic agents that inhibit KIT, and especially agents that inhibit mutant KIT.

Platelet-derived growth factor receptors (PDGF-R) are cell surface tyrosine kinase receptors for members of the platelet-derived growth factor (PDGF) family. PDGF subunits -A and -B are important factors regulating cell proliferation, cellular differentiation, cell growth, development and many diseases including cancer. A PDGFRA D842V mutation has been found in a distinct subset of GIST, typically from the stomach. The D842V mutation is known to be associated with tyrosine kinase inhibitor resistance. As such, there is a need for agents that target this mutation.

SUMMARY OF THE INVENTION

The present invention provides compounds and compositions for treating or preventing conditions such as mastocytosis by modulating the activity of Kit, such compounds having the structural Formula I:

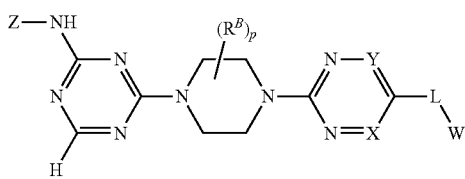

Formula I or a pharmaceutically acceptable salt thereof, wherein:
W is selected from hydrogen, halo and

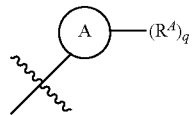

wherein Ring A is selected from monocyclic or bicyclic aryl, monocyclic or bicyclic heteroaryl, cycloalkyl and heterocyclyl;

each X and Y is independently selected from $CR^1$ and N;

Z is selected from $C_1$-$C_6$ alkyl, cycloalkyl, monocyclic or bicyclic aryl, monocyclic or bicyclic aralkyl, monocyclic or bicyclic heteroaryl, monocyclic or bicyclic heterocyclyl, and monocyclic or bicyclic heterocyclylalkyl; wherein each of $C_1$-$C_6$ alkyl, cycloalkyl, monocyclic or bicyclic aryl, monocyclic or bicyclic aralkyl, monocyclic or bicyclic heteroaryl, monocyclic or bicyclic heterocyclyl, and monocyclic or bicyclic heterocyclylalkyl is substituted with 0-5 occurrences of $R^C$;

L is selected from a bond, —$(C(R^2)(R^2))_m$—, —$(C_2$-$C_6$ alkynylene)-, —$(C_2$-$C_6$ alkenylene)-, —$(C_1$-$C_6$ haloalkylene)-, —$(C_1$-$C_6$ heteroalkylene)-, —$(C_1$-$C_6$ hydroxyalkylene)-, —C(O)—, —O—, —S—, —S(O), —$SO_2$—, —$N(R^2)$—, —O—$(C_1$-$C_6$ alkylene)-, —$(C_1$-$C_6$ alkylene)-O—, —$N(R^2)$—CO—, —CO—$N(R^2)$—, —$(C_1$-$C_6$ alkylene)-$N(R^2)$—, —$N(R^2)$—$(C_1$-$C_6$ alkylene)-, —$N(R^2)$—CO—$(C_1$-$C_6$ alkylene)-, —CO—$N(R^2)$—$(C_1$-$C_6$ alkylene)-, —$N(R^2)$—$SO_2$—, —$SO_2$—$N(R^2)$—, —$N(R^2)$—$SO_2$—$(C_1$-$C_6$ alkylene)-, and —$SO_2$—$N(R^2)$—$(C_1$-$C_6$ alkylene)-;

each $R^A$ and $R^B$ is independently selected from $C_1$-$C_6$ alkyl, halo, $C_1$-$C_6$ haloalkyl, $C_1$-$C_6$ hydroxyalkyl, $C_1$-$C_6$ heteroalkyl, monocyclic or bicyclic aralkyl, —$N(R^2)(R^2)$, cyano, and —$OR^2$;

each $R^C$ is independently selected from $C_1$-$C_6$ alkyl, $C_1$-$C_6$ alkynyl, halo, $C_1$-$C_6$ heteroalkyl, $C_1$-$C_6$ haloalkyl, $C_1$-$C_6$ haloalkoxy, $C_1$-$C_6$ hydroxyalkyl, cycloalkyl, monocyclic or bicyclic aryl, monocyclic or bicyclic aryloxy, monocyclic or bicyclic aralkyl, monocyclic or bicyclic heterocyclyl, monocyclic or bicyclic heterocyclylalkyl, nitro, cyano, —$C(O)R^2$, —$OC(O)R^2$, —$C(O)OR^2$, —$SR^2$, —$S(O)_2R^2$, —$S(O)_2$—N$(R^2)(R^2)$, —$(C_1$-$C_6$ alkylene)-$S(O)_2$—$N(R^2)(R^2)$, —$N(R^2)(R^2)$, —C(O)—$N(R^2)(R^2)$, —$N(R^2)(R^2)$—$C(O)R^2$, —$(C_1$-$C_6$ alkylene)-$N(R^2)$—$C(O)R^2$, —$NR^2S(O)_2R^2$, —$P(O)(R^2)(R^2)$, and —$OR^2$; wherein each of heteroalkyl, haloalkyl, haloalkoxy, alkyl, alkynyl, cycloalkyl, aryl, aryloxy, aralkyl, heterocyclyl, and heterocyclylalkyl is substituted with 0-5 occurrences of $R^a$; or 2 $R^C$ together with the carbon atom(s) to which they are attached form a cycloalkyl or heterocyclyl ring substituted with 0-5 occurrences of $R^a$;

each $R^1$ is independently selected from hydrogen, $C_1$-$C_6$ alkyl, monocyclic aralkyl, $C_1$-$C_6$ hydroxyalkyl, halo, $C_1$-$C_6$ haloalkyl, —$N(R^2)(R^2)$, and —$OR^2$;

each $R^2$ is independently selected from hydrogen, hydroxyl, halo, $C_1$-$C_6$ alkyl, $C_1$-$C_6$ haloalkyl, $C_1$-$C_6$ hydroxyalkyl, cycloalkyl, cycloalkylalkyl, heterocyclyl, and heterocyclylalkyl; wherein each of $C_1$-$C_6$ alkyl, cycloalkyl and heterocyclyl is substituted with 0-5 occurrences of $R^b$, or 2 $R^2$ together with the carbon or nitrogen atom to which they are attached form a cycloalkyl or heterocyclyl ring;

each $R^a$ and $R^b$ is independently selected from halo, hydroxyl, —C(O)R', $C_1$-$C_6$ alkyl, $C_1$-$C_6$ haloalkyl, $C_1$-$C_6$ heteroalkyl, $C_1$-$C_6$ hydroxyalkyl, —NR'R', and cycloalkyl; wherein cycloalkyl is substituted with 0-5 occurrences of R';

R' is hydrogen, hydroxyl, or $C_1$-$C_6$ alkyl; and m, p, and q are each independently 0, 1, 2, 3, or 4.

Any of the compounds disclosed herein may be used to treat any of the diseases disclosed herein.

BRIEF DESCRIPTION OF THE DRAWINGS

FIG. 1 is a line graph depicting tumor growth curves for the different treatment groups: vehicle (♦), Dasatinib at 25 milligrams per kilogram (mpk) orally twice a day (po bid) (■), Compound 165 at 25 mpk po bid (▼), Compound 165 at 50 mpk po bid (●), and Compound 165 at 100 mpk po bid (▲).

DETAILED DESCRIPTION OF THE INVENTION

"Aliphatic group" means a straight-chain, branched-chain, or cyclic hydrocarbon group and includes saturated and unsaturated groups, such as an alkyl group, an alkenyl group, and an alkynyl group.

"Alkylene" refers to a divalent radical of an alkyl group, e.g., —CH$_2$—, —CH$_2$CH$_2$—, and CH$_2$CH$_2$CH$_2$—.

"Alkenyl" means an aliphatic group containing at least one double bond.

"Alkoxyl" or "alkoxy" means an alkyl group having an oxygen radical attached thereto. Representative alkoxyl groups include methoxy, ethoxy, propyloxy, tert-butoxy and the like.

"Alkyl" refers to a monovalent radical of a saturated straight or branched hydrocarbon, such as a straight or branched group of 1-12, 1-10, or 1-6 carbon atoms, referred to herein as C$_1$-C$_{12}$ alkyl, C$_1$-C$_{10}$ alkyl, and C$_1$-C$_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

"Alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

"Hydroxyalkylene" or "hydroxyalkyl" refers to an alkylene or alkyl moiety in which an alkylene or alkyl hydrogen atom is replaced by a hydroxyl group. Hydroxyalkylene or hydroxyalkyl includes groups in which more than one hydrogen atom has been replaced by a hydroxyl group.

"Aromatic ring system" is art-recognized and refers to a monocyclic, bicyclic or polycyclic hydrocarbon ring system, wherein at least one ring is aromatic.

"Aryl" refers to a monovalent radical of an aromatic ring system. Representative aryl groups include fully aromatic ring systems, such as phenyl, naphthyl, and anthracenyl, and ring systems where an aromatic carbon ring is fused to one or more non-aromatic carbon rings, such as indanyl, phthalimidyl, naphthimidyl, or tetrahydronaphthyl, and the like.

"Arylalkyl" or "aralkyl" refers to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

"Aryloxy" refers to —O-(aryl), wherein the heteroaryl moiety is as defined herein.

"Halo" refers to a radical of any halogen, e.g., —F, —Cl, —Br, or —I.

"Haloalkyl" and "haloalkoxy" refers to alkyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl" refers to an optionally substituted alkyl, which has one or more skeletal chain atoms selected from an atom other than carbon, e.g., oxygen, nitrogen, sulfur, phosphorus or combinations thereof. A numerical range may be given, e.g. C$_1$-C$_6$ heteroalkyl which refers to the number of carbons in the chain, which in this example includes 1 to 6 carbon atoms. For example, a —CH$_2$OCH$_2$CH$_3$ radical is referred to as a "C$_3$" heteroalkyl. Connection to the rest of the molecule may be through either a heteroatom or a carbon in the heteroalkyl chain.

"Carbocyclic ring system" refers to a monocyclic, bicyclic or polycyclic hydrocarbon ring system, wherein each ring is either completely saturated or contains one or more units of unsaturation, but where no ring is aromatic.

"Carbocyclyl" refers to a monovalent radical of a carbocyclic ring system. Representative carbocyclyl groups include cycloalkyl groups (e.g., cyclopentyl, cyclobutyl, cyclopentyl, cyclohexyl and the like), and cycloalkenyl groups (e.g., cyclopentenyl, cyclohexenyl, cyclopentadienyl, and the like).

"Cycloalkyl" refers to a cyclic, bicyclic, tricyclic, or polycyclic non-aromatic hydrocarbon groups having 3 to 12 carbons. Any substitutable ring atom can be substituted (e.g., by one or more substituents). The cycloalkyl groups can contain fused or spiro rings. Fused rings are rings that share a common carbon atom. Examples of cycloalkyl moieties include, but are not limited to, cyclopropyl, cyclohexyl, methylcyclohexyl, adamantyl, and norbornyl.

"Cycloalkylalkyl" refers to a -(cycloalkyl)-alkyl radical where cycloalkyl and alkyl are as disclosed herein. The "cycloalkylalkyl" is bonded to the parent molecular structure through the cycloalkyl group.

"Heteroaromatic ring system" is art-recognized and refers to monocyclic, bicyclic or polycyclic ring system wherein at least one ring is both aromatic and comprises at least one heteroatom (e.g., N, O or S); and wherein no other rings are heterocyclyl (as defined below). In certain instances, a ring which is aromatic and comprises a heteroatom contains 1, 2, 3, or 4 ring heteroatoms in such ring.

"Heteroaryl" refers to a monovalent radical of a heteroaromatic ring system. Representative heteroaryl groups include ring systems where (i) each ring comprises a heteroatom and is aromatic, e.g., imidazolyl, oxazolyl, isoxazolyl, thiazolyl, triazolyl, pyrrolyl, furanyl, thiophenyl pyrazolyl, pyridinyl, pyrazinyl, pyridazinyl, pyrimidinyl, indolizinyl, purinyl, naphthyridinyl, and pteridinyl; (ii) each ring is aromatic or carbocyclyl, at least one aromatic ring comprises a heteroatom and at least one other ring is a hydrocarbon ring or e.g., indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, pyrido[2,3-b]-1,4-oxazin-3-(4H)-one, 5,6,7,8-tetrahydroquinolinyl and 5,6,7,8-tetrahydroisoquinolinyl; and (iii) each ring is aromatic or carbocyclyl, and at least one aromatic ring shares a bridgehead heteroatom with another aromatic ring, e.g., 4H-quinolizinyl.

"Heterocyclic ring system" refers to monocyclic, bicyclic and polycyclic ring systems where at least one ring is saturated or partially unsaturated (but not aromatic) and comprises at least one heteroatom. A heterocyclic ring system can be attached to its pendant group at any heteroatom or carbon atom that results in a stable structure and any of the ring atoms can be optionally substituted.

"Heterocyclyl" refers to a monovalent radical of a heterocyclic ring system. Representative heterocyclyls include ring systems in which (i) every ring is non-aromatic and at least one ring comprises a heteroatom, e.g., tetrahydrofuranyl, tetrahydropyranyl, oxetanyl, azetidinyl, tetrahydrothienyl, pyrrolidinyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl; (ii) at least one ring is non-aromatic and comprises a heteroatom and at least one other ring is an aromatic carbon ring, e.g., 1,2,3,4-tetrahydroquinolinyl, 1,2,3,4-tetrahydroisoquinolinyl; and (iii) at least one ring is non-aromatic and comprises a heteroatom and at least one other ring is aromatic and comprises a heteroatom, e.g., 3,4-dihydro-1H-pyrano[4,3-c]pyridine, and 1,2,3,4-tetrahydro-2,6-naphthyridine. In some embodiments, heterocyclyl can include:

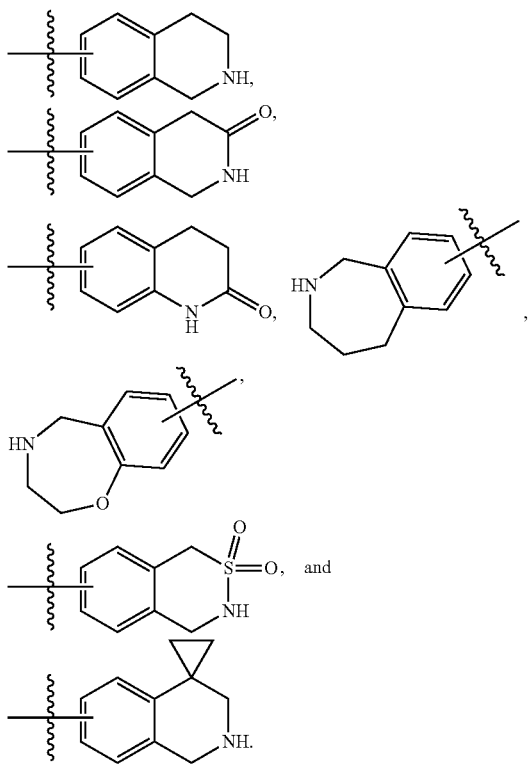

"Heterocyclylalkyl" refers to an alkyl group substituted with a heterocycle group.

"Cyano" refers to a —CN radical.

"Nitro" refers to —NO$_2$.

"Hydroxy" or "hydroxyl" refers to —OH.

"Substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

As used herein, the definition of each expression, e.g., alkyl, m, n, etc., when it occurs more than once in any structure, is intended to be independent of its definition elsewhere in the same structure.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Unless otherwise indicated, when a disclosed compound is named or depicted by a structure without specifying the stereochemistry and has one or more chiral centers, it is understood to represent all possible stereoisomers of the compound, as well as enantiomeric mixtures thereof.

The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer.

$$ee=(90-10)/100=80\%.$$

Thus, a composition containing 90% of one enantiomer and 10% of the other enantiomer is said to have an enantiomeric excess of 80%.

The compounds or compositions described herein may contain an enantiomeric excess of at least 50%, 75%, 90%, 95%, or 99% of one form of the compound, e.g., the S-enantiomer. In other words such compounds or compositions contain an enantiomeric excess of the S enantiomer over the R enantiomer.

The compounds described herein may also contain unnatural proportions of atomic isotopes at one or more of the atoms that constitute such compounds. For example, the compounds may be radiolabeled with radioactive isotopes, such as for example deuterium ($^2$H), tritium ($^3$H), carbon-13 ($^{13}$C), or carbon-14 ($^{14}$C). All isotopic variations of the compounds disclosed herein, whether radioactive or not, are intended to be encompassed within the scope of the present invention. In addition, all tautomeric forms of the compounds described herein are intended to be within the scope of the invention.

The compound can be useful as the free base or as a salt. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19.)

Certain compounds disclosed herein can exist in unsolvated forms as well as solvated forms, including hydrated forms. The term "hydrate" or "hydrated" as used herein, refers to a compound formed by the union of water with the parent compound.

In general, the solvated forms are equivalent to unsolvated forms and are encompassed within the scope of the present invention. Certain compounds disclosed herein may exist in multiple crystalline or amorphous forms. In general, all physical forms are equivalent for the uses contemplated by the present invention and are intended to be within the scope of the present invention.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably includes humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

Compounds

In one embodiment, the invention provides a compound having structural Formula I:

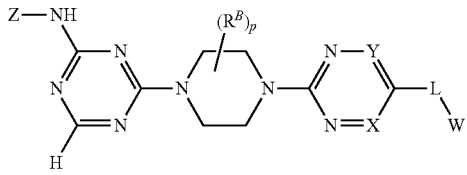

Formula I or a pharmaceutically acceptable salt thereof, wherein:
W is selected from hydrogen, halo and

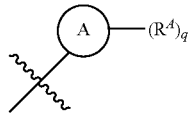

wherein Ring A is selected from monocyclic or bicyclic aryl, monocyclic or bicyclic heteroaryl, cycloalkyl and heterocyclyl;

each X and Y is independently selected from $CR^1$ and N;

Z is selected from $C_1$-$C_6$ alkyl, cycloalkyl, monocyclic or bicyclic aryl, monocyclic or bicyclic aralkyl, monocyclic or bicyclic heteroaryl, monocyclic or bicyclic heterocyclyl, and monocyclic or bicyclic heterocyclylalkyl; wherein each of $C_1$-$C_6$ alkyl, cycloalkyl, monocyclic or bicyclic aryl, monocyclic or bicyclic aralkyl, monocyclic or bicyclic heteroaryl, monocyclic or bicyclic heterocyclyl, and monocyclic or bicyclic heterocyclylalkyl is substituted with 0-5 occurrences of $R^C$;

L is selected from a bond, —$(C(R^2)(R^2))_m$—, —$(C_2$-$C_6$ alkynylene)-, —$(C_2$-$C_6$ alkenylene)-, —$(C_1$-$C_6$ haloalkylene)-, —$(C_1$-$C_6$ heteroalkylene)-, —$(C_1$-$C_6$ hydroxyalkylene)-, —C(O)—, —O—, —S—, —S(O)—, —$SO_2$—, —$N(R^2)$—, —O—$(C_1$-$C_6$ alkylene)-, —$(C_1$-$C_6$ alkylene)-O—, —$N(R^2)$—CO—, —CO—$N(R^2)$—, —$(C_1$-$C_6$ alkylene)-$N(R^2)$—, —$N(R^2)$—$(C_1$-$C_6$ alkylene)-, —$N(R^2)$—CO—$(C_1$-$C_6$ alkylene)-, —CO—$N(R^2)$—$(C_1$-$C_6$ alkylene)-, —$N(R^2)$—$SO_2$—, —$SO_2$—$N(R^2)$—, —$N(R^2)$—$SO_2$—$(C_1$-$C_6$ alkylene)-, and —$SO_2$—$N(R^2)$—$(C_1$-$C_6$ alkylene)-;

each $R^A$ and $R^B$ is independently selected from $C_1$-$C_6$ alkyl, halo, $C_1$-$C_6$ haloalkyl, $C_1$-$C_6$ hydroxyalkyl, $C_1$-$C_6$ heteroalkyl, monocyclic or bicyclic aralkyl, —$N(R^2)(R^2)$, cyano, and —$OR^2$;

each $R^C$ is independently selected from $C_1$-$C_6$ alkyl, $C_1$-$C_6$ alkynyl, halo, $C_1$-$C_6$ heteroalkyl, $C_1$-$C_6$ haloalkyl, $C_1$-$C_6$ haloalkoxy, $C_1$-$C_6$ hydroxyalkyl, cycloalkyl, monocyclic or bicyclic aryl, monocyclic or bicyclic aryloxy, monocyclic or bicyclic aralkyl, monocyclic or bicyclic heterocyclyl, monocyclic or bicyclic heterocyclylalkyl, nitro, cyano, —$C(O)R^2$, —$OC(O)R^2$, —$C(O)OR^2$, —$SR^2$, —$S(O)_2R^2$, —$S(O)_2$—$N(R^2)(R^2)$, —$(C_1$-$C_6$ alkylene)-$S(O)_2$—$N(R^2)(R^2)$, —$N(R^2)(R^2)$, —$C(O)$—$N(R^2)(R^2)$, —$N(R^2)(R^2)$—$C(O)R^2$, —$(C_1$-$C_6$ alkylene)-$N(R^2)$—$C(O)R^2$, —$NR^2S(O)_2R^2$, —$P(O)(R^2)(R^2)$, and —$OR^2$; wherein each of heteroalkyl, haloalkyl, haloalkoxy, alkyl, alkynyl, cycloalkyl, aryl, aryloxy, aralkyl, heterocyclyl, and heterocyclylalkyl is substituted with 0-5 occurrences of $R^a$; or 2 $R^C$ together with the carbon atom(s) to which they are attached form a cycloalkyl or heterocyclyl ring substituted with 0-5 occurrences of $R^a$;

each $R^1$ is independently selected from hydrogen, $C_1$-$C_6$ alkyl, monocyclic aralkyl, $C_1$-$C_6$ hydroxyalkyl, halo, $C_1$-$C_6$ haloalkyl, —$N(R^2)(R^2)$, and —$OR^2$;

each $R^2$ is independently selected from hydrogen, hydroxyl, halo, $C_1$-$C_6$ alkyl, $C_1$-$C_6$ haloalkyl, $C_1$-$C_6$ hydroxyalkyl, cycloalkyl, cycloalkylalkyl, heterocyclyl, and heterocyclylalkyl; wherein each of $C_1$-$C_6$ alkyl, cycloalkyl and heterocyclyl is substituted with 0-5 occurrences of $R^b$, or 2 $R^2$ together with the carbon or nitrogen atom to which they are attached form a cycloalkyl or heterocyclyl ring;

each $R^a$ and $R^b$ is independently selected from halo, hydroxyl, —C(O)R', $C_1$-$C_6$ alkyl, $C_1$-$C_6$ haloalkyl, $C_1$-$C_6$ heteroalkyl, $C_1$-$C_6$ hydroxyalkyl, —NR'R', and cycloalkyl; wherein cycloalkyl is substituted with 0-5 occurrences of R';

R' is hydrogen, hydroxyl, or $C_1$-$C_6$ alkyl; and m, p, and q are each independently 0, 1, 2, 3, or 4.

In some embodiments, W is H. In some embodiments, W is halo. In some embodiments, W is

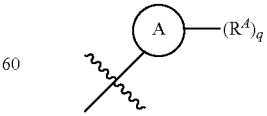

wherein Ring A is selected from monocyclic or bicyclic aryl, monocyclic or bicyclic heteroaryl, cycloalkyl and heterocyclyl. In some embodiments, Ring A is selected from phenyl, cycloalkyl, monocyclic heteroaryl, and heterocyclyl. In some embodiments, Ring A is optionally substituted phenyl. In some embodiments, Ring A is substituted phenyl. In some embodiments, Ring A is unsubstituted phenyl. In some embodiments, Ring A is phenyl substituted with halo.

In some embodiments, each $R^A$ is independently selected from $C_1$-$C_6$ alkyl, halo, $C_1$-$C_6$ haloalkyl, $C_1$-$C_6$ hydroxyalkyl, —N($R^2$)($R^2$), cyano, and —O$R^2$. In some embodiments, $R^A$ is independently selected from $C_1$-$C_6$ alkyl and halo. In some embodiments, q is 0, 1 or 2.

In some embodiments, each $R^B$ is independently selected from $C_1$-$C_6$ alkyl, $C_1$-$C_6$ hydroxyalkyl, $C_1$-$C_6$ heteroalkyl, —N($R^2$)($R^2$), cyano and —O$R^2$. In some embodiments, each $R^B$ is independently selected from $C_1$-$C_6$ alkyl and $C_1$-$C_6$ hydroxyalkyl. In some embodiments, p is 0, 1 or 2. In some embodiments, p is 0. In some embodiments, p is 1.

In some embodiments, at least one of X and Y is N. In some embodiments, X and Y are both N. In some embodiments, X and Y are both $CR^1$. In some embodiments, X and Y are both CH.

In some embodiments, Z is $C_1$-$C_6$ alkyl. In some embodiments, Z is cycloalkyl, monocyclic or bicyclic aryl, monocyclic or bicyclic aralkyl, monocyclic or bicyclic heteroaryl, monocyclic or bicyclic heterocyclyl, or monocyclic or bicyclic heterocyclylalkyl; wherein each of $C_1$-$C_6$ alkyl, cycloalkyl, monocyclic or bicyclic aryl, monocyclic or bicyclic aralkyl, monocyclic or bicyclic heteroaryl, monocyclic or bicyclic heterocyclyl, and monocyclic and bicyclic heterocyclylalkyl is substituted with 0-5 occurrences of $R^C$. In some embodiments, Z is bicyclic heteroaryl, bicyclic heterocyclyl, monocyclic heteroaryl, monocyclic heterocyclylalkyl, or monocyclic aryl. In some embodiments, Z is aryl or heteroaryl substituted with 0-5 occurrences of $R^C$. In some embodiments, Z is phenyl substituted with 0-5 occurrences of $R^C$. In some embodiments, Z is phenyl substituted with 1 or 2 occurrences of $R^C$. In some embodiments, Z is phenyl substituted with —N($R^2$)($R^2$), $C_1$-$C_6$ alkyl, or $C_1$-$C_6$ hydroxyalkyl. In some embodiments, Z is heteroaryl substituted with 0-5 occurrences of $R^C$. In some embodiments, Z is a heteroaryl ring substituted with 0-5 occurrences of $R^C$.

In some embodiments, each $R^C$ is independently selected from $C_1$-$C_6$ alkyl, $C_1$-$C_6$ heteroalkyl, $C_1$-$C_6$ hydroxyalkyl, cycloalkyl, monocyclic or bicyclic heterocyclyl, monocyclic or bicyclic heterocyclylalkyl, —C(O)$R^2$, —C(O)O$R^2$, —S$R^2$, —S(O)$_2R^2$, and —O$R^2$; wherein each of heteroalkyl, alkyl, cycloalkyl, heterocyclyl, and heterocyclylalkyl is substituted with 0-5 occurrences of $R^a$.

In some embodiments, L is selected from a bond, —O—, —(C($R^2$)($R^2$))$_m$—, —O—($C_1$-$C_6$ alkylene)-, —($C_1$-$C_6$ alkylene)-O—, —($C_2$-$C_6$ alkynylene)-, —($C_1$-$C_6$ haloalkylene)-, —($C_1$-$C_6$ hydroxyalkylene)-, —O—, —S(O), —SO$_2$—, and —N($R^2$)—. In some embodiments, L is selected from a bond, —(C($R^2$)($R^2$))$_m$—, —S—, and —SO$_2$—. In some embodiments, L is —(C($R^2$)($R^2$))$_m$—. In some embodiments, L is a bond or CH$_2$. In some embodiments, L is —(C($R^2$)($R^2$))$_m$—, wherein each $R^2$ is independently selected from hydrogen, hydroxyl, —NR"R", $C_1$-$C_6$ alkyl, $C_1$-$C_6$ haloalkyl, $C_1$-$C_6$ hydroxyalkyl, and cycloalkyl; and m is 1 or 2.

In some embodiments, the compound is a compound of Formula II, or a pharmaceutically acceptable salt thereof, where the substituents are as defined above.

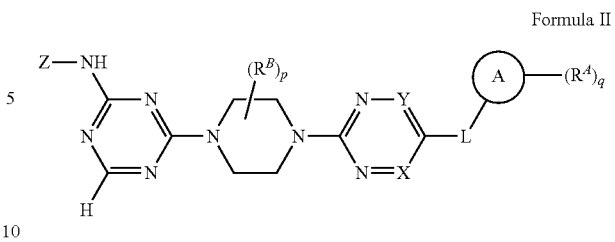

Formula II

In some embodiments, L is —(C($R^2$)($R^2$))$_m$—. In some embodiments, X and Y are CR$^1$. In some embodiments, Z is phenyl, Z is pyridinyl, Z is isoxazolyl, Z is pyrazolyl, or Z is dihydroisoquinolinyl.

In some embodiments, Ring A is selected from monocyclic or bicyclic aryl, monocyclic or bicyclic heteroaryl, cycloalkyl and heterocyclyl. In some embodiments, Ring A is selected from phenyl, cycloalkyl, monocyclic heteroaryl, and heterocyclyl. In some embodiments, Ring A is optionally substituted phenyl. In some embodiments, Ring A is substituted phenyl. In some embodiments, Ring A is unsubstituted phenyl. In some embodiments, Ring A is phenyl substituted with halo.

In some embodiments, each $R^A$ is independently selected from $C_1$-$C_6$ alkyl, halo, $C_1$-$C_6$ haloalkyl, $C_1$-$C_6$ hydroxyalkyl, —N($R^2$)($R^2$), cyano, and —O$R^2$. In some embodiments, $R^A$ is independently selected from $C_1$-$C_6$ alkyl and halo. In some embodiments, q is 0, 1 or 2.

In some embodiments, each $R^B$ is independently selected from $C_1$-$C_6$ alkyl, $C_1$-$C_6$ hydroxyalkyl, $C_1$-$C_6$ heteroalkyl, —N($R^2$)($R^2$), cyano and —O$R^2$. In some embodiments, each $R^B$ is independently selected from $C_1$-$C_6$ alkyl and $C_1$-$C_6$ hydroxyalkyl. In some embodiments, p is 0, 1 or 2. In some embodiments, p is 0. In some embodiments, p is 1.

In some embodiments, at least one of X and Y is N. In some embodiments, X and Y are both N. In some embodiments, X and Y are both $CR^1$. In some embodiments, X and Y are both CH.

In some embodiments, Z is $C_1$-$C_6$ alkyl. In some embodiments, Z is cycloalkyl, monocyclic or bicyclic aryl, monocyclic or bicyclic aralkyl, monocyclic or bicyclic heteroaryl, monocyclic or bicyclic heterocyclyl, or monocyclic or bicyclic heterocyclylalkyl; wherein each of $C_1$-$C_6$ alkyl, cycloalkyl, monocyclic or bicyclic aryl, monocyclic or bicyclic aralkyl, monocyclic or bicyclic heteroaryl, monocyclic or bicyclic heterocyclyl, and monocyclic and bicyclic heterocyclylalkyl is substituted with 0-5 occurrences of $R^C$. In some embodiments, Z is bicyclic heteroaryl, bicyclic heterocyclyl, monocyclic heteroaryl, monocyclic heterocyclylalkyl, or monocyclic aryl. In some embodiments, Z is aryl or heteroaryl substituted with 0-5 occurrences of $R^C$. In some embodiments, Z is phenyl substituted with 0-5 occurrences of $R^C$. In some embodiments, Z is phenyl substituted with 1 or 2 occurrences of $R^C$. In some embodiments, Z is phenyl substituted with —N($R^2$)($R^2$), $C_1$-$C_6$ alkyl, or $C_1$-$C_6$ hydroxyalkyl. In some embodiments, Z is heteroaryl substituted with 0-5 occurrences of $R^C$. In some embodiments, Z is a heteroaryl ring substituted with 0-5 occurrences of $R^C$.

In some embodiments, each $R^C$ is independently selected from $C_1$-$C_6$ alkyl, $C_1$-$C_6$ heteroalkyl, $C_1$-$C_6$ hydroxyalkyl, cycloalkyl, monocyclic or bicyclic heterocyclyl, monocyclic or bicyclic heterocyclylalkyl, —C(O)$R^2$, —C(O)O$R^2$, —S$R^2$, —S(O)$_2R^2$, and —O$R^2$; wherein each of heteroalkyl, alkyl, cycloalkyl, heterocyclyl, and heterocyclylalkyl is substituted with 0-5 occurrences of $R^a$.

In some embodiments, L is selected from a bond, —O—, —(C($R^2$)($R^2$))$_m$—, —O—($C_1$-$C_6$ alkylene)-, —($C_1$-$C_6$ alkylene)-O—, —($C_2$-$C_6$ alkynylene)-, —($C_1$-$C_6$ haloalkylene)-, —($C_1$-$C_6$ hydroxyalkylene)-, —S—, —S(O), —$SO_2$—, and —N($R^2$)—. In some embodiments, L is selected from a bond, —(C($R^2$)($R^2$))$_m$—, —S—, and —$SO_2$—. In some embodiments, L is —(C($R^2$)($R^2$))$_m$—. In some embodiments, L is a bond or $CH_2$. In some embodiments, L is —(C($R^2$)($R^2$))$_m$—, wherein each $R^2$ is independently selected from hydrogen, hydroxyl, —NR"R", $C_1$-$C_6$ alkyl, $C_1$-$C_6$ haloalkyl, $C_1$-$C_6$ hydroxyalkyl, and cycloalkyl; and m is 1 or 2.

In other embodiments, the compound is a compound of Formula II(a), or a pharmaceutically acceptable salt thereof, where the substituents are as defined above.

Formula II(a)

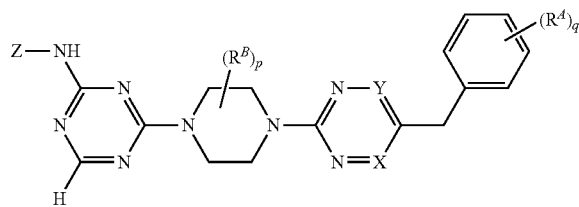

In some embodiments, Z is phenyl, Z is pyridinyl, Z is isoxazolyl, Z is pyrazolyl, or Z is dihydroisoquinolinyl. In some embodiments, $R^C$ is piperidinyl.

In some embodiments, each $R^A$ is independently selected from $C_1$-$C_6$ alkyl, halo, $C_1$-$C_6$ haloalkyl, $C_1$-$C_6$ hydroxyalkyl, —N($R^2$)($R^2$), cyano, and —$OR^2$. In some embodiments, $R^A$ is independently selected from $C_1$-$C_6$ alkyl and halo. In some embodiments, q is 0, 1 or 2.

In some embodiments, each $R^B$ is independently selected from $C_1$-$C_6$ alkyl, $C_1$-$C_6$ hydroxyalkyl, $C_1$-$C_6$ heteroalkyl, —N($R^2$)($R^2$), cyano and —$OR^2$. In some embodiments, each $R^B$ is independently selected from $C_1$-$C_6$ alkyl and $C_1$-$C_6$ hydroxyalkyl. In some embodiments, p is 0, 1 or 2. In some embodiments, p is 0. In some embodiments, p is 1.

In some embodiments, at least one of X and Y is N. In some embodiments, X and Y are both N. In some embodiments, X and Y are both $CR^1$. In some embodiments, X and Y are both CH.

In some embodiments, Z is $C_1$-$C_6$ alkyl. In some embodiments, Z is cycloalkyl, monocyclic or bicyclic aryl, monocyclic or bicyclic aralkyl, monocyclic or bicyclic heteroaryl, monocyclic or bicyclic heterocyclyl, or monocyclic or bicyclic heterocyclylalkyl; wherein each of $C_1$-$C_6$ alkyl, cycloalkyl, monocyclic or bicyclic aryl, monocyclic or bicyclic aralkyl, monocyclic or bicyclic heteroaryl, monocyclic or bicyclic heterocyclyl, and monocyclic and bicyclic heterocyclylalkyl is substituted with 0-5 occurrences of $R^C$. In some embodiments, Z is bicyclic heteroaryl, bicyclic heterocyclyl, monocyclic heteroaryl, monocyclic heterocyclylalkyl, or monocyclic aryl. In some embodiments, Z is aryl or heteroaryl substituted with 0-5 occurrences of $R^C$. In some embodiments, Z is phenyl substituted with 0-5 occurrences of $R^C$. In some embodiments, Z is phenyl substituted with 1 or 2 occurrences of $R^C$. In some embodiments, Z is phenyl substituted with —N($R^2$)($R^2$), $C_1$-$C_6$ alkyl, or $C_1$-$C_6$ hydroxyalkyl. In some embodiments, Z is heteroaryl substituted with 0-5 occurrences of $R^C$. In some embodiments, Z is a heteroaryl ring substituted with 0-5 occurrences of $R^C$.

In some embodiments, each $R^C$ is independently selected from $C_1$-$C_6$ alkyl, $C_1$-$C_6$ heteroalkyl, $C_1$-$C_6$ hydroxyalkyl, cycloalkyl, monocyclic or bicyclic heterocyclyl, monocyclic or bicyclic heterocyclylalkyl, —C(O)$R^2$, —C(O)O$R^2$, —S$R^2$, —S(O)$_2R^2$, and —$OR^2$; wherein each of heteroalkyl, alkyl, cycloalkyl, heterocyclyl, and heterocyclylalkyl is substituted with 0-5 occurrences of $R^a$.

The invention also features pharmaceutical compositions comprising a pharmaceutically acceptable carrier and any compound of Formulas I-III.

The table below shows the structures of compounds described herein.

| Compound Number | Structure |
|---|---|
| 1 | ![structure of compound 1: methylamino-triazine linked via piperazine to pyrimidine bearing NH2 and benzyl substituents] |

-continued
| Compound Number | Structure |
|---|---|
| 2 | 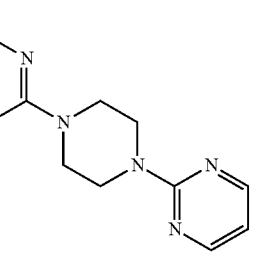 |
| 3 | 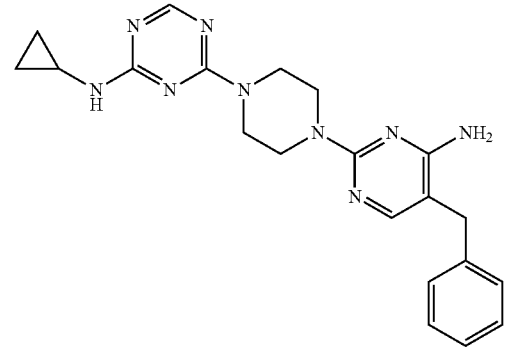 [SMILES: Nc1nc(N2CCN(c3ncnc(NC4CC4)n3)CC2)ncc1Cc1ccccc1] |
| 4 | 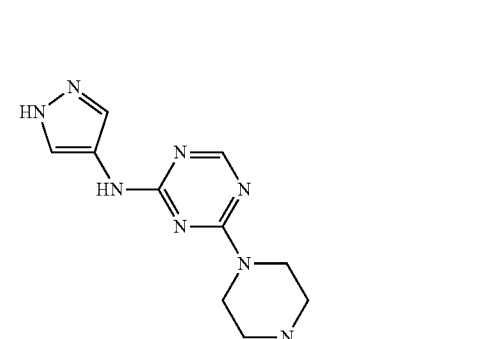 |

-continued
| Compound Number | Structure |
|---|---|
| 5 | 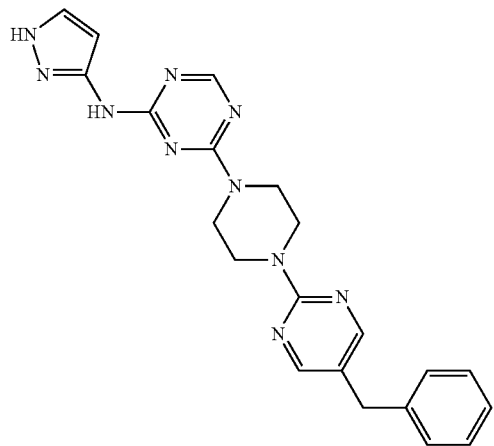 [SMILES: c1ccc(Cc2cnc(N3CCN(c4ncnc(Nc5cc[nH]n5)n4)CC3)nc2)cc1] |
| 6 | 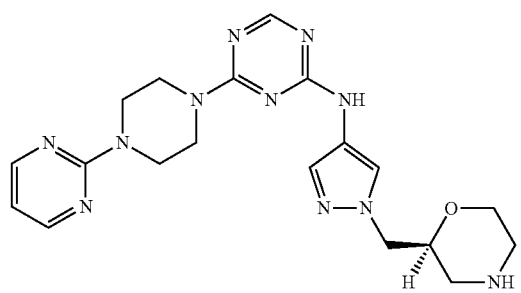 [SMILES: c1cnc(N2CCN(c3ncnc(Nc4cnn(C[C@@H]5CNCCO5)c4)n3)CC2)nc1] |
| 7 | 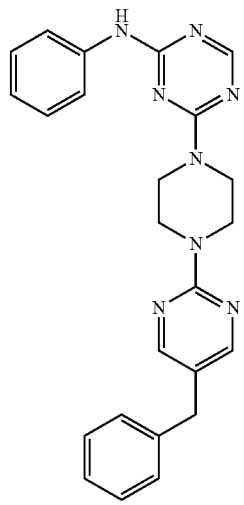 [SMILES: c1ccc(Cc2cnc(N3CCN(c4ncnc(Nc5ccccc5)n4)CC3)nc2)cc1] |

-continued
| Compound Number | Structure |
|---|---|
| 8 | 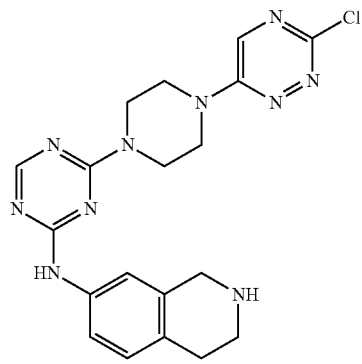 [SMILES: Clc1ncc(N2CCN(c3ncnc(Nc4ccc5c(c4)CNCC5)n3)CC2)nn1] |
| 9 | 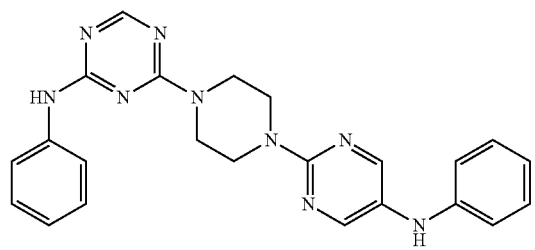 [SMILES: c1ccc(Nc2cnc(N3CCN(c4ncnc(Nc5ccccc5)n4)CC3)nc2)cc1] |
| 10 | 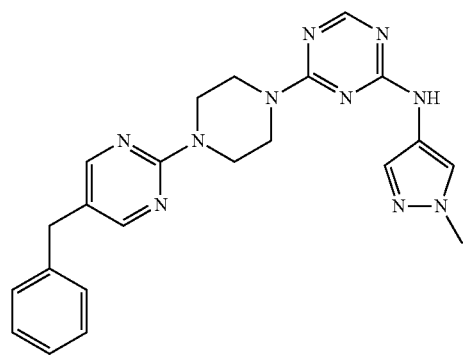 [SMILES: Cn1cc(Nc2ncnc(N3CCN(c4ncc(Cc5ccccc5)cn4)CC3)n2)cn1] |
| 11 | 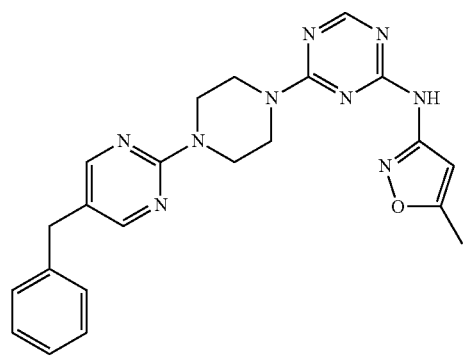 [SMILES: Cc1cc(Nc2ncnc(N3CCN(c4ncc(Cc5ccccc5)cn4)CC3)n2)no1] |

| Compound Number | Structure |
|---|---|
| 12 | 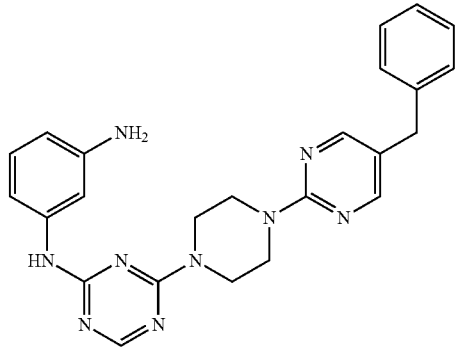 [SMILES: Nc1cccc(Nc2ncnc(N3CCN(c4ncc(Cc5ccccc5)cn4)CC3)n2)c1] |
| 13 | 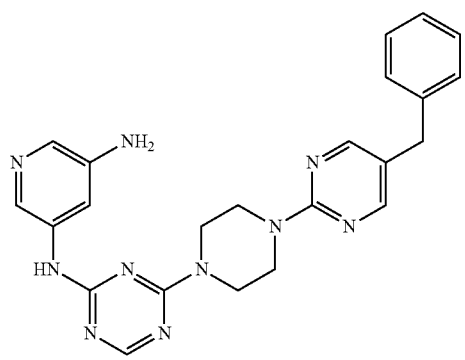 [SMILES: Nc1cncc(Nc2ncnc(N3CCN(c4ncc(Cc5ccccc5)cn4)CC3)n2)c1] |
| 14 | 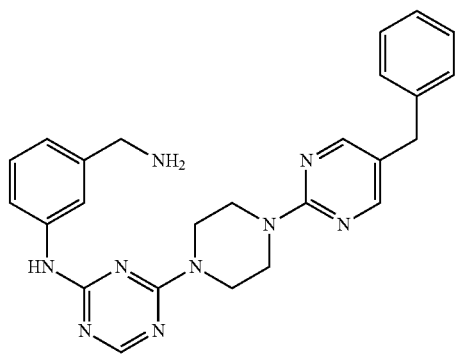 [SMILES: NCc1cccc(Nc2ncnc(N3CCN(c4ncc(Cc5ccccc5)cn4)CC3)n2)c1] |
| 15 | 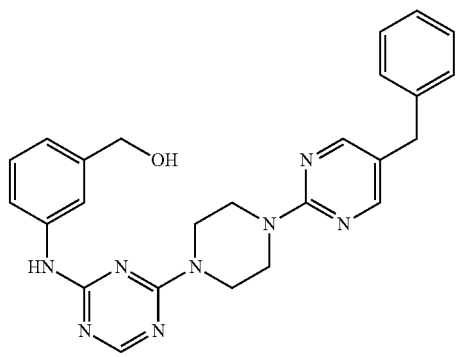 [SMILES: OCc1cccc(Nc2ncnc(N3CCN(c4ncc(Cc5ccccc5)cn4)CC3)n2)c1] |

-continued
| Compound Number | Structure |
|---|---|
| 16 | 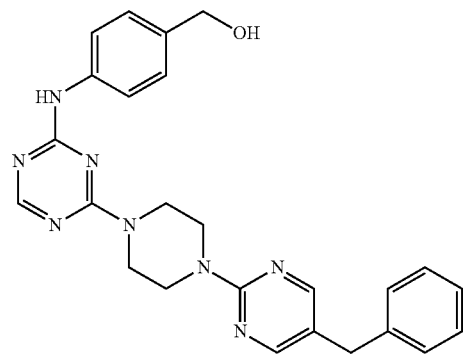 [SMILES: OCc1ccc(Nc2ncnc(N3CCN(c4ncc(Cc5ccccc5)cn4)CC3)n2)cc1] |
| 17 | 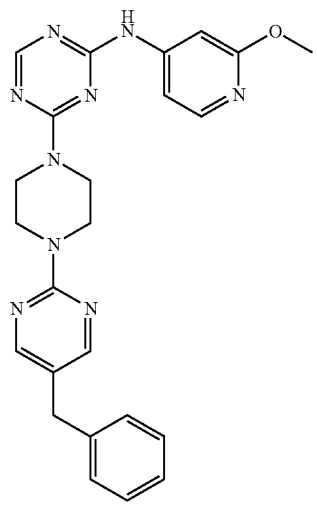 [SMILES: COc1cc(Nc2ncnc(N3CCN(c4ncc(Cc5ccccc5)cn4)CC3)n2)ccn1] |
| 18 | 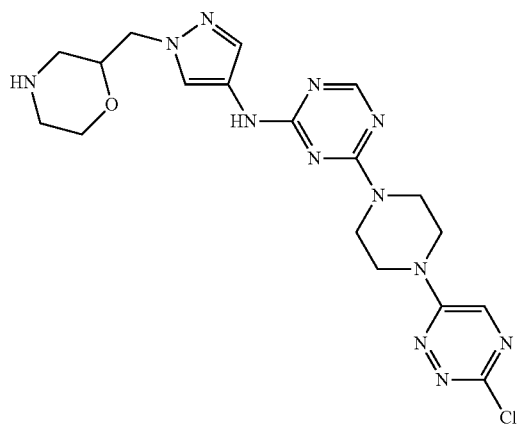 [SMILES: Clc1ncc(N2CCN(c3ncnc(Nc4cnn(CC5CNCCO5)c4)n3)CC2)nn1] |

-continued
| Compound Number | Structure |
|---|---|
| 19 | 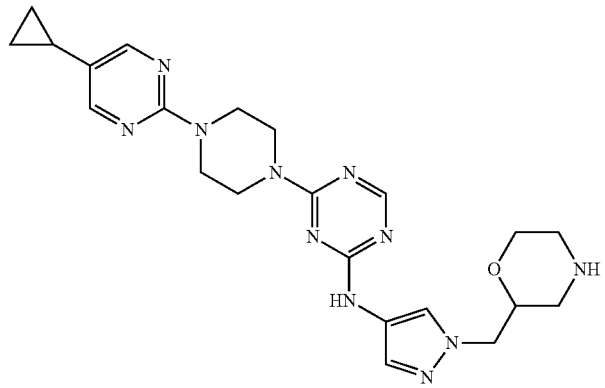 [SMILES: c1nc(Nc2cnn(CC3CNCCO3)c2)nc(N2CCN(c3ncc(C4CC4)cn3)CC2)n1] |
| 20 | 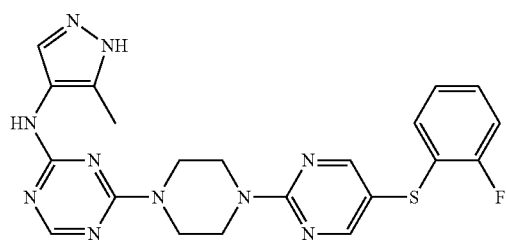 [SMILES: Cc1[nH]ncc1Nc1ncnc(N2CCN(c3ncc(Sc4ccccc4F)cn3)CC2)n1] |
| 21 | 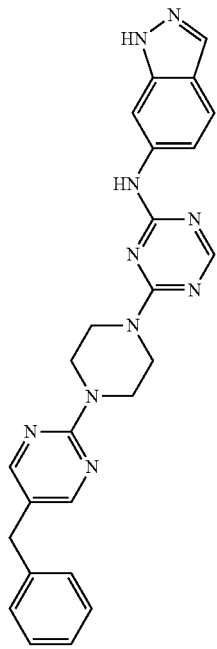 [SMILES: c1ccc(Cc2cnc(N3CCN(c4ncnc(Nc5ccc6cn[nH]c6c5)n4)CC3)nc2)cc1] |

-continued
| Compound Number | Structure |
|---|---|
| 22 | 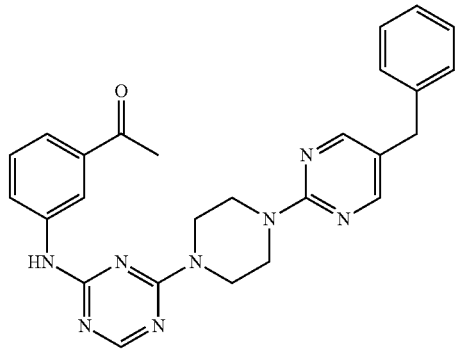 [SMILES: CC(=O)c1cccc(Nc2ncnc(N3CCN(c4ncc(Cc5ccccc5)cn4)CC3)n2)c1] |
| 23 | 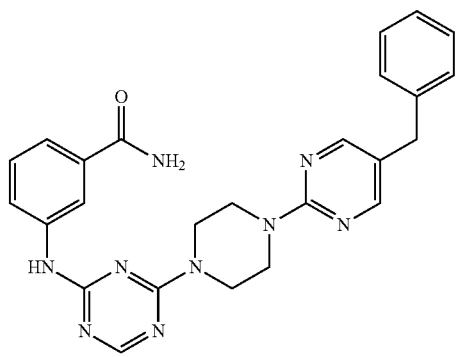 [SMILES: NC(=O)c1cccc(Nc2ncnc(N3CCN(c4ncc(Cc5ccccc5)cn4)CC3)n2)c1] |
| 24 | 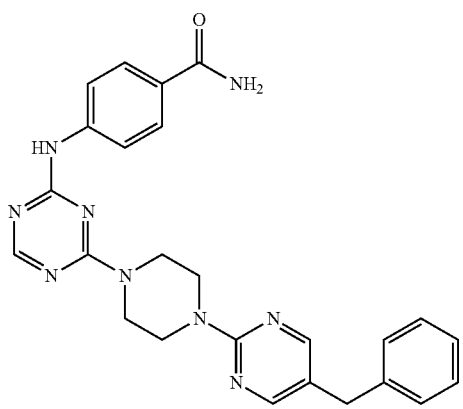 [SMILES: NC(=O)c1ccc(Nc2ncnc(N3CCN(c4ncc(Cc5ccccc5)cn4)CC3)n2)cc1] |
| 25 | 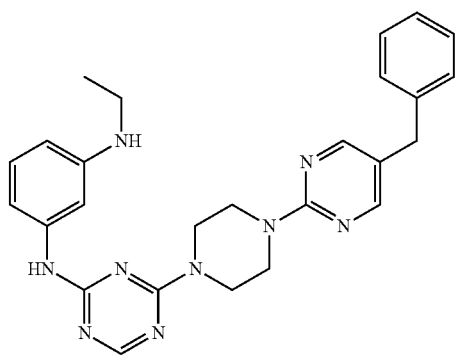 [SMILES: CCNc1cccc(Nc2ncnc(N3CCN(c4ncc(Cc5ccccc5)cn4)CC3)n2)c1] |

| Compound Number | Structure |
|---|---|
| 26 | 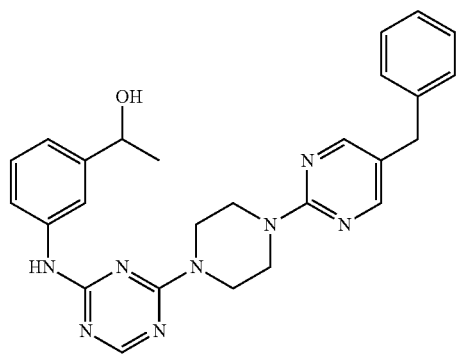 [SMILES: CC(O)c1cccc(Nc2ncnc(N3CCN(c4ncc(Cc5ccccc5)cn4)CC3)n2)c1] |
| 27 | 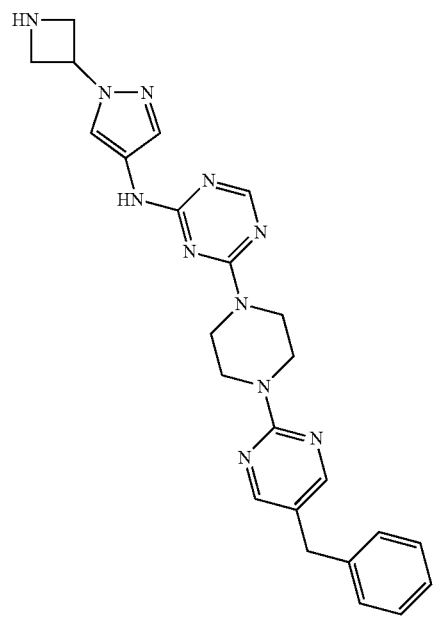 [SMILES: c1ccc(Cc2cnc(N3CCN(c4ncnc(Nc5cnn(C6CNC6)c5)n4)CC3)nc2)cc1] |
| 28 | 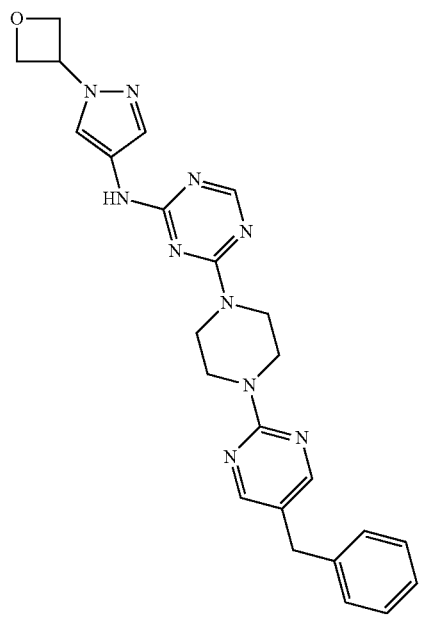 [SMILES: c1ccc(Cc2cnc(N3CCN(c4ncnc(Nc5cnn(C6COC6)c5)n4)CC3)nc2)cc1] |

| Compound Number | Structure |
|---|---|
| 29 | 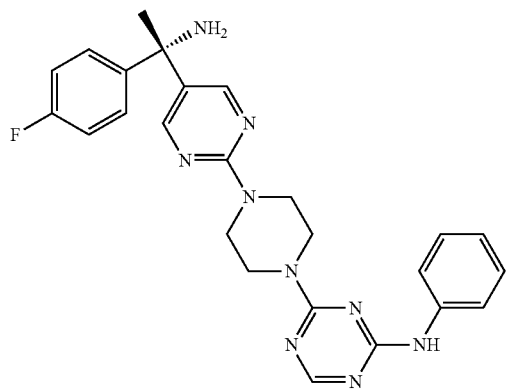 [SMILES: C[C@](N)(c1ccc(F)cc1)c1cnc(N2CCN(c3ncnc(Nc4ccccc4)n3)CC2)nc1] |
| 30 | 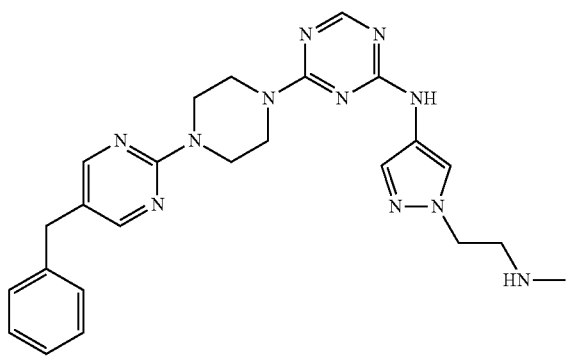 [SMILES: CNCCn1cc(Nc2ncnc(N3CCN(c4ncc(Cc5ccccc5)cn4)CC3)n2)cn1] |
| 31 | 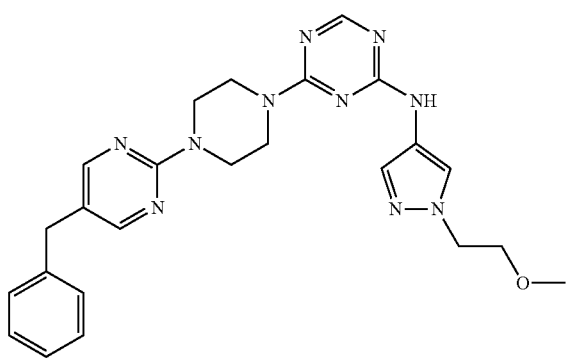 [SMILES: COCCn1cc(Nc2ncnc(N3CCN(c4ncc(Cc5ccccc5)cn4)CC3)n2)cn1] |
| 32 | 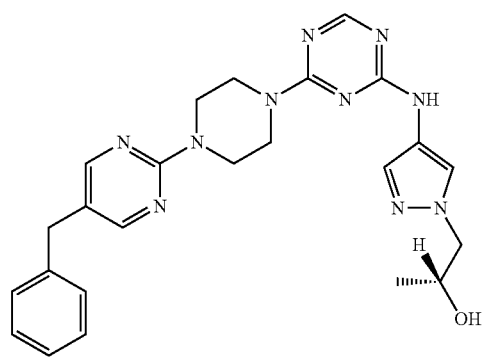 [SMILES: C[C@@H](O)Cn1cc(Nc2ncnc(N3CCN(c4ncc(Cc5ccccc5)cn4)CC3)n2)cn1] |

-continued
| Compound Number | Structure |
|---|---|
| 33 | 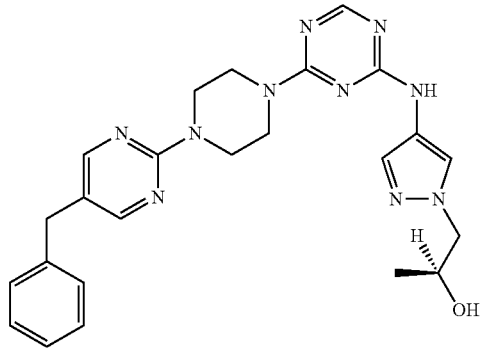 [SMILES: C[C@H](O)Cn1cc(Nc2ncnc(N3CCN(c4ncc(Cc5ccccc5)cn4)CC3)n2)cn1] |
| 34 | 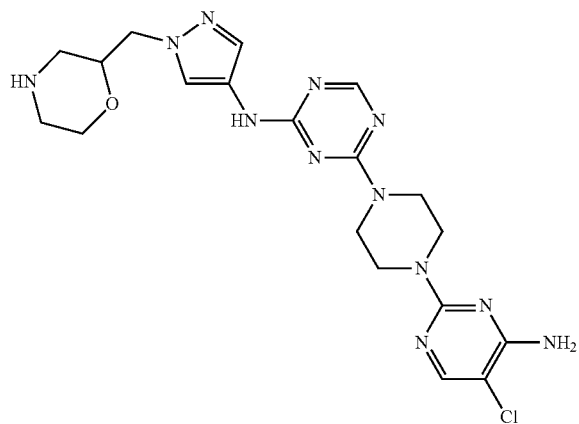 [SMILES: Nc1nc(N2CCN(c3ncnc(Nc4cnn(CC5CNCCO5)c4)n3)CC2)ncc1Cl] |
| 35 | 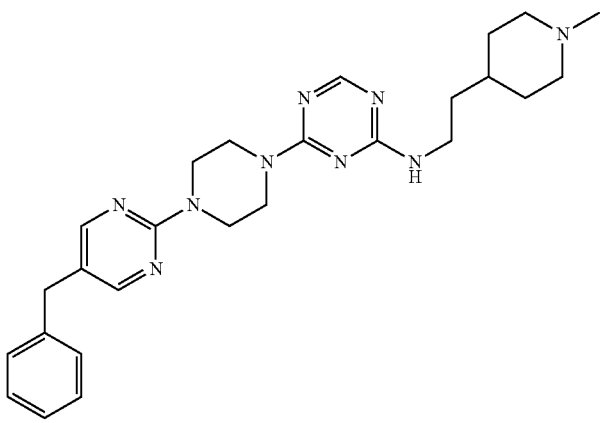 [SMILES: CN1CCC(CCNc2ncnc(N3CCN(c4ncc(Cc5ccccc5)cn4)CC3)n2)CC1] |

| Compound Number | Structure |
|---|---|
| 36 | 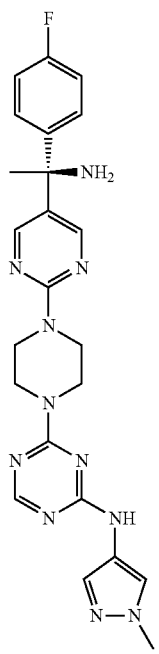 [SMILES: Cn1cc(Nc2ncnc(N3CCN(c4ncc([C@@](C)(N)c5ccc(F)cc5)cn4)CC3)n2)cn1] |
| 37 | 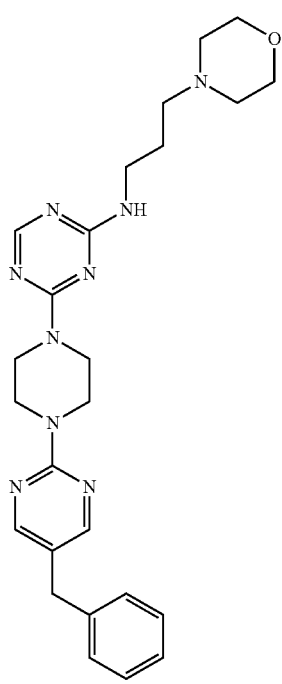 [SMILES: c1ccc(Cc2cnc(N3CCN(c4ncnc(NCCCN5CCOCC5)n4)CC3)nc2)cc1] |

-continued
| Compound Number | Structure |
|---|---|
| 38 | 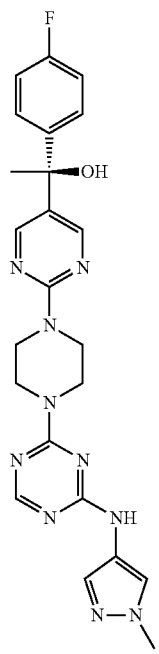 [SMILES: Cn1cc(Nc2ncnc(N3CCN(c4ncc([C@@](C)(O)c5ccc(F)cc5)cn4)CC3)n2)cn1] |
| 39 | 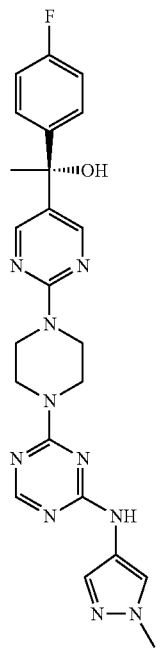 [SMILES: Cn1cc(Nc2ncnc(N3CCN(c4ncc([C@](C)(O)c5ccc(F)cc5)cn4)CC3)n2)cn1] |
| 40 | 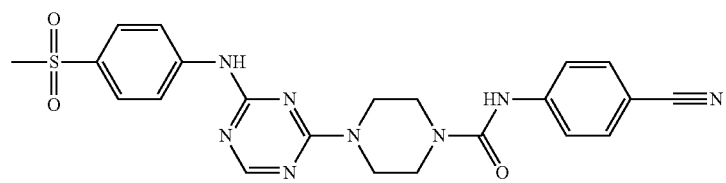 [SMILES: CS(=O)(=O)c1ccc(Nc2ncnc(N3CCN(C(=O)Nc4ccc(C#N)cc4)CC3)n2)cc1] |

-continued
| Compound Number | Structure |
|---|---|
| 41 | 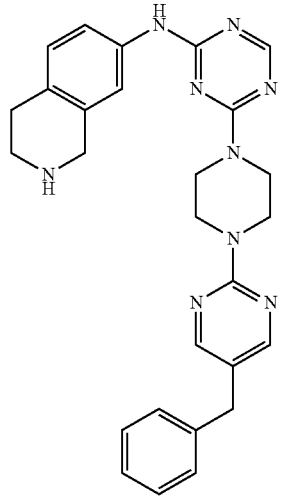 [SMILES: c1ccc(Cc2cnc(N3CCN(c4ncnc(Nc5ccc6c(c5)CNCC6)n4)CC3)nc2)cc1] |
| 42 | 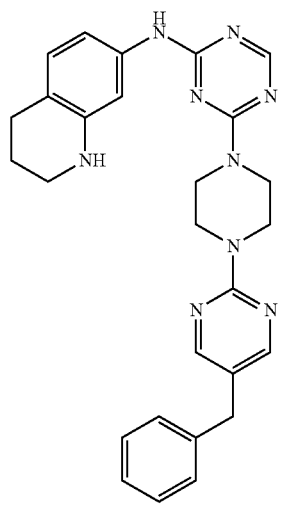 [SMILES: c1ccc(Cc2cnc(N3CCN(c4ncnc(Nc5ccc6c(c5)NCCC6)n4)CC3)nc2)cc1] |
| 43 | 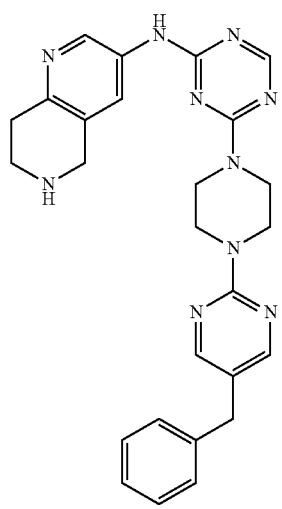 [SMILES: c1ccc(Cc2cnc(N3CCN(c4ncnc(Nc5cnc6c(c5)CNCC6)n4)CC3)nc2)cc1] |

-continued
| Compound Number | Structure |
|---|---|
| 44 | 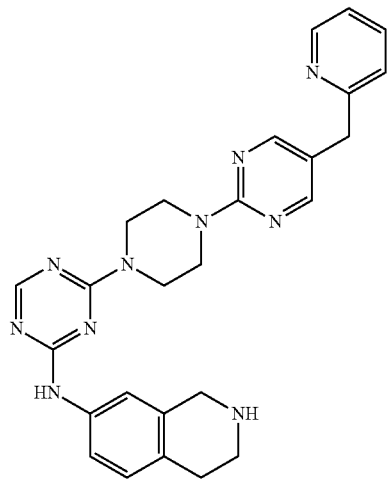 [SMILES: c1ccc(Cc2cnc(N3CCN(c4ncnc(Nc5ccc6c(c5)CNCC6)n4)CC3)nc2)nc1] |
| 45 | 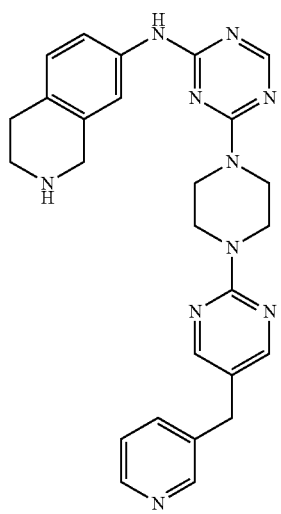 [SMILES: c1cncc(Cc2cnc(N3CCN(c4ncnc(Nc5ccc6c(c5)CNCC6)n4)CC3)nc2)c1] |
| 46 | 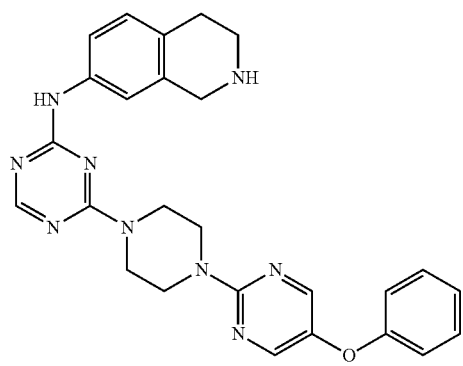 [SMILES: c1ccc(Oc2cnc(N3CCN(c4ncnc(Nc5ccc6c(c5)CNCC6)n4)CC3)nc2)cc1] |

-continued
| Compound Number | Structure |
|---|---|
| 47 | 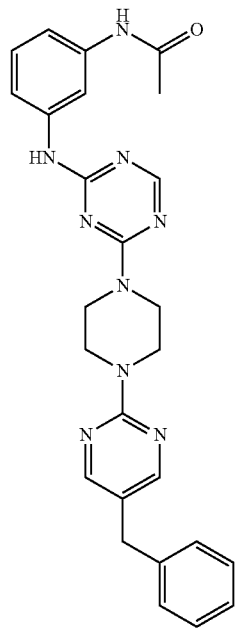 [SMILES: CC(=O)Nc1cccc(Nc2ncnc(N3CCN(c4ncc(Cc5ccccc5)cn4)CC3)n2)c1] |
| 48 | 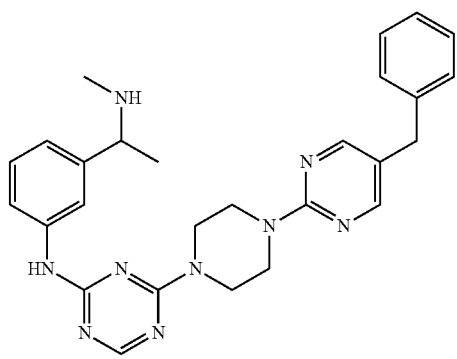 [SMILES: CNC(C)c1cccc(Nc2ncnc(N3CCN(c4ncc(Cc5ccccc5)cn4)CC3)n2)c1] |
| 49 | 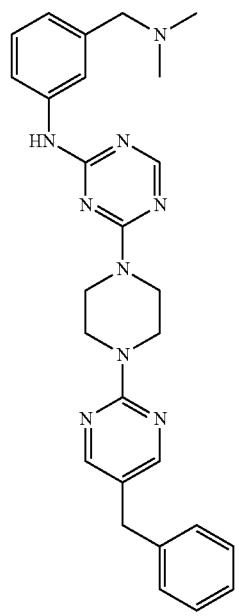 [SMILES: CN(C)Cc1cccc(Nc2ncnc(N3CCN(c4ncc(Cc5ccccc5)cn4)CC3)n2)c1] |

-continued
| Compound Number | Structure |
|---|---|
| 50 | 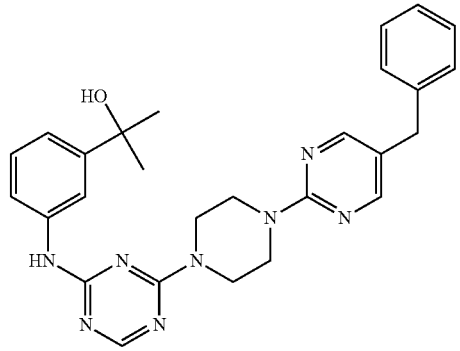 [SMILES: CC(C)(O)c1cccc(Nc2ncnc(N3CCN(c4ncc(Cc5ccccc5)cn4)CC3)n2)c1] |
| 51 | 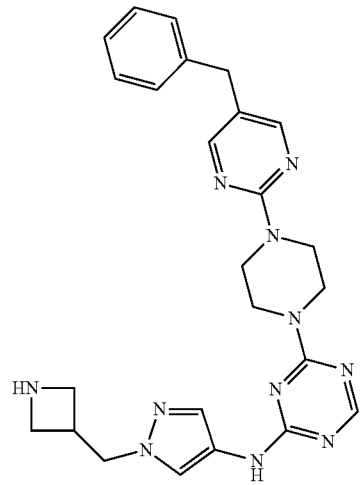 [SMILES: c1ccc(Cc2cnc(N3CCN(c4ncnc(Nc5cnn(CC6CNC6)c5)n4)CC3)nc2)cc1] |
| 52 | 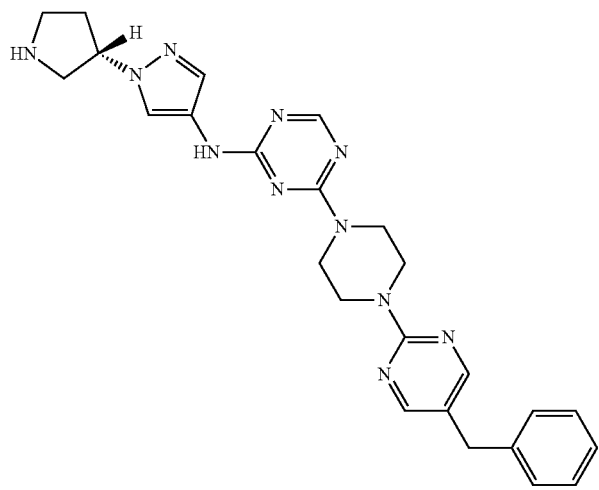 [SMILES: c1ccc(Cc2cnc(N3CCN(c4ncnc(Nc5cnn([C@H]6CCNC6)c5)n4)CC3)nc2)cc1] |

-continued
| Compound Number | Structure |
|---|---|
| 53 | 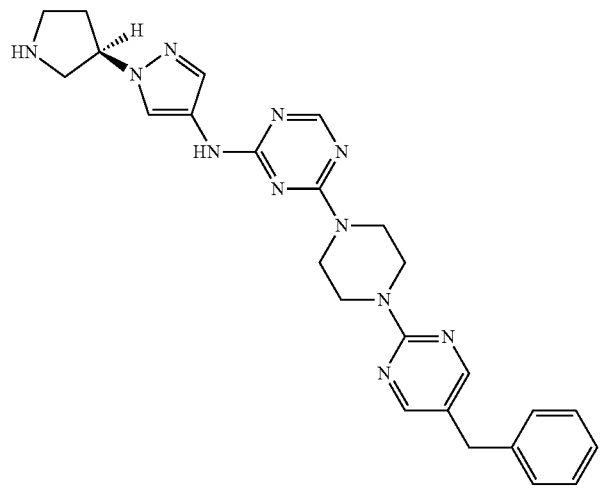 [SMILES: c1ccc(Cc2cnc(N3CCN(c4ncnc(Nc5cnn([C@@H]6CCNC6)c5)n4)CC3)nc2)cc1] |
| 54 | 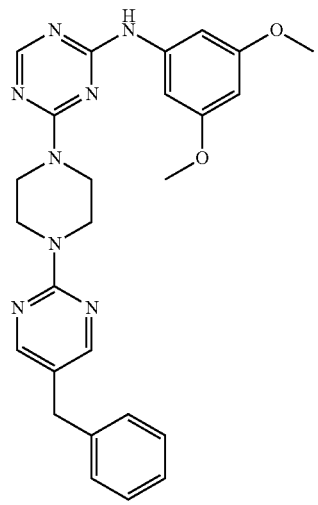 [SMILES: COc1cc(Nc2ncnc(N3CCN(c4ncc(Cc5ccccc5)cn4)CC3)n2)cc(OC)c1] |
| 55 | 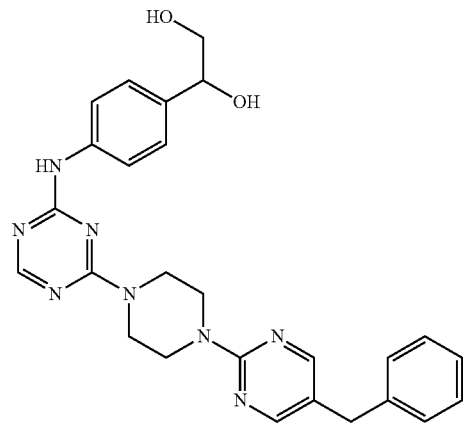 [SMILES: OCC(O)c1ccc(Nc2ncnc(N3CCN(c4ncc(Cc5ccccc5)cn4)CC3)n2)cc1] |

| Compound Number | Structure |
|---|---|
| 56 | 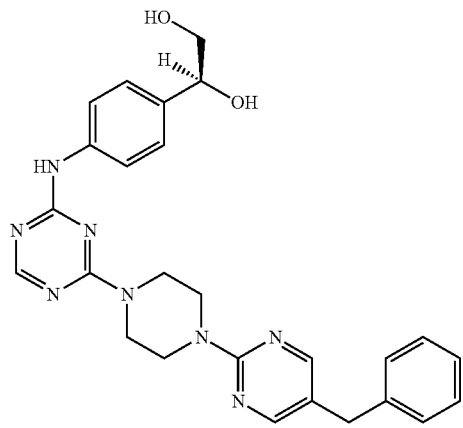 [SMILES: OC[C@@H](O)c1ccc(Nc2ncnc(N3CCN(c4ncc(Cc5ccccc5)cn4)CC3)n2)cc1] |
| 57 | 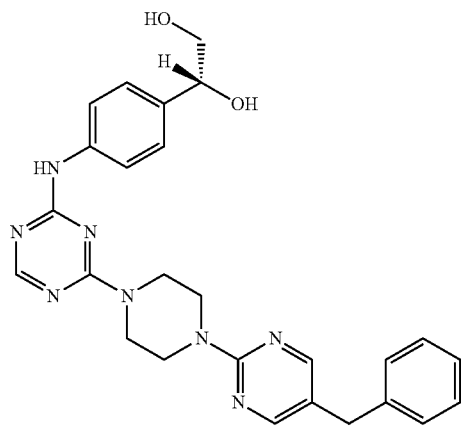 [SMILES: OC[C@H](O)c1ccc(Nc2ncnc(N3CCN(c4ncc(Cc5ccccc5)cn4)CC3)n2)cc1] |
| 58 | 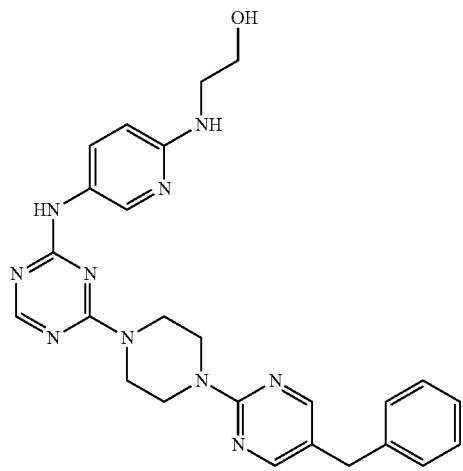 [SMILES: OCCNc1ccc(Nc2ncnc(N3CCN(c4ncc(Cc5ccccc5)cn4)CC3)n2)cn1] |

-continued
| Compound Number | Structure |
|---|---|
| 59 | 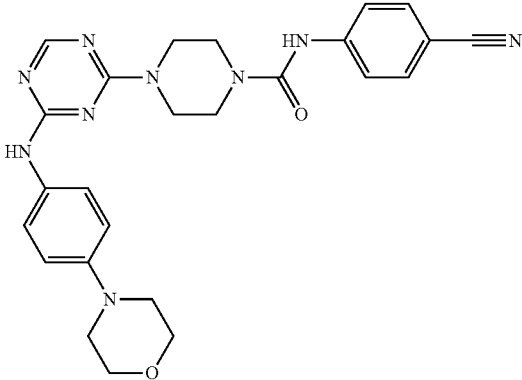 [SMILES: N#Cc1ccc(NC(=O)N2CCN(c3ncnc(Nc4ccc(N5CCOCC5)cc4)n3)CC2)cc1] |
| 60 | 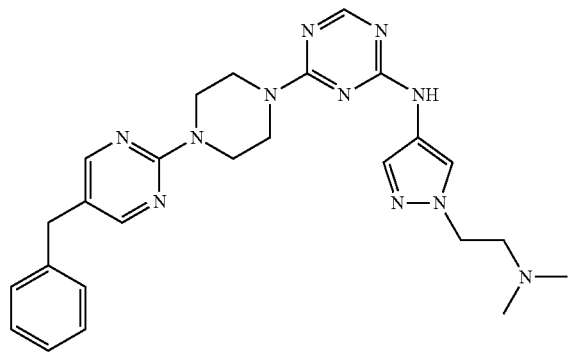 [SMILES: CN(C)CCn1cc(Nc2ncnc(N3CCN(c4ncc(Cc5ccccc5)cn4)CC3)n2)cn1] |
| 61 | 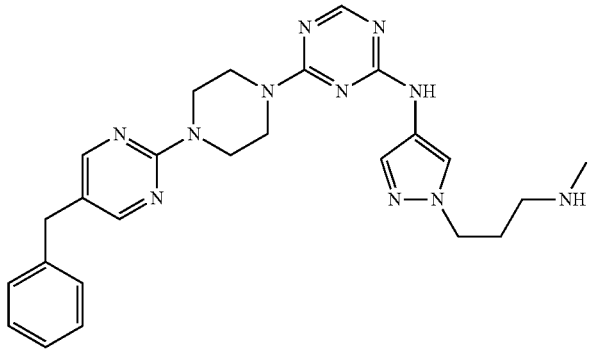 [SMILES: CNCCCn1cc(Nc2ncnc(N3CCN(c4ncc(Cc5ccccc5)cn4)CC3)n2)cn1] |
| 62 | 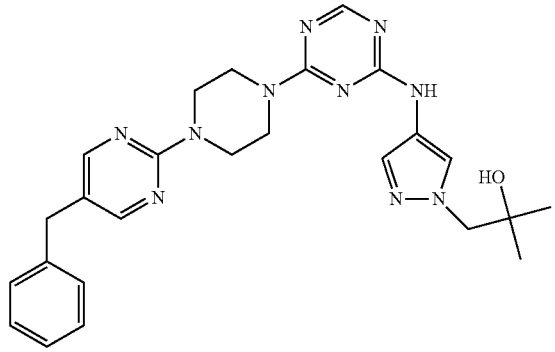 [SMILES: CC(C)(O)Cn1cc(Nc2ncnc(N3CCN(c4ncc(Cc5ccccc5)cn4)CC3)n2)cn1] |

-continued
| Compound Number | Structure |
|---|---|
| 63 | 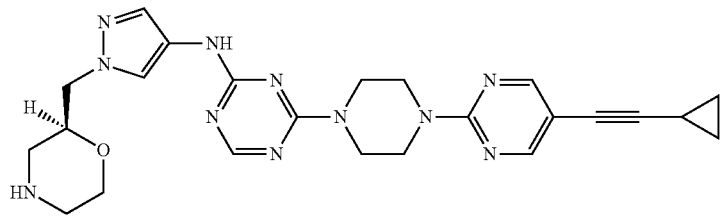 [SMILES: C(#CC1CC1)c1cnc(N2CCN(c3ncnc(Nc4cnn(C[C@@H]5CNCCO5)c4)n3)CC2)nc1] |
| 64 | 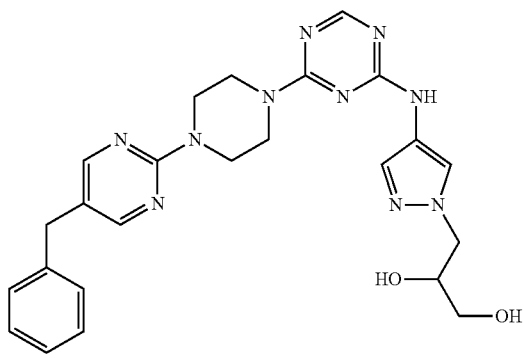 [SMILES: OCC(O)Cn1cc(Nc2ncnc(N3CCN(c4ncc(Cc5ccccc5)cn4)CC3)n2)cn1] |
| 65 | 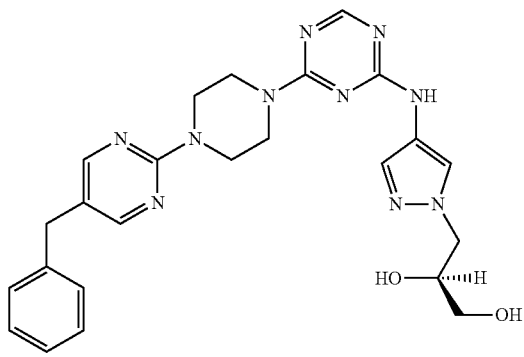 [SMILES: OC[C@@H](O)Cn1cc(Nc2ncnc(N3CCN(c4ncc(Cc5ccccc5)cn4)CC3)n2)cn1] |
| 66 | 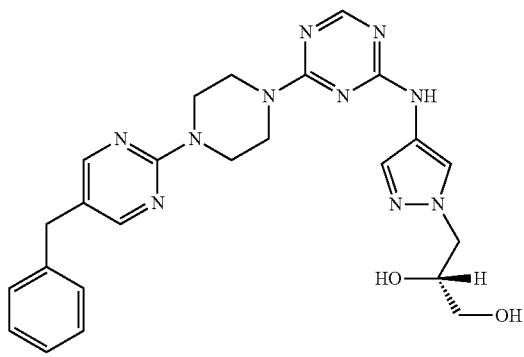 [SMILES: OC[C@H](O)Cn1cc(Nc2ncnc(N3CCN(c4ncc(Cc5ccccc5)cn4)CC3)n2)cn1] |

| Compound Number | Structure |
|---|---|
| 67 | 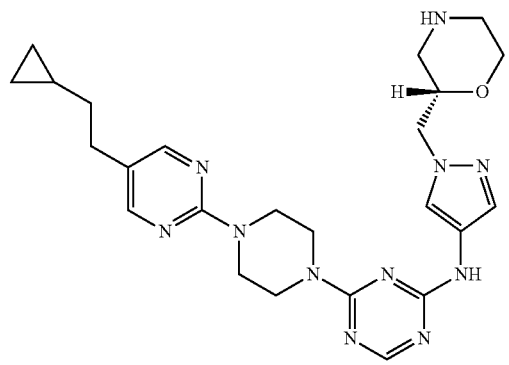 [SMILES: c1nc(Nc2cnn(C[C@@H]3CNCCO3)c2)nc(N2CCN(c3ncc(CCC4CC4)cn3)CC2)n1] |
| 68 | 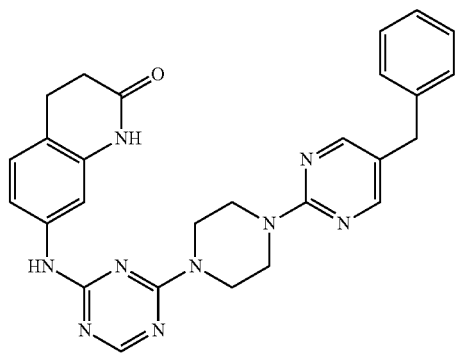 [SMILES: O=C1CCc2ccc(Nc3ncnc(N4CCN(c5ncc(Cc6ccccc6)cn5)CC4)n3)cc2N1] |
| 69 | 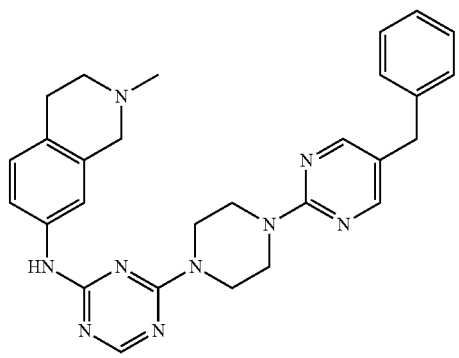 [SMILES: CN1CCc2ccc(Nc3ncnc(N4CCN(c5ncc(Cc6ccccc6)cn5)CC4)n3)cc2C1] |
| 70 | 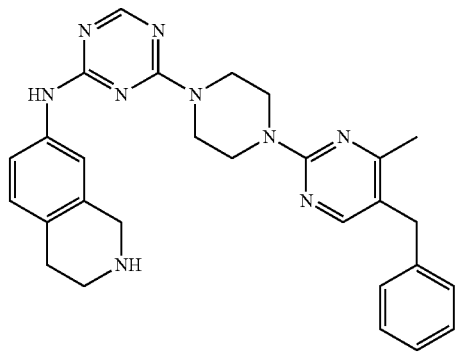 [SMILES: Cc1nc(N2CCN(c3ncnc(Nc4ccc5c(c4)CNCC5)n3)CC2)ncc1Cc1ccccc1] |

| Compound Number | Structure |
|---|---|
| 71 | 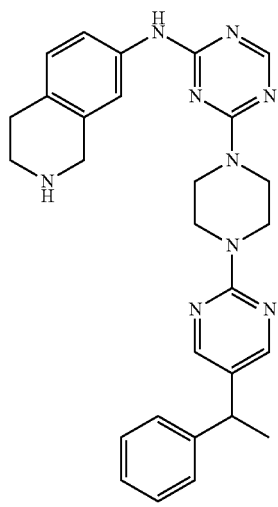 [SMILES: CC(c1ccccc1)c1cnc(N2CCN(c3ncnc(Nc4ccc5c(c4)CNCC5)n3)CC2)nc1] |
| 72 | 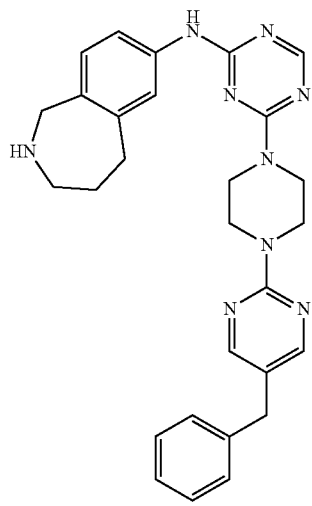 [SMILES: c1ccc(Cc2cnc(N3CCN(c4ncnc(Nc5ccc6c(c5)CCCNC6)n4)CC3)nc2)cc1] |
| 73 | 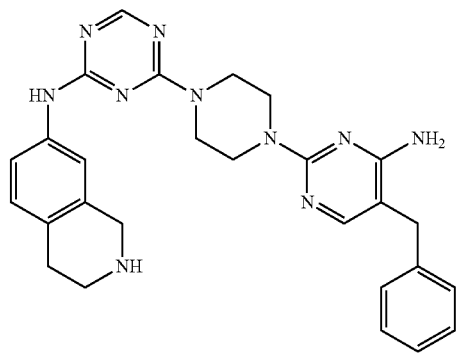 [SMILES: Nc1nc(N2CCN(c3ncnc(Nc4ccc5c(c4)CNCC5)n3)CC2)ncc1Cc1ccccc1] |

-continued
| Compound Number | Structure |
|---|---|
| 74 | 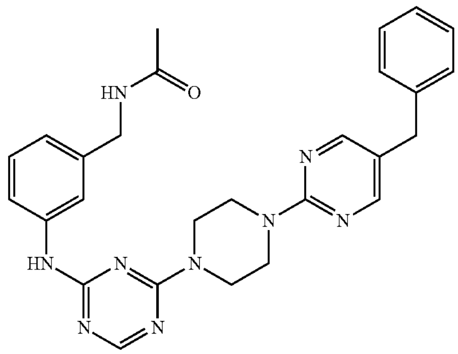 [SMILES: CC(=O)NCc1cccc(Nc2ncnc(N3CCN(c4ncc(Cc5ccccc5)cn4)CC3)n2)c1] |
| 75 | 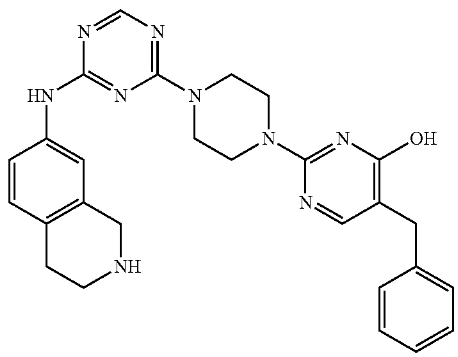 [SMILES: Oc1nc(N2CCN(c3ncnc(Nc4ccc5c(c4)CNCC5)n3)CC2)ncc1Cc1ccccc1] |
| 76 | 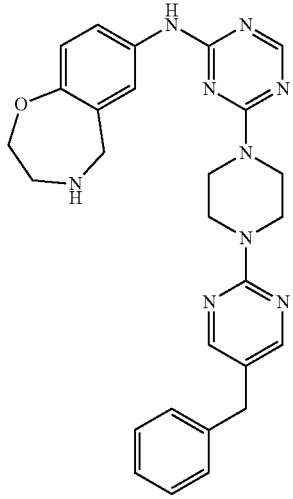 [SMILES: c1ccc(Cc2cnc(N3CCN(c4ncnc(Nc5ccc6c(c5)CNCCO6)n4)CC3)nc2)cc1] |
| 77 | 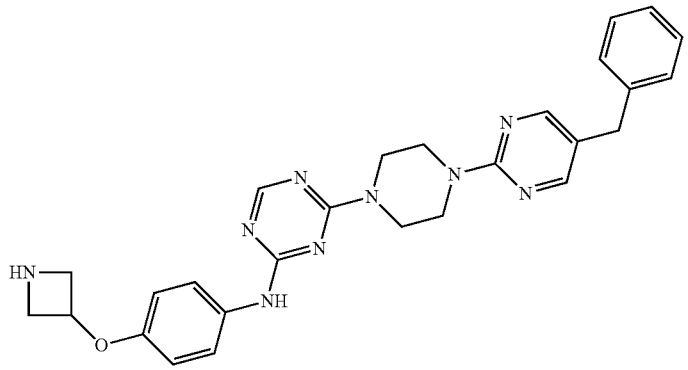 [SMILES: c1ccc(Cc2cnc(N3CCN(c4ncnc(Nc5ccc(OC6CNC6)cc5)n4)CC3)nc2)cc1] |

| Compound Number | Structure |
|---|---|
| 78 | 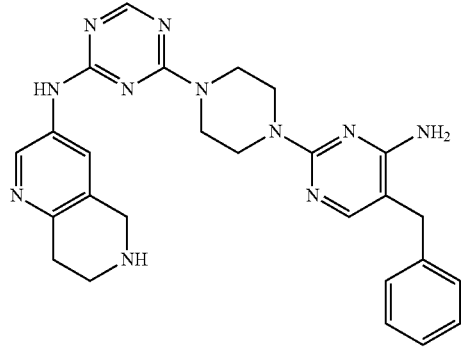 [SMILES: Nc1nc(N2CCN(c3ncnc(Nc4cnc5c(c4)CNCC5)n3)CC2)ncc1Cc1ccccc1] |
| 79 | 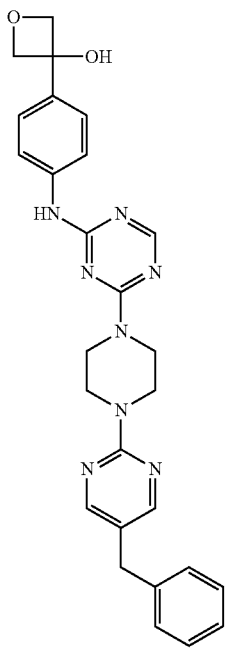 [SMILES: OC1(c2ccc(Nc3ncnc(N4CCN(c5ncc(Cc6ccccc6)cn5)CC4)n3)cc2)COC1] |
| 80 | 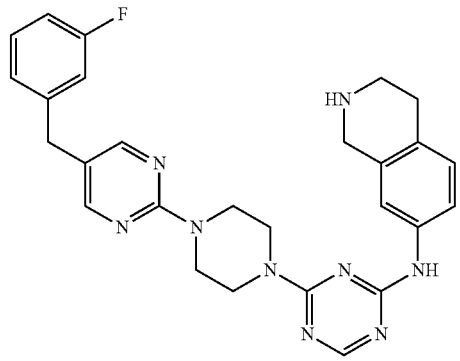 [SMILES: Fc1cccc(Cc2cnc(N3CCN(c4ncnc(Nc5ccc6c(c5)CNCC6)n4)CC3)nc2)c1] |

-continued
| Compound Number | Structure |
|---|---|
| 81 | 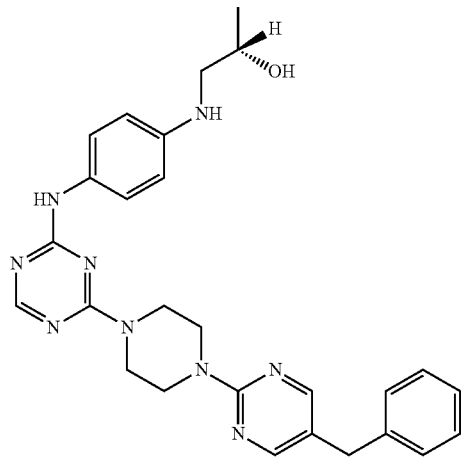 [SMILES: C[C@H](O)CNc1ccc(Nc2ncnc(N3CCN(c4ncc(Cc5ccccc5)cn4)CC3)n2)cc1] |
| 82 | 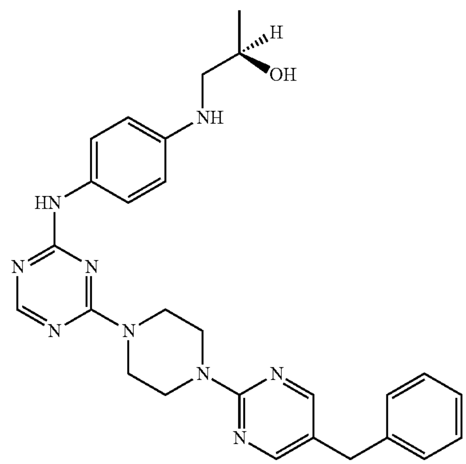 [SMILES: C[C@@H](O)CNc1ccc(Nc2ncnc(N3CCN(c4ncc(Cc5ccccc5)cn4)CC3)n2)cc1] |
| 83 | 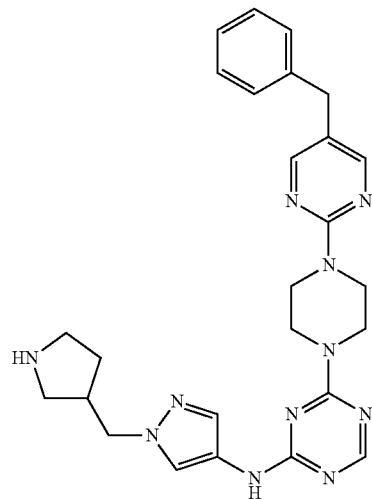 [SMILES: c1ccc(Cc2cnc(N3CCN(c4ncnc(Nc5cnn(CC6CCNC6)c5)n4)CC3)nc2)cc1] |

| Compound Number | Structure |
|---|---|
| 84 | 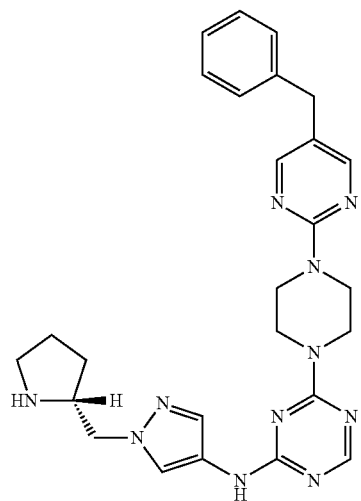 [SMILES: c1ccc(Cc2cnc(N3CCN(c4ncnc(Nc5cnn(C[C@H]6CCCN6)c5)n4)CC3)nc2)cc1] |
| 85 | 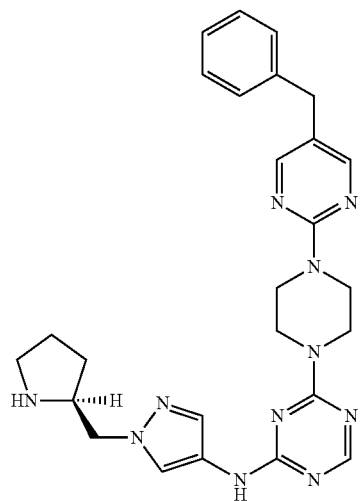 [SMILES: c1ccc(Cc2cnc(N3CCN(c4ncnc(Nc5cnn(C[C@@H]6CCCN6)c5)n4)CC3)nc2)cc1] |
| 86 | 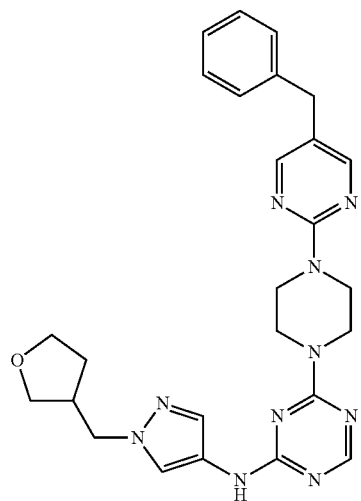 [SMILES: c1ccc(Cc2cnc(N3CCN(c4ncnc(Nc5cnn(CC6CCOC6)c5)n4)CC3)nc2)cc1] |

| Compound Number | Structure |
| --- | --- |
| 87 | 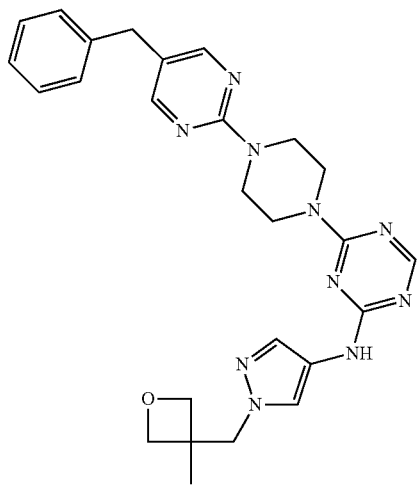 [SMILES: CC1(Cn2cc(Nc3ncnc(N4CCN(c5ncc(Cc6ccccc6)cn5)CC4)n3)cn2)COC1] |
| 88 | 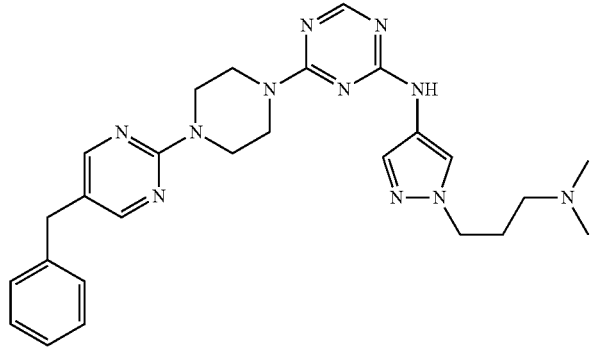 [SMILES: CN(C)CCCn1cc(Nc2ncnc(N3CCN(c4ncc(Cc5ccccc5)cn4)CC3)n2)cn1] |
| 89 | 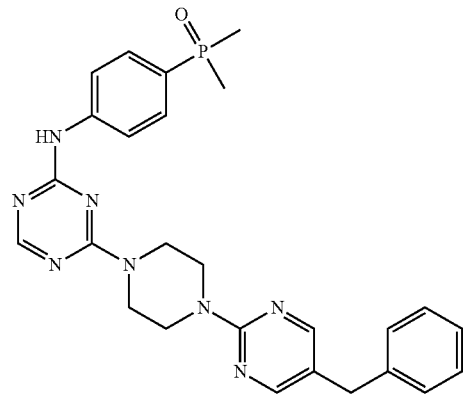 [SMILES: CP(C)(=O)c1ccc(Nc2ncnc(N3CCN(c4ncc(Cc5ccccc5)cn4)CC3)n2)cc1] |

| Compound Number | Structure |
|---|---|
| 90 | 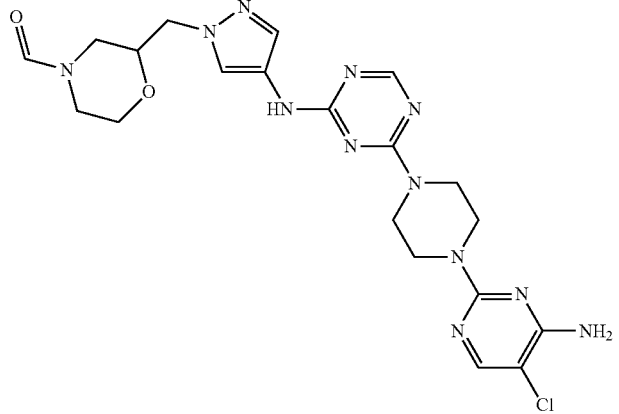 [SMILES: Nc1nc(N2CCN(c3ncnc(Nc4cnn(CC5CN(C=O)CCO5)c4)n3)CC2)ncc1Cl] |
| 91 | 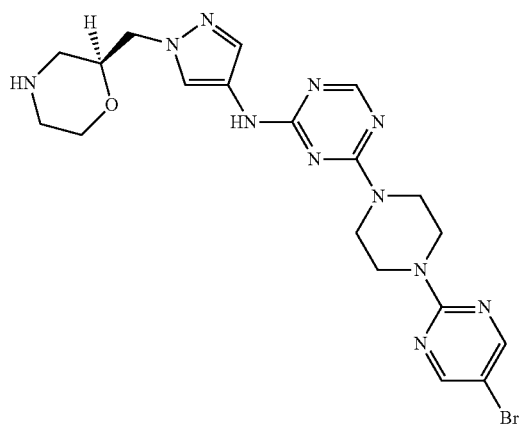 [SMILES: Brc1cnc(N2CCN(c3ncnc(Nc4cnn(C[C@@H]5CNCCO5)c4)n3)CC2)nc1] |
| 92 | 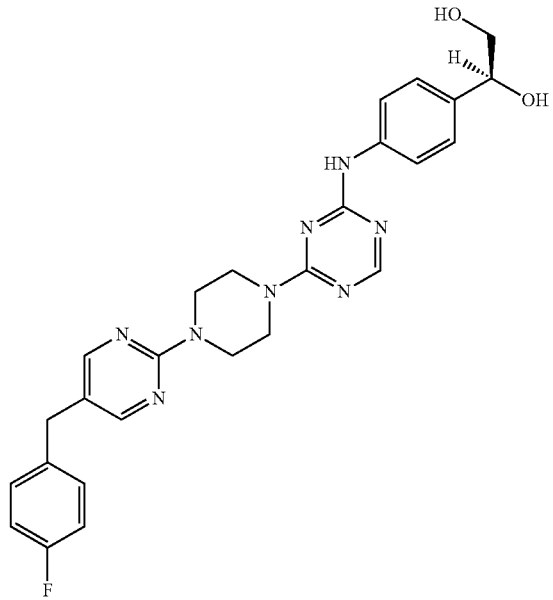 [SMILES: OC[C@@H](O)c1ccc(Nc2ncnc(N3CCN(c4ncc(Cc5ccc(F)cc5)cn4)CC3)n2)cc1] |

| Compound Number | Structure |
|---|---|
| 93 | 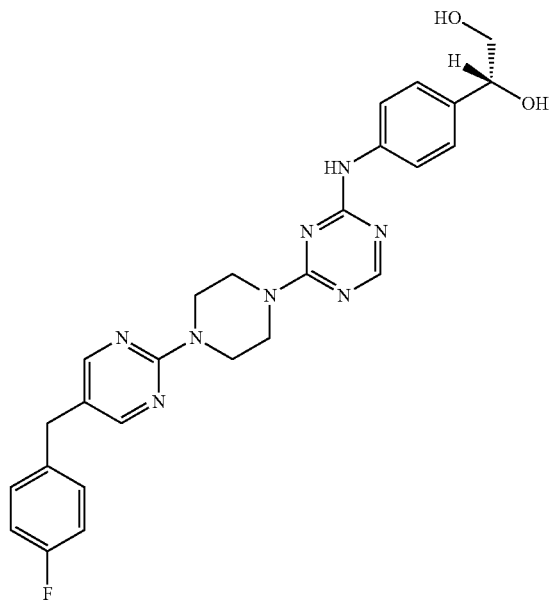 [SMILES: OC[C@H](O)c1ccc(Nc2ncnc(N3CCN(c4ncc(Cc5ccc(F)cc5)cn4)CC3)n2)cc1] |
| 94 | 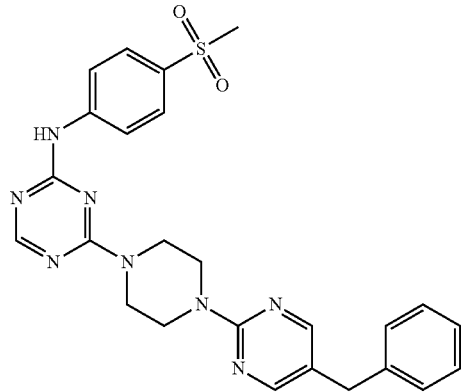 [SMILES: CS(=O)(=O)c1ccc(Nc2ncnc(N3CCN(c4ncc(Cc5ccccc5)cn4)CC3)n2)cc1] |
| 95 | 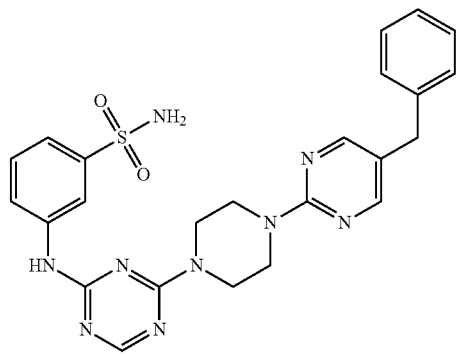 [SMILES: NS(=O)(=O)c1cccc(Nc2ncnc(N3CCN(c4ncc(Cc5ccccc5)cn4)CC3)n2)c1] |

| Compound Number | Structure |
|---|---|
| 96 | 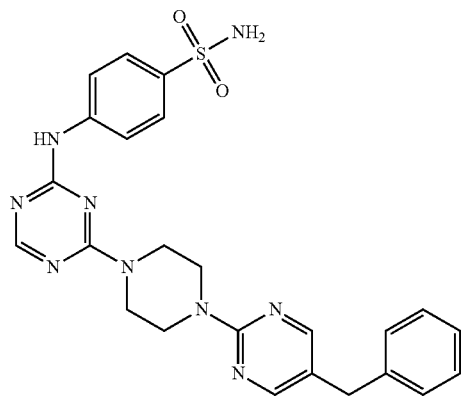 [SMILES: NS(=O)(=O)c1ccc(Nc2ncnc(N3CCN(c4ncc(Cc5ccccc5)cn4)CC3)n2)cc1] |
| 97 | 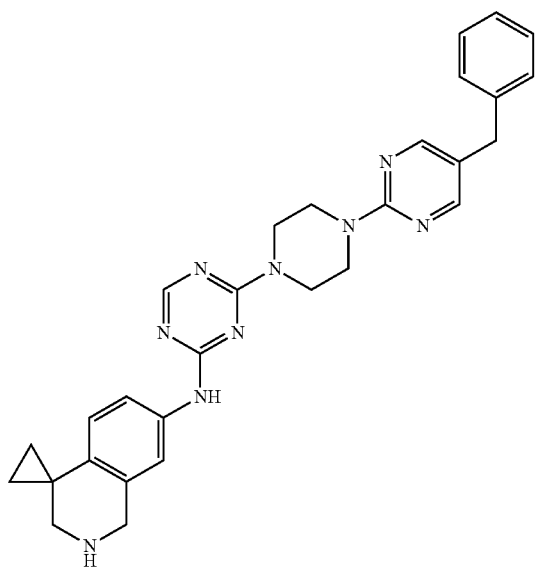 [SMILES: c1ccc(Cc2cnc(N3CCN(c4ncnc(Nc5ccc6c(c5)CNCC65CC5)n4)CC3)nc2)cc1] |
| 98 | 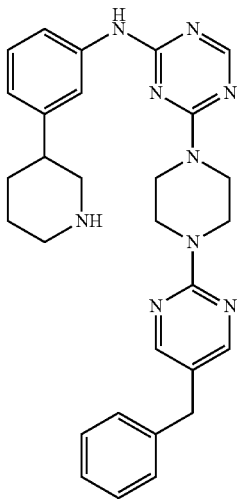 [SMILES: c1ccc(Cc2cnc(N3CCN(c4ncnc(Nc5cccc(C6CCCNC6)c5)n4)CC3)nc2)cc1] |

| Compound Number | Structure |
|---|---|
| 99 | 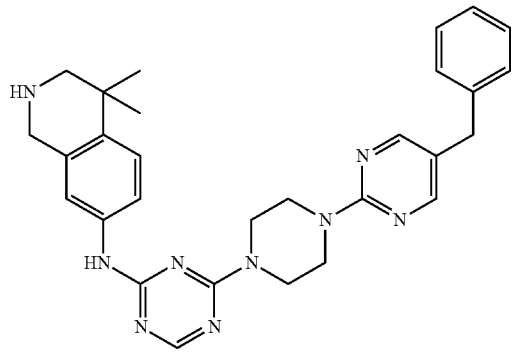 [SMILES: CC1(C)CNCc2cc(Nc3ncnc(N4CCN(c5ncc(Cc6ccccc6)cn5)CC4)n3)ccc21] |
| 100 | 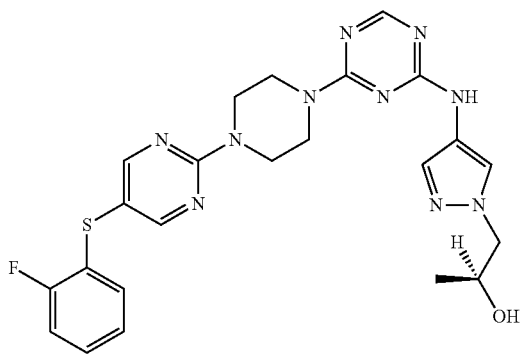 [SMILES: C[C@H](O)Cn1cc(Nc2ncnc(N3CCN(c4ncc(Sc5ccccc5F)cn4)CC3)n2)cn1] |
| 101 | 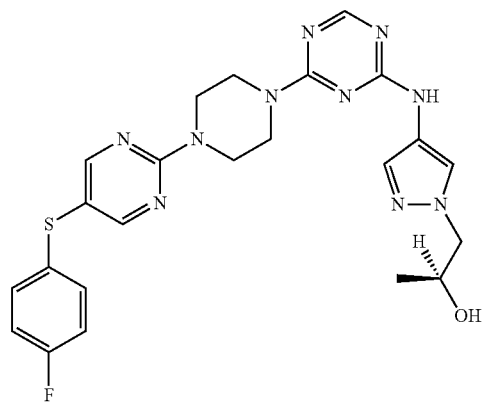 [SMILES: C[C@H](O)Cn1cc(Nc2ncnc(N3CCN(c4ncc(Sc5ccc(F)cc5)cn4)CC3)n2)cn1] |

-continued
| Compound Number | Structure |
|---|---|
| 102 | 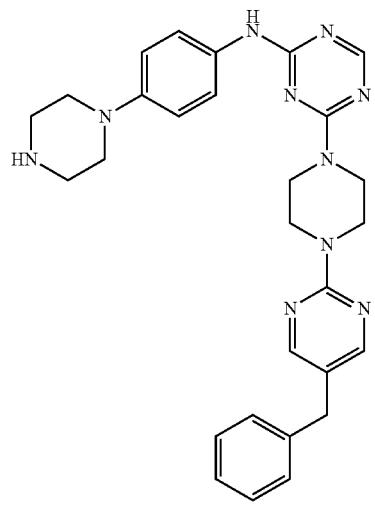 [SMILES: c1ccc(Cc2cnc(N3CCN(c4ncnc(Nc5ccc(N6CCNCC6)cc5)n4)CC3)nc2)cc1] |
| 103 | 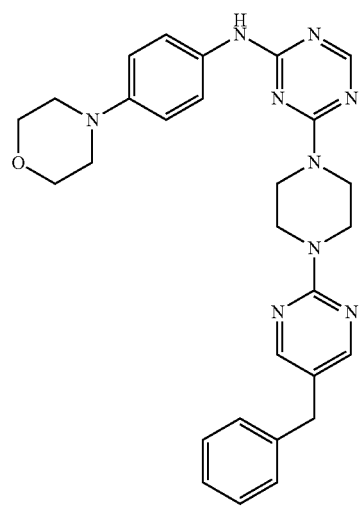 [SMILES: c1ccc(Cc2cnc(N3CCN(c4ncnc(Nc5ccc(N6CCOCC6)cc5)n4)CC3)nc2)cc1] |
| 104 | 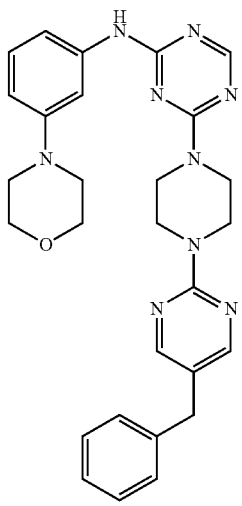 [SMILES: c1ccc(Cc2cnc(N3CCN(c4ncnc(Nc5cccc(N6CCOCC6)c5)n4)CC3)nc2)cc1] |

-continued
| Compound Number | Structure |
|---|---|
| 105 | 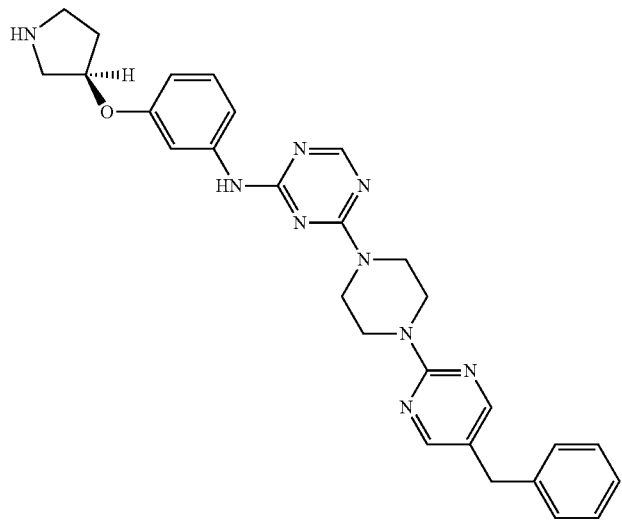 [SMILES: c1ccc(Cc2cnc(N3CCN(c4ncnc(Nc5cccc(O[C@@H]6CCNC6)c5)n4)CC3)nc2)cc1] |
| 106 | 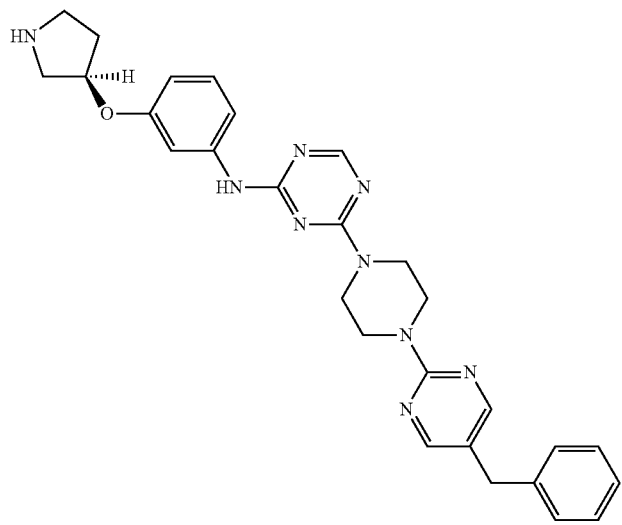 [SMILES: c1ccc(Cc2cnc(N3CCN(c4ncnc(Nc5cccc(O[C@@H]6CCNC6)c5)n4)CC3)nc2)cc1] |
| 107 | 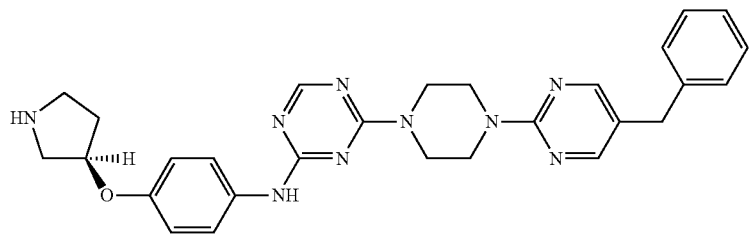 [SMILES: c1ccc(Cc2cnc(N3CCN(c4ncnc(Nc5ccc(O[C@@H]6CCNC6)cc5)n4)CC3)nc2)cc1] |
| 108 | 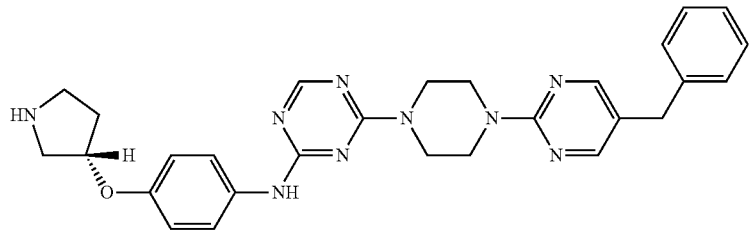 [SMILES: c1ccc(Cc2cnc(N3CCN(c4ncnc(Nc5ccc(O[C@H]6CCNC6)cc5)n4)CC3)nc2)cc1] |

-continued
| Compound Number | Structure |
|---|---|
| 109 | 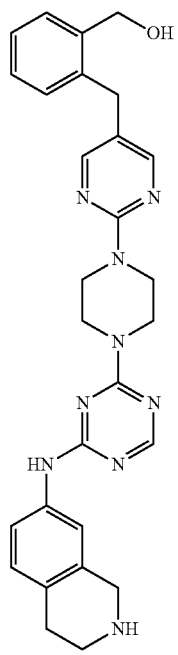 [SMILES: OCc1ccccc1Cc1cnc(N2CCN(c3ncnc(Nc4ccc5c(c4)CNCC5)n3)CC2)nc1] |
| 110 | 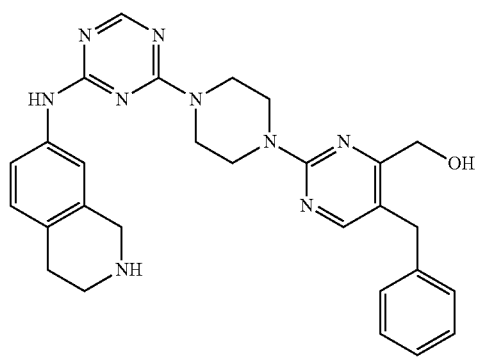 [SMILES: OCc1nc(N2CCN(c3ncnc(Nc4ccc5c(c4)CNCC5)n3)CC2)ncc1Cc1ccccc1] |
| 111 | 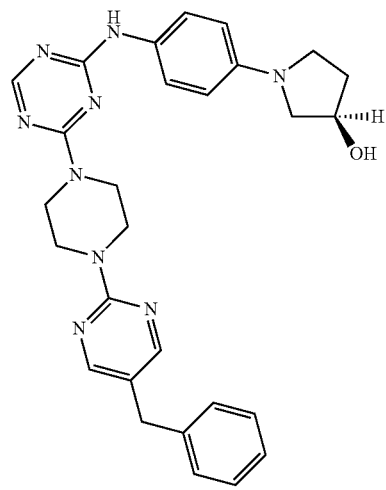 [SMILES: O[C@@H]1CCN(c2ccc(Nc3ncnc(N4CCN(c5ncc(Cc6ccccc6)cn5)CC4)n3)cc2)C1] |

-continued
| Compound Number | Structure |
|---|---|
| 112 | 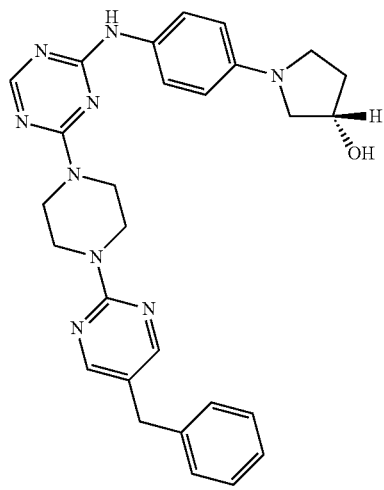 [SMILES: O[C@H]1CCN(c2ccc(Nc3ncnc(N4CCN(c5ncc(Cc6ccccc6)cn5)CC4)n3)cc2)C1] |
| 113 | 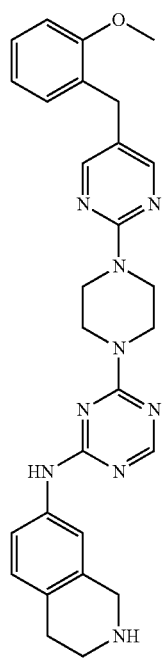 [SMILES: COc1ccccc1Cc1cnc(N2CCN(c3ncnc(Nc4ccc5c(c4)CNCC5)n3)CC2)nc1] |

-continued
| Compound Number | Structure |
|---|---|
| 114 | 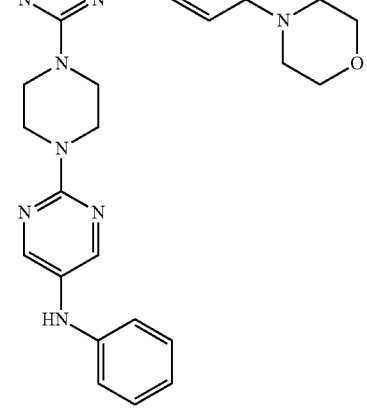 |
| 115 | 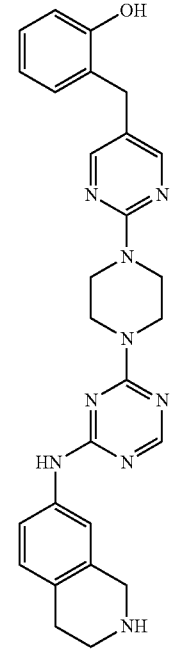 [SMILES: Oc1ccccc1Cc1cnc(N2CCN(c3ncnc(Nc4ccc5c(c4)CNCC5)n3)CC2)nc1] |
| 116 | 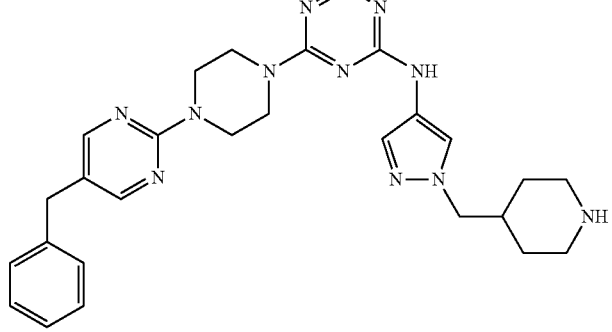 |

| Compound Number | Structure |
|---|---|
| 117 | 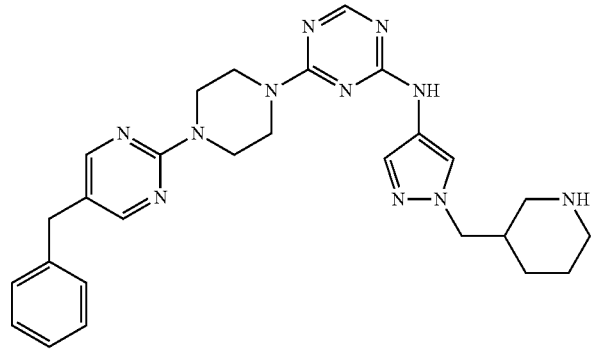 [SMILES: c1ccc(Cc2cnc(N3CCN(c4ncnc(Nc5cnn(CC6CCCNC6)c5)n4)CC3)nc2)cc1] |
| 118 | 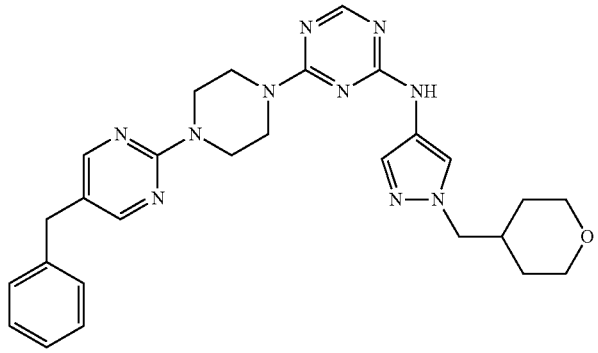 [SMILES: c1ccc(Cc2cnc(N3CCN(c4ncnc(Nc5cnn(CC6CCOCC6)c5)n4)CC3)nc2)cc1] |
| 119 | 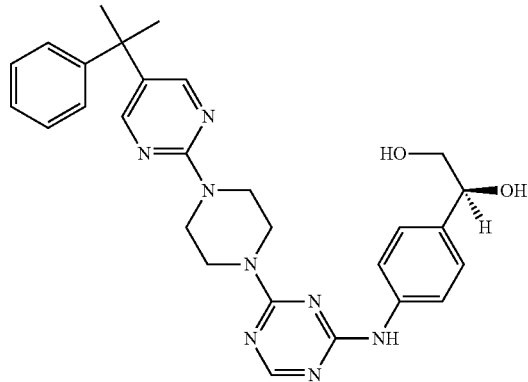 [SMILES: CC(C)(c1ccccc1)c1cnc(N2CCN(c3ncnc(Nc4ccc([C@H](O)CO)cc4)n3)CC2)nc1] |
| 120 | 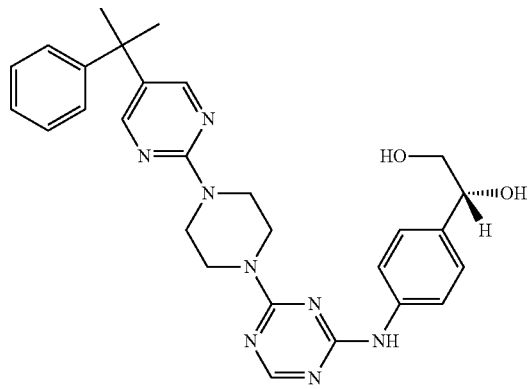 [SMILES: CC(C)(c1ccccc1)c1cnc(N2CCN(c3ncnc(Nc4ccc([C@@H](O)CO)cc4)n3)CC2)nc1] |

| Compound Number | Structure |
|---|---|
| 121 | 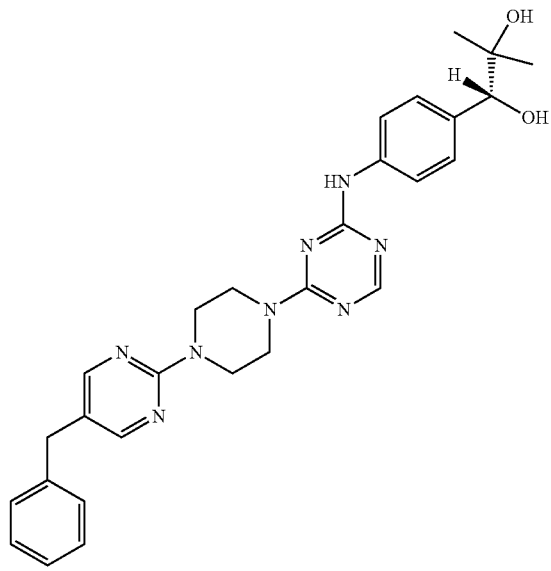 [SMILES: CC(C)(O)[C@H](O)c1ccc(Nc2ncnc(N3CCN(c4ncc(Cc5ccccc5)cn4)CC3)n2)cc1] |
| 122 | 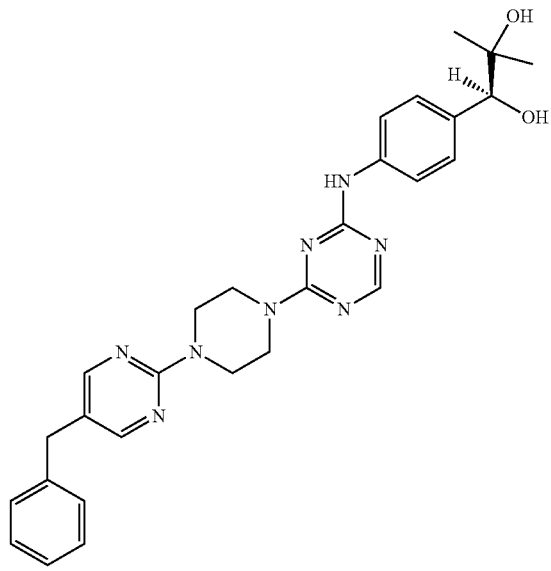 [SMILES: CC(C)(O)[C@@H](O)c1ccc(Nc2ncnc(N3CCN(c4ncc(Cc5ccccc5)cn4)CC3)n2)cc1] |
| 123 | 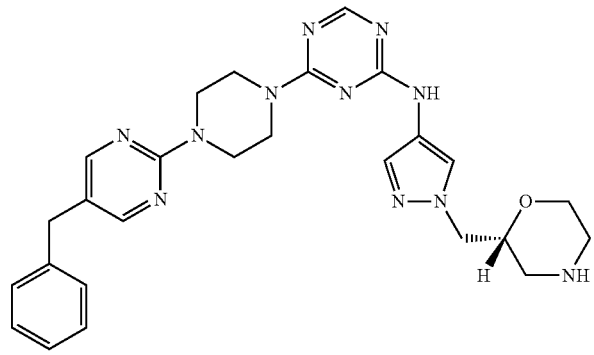 [SMILES: c1ccc(Cc2cnc(N3CCN(c4ncnc(Nc5cnn(C[C@H]6CNCCO6)c5)n4)CC3)nc2)cc1] |

-continued
| Compound Number | Structure |
|---|---|
| 124 | 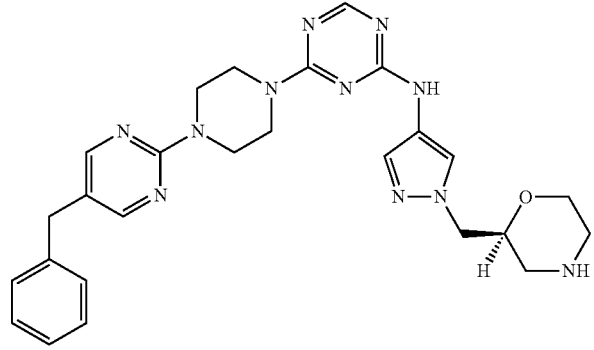 [SMILES: c1ccc(Cc2cnc(N3CCN(c4ncnc(Nc5cnn(C[C@@H]6CNCCO6)c5)n4)CC3)nc2)cc1] |
| 125 | 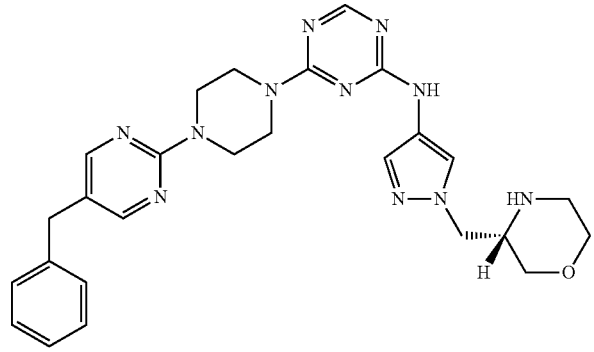 [SMILES: c1ccc(Cc2cnc(N3CCN(c4ncnc(Nc5cnn(C[C@H]6COCCN6)c5)n4)CC3)nc2)cc1] |
| 126 | 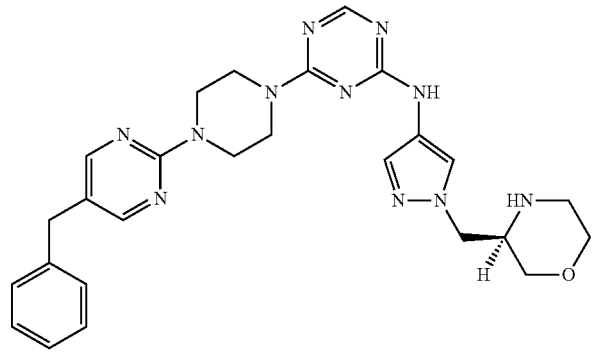 [SMILES: c1ccc(Cc2cnc(N3CCN(c4ncnc(Nc5cnn(C[C@@H]6COCCN6)c5)n4)CC3)nc2)cc1] |
| 127 | 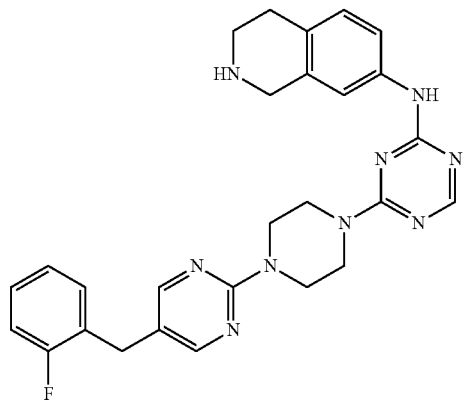 [SMILES: Fc1ccccc1Cc1cnc(N2CCN(c3ncnc(Nc4ccc5c(c4)CNCC5)n3)CC2)nc1] |

-continued
| Compound Number | Structure |
|---|---|
| 128 | 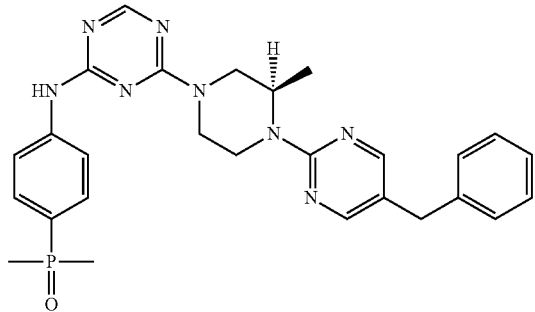 [SMILES: C[C@@H]1CN(c2ncnc(Nc3ccc(P(C)(C)=O)cc3)n2)CCN1c1ncc(Cc2ccccc2)cn1] |
| 129 | 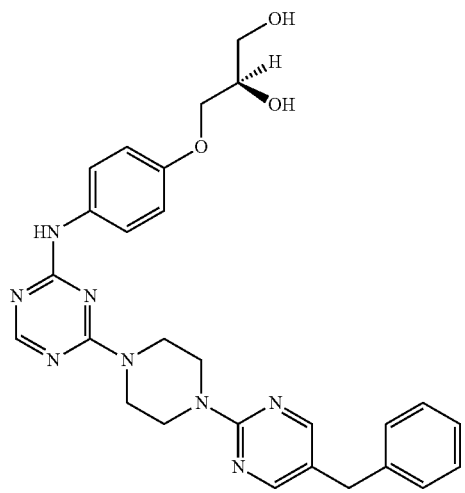 [SMILES: OC[C@@H](O)COc1ccc(Nc2ncnc(N3CCN(c4ncc(Cc5ccccc5)cn4)CC3)n2)cc1] |
| 130 | 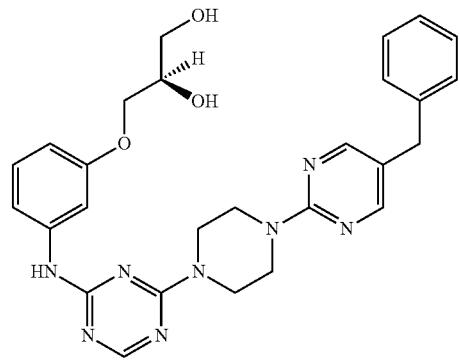 [SMILES: OC[C@@H](O)COc1cccc(Nc2ncnc(N3CCN(c4ncc(Cc5ccccc5)cn4)CC3)n2)c1] |

-continued
| Compound Number | Structure |
|---|---|
| 131 | 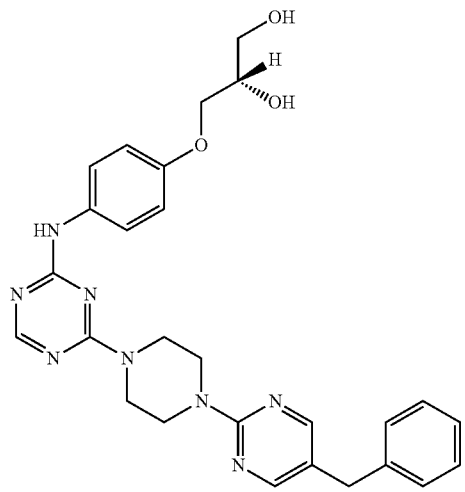 [SMILES: OC[C@H](O)COc1ccc(Nc2ncnc(N3CCN(c4ncc(Cc5ccccc5)cn4)CC3)n2)cc1] |
| 132 | 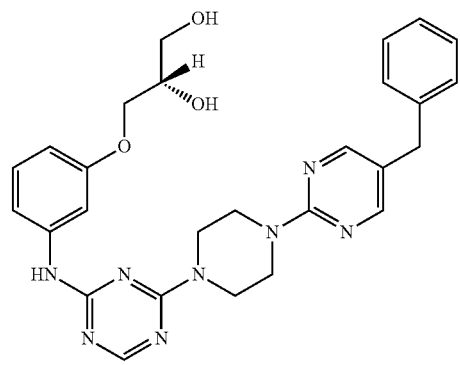 [SMILES: OC[C@H](O)COc1cccc(Nc2ncnc(N3CCN(c4ncc(Cc5ccccc5)cn4)CC3)n2)c1] |
| 133 | 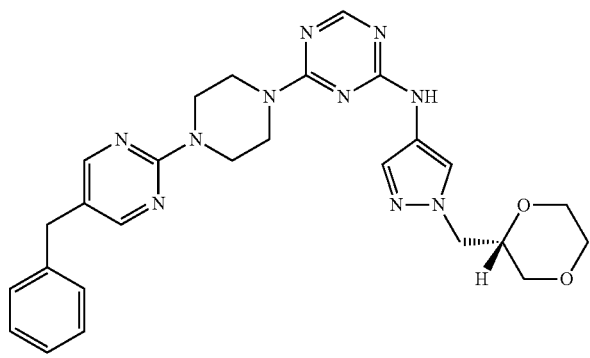 [SMILES: c1ccc(Cc2cnc(N3CCN(c4ncnc(Nc5cnn(C[C@H]6COCCO6)c5)n4)CC3)nc2)cc1] |
| 134 | 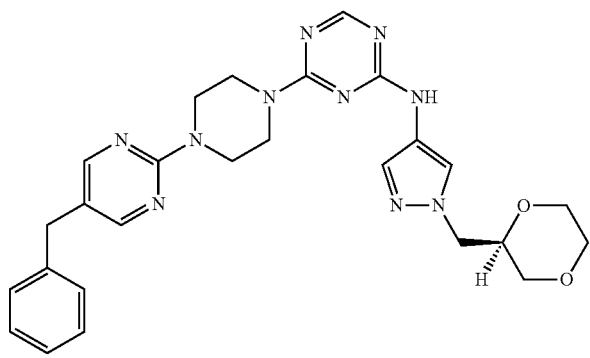 [SMILES: c1ccc(Cc2cnc(N3CCN(c4ncnc(Nc5cnn(C[C@@H]6COCCO6)c5)n4)CC3)nc2)cc1] |

| Compound Number | Structure |
|---|---|
| 135 | 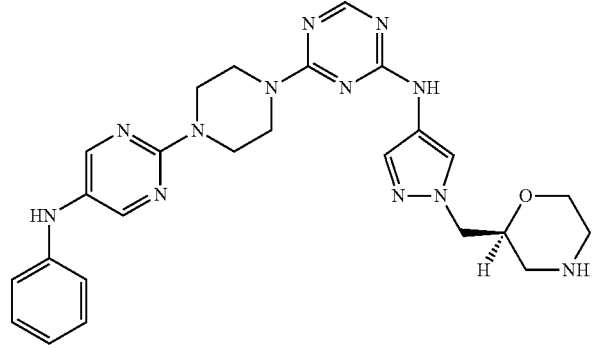 [SMILES: c1ccc(Nc2cnc(N3CCN(c4ncnc(Nc5cnn(C[C@@H]6CNCCO6)c5)n4)CC3)nc2)cc1] |
| 136 | 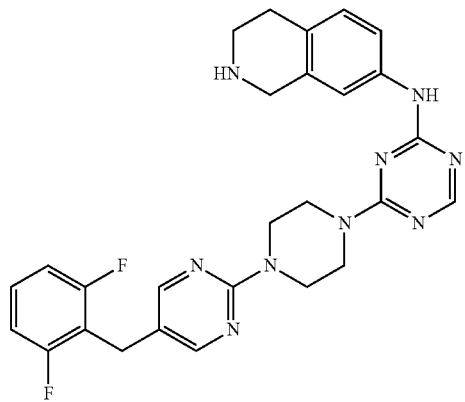 [SMILES: Fc1cccc(F)c1Cc1cnc(N2CCN(c3ncnc(Nc4ccc5c(c4)CNCC5)n3)CC2)nc1] |
| 137 | 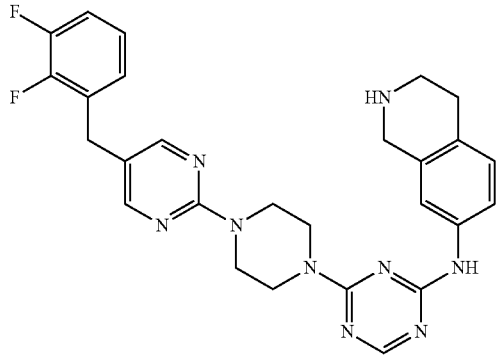 [SMILES: Fc1cccc(Cc2cnc(N3CCN(c4ncnc(Nc5ccc6c(c5)CNCC6)n4)CC3)nc2)c1F] |

| Compound Number | Structure |
|---|---|
| 138 | 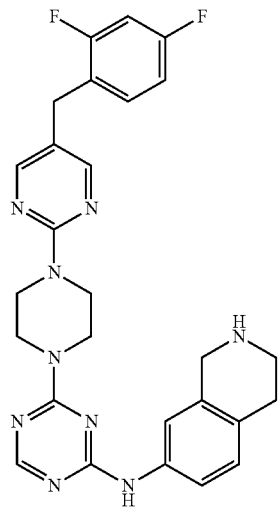 [SMILES: Fc1ccc(Cc2cnc(N3CCN(c4ncnc(Nc5ccc6c(c5)CNCC6)n4)CC3)nc2)c(F)c1] |
| 139 | 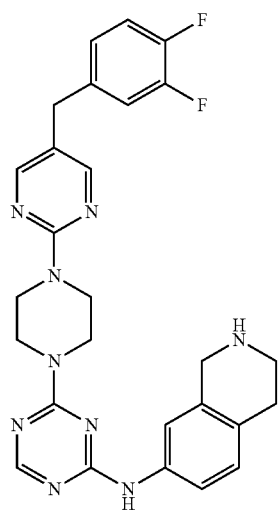 [SMILES: Fc1ccc(Cc2cnc(N3CCN(c4ncnc(Nc5ccc6c(c5)CNCC6)n4)CC3)nc2)cc1F] |
| 140 | 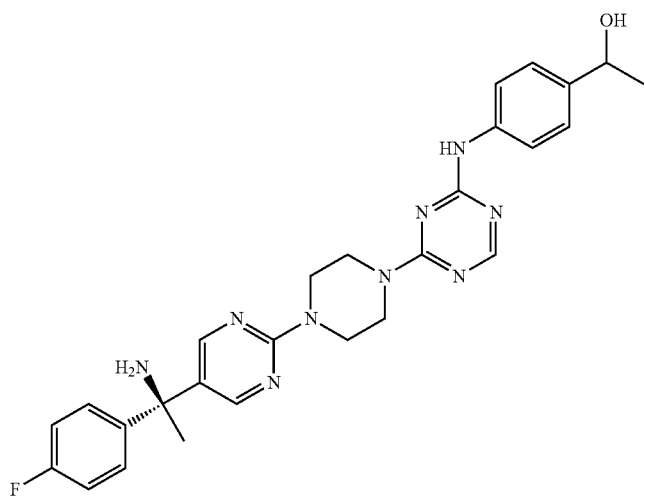 [SMILES: CC(O)c1ccc(Nc2ncnc(N3CCN(c4ncc([C@@](C)(N)c5ccc(F)cc5)cn4)CC3)n2)cc1] |

-continued

| Compound Number | Structure |
|---|---|
| 141 | 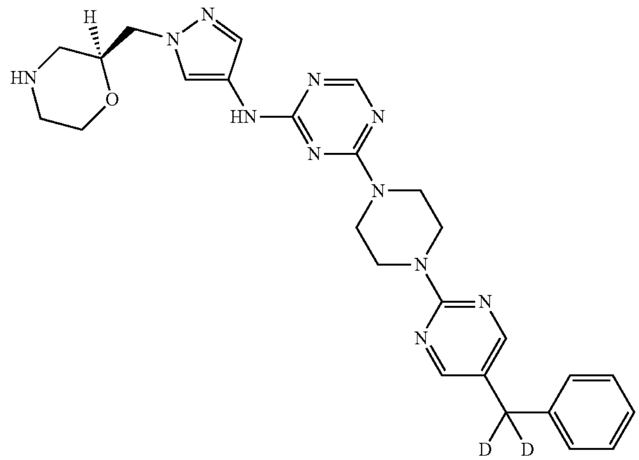 [SMILES: [2H]C([2H])(c1ccccc1)c1cnc(N2CCN(c3ncnc(Nc4cnn(C[C@@H]5CNCCO5)c4)n3)CC2)nc1] |
| 142 | 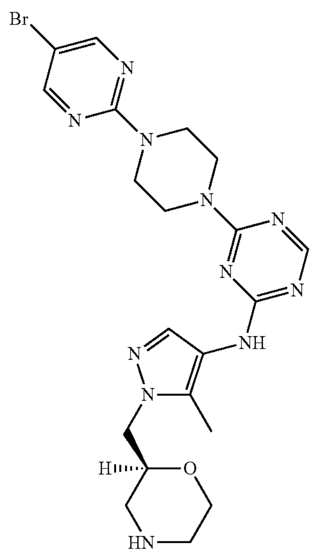 [SMILES: Cc1c(Nc2ncnc(N3CCN(c4ncc(Br)cn4)CC3)n2)cnn1C[C@@H]1CNCCO1] |
| 143 | 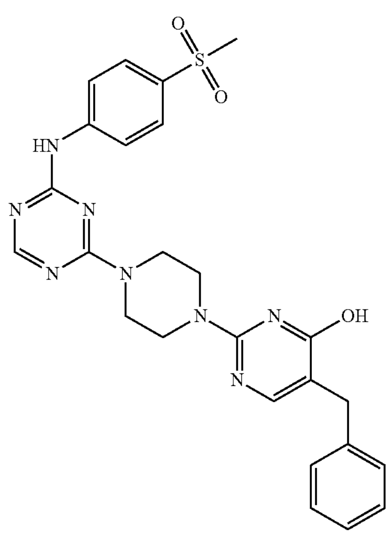 [SMILES: CS(=O)(=O)c1ccc(Nc2ncnc(N3CCN(c4ncc(Cc5ccccc5)c(O)n4)CC3)n2)cc1] |

-continued
| Compound Number | Structure |
|---|---|
| 144 | 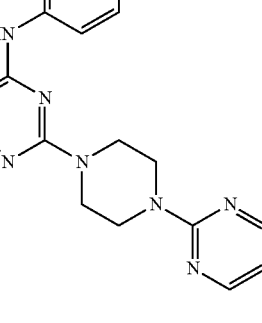 |
| 145 | 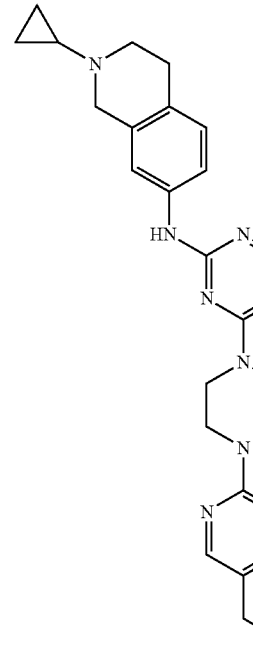 |
| 146 | 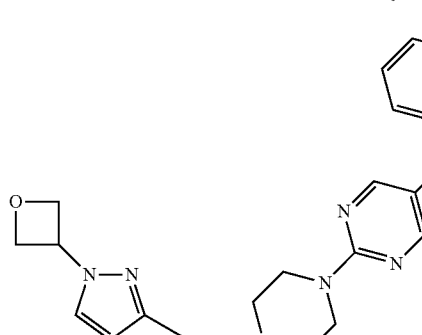 |

| Compound Number | Structure |
|---|---|
| 147 | 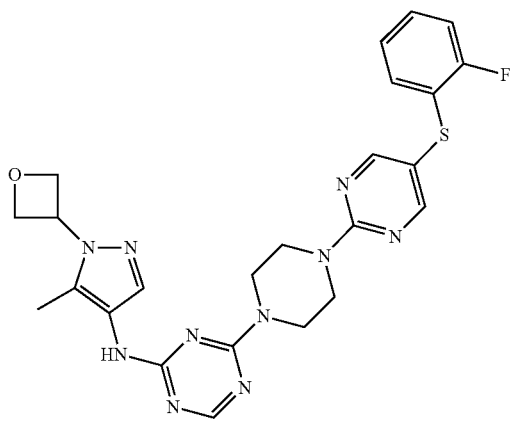 [SMILES: Cc1c(Nc2ncnc(N3CCN(c4ncc(Sc5ccccc5F)cn4)CC3)n2)cnn1C1COC1] |
| 148 | 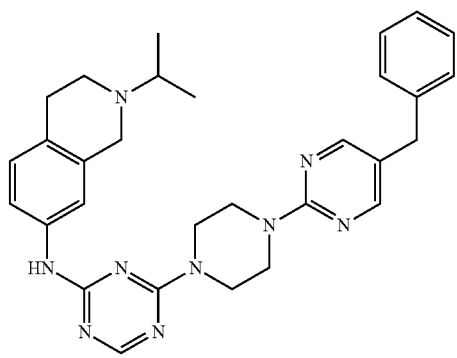 [SMILES: CC(C)N1CCc2ccc(Nc3ncnc(N4CCN(c5ncc(Cc6ccccc6)cn5)CC4)n3)cc2C1] |
| 149 | 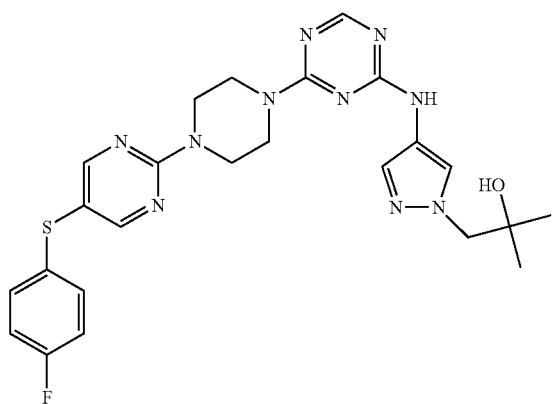 [SMILES: CC(C)(O)Cn1cc(Nc2ncnc(N3CCN(c4ncc(Sc5ccc(F)cc5)cn4)CC3)n2)cn1] |
| 150 | 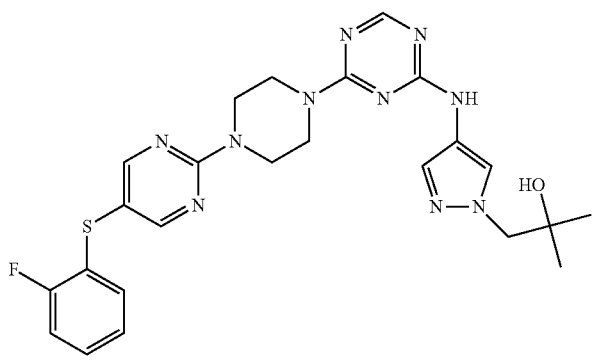 [SMILES: CC(C)(O)Cn1cc(Nc2ncnc(N3CCN(c4ncc(Sc5ccccc5F)cn4)CC3)n2)cn1] |

| Compound Number | Structure |
|---|---|
| 151 | 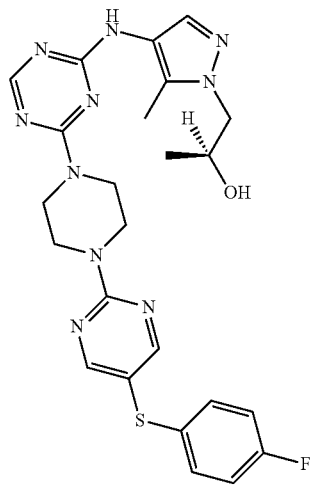 [SMILES: Cc1c(Nc2ncnc(N3CCN(c4ncc(Sc5ccc(F)cc5)cn4)CC3)n2)cnn1C[C@H](C)O] |
| 152 | 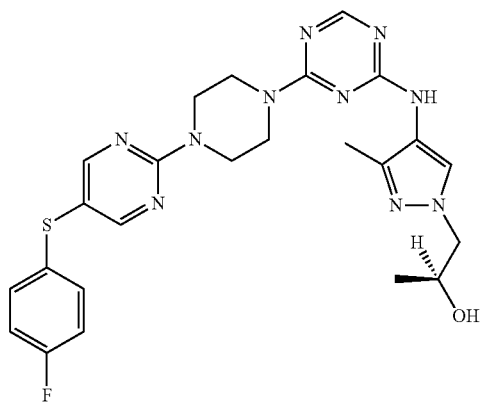 [SMILES: Cc1nn(C[C@H](C)O)cc1Nc1ncnc(N2CCN(c3ncc(Sc4ccc(F)cc4)cn3)CC2)n1] |
| 153 | 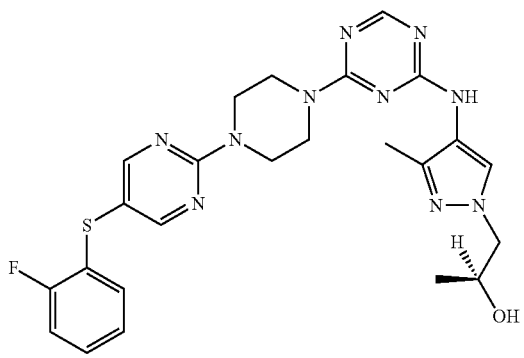 [SMILES: Cc1nn(C[C@H](C)O)cc1Nc1ncnc(N2CCN(c3ncc(Sc4ccccc4F)cn3)CC2)n1] |

| Compound Number | Structure |
|---|---|
| 154 | 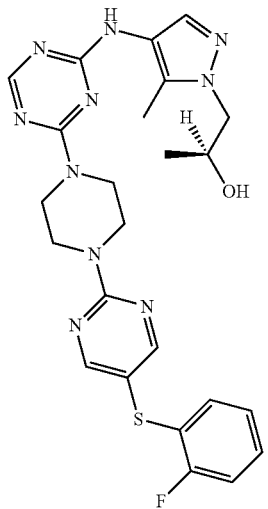 [SMILES: Cc1c(Nc2ncnc(N3CCN(c4ncc(Sc5ccccc5F)cn4)CC3)n2)cnn1C[C@H](C)O] |
| 155 | 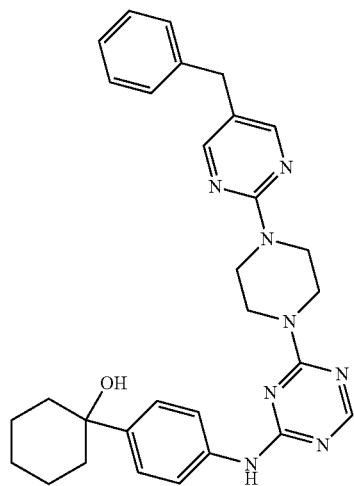 [SMILES: OC1(c2ccc(Nc3ncnc(N4CCN(c5ncc(Cc6ccccc6)cn5)CC4)n3)cc2)CCCCC1] |
| 156 | 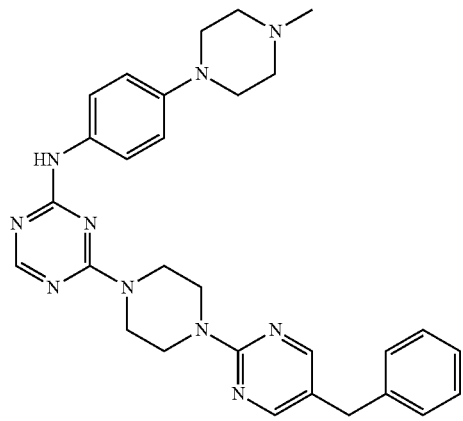 [SMILES: CN1CCN(c2ccc(Nc3ncnc(N4CCN(c5ncc(Cc6ccccc6)cn5)CC4)n3)cc2)CC1] |

| Compound Number | Structure |
|---|---|
| 157 | 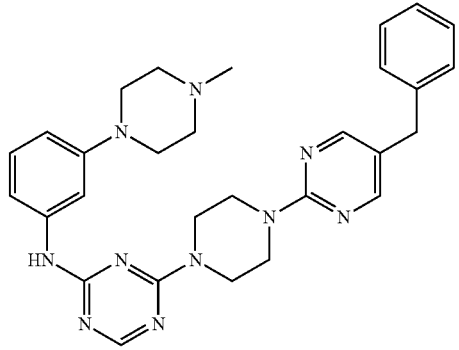 [SMILES: CN1CCN(c2cccc(Nc3ncnc(N4CCN(c5ncc(Cc6ccccc6)cn5)CC4)n3)c2)CC1] |
| 158 | 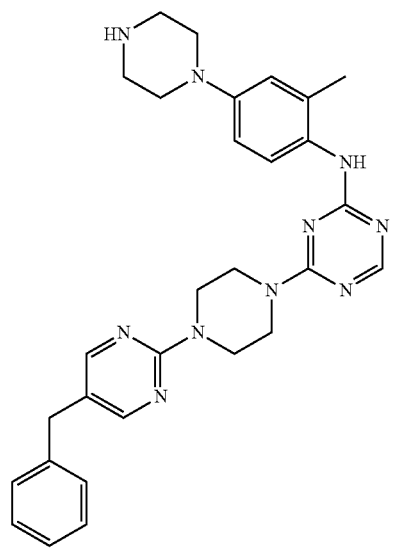 [SMILES: Cc1cc(N2CCNCC2)ccc1Nc1ncnc(N2CCN(c3ncc(Cc4ccccc4)cn3)CC2)n1] |
| 159 | 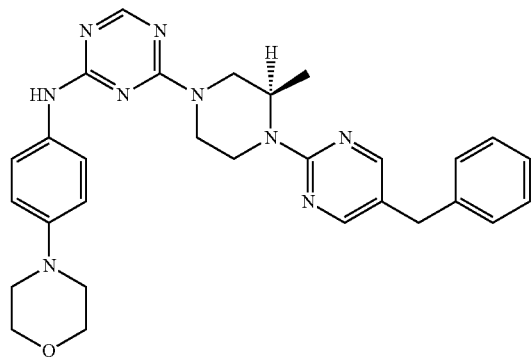 [SMILES: C[C@@H]1CN(c2ncnc(Nc3ccc(N4CCOCC4)cc3)n2)CCN1c1ncc(Cc2ccccc2)cn1] |

-continued
| Compound Number | Structure |
|---|---|
| 160 | 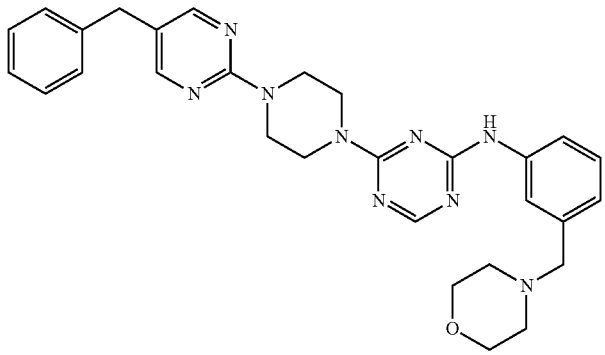 [SMILES: c1ccc(Cc2cnc(N3CCN(c4ncnc(Nc5cccc(CN6CCOCC6)c5)n4)CC3)nc2)cc1] |
| 161 | 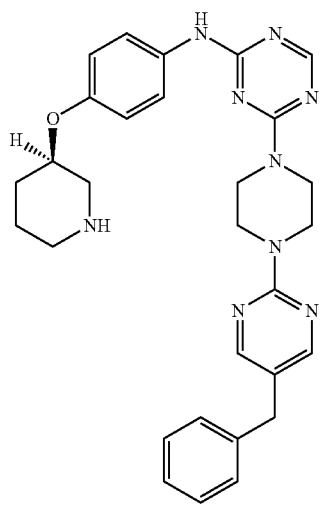 [SMILES: c1ccc(Cc2cnc(N3CCN(c4ncnc(Nc5ccc(O[C@@H]6CCCNC6)cc5)n4)CC3)nc2)cc1] |
| 162 | 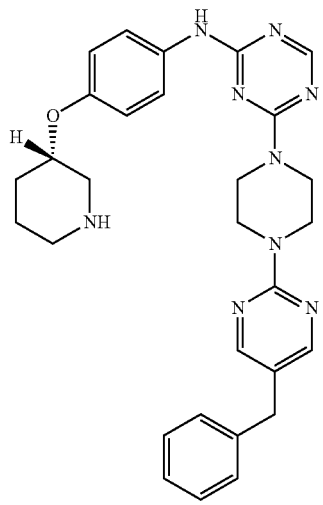 [SMILES: c1ccc(Cc2cnc(N3CCN(c4ncnc(Nc5ccc(O[C@H]6CCCNC6)cc5)n4)CC3)nc2)cc1] |

-continued
| Compound Number | Structure |
|---|---|
| 163 | 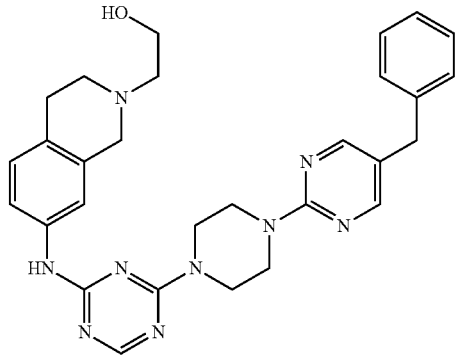 [SMILES: OCCN1CCc2ccc(Nc3ncnc(N4CCN(c5ncc(Cc6ccccc6)cn5)CC4)n3)cc2C1] |
| 164 | 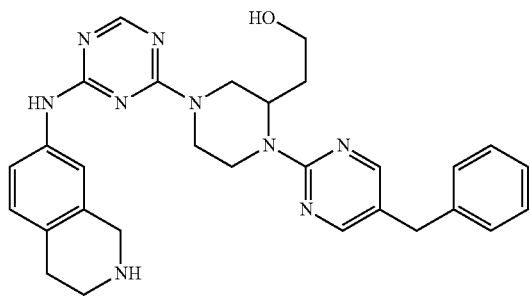 [SMILES: OCCC1CN(c2ncnc(Nc3ccc4c(c3)CNCC4)n2)CCN1c1ncc(Cc2ccccc2)cn1] |
| 165 | 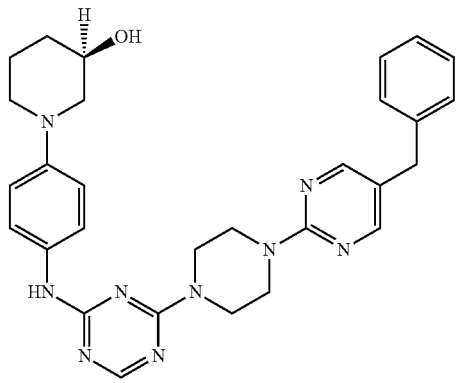 [SMILES: O[C@@H]1CCCN(c2ccc(Nc3ncnc(N4CCN(c5ncc(Cc6ccccc6)cn5)CC4)n3)cc2)C1] |
| 166 | 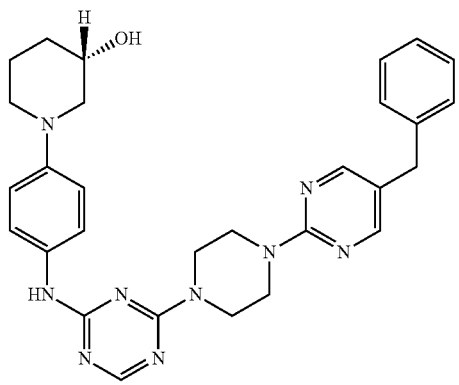 [SMILES: O[C@H]1CCCN(c2ccc(Nc3ncnc(N4CCN(c5ncc(Cc6ccccc6)cn5)CC4)n3)cc2)C1] |

-continued
| Compound Number | Structure |
|---|---|
| 167 | 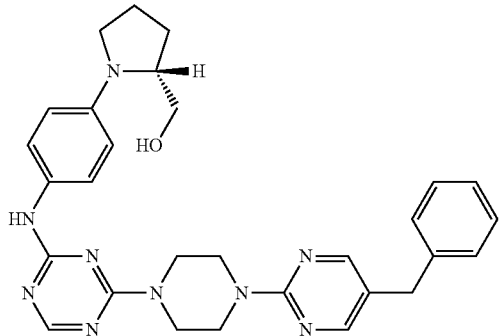 [SMILES: OC[C@H]1CCCN1c1ccc(Nc2ncnc(N3CCN(c4ncc(Cc5ccccc5)cn4)CC3)n2)cc1] |
| 168 | 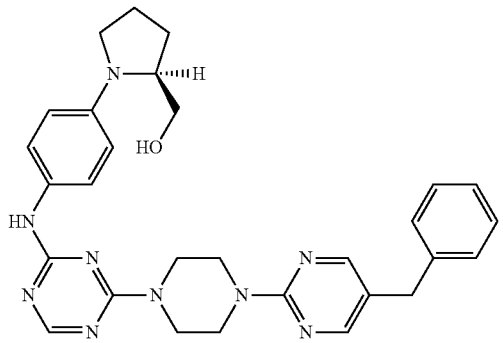 [SMILES: OC[C@@H]1CCCN1c1ccc(Nc2ncnc(N3CCN(c4ncc(Cc5ccccc5)cn4)CC3)n2)cc1] |
| 169 | 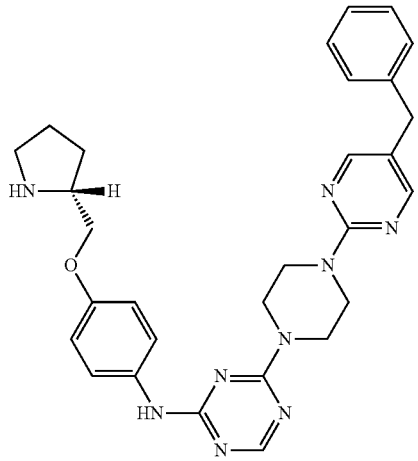 [SMILES: c1ccc(Cc2cnc(N3CCN(c4ncnc(Nc5ccc(OC[C@H]6CCCN6)cc5)n4)CC3)nc2)cc1] |

| Compound Number | Structure |
|---|---|
| 170 | 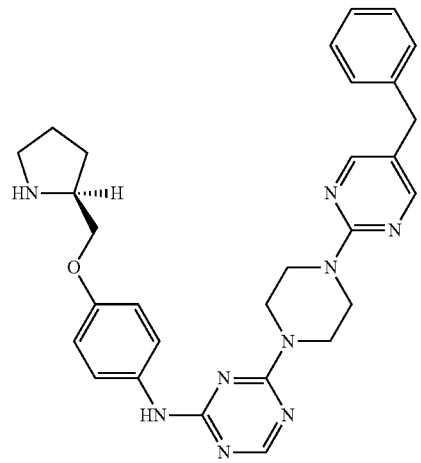 [SMILES: c1ccc(Cc2cnc(N3CCN(c4ncnc(Nc5ccc(OC[C@@H]6CCCN6)cc5)n4)CC3)nc2)cc1] |
| 171 | 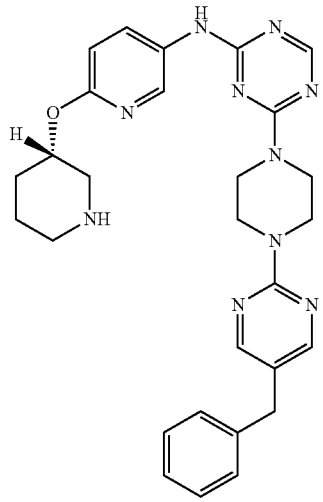 [SMILES: c1ccc(Cc2cnc(N3CCN(c4ncnc(Nc5ccc(O[C@H]6CCCNC6)nc5)n4)CC3)nc2)cc1] |

-continued
| Compound Number | Structure |
|---|---|
| 172 | 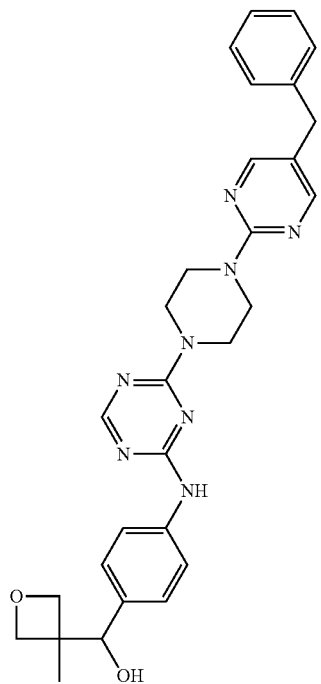 [SMILES: CC1(C(O)c2ccc(Nc3ncnc(N4CCN(c5ncc(Cc6ccccc6)cn5)CC4)n3)cc2)COC1] |
| 173 | 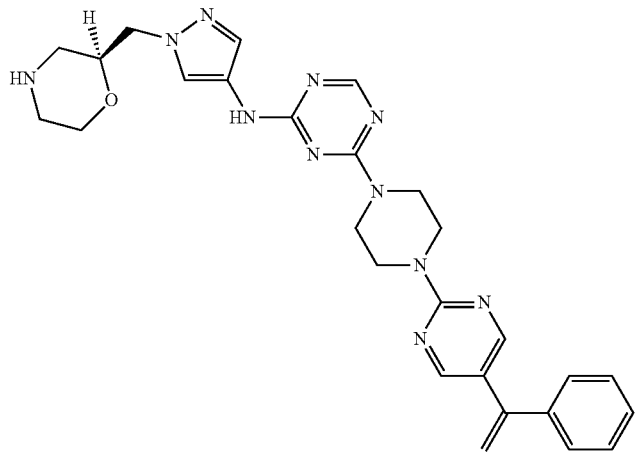 [SMILES: C=C(c1ccccc1)c1cnc(N2CCN(c3ncnc(Nc4cnn(C[C@@H]5CNCCO5)c4)n3)CC2)nc1] |
| 174 | 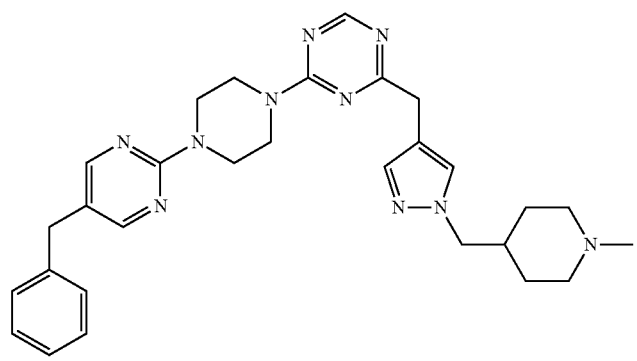 [SMILES: CN1CCC(Cn2cc(Cc3ncnc(N4CCN(c5ncc(Cc6ccccc6)cn5)CC4)n3)cn2)CC1] |

-continued
| Compound Number | Structure |
|---|---|
| 175 | 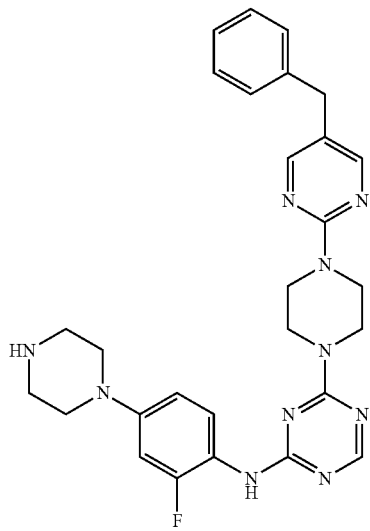 [SMILES: Fc1cc(N2CCNCC2)ccc1Nc1ncnc(N2CCN(c3ncc(Cc4ccccc4)cn3)CC2)n1] |
| 176 | 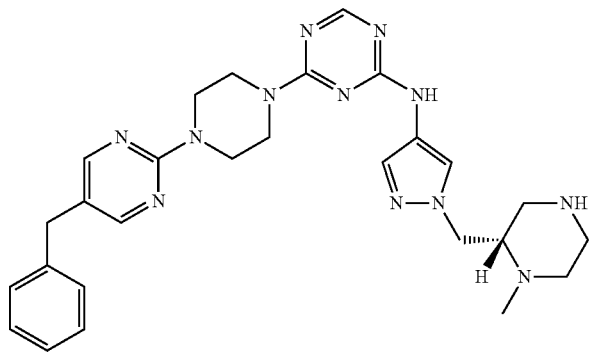 [SMILES: CN1CCNC[C@H]1Cn1cc(Nc2ncnc(N3CCN(c4ncc(Cc5ccccc5)cn4)CC3)n2)cn1] |
| 177 | 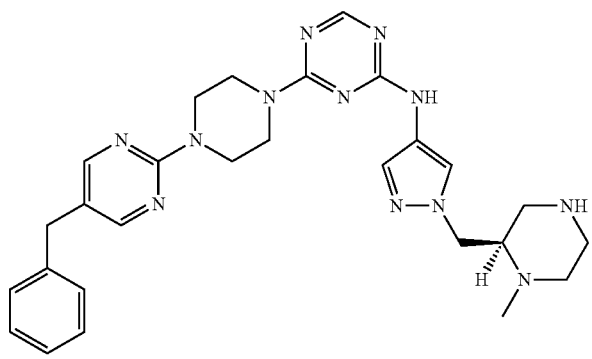 [SMILES: CN1CCNC[C@@H]1Cn1cc(Nc2ncnc(N3CCN(c4ncc(Cc5ccccc5)cn4)CC3)n2)cn1] |

| Compound Number | Structure |
|---|---|
| 178 | 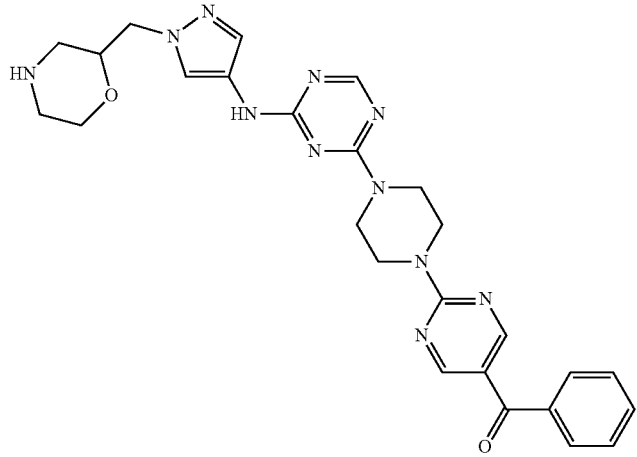 [SMILES: O=C(c1ccccc1)c1cnc(N2CCN(c3ncnc(Nc4cnn(CC5CNCCO5)c4)n3)CC2)nc1] |
| 179 | 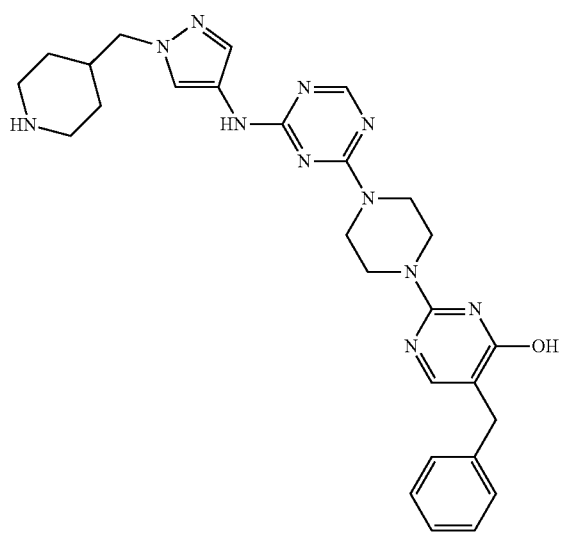 [SMILES: Oc1nc(N2CCN(c3ncnc(Nc4cnn(CC5CCNCC5)c4)n3)CC2)ncc1Cc1ccccc1] |
| 180 | 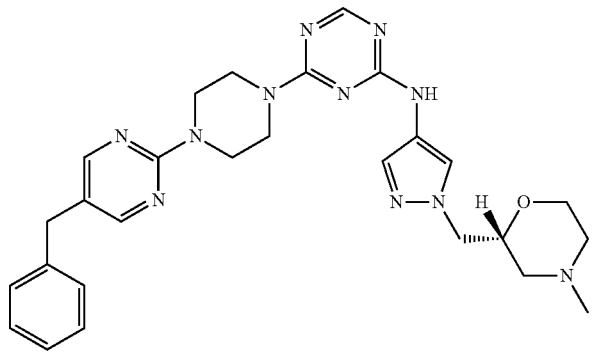 [SMILES: CN1CCO[C@@H](Cn2cc(Nc3ncnc(N4CCN(c5ncc(Cc6ccccc6)cn5)CC4)n3)cn2)C1] |

-continued
| Compound Number | Structure |
|---|---|
| 181 | 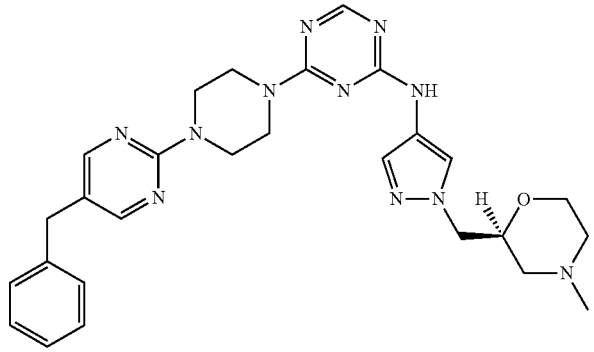 [SMILES: CN1CCO[C@H](Cn2cc(Nc3ncnc(N4CCN(c5ncc(Cc6ccccc6)cn5)CC4)n3)cn2)C1] |
| 182 | 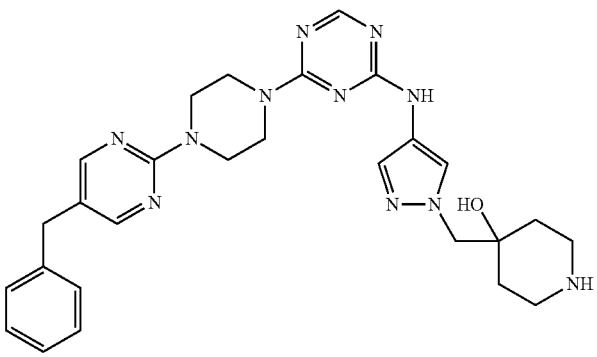 [SMILES: OC1(Cn2cc(Nc3ncnc(N4CCN(c5ncc(Cc6ccccc6)cn5)CC4)n3)cn2)CCNCC1] |
| 183 | 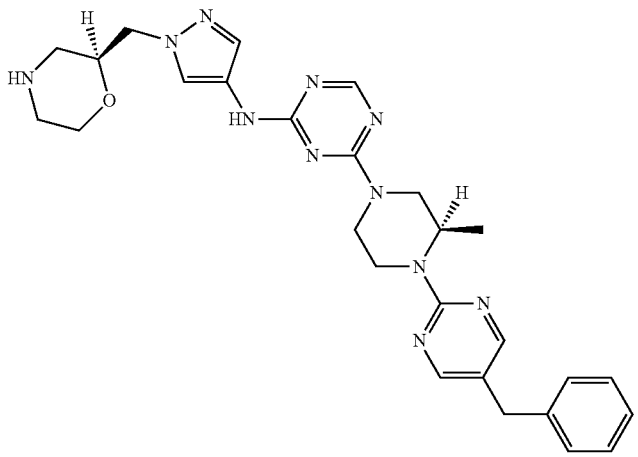 |
| 184 | 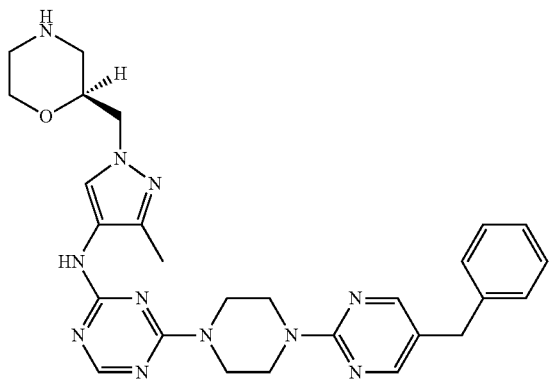 [SMILES: Cc1nn(C[C@@H]2CNCCO2)cc1Nc1ncnc(N2CCN(c3ncc(Cc4ccccc4)cn3)CC2)n1] |

| Compound Number | Structure |
|---|---|
| 185 | 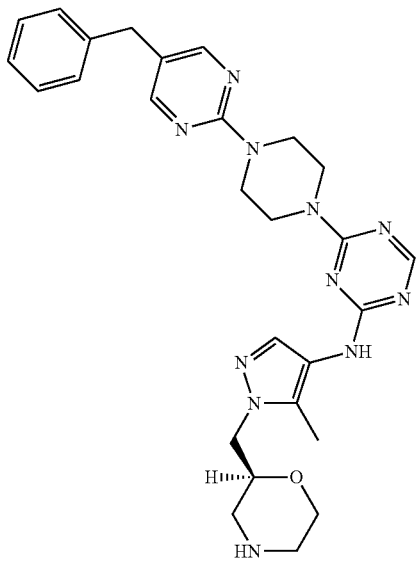 [SMILES: Cc1c(Nc2ncnc(N3CCN(c4ncc(Cc5ccccc5)cn4)CC3)n2)cnn1C[C@@H]1CNCCO1] |
| 186 | 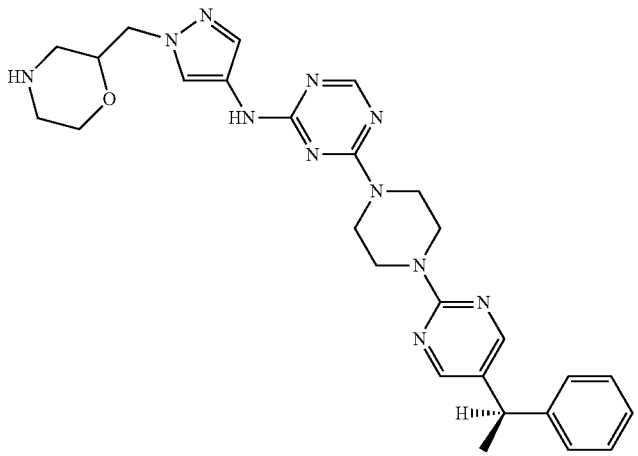 [SMILES: C[C@H](c1ccccc1)c1cnc(N2CCN(c3ncnc(Nc4cnn(CC5CNCCO5)c4)n3)CC2)nc1] |
| 187 | 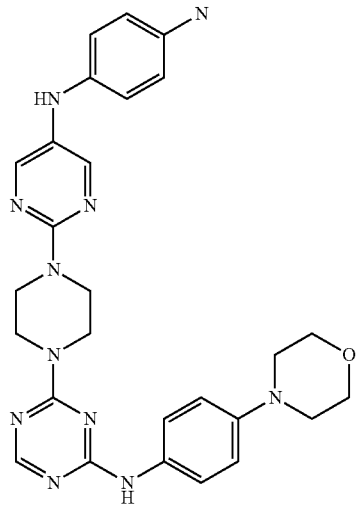 [SMILES: Nc1ccc(Nc2cnc(N3CCN(c4ncnc(Nc5ccc(N6CCOCC6)cc5)n4)CC3)nc2)cc1] |

| Compound Number | Structure |
|---|---|
| 188 | 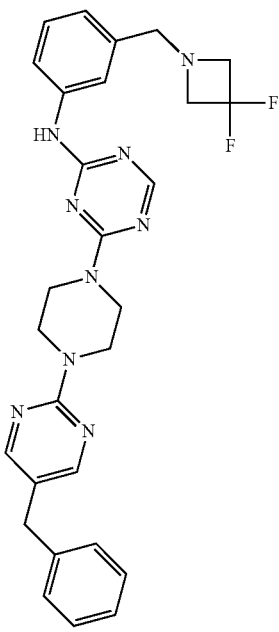 [SMILES: FC1(F)CN(Cc2cccc(Nc3ncnc(N4CCN(c5ncc(Cc6ccccc6)cn5)CC4)n3)c2)C1] |
| 189 | 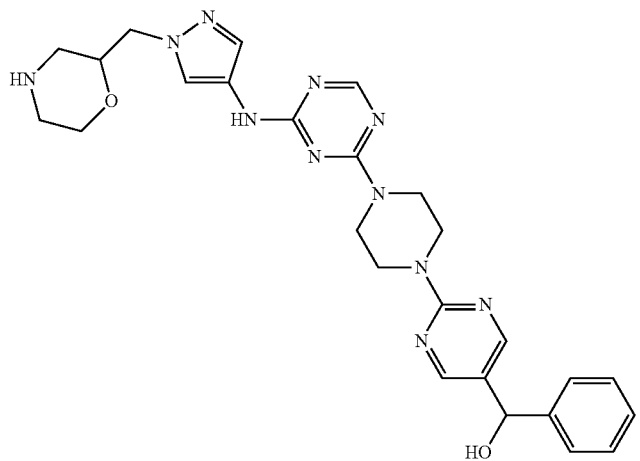 [SMILES: OC(c1ccccc1)c1cnc(N2CCN(c3ncnc(Nc4cnn(CC5CNCCO5)c4)n3)CC2)nc1] |

| Compound Number | Structure |
|---|---|
| 190 | 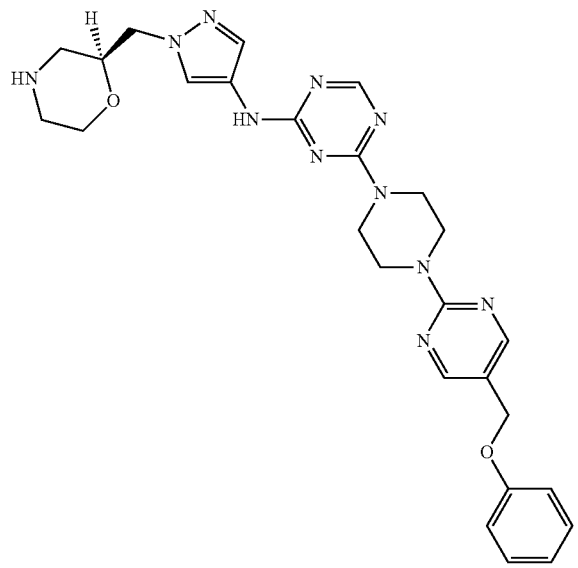 [SMILES: c1ccc(OCc2cnc(N3CCN(c4ncnc(Nc5cnn(C[C@@H]6CNCCO6)c5)n4)CC3)nc2)cc1] |
| 191 | 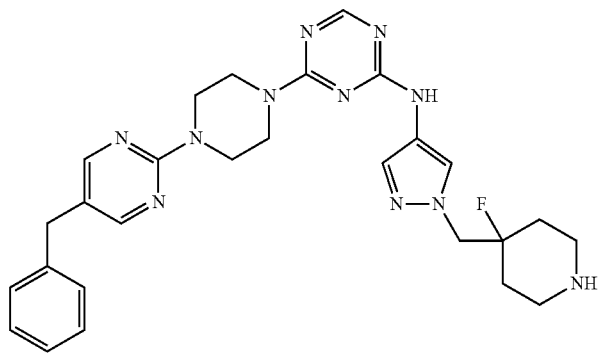 [SMILES: FC1(Cn2cc(Nc3ncnc(N4CCN(c5ncc(Cc6ccccc6)cn5)CC4)n3)cn2)CCNCC1] |
| 192 | 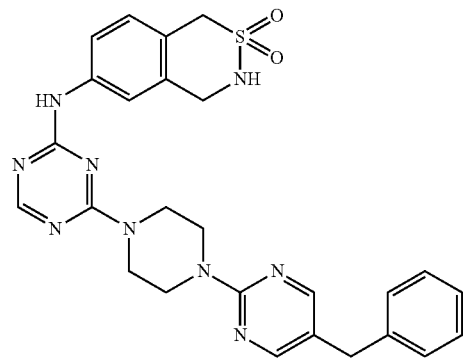 [SMILES: O=S1(=O)Cc2ccc(Nc3ncnc(N4CCN(c5ncc(Cc6ccccc6)cn5)CC4)n3)cc2CN1] |

| Compound Number | Structure |
|---|---|
| 193 | 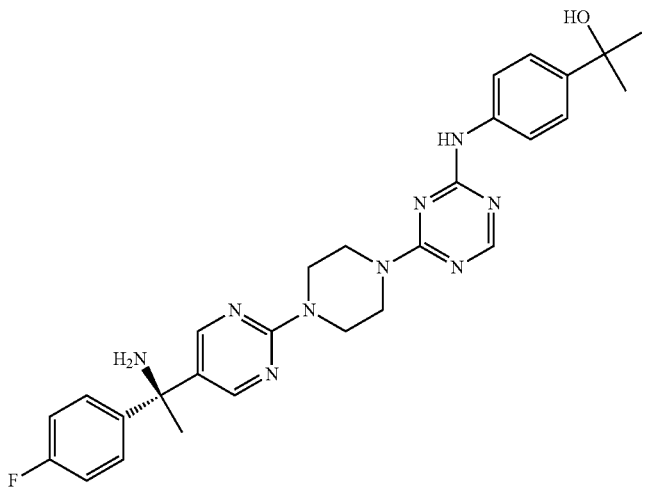 [SMILES: CC(C)(O)c1ccc(Nc2ncnc(N3CCN(c4ncc([C@@](C)(N)c5ccc(F)cc5)cn4)CC3)n2)cc1] |
| 194 | 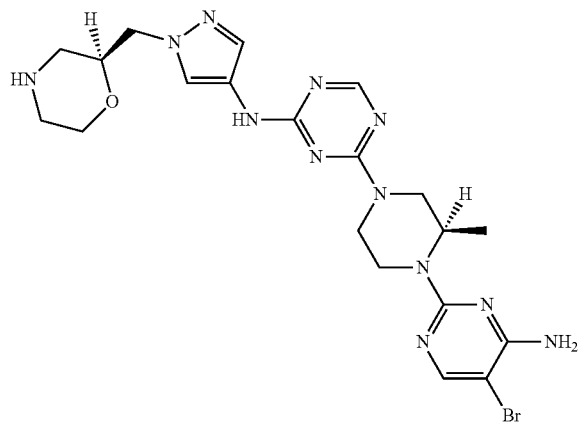 [SMILES: C[C@@H]1CN(c2ncnc(Nc3cnn(C[C@@H]4CNCCO4)c3)n2)CCN1c1ncc(Br)c(N)n1] |
| 195 | 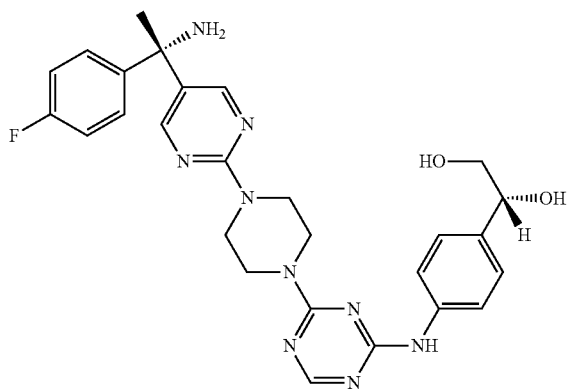 [SMILES: C[C@](N)(c1ccc(F)cc1)c1cnc(N2CCN(c3ncnc(Nc4ccc([C@@H](O)CO)cc4)n3)CC2)nc1] |

US 9,334,263 B2
135                                                                 136
-continued
| Compound Number | Structure |
|---|---|
| 196 | 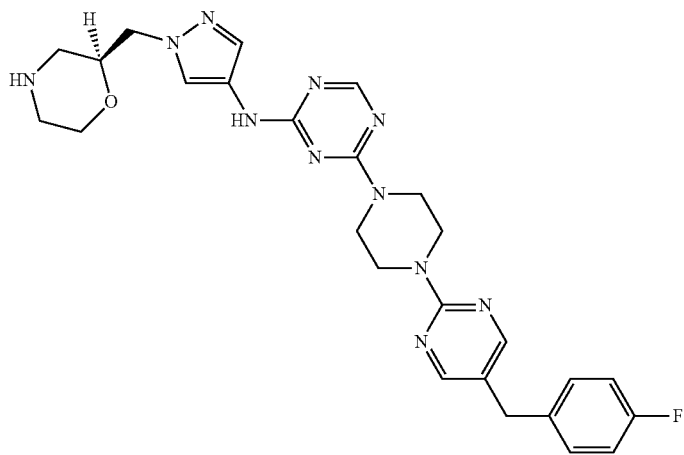 [SMILES: Fc1ccc(Cc2cnc(N3CCN(c4ncnc(Nc5cnn(C[C@@H]6CNCCO6)c5)n4)CC3)nc2)cc1] |
| 197 | 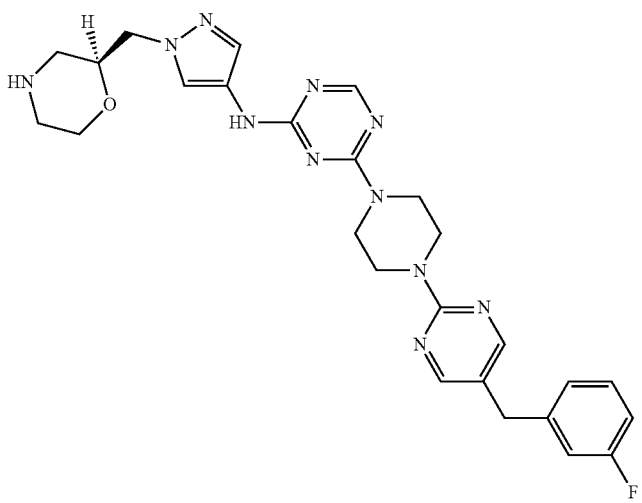 [SMILES: Fc1cccc(Cc2cnc(N3CCN(c4ncnc(Nc5cnn(C[C@@H]6CNCCO6)c5)n4)CC3)nc2)c1] |
| 198 | 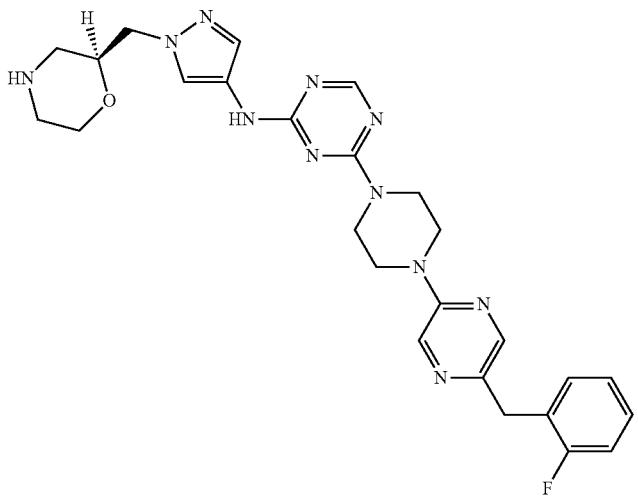 [SMILES: Fc1ccccc1Cc1cnc(N2CCN(c3ncnc(Nc4cnn(C[C@@H]5CNCCO5)c4)n3)CC2)cn1] |

| Compound Number | Structure |
|---|---|
| 199 | 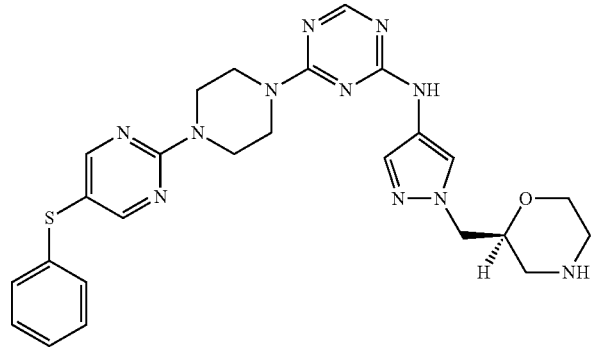 |
| 200 | 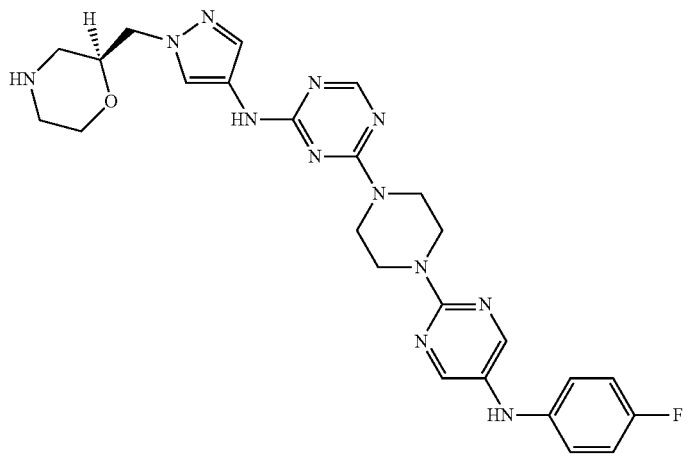 [SMILES: Fc1ccc(Nc2cnc(N3CCN(c4ncnc(Nc5cnn(C[C@@H]6CNCCO6)c5)n4)CC3)nc2)cc1] |
| 201 | 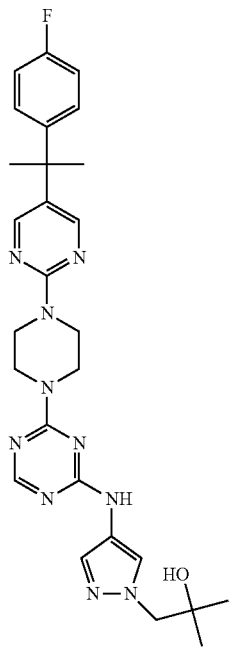 [SMILES: CC(C)(O)Cn1cc(Nc2ncnc(N3CCN(c4ncc(C(C)(C)c5ccc(F)cc5)cn4)CC3)n2)cn1] |

-continued
| Compound Number | Structure |
|---|---|
| 202 | 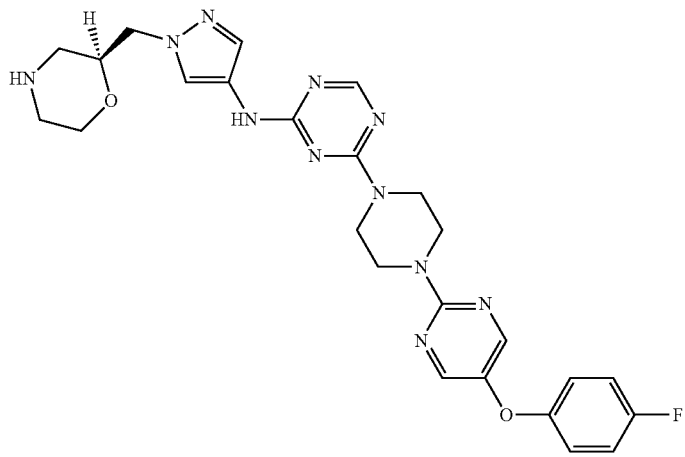 [SMILES: Fc1ccc(Oc2cnc(N3CCN(c4ncnc(Nc5cnn(C[C@@H]6CNCCO6)c5)n4)CC3)nc2)cc1] |
| 203 | 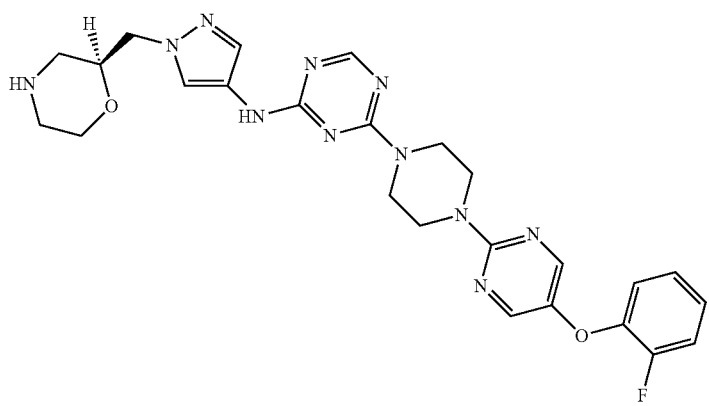 [SMILES: Fc1ccccc1Oc1cnc(N2CCN(c3ncnc(Nc4cnn(C[C@@H]5CNCCO5)c4)n3)CC2)nc1] |
| 204 | 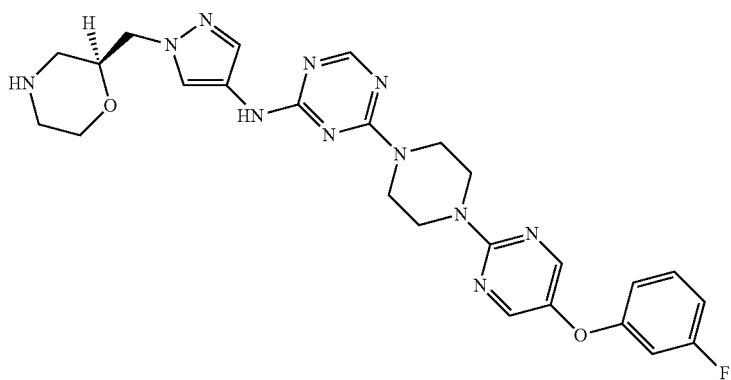 [SMILES: Fc1cccc(Oc2cnc(N3CCN(c4ncnc(Nc5cnn(C[C@@H]6CNCCO6)c5)n4)CC3)nc2)c1] |

| Compound Number | Structure |
|---|---|
| 205 | 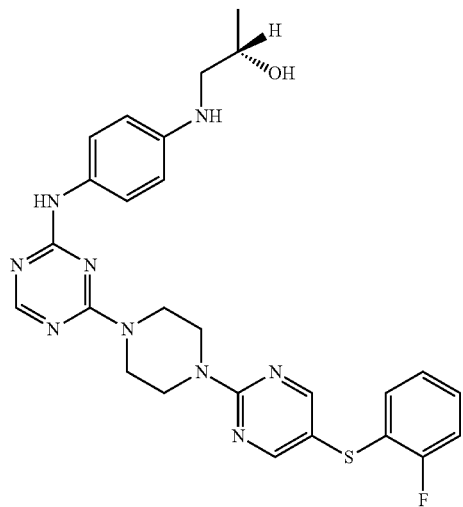 [SMILES: C[C@H](O)CNc1ccc(Nc2ncnc(N3CCN(c4ncc(Sc5ccccc5F)cn4)CC3)n2)cc1] |
| 206 | 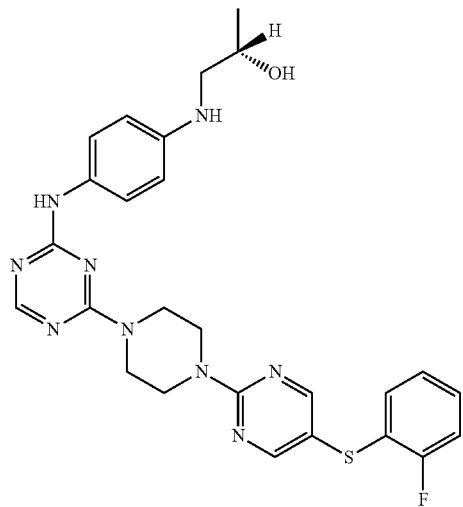 |

-continued
| Compound Number | Structure |
|---|---|
| 207 | 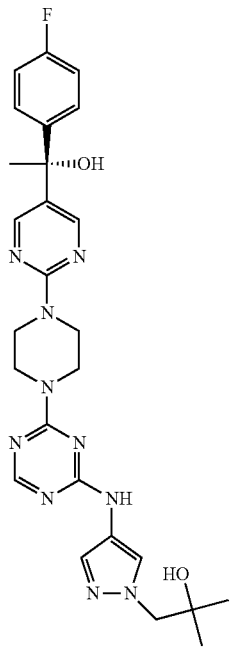 [SMILES: CC(C)(O)Cn1cc(Nc2ncnc(N3CCN(c4ncc([C@](C)(O)c5ccc(F)cc5)cn4)CC3)n2)cn1] |
| 208 | 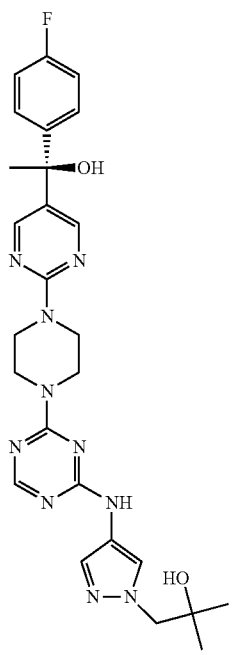 [SMILES: CC(C)(O)Cn1cc(Nc2ncnc(N3CCN(c4ncc([C@@](C)(O)c5ccc(F)cc5)cn4)CC3)n2)cn1] |

| Compound Number | Structure |
|---|---|
| 209 | 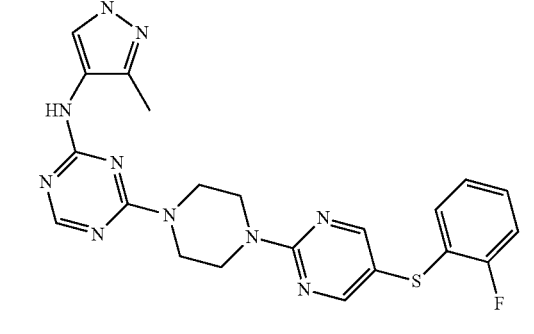 |
| 210 | 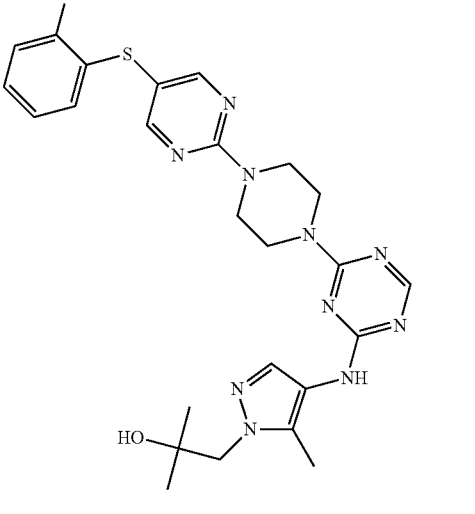 |
| 211 | 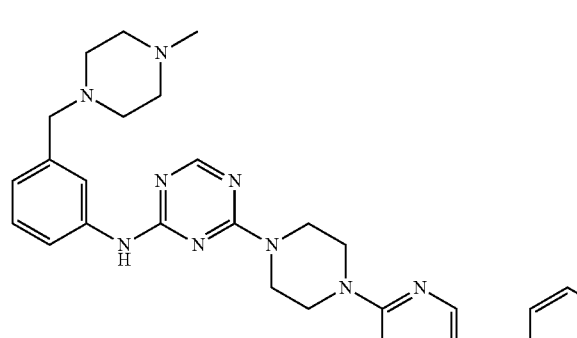 |

| Compound Number | Structure |
|---|---|
| 212 | 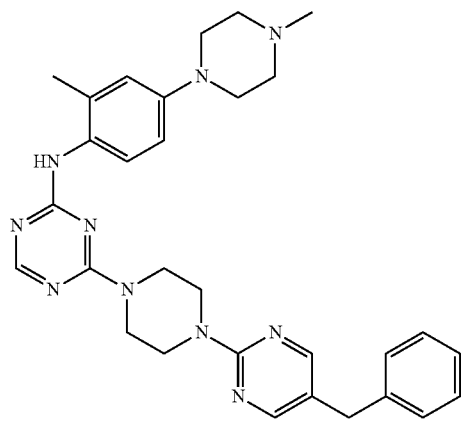 [SMILES: Cc1cc(N2CCN(C)CC2)ccc1Nc1ncnc(N2CCN(c3ncc(Cc4ccccc4)cn3)CC2)n1] |
| 213 | 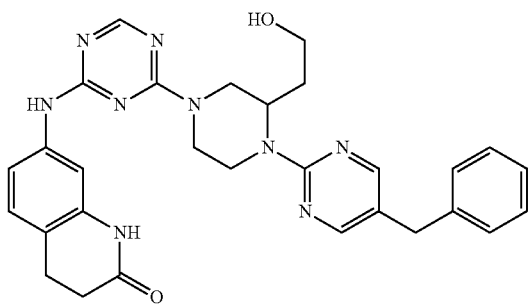 [SMILES: O=C1CCc2ccc(Nc3ncnc(N4CCN(c5ncc(Cc6ccccc6)cn5)C(CCO)C4)n3)cc2N1] |
| 214 | 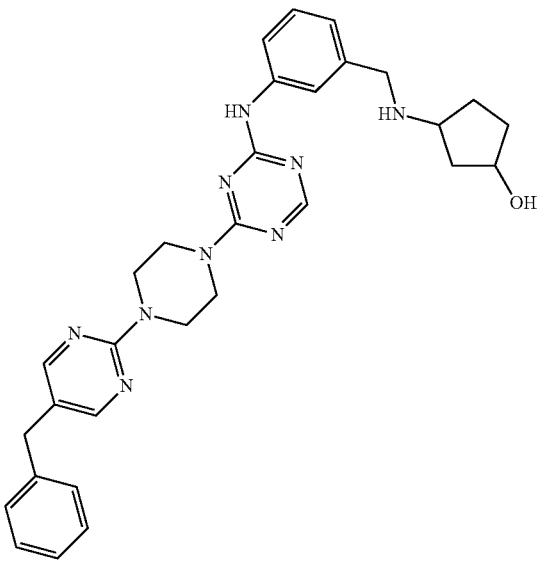 [SMILES: OC1CCC(NCc2cccc(Nc3ncnc(N4CCN(c5ncc(Cc6ccccc6)cn5)CC4)n3)c2)C1] |

-continued
| Compound Number | Structure |
|---|---|
| 215 | 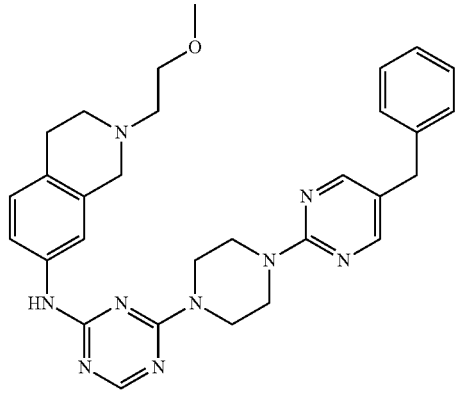 [SMILES: COCCN1CCc2ccc(Nc3ncnc(N4CCN(c5ncc(Cc6ccccc6)cn5)CC4)n3)cc2C1] |
| 216 | 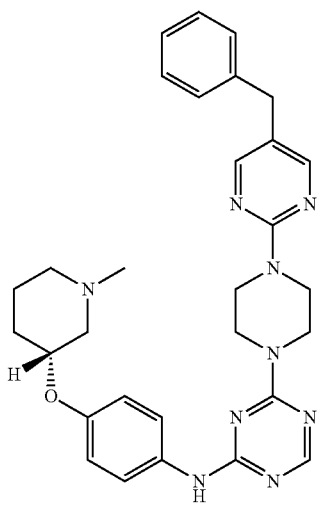 [SMILES: CN1CCC[C@@H](Oc2ccc(Nc3ncnc(N4CCN(c5ncc(Cc6ccccc6)cn5)CC4)n3)cc2)C1] |
| 217 | 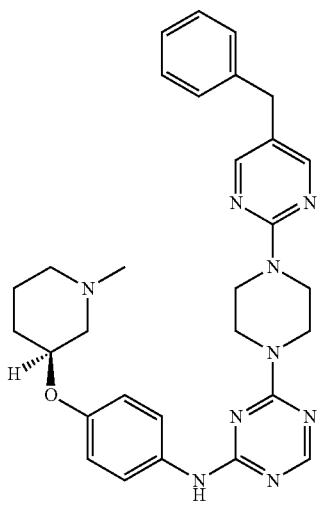 [SMILES: CN1CCC[C@H](Oc2ccc(Nc3ncnc(N4CCN(c5ncc(Cc6ccccc6)cn5)CC4)n3)cc2)C1] |

| Compound Number | Structure |
|---|---|
| 218 | 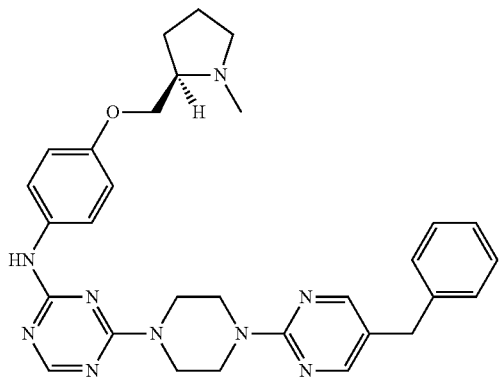 [SMILES: CN1CCC[C@@H]1COc1ccc(Nc2ncnc(N3CCN(c4ncc(Cc5ccccc5)cn4)CC3)n2)cc1] |
| 219 | 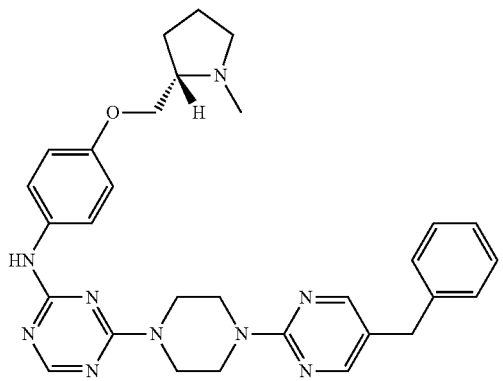 [SMILES: CN1CCC[C@H]1COc1ccc(Nc2ncnc(N3CCN(c4ncc(Cc5ccccc5)cn4)CC3)n2)cc1] |
| 220 | 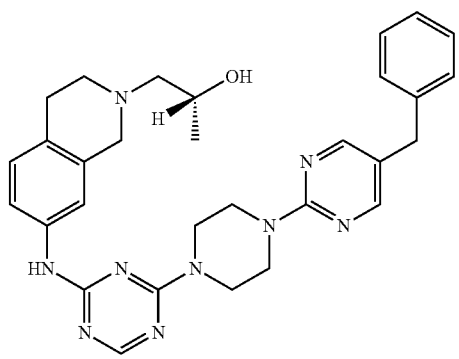 [SMILES: C[C@@H](O)CN1CCc2ccc(Nc3ncnc(N4CCN(c5ncc(Cc6ccccc6)cn5)CC4)n3)cc2C1] |
| 221 | 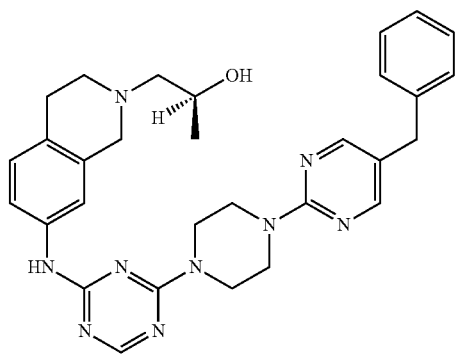 [SMILES: C[C@H](O)CN1CCc2ccc(Nc3ncnc(N4CCN(c5ncc(Cc6ccccc6)cn5)CC4)n3)cc2C1] |

-continued
| Compound Number | Structure |
|---|---|
| 222 | 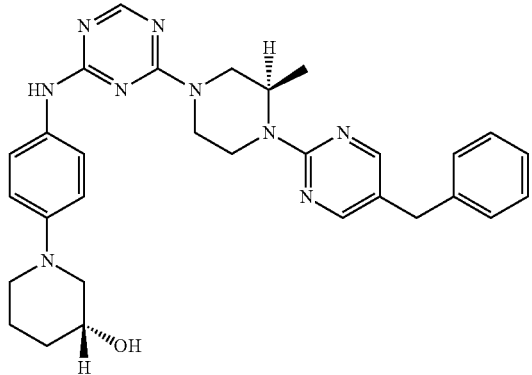 [SMILES: C[C@@H]1CN(c2ncnc(Nc3ccc(N4CCC[C@@H](O)C4)cc3)n2)CCN1c1ncc(Cc2ccccc2)cn1] |
| 223 | 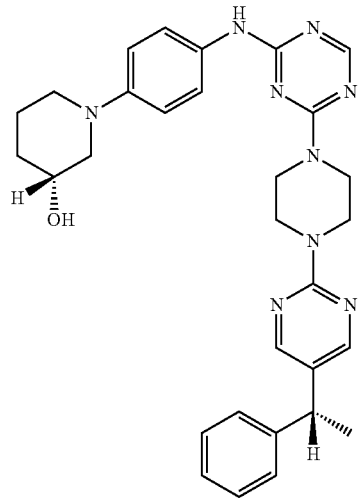 [SMILES: C[C@H](c1ccccc1)c1cnc(N2CCN(c3ncnc(Nc4ccc(N5CCC[C@@H](O)C5)cc4)n3)CC2)nc1] |
| 224 | 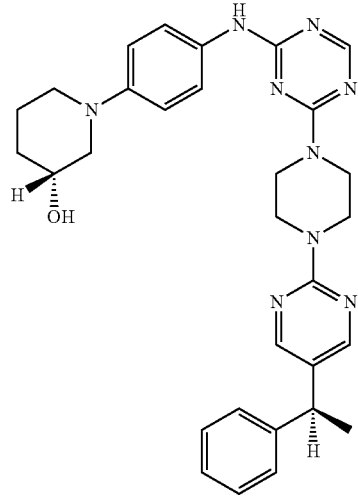 [SMILES: C[C@@H](c1ccccc1)c1cnc(N2CCN(c3ncnc(Nc4ccc(N5CCC[C@@H](O)C5)cc4)n3)CC2)nc1] |

-continued
| Compound Number | Structure |
|---|---|
| 225 | 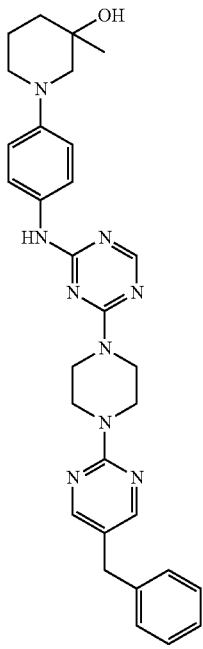 [SMILES: CC1(O)CCCN(c2ccc(Nc3ncnc(N4CCN(c5ncc(Cc6ccccc6)cn5)CC4)n3)cc2)C1] |
| 226 | 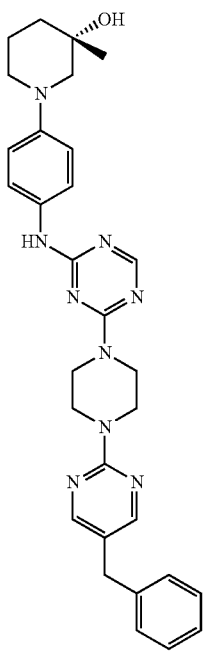 [SMILES: C[C@]1(O)CCCN(c2ccc(Nc3ncnc(N4CCN(c5ncc(Cc6ccccc6)cn5)CC4)n3)cc2)C1] |

-continued
| Compound Number | Structure |
|---|---|
| 227 | 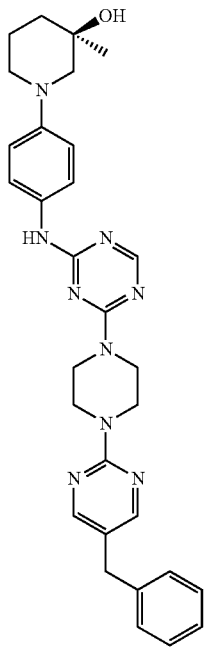 [SMILES: C[C@@]1(O)CCCN(c2ccc(Nc3ncnc(N4CCN(c5ncc(Cc6ccccc6)cn5)CC4)n3)cc2)C1] |
| 228 | 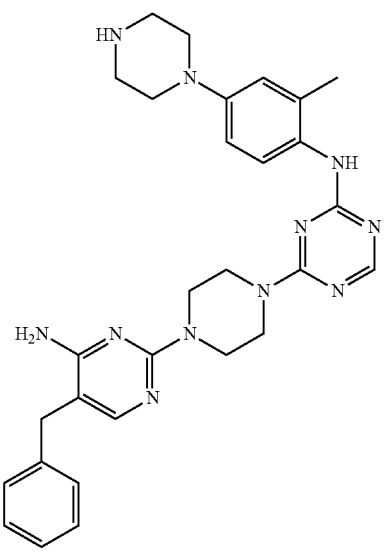 [SMILES: Cc1cc(N2CCNCC2)ccc1Nc1ncnc(N2CCN(c3ncc(Cc4ccccc4)c(N)n3)CC2)n1] |
| 229 | 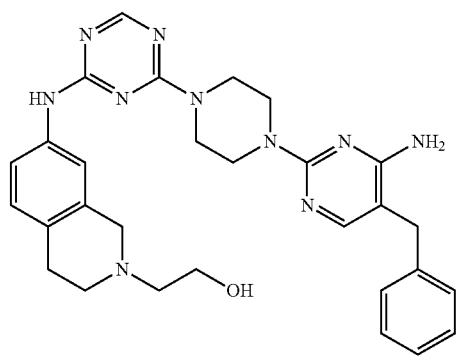 [SMILES: Nc1nc(N2CCN(c3ncnc(Nc4ccc5c(c4)CN(CCO)CC5)n3)CC2)ncc1Cc1ccccc1] |

| Compound Number | Structure |
|---|---|
| 230 | 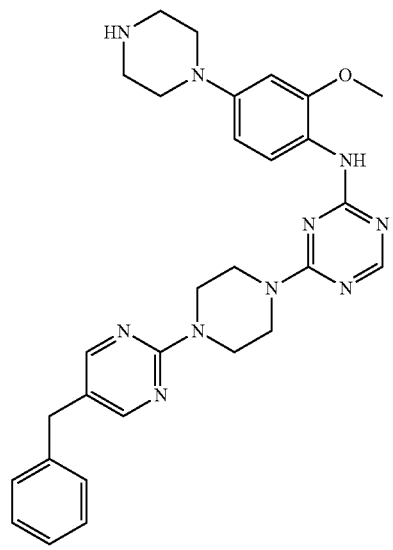 [SMILES: COc1cc(N2CCNCC2)ccc1Nc1ncnc(N2CCN(c3ncc(Cc4ccccc4)cn3)CC2)n1] |
| 231 | 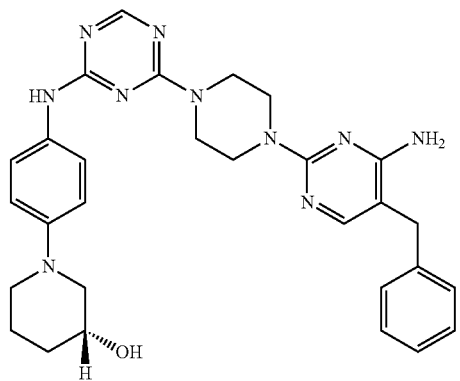 [SMILES: Nc1nc(N2CCN(c3ncnc(Nc4ccc(N5CCC[C@@H](O)C5)cc4)n3)CC2)ncc1Cc1ccccc1] |
| 232 | 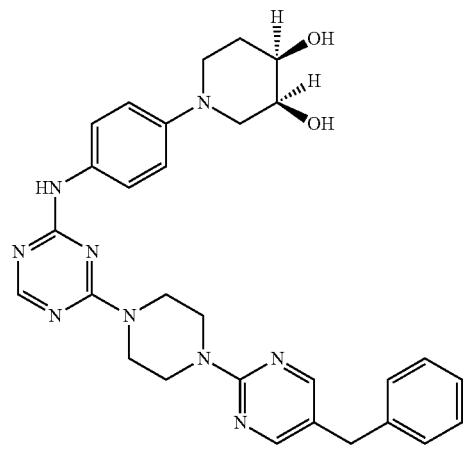 [SMILES: O[C@@H]1CCN(c2ccc(Nc3ncnc(N4CCN(c5ncc(Cc6ccccc6)cn5)CC4)n3)cc2)C[C@@H]1O] |

-continued
| Compound Number | Structure |
|---|---|
| 233 | 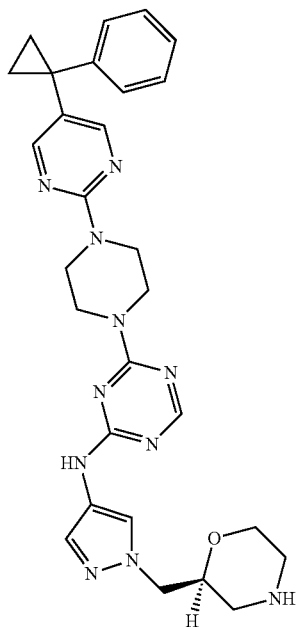 [SMILES: c1ccc(C2(c3cnc(N4CCN(c5ncnc(Nc6cnn(C[C@@H]7CNCCO7)c6)n5)CC4)nc3)CC2)cc1] |
| 234 | 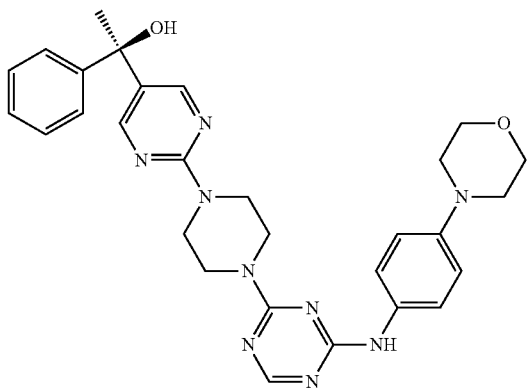 [SMILES: C[C@@](O)(c1ccccc1)c1cnc(N2CCN(c3ncnc(Nc4ccc(N5CCOCC5)cc4)n3)CC2)nc1] |
| 235 | 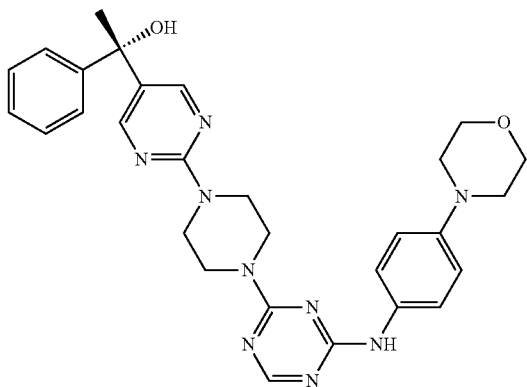 [SMILES: C[C@](O)(c1ccccc1)c1cnc(N2CCN(c3ncnc(Nc4ccc(N5CCOCC5)cc4)n3)CC2)nc1] |

| Compound Number | Structure |
|---|---|
| 236 | 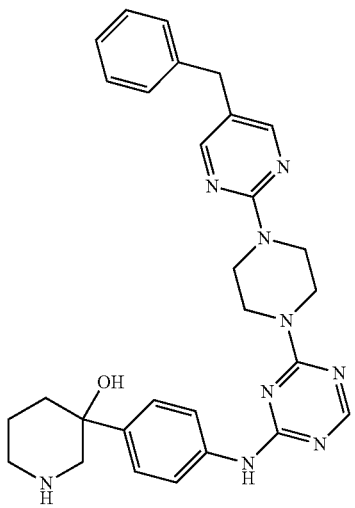 [SMILES: OC1(c2ccc(Nc3ncnc(N4CCN(c5ncc(Cc6ccccc6)cn5)CC4)n3)cc2)CCCNC1] |
| 237 | 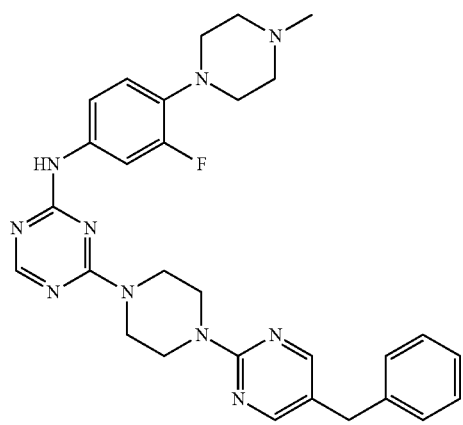 [SMILES: CN1CCN(c2ccc(Nc3ncnc(N4CCN(c5ncc(Cc6ccccc6)cn5)CC4)n3)cc2F)CC1] |
| 238 | 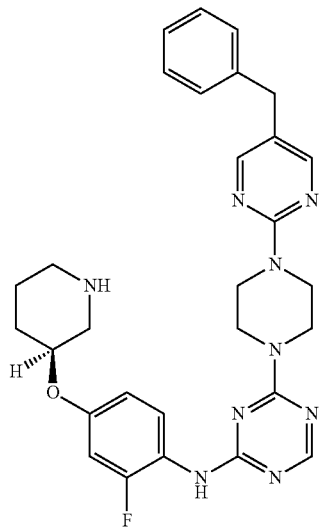 [SMILES: Fc1cc(O[C@H]2CCCNC2)ccc1Nc1ncnc(N2CCN(c3ncc(Cc4ccccc4)cn3)CC2)n1] |

| Compound Number | Structure |
|---|---|
| 239 | 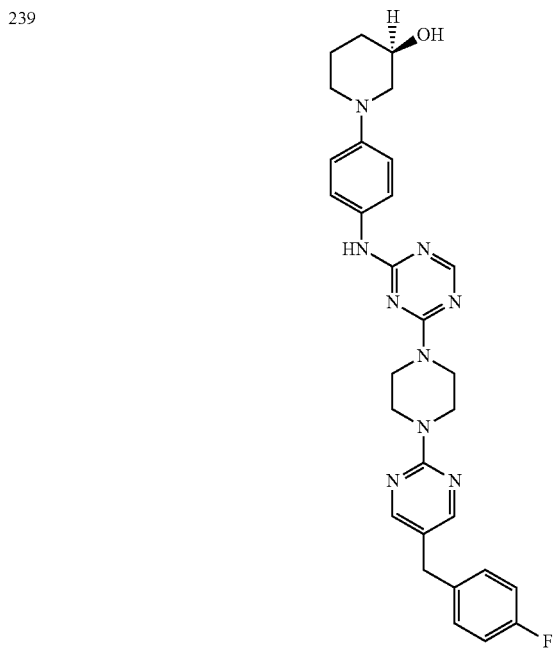 |
| 240 | 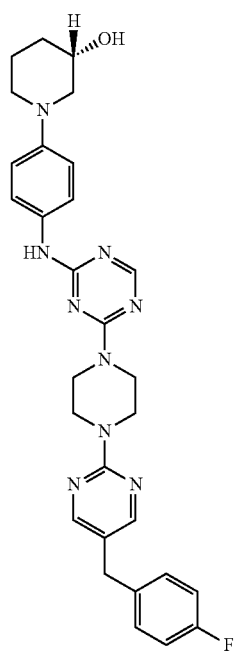 [SMILES: O[C@H]1CCCN(c2ccc(Nc3ncnc(N4CCN(c5ncc(Cc6ccc(F)cc6)cn5)CC4)n3)cc2)C1] |

| Compound Number | Structure |
|---|---|
| 241 | 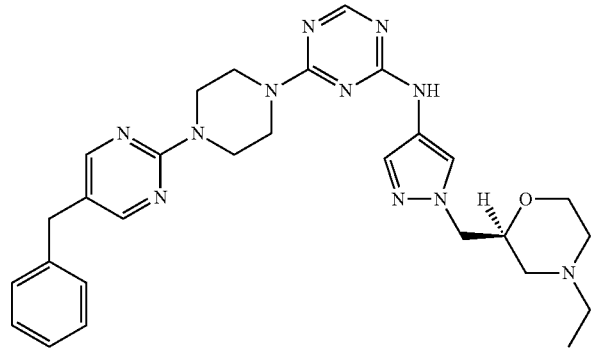 [SMILES: CCN1CCO[C@H](Cn2cc(Nc3ncnc(N4CCN(c5ncc(Cc6ccccc6)cn5)CC4)n3)cn2)C1] |
| 242 | 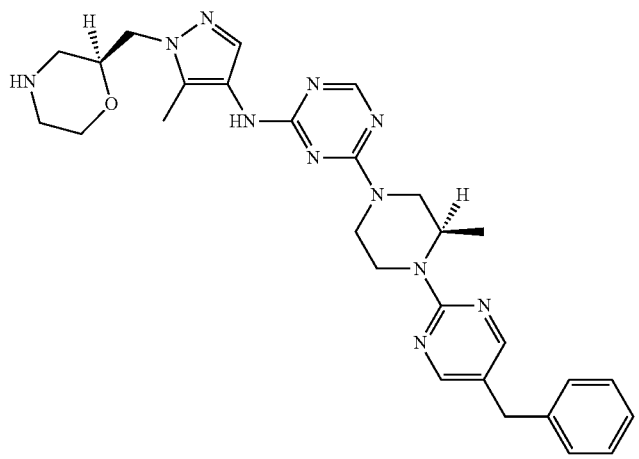 [SMILES: Cc1c(Nc2ncnc(N3CCN(c4ncc(Cc5ccccc5)cn4)[C@H](C)C3)n2)cnn1C[C@@H]1CNCCO1] |
| 243 | 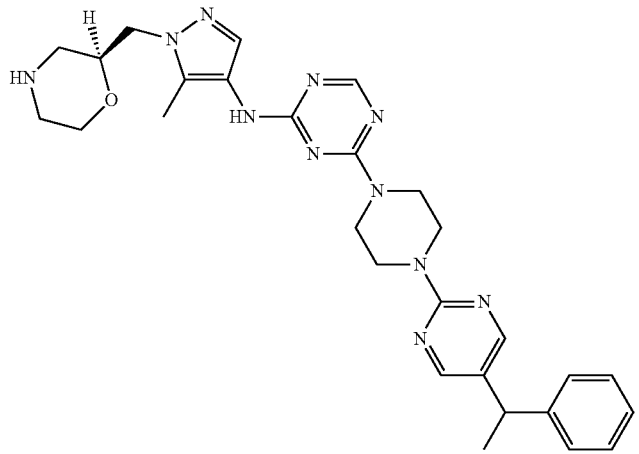 [SMILES: Cc1c(Nc2ncnc(N3CCN(c4ncc(C(C)c5ccccc5)cn4)CC3)n2)cnn1C[C@@H]1CNCCO1] |

-continued
| Compound Number | Structure |
|---|---|
| 244 | 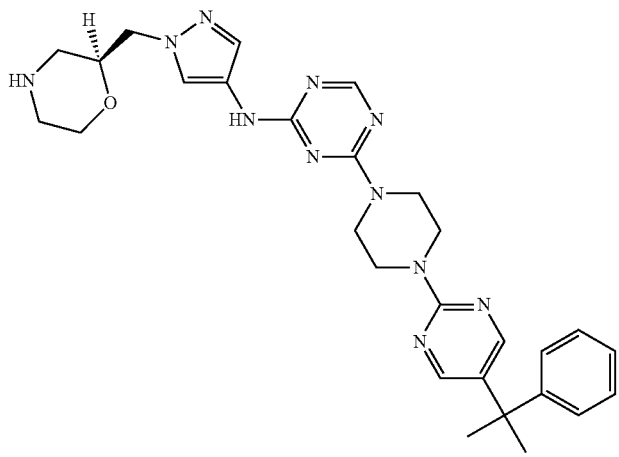 [SMILES: CC(C)(c1ccccc1)c1cnc(N2CCN(c3ncnc(Nc4cnn(C[C@@H]5CNCCO5)c4)n3)CC2)nc1] |
| 245 | 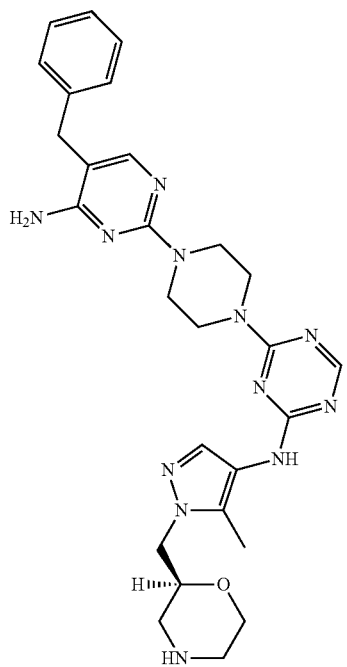 [SMILES: Cc1c(Nc2ncnc(N3CCN(c4ncc(Cc5ccccc5)c(N)n4)CC3)n2)cnn1C[C@@H]1CNCCO1] |

| Compound Number | Structure |
|---|---|
| 246 | 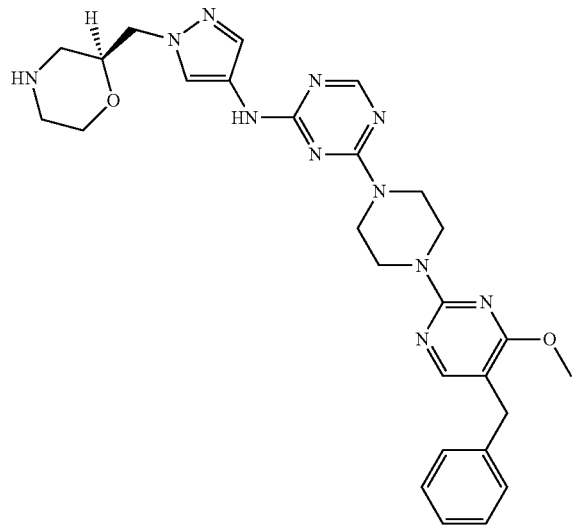 [SMILES: COc1nc(N2CCN(c3ncnc(Nc4cnn(C[C@@H]5CNCCO5)c4)n3)CC2)ncc1Cc1ccccc1] |
| 247 | 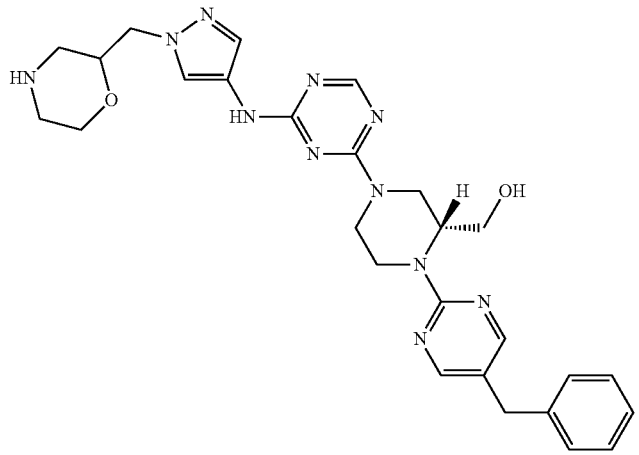 [SMILES: OC[C@H]1CN(c2ncnc(Nc3cnn(CC4CNCCO4)c3)n2)CCN1c1ncc(Cc2ccccc2)cn1] |
| 248 | 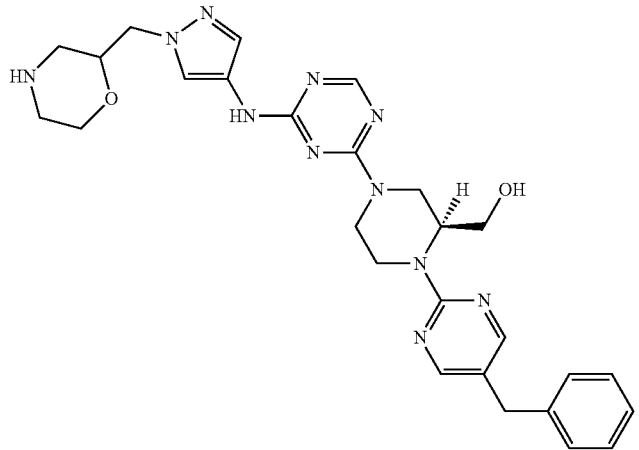 [SMILES: OC[C@@H]1CN(c2ncnc(Nc3cnn(CC4CNCCO4)c3)n2)CCN1c1ncc(Cc2ccccc2)cn1] |

| Compound Number | Structure |
|---|---|
| 249 | 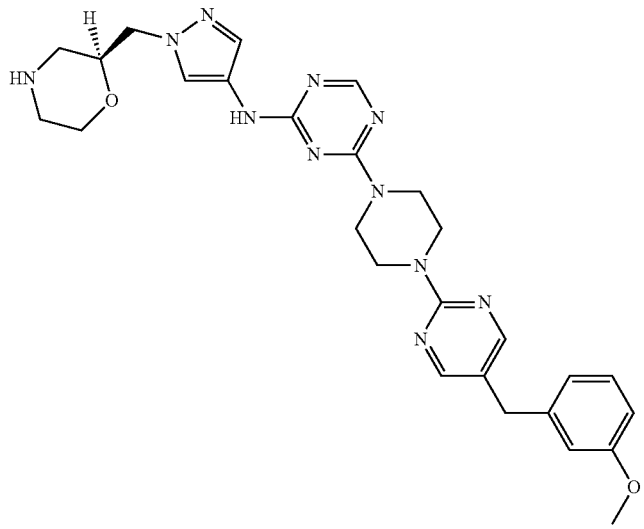 [SMILES: COc1cccc(Cc2cnc(N3CCN(c4ncnc(Nc5cnn(C[C@@H]6CNCCO6)c5)n4)CC3)nc2)c1] |
| 250 | 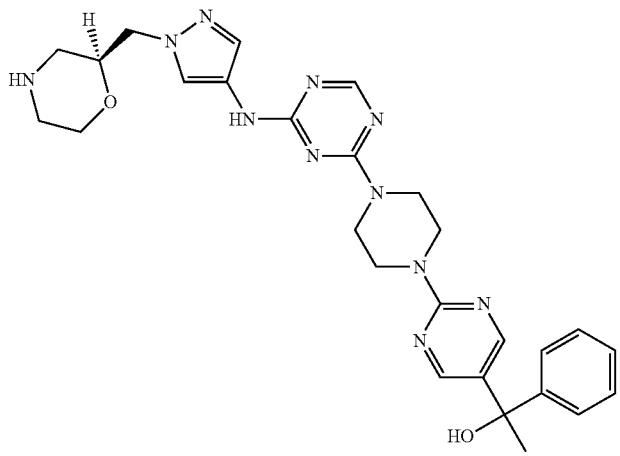 [SMILES: CC(O)(c1ccccc1)c1cnc(N2CCN(c3ncnc(Nc4cnn(C[C@@H]5CNCCO5)c4)n3)CC2)nc1] |
| 251 | 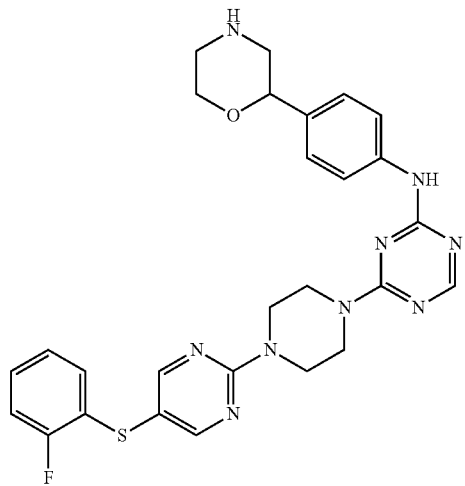 [SMILES: Fc1ccccc1Sc1cnc(N2CCN(c3ncnc(Nc4ccc(C5CNCCO5)cc4)n3)CC2)nc1] |

-continued
| Compound Number | Structure |
|---|---|
| 252 | 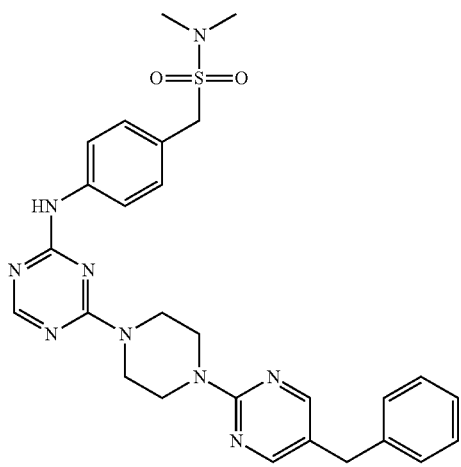 [SMILES: CN(C)S(=O)(=O)Cc1ccc(Nc2ncnc(N3CCN(c4ncc(Cc5ccccc5)cn4)CC3)n2)cc1] |
| 253 | 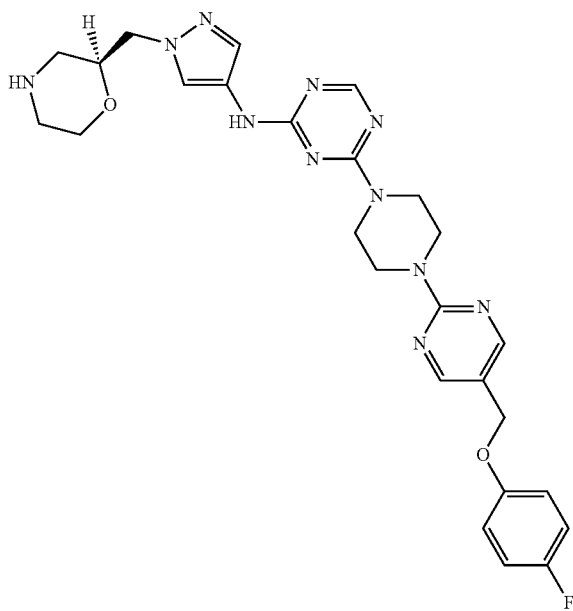 [SMILES: Fc1ccc(OCc2cnc(N3CCN(c4ncnc(Nc5cnn(C[C@@H]6CNCCO6)c5)n4)CC3)nc2)cc1] |
| 254 | 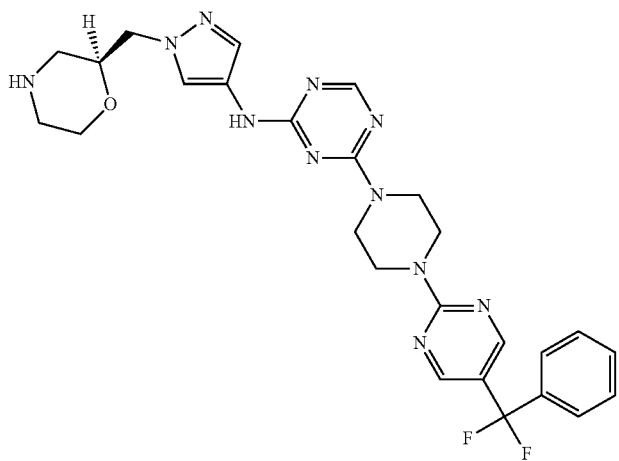 [SMILES: FC(F)(c1ccccc1)c1cnc(N2CCN(c3ncnc(Nc4cnn(C[C@@H]5CNCCO5)c4)n3)CC2)nc1] |

| Compound Number | Structure |
|---|---|
| 255 | 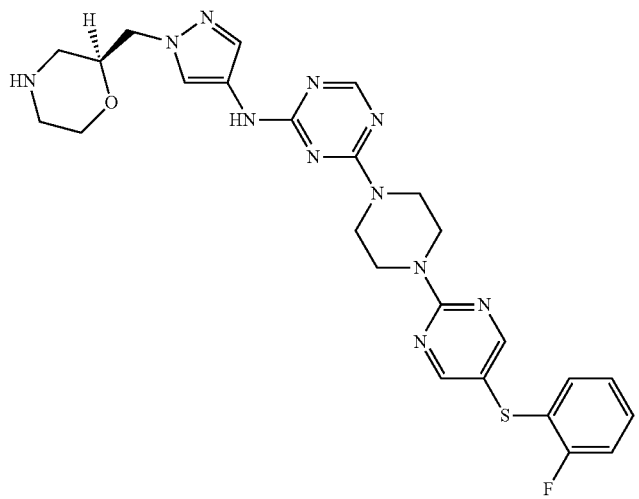 [SMILES: Fc1ccccc1Sc1cnc(N2CCN(c3ncnc(Nc4cnn(C[C@@H]5CNCCO5)c4)n3)CC2)nc1] |
| 256 | 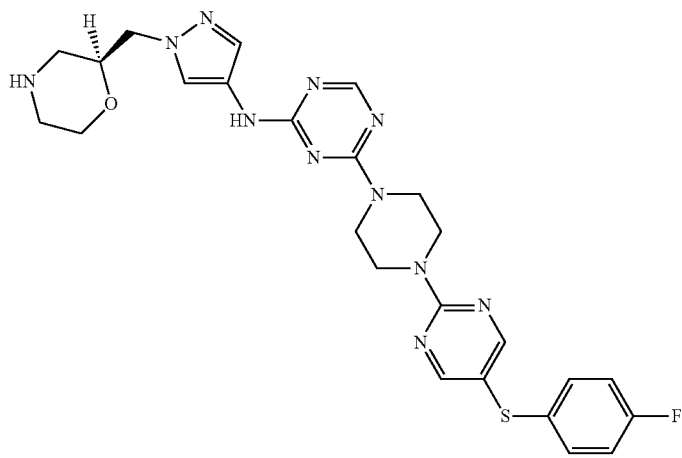 [SMILES: Fc1ccc(Sc2cnc(N3CCN(c4ncnc(Nc5cnn(C[C@@H]6CNCCO6)c5)n4)CC3)nc2)cc1] |
| 257 | 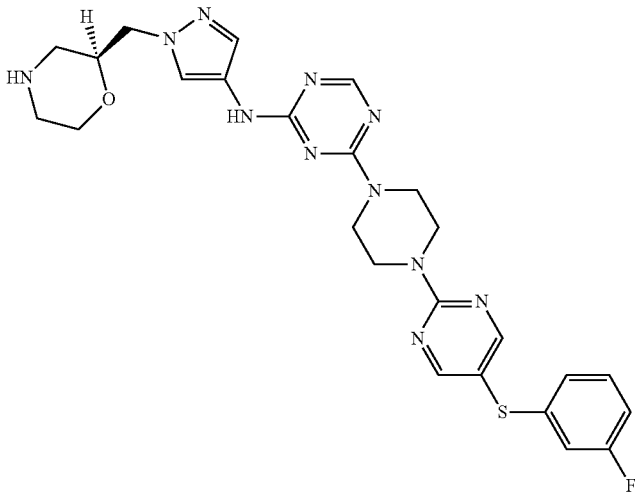 [SMILES: Fc1cccc(Sc2cnc(N3CCN(c4ncnc(Nc5cnn(C[C@@H]6CNCCO6)c5)n4)CC3)nc2)c1] |

| Compound Number | Structure |
|---|---|
| 258 | 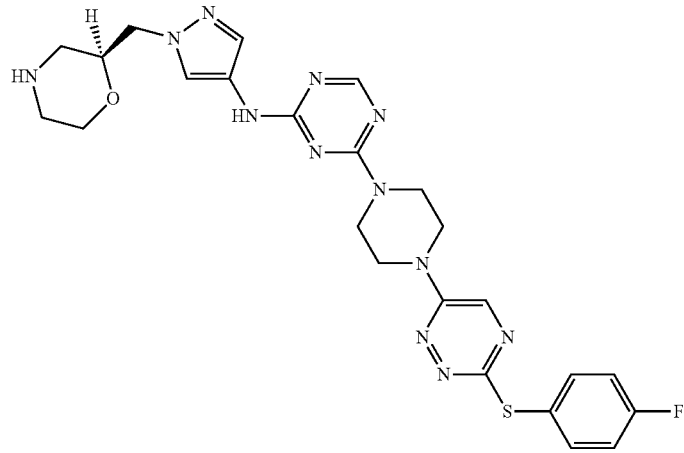 |
| 259 | 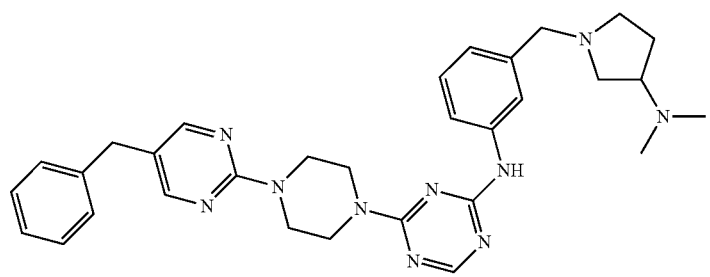 [SMILES: CN(C)C1CCN(Cc2cccc(Nc3ncnc(N4CCN(c5ncc(Cc6ccccc6)cn5)CC4)n3)c2)C1] |
| 260 | 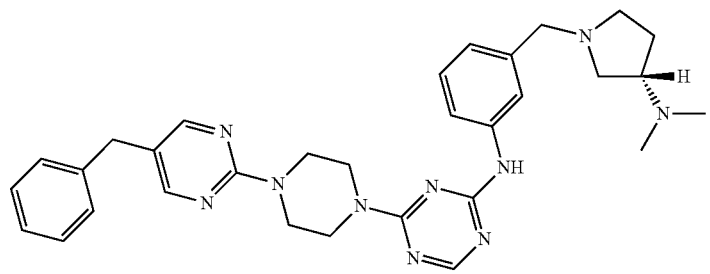 [SMILES: CN(C)[C@H]1CCN(Cc2cccc(Nc3ncnc(N4CCN(c5ncc(Cc6ccccc6)cn5)CC4)n3)c2)C1] |
| 261 | 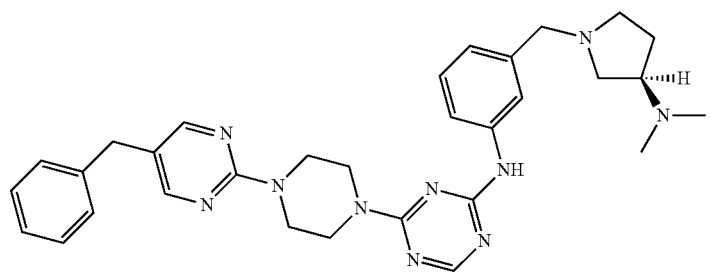 [SMILES: CN(C)[C@@H]1CCN(Cc2cccc(Nc3ncnc(N4CCN(c5ncc(Cc6ccccc6)cn5)CC4)n3)c2)C1] |

| Compound Number | Structure |
|---|---|
| 262 | 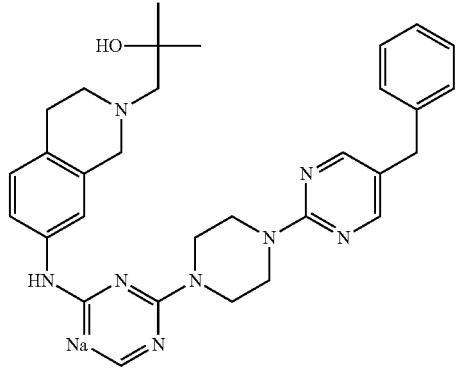 |
| 263 | 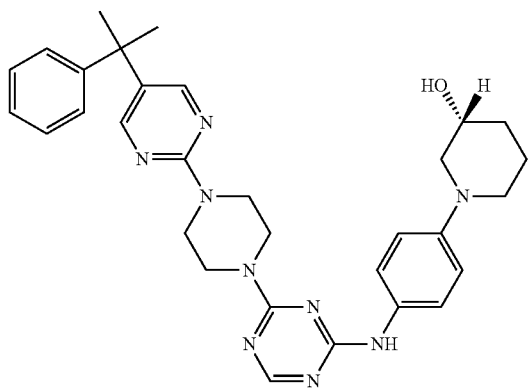 [SMILES: CC(C)(c1ccccc1)c1cnc(N2CCN(c3ncnc(Nc4ccc(N5CCC[C@@H](O)C5)cc4)n3)CC2)nc1] |
| 264 | 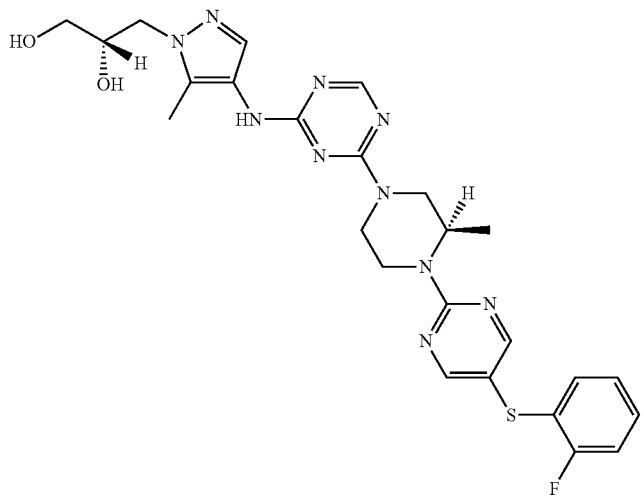 [SMILES: Cc1c(Nc2ncnc(N3CCN(c4ncc(Sc5ccccc5F)cn4)[C@H](C)C3)n2)cnn1C[C@H](O)CO] |

| Compound Number | Structure |
|---|---|
| 265 | 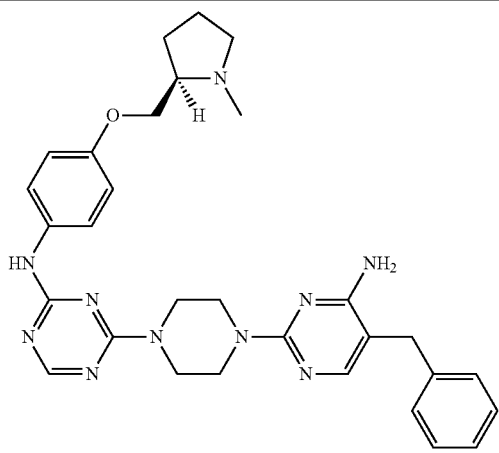 |
| 266 | 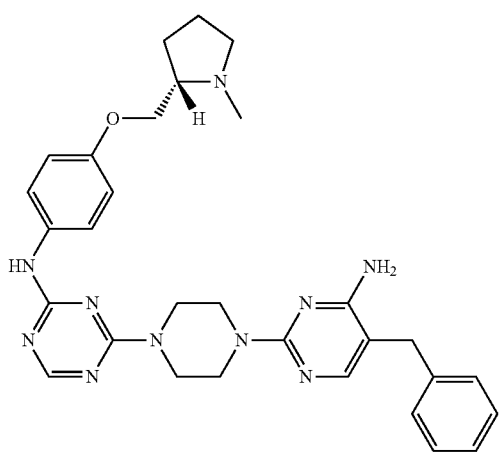 [SMILES: CN1CCC[C@H]1COc1ccc(Nc2ncnc(N3CCN(c4ncc(Cc5ccccc5)c(N)n4)CC3)n2)cc1] |
| 267 | 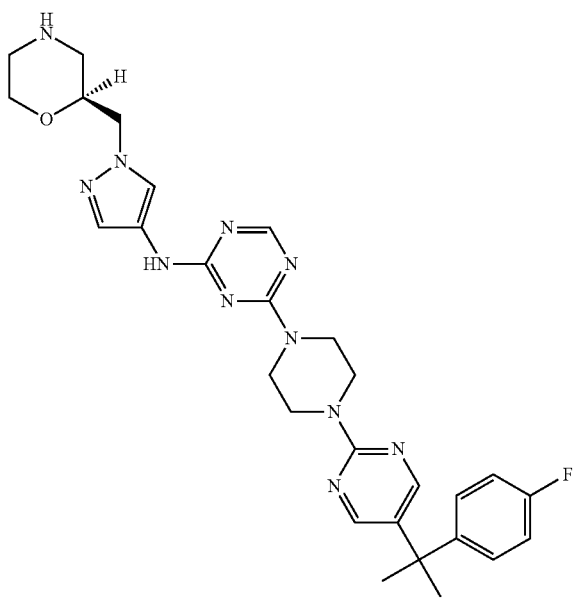 [SMILES: CC(C)(c1ccc(F)cc1)c1cnc(N2CCN(c3ncnc(Nc4cnn(C[C@@H]5CNCCO5)c4)n3)CC2)nc1] |

| Compound Number | Structure |
|---|---|
| 268 | 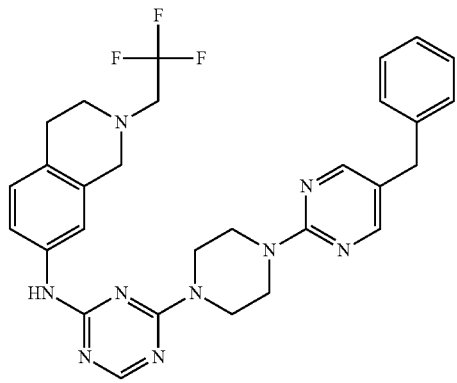 [SMILES: FC(F)(F)CN1CCc2ccc(Nc3ncnc(N4CCN(c5ncc(Cc6ccccc6)cn5)CC4)n3)cc2C1] |
| 269 | 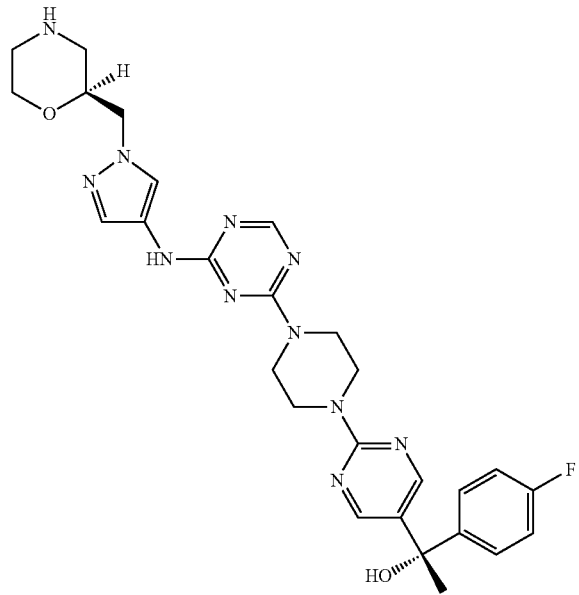 [SMILES: C[C@](O)(c1ccc(F)cc1)c1cnc(N2CCN(c3ncnc(Nc4cnn(C[C@@H]5CNCCO5)c4)n3)CC2)nc1] |
| 270 | 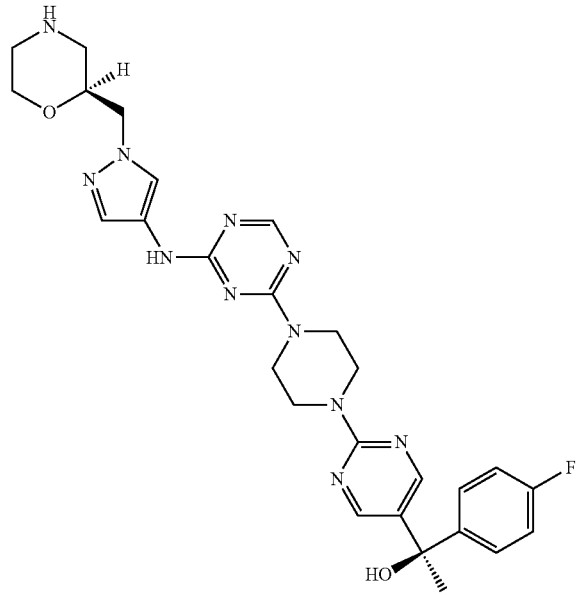 [SMILES: C[C@@](O)(c1ccc(F)cc1)c1cnc(N2CCN(c3ncnc(Nc4cnn(C[C@@H]5CNCCO5)c4)n3)CC2)nc1] |

| Compound Number | Structure |
|---|---|
| 271 | 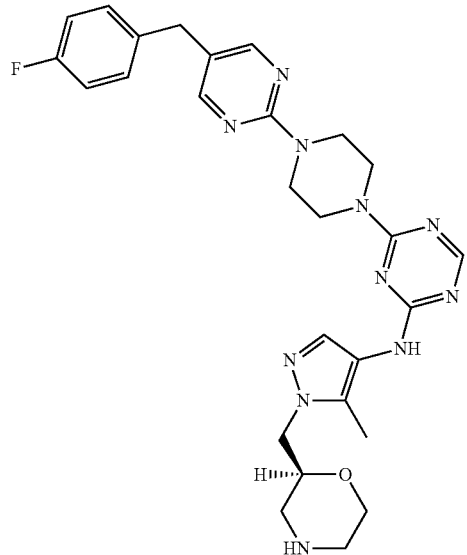 [SMILES: Cc1c(Nc2ncnc(N3CCN(c4ncc(Cc5ccc(F)cc5)cn4)CC3)n2)cnn1C[C@@H]1CNCCO1] |
| 272 | 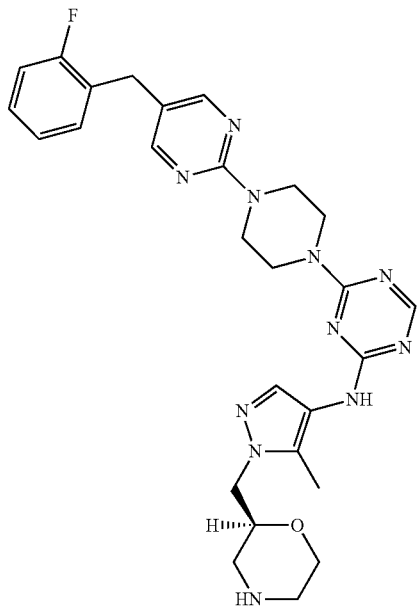 [SMILES: Cc1c(Nc2ncnc(N3CCN(c4ncc(Cc5ccccc5F)cn4)CC3)n2)cnn1C[C@@H]1CNCCO1] |

-continued
| Compound Number | Structure |
|---|---|
| 273 | 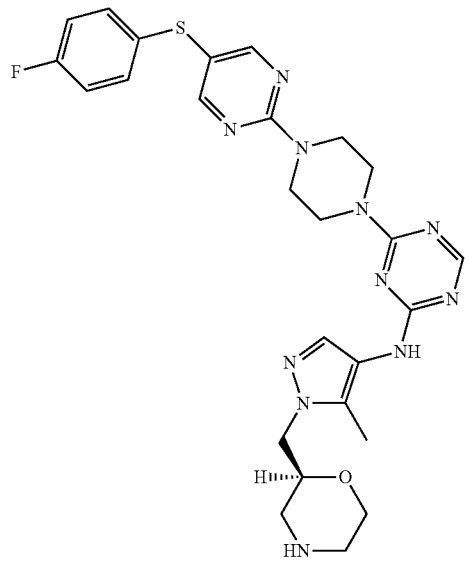 [SMILES: Cc1c(Nc2ncnc(N3CCN(c4ncc(Sc5ccc(F)cc5)cn4)CC3)n2)cnn1C[C@@H]1CNCCO1] |
| 274 | 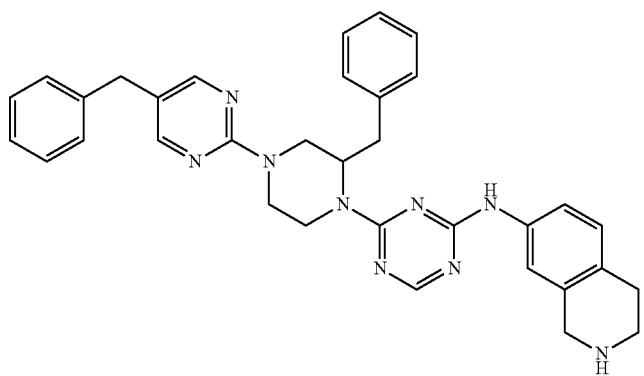 [SMILES: c1ccc(Cc2cnc(N3CCN(c4ncnc(Nc5ccc6c(c5)CNCC6)n4)C(Cc4ccccc4)C3)nc2)cc1] |
| 275 | 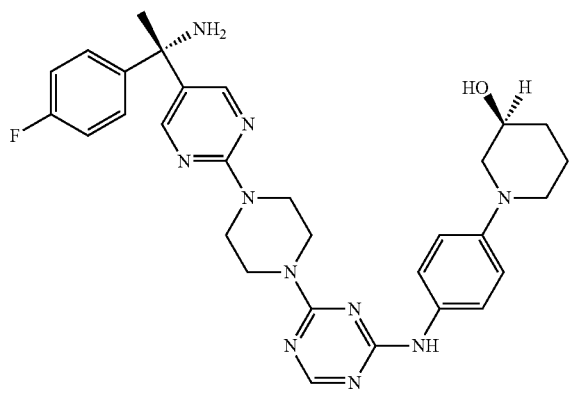 [SMILES: C[C@](N)(c1ccc(F)cc1)c1cnc(N2CCN(c3ncnc(Nc4ccc(N5CCC[C@H](O)C5)cc4)n3)CC2)nc1] |

| Compound Number | Structure |
|---|---|
| 276 | 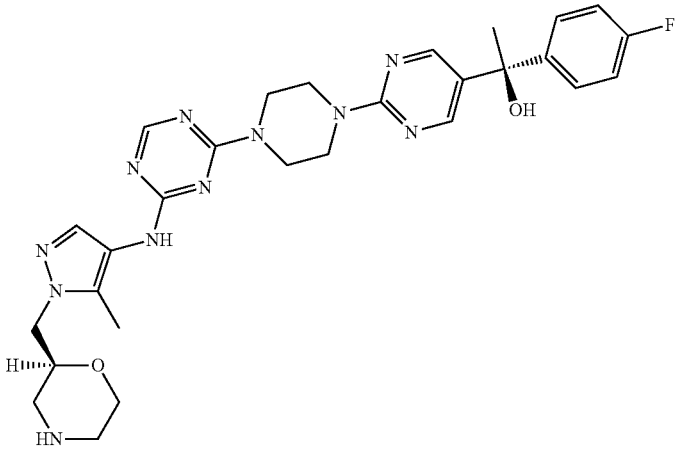 [SMILES: Cc1c(Nc2ncnc(N3CCN(c4ncc([C@@](C)(O)c5ccc(F)cc5)cn4)CC3)n2)cnn1C[C@@H]1CNCCO1] |
| 277 | 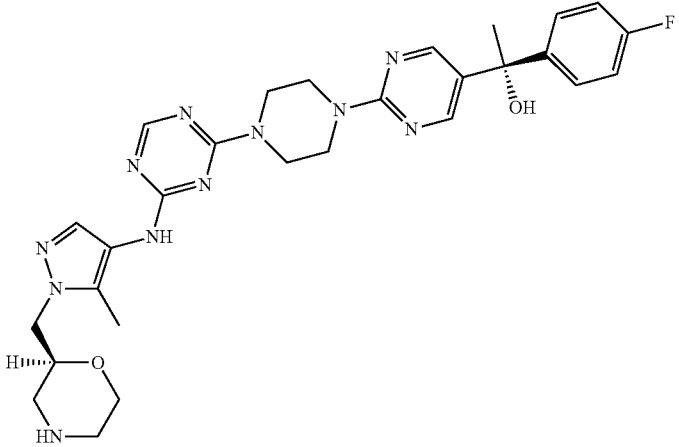 [SMILES: Cc1c(Nc2ncnc(N3CCN(c4ncc([C@](C)(O)c5ccc(F)cc5)cn4)CC3)n2)cnn1C[C@@H]1CNCCO1] |

Synthesis

Compounds of the invention, including salts and N-oxides thereof, can be prepared using known organic synthesis techniques and can be synthesized according to any of numerous possible synthetic routes, such as those in the Schemes below. The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 4th ed., John Wiley & Sons: New Jersey, (2006), which is incorporated herein by reference in its entirety.

Reactions can be monitored according to any suitable method known in the art. For example, product formation can be monitored by spectroscopic means, such as nuclear magnetic resonance (NMR) spectroscopy (e.g., $^1$H or $^{13}$C), infrared (IR) spectroscopy, spectrophotometry (e.g., UV-visible), mass spectrometry (MS), or by chromatographic methods such as high performance liquid chromatography (HPLC) or thin layer chromatography (TLC).

Indications

The compounds described herein can be useful for treating conditions associated with aberrant KIT activity, in humans or non-humans. Activating mutations in KIT are found in multiple indications, including systemic mastocytosis, GIST (gastrointestinal stromal tumors), AML (acute myeloid leukemia), melanoma, seminoma, intercranial germ cell tumors, and mediastinal B-cell lymphoma.

Mastocytosis refers to a group of disorders characterized by excessive mast cell accumulation in one tissue, or in multiple tissues. Mastocytosis is subdivided into two groups of disorders: (1) cutaneous mastocytosis (CM) describes forms that are limited to the skin; and (2) systemic mastocytosis (SM) describes forms in which mast cells infiltrate extracutaneous organs, with or without skin involvement. SM is further subdivided into five forms: indolent (ISM), smoldering (SSM), aggressive (ASM), SM with associated hemotologic non-mast cell lineage disease (SM-AHNMD), and mast cell leukemia (MCL).

Diagnosis of systemic mastocytosis is based in part on histological and cytological studies of bone marrow showing infiltration by mast cells of frequently atypical morphology, which frequently abnormally express non-mast cell markers (CD25 and/or CD2). Diagnosis of SM is confirmed when bone marrow mast cell infiltration occurs in the context of one of the following: (1) abnormal mast cell morphology (spindle-shaped cells); (2) elevated level of serum tryptase above 20 ng/mL; or (3) the presence of the activating KIT D816V mutation.

Activating mutations at the D816 position are found in the vast majority of mastocytosis cases (90-98%), with the most common mutations being D816V and D816H, and D816Y. The D816V mutation is found in the activation loop of the kinase domain, and leads to constitutive activation of KIT kinase.

The compounds described herein may also be useful to treat GIST. Complete surgical resection remains the principal treatment of choice for patients with a primary GIST. Surgery is effective in approximately 50% of patients with GIST; of the remaining patients, tumor recurrence is frequent. Primary treatment with a KIT inhibitor such as imatinib has also been shown to be sufficient for initial treatment. However, resistance to imatinib occurs within months through somatic mutation. These secondary imatinib resistant mutations are most frequently located on Exon 11, 13, 14, 17 or 18. Sunitinib is the standard of care second line treatment for most imatinib resistant tumors and is effective for those containing mutations in exons 11, 13 and 14. However, secondary KIT mutations in exons 17 and 18 are resistant to sunitinib treatment and furthermore, tumors containing tertiary resistance mutations in exon 17 and 18 emerge several months after sunitinib treatment. Regorafenib has shown promising results in a phase 3 clinical trial of imatinib, sunitinib resistant GISTs with activity against several but not all exon 17 and 18 mutations, of which D816 is one. Thus, there is a need for therapeutic agents to treat GIST patients with exon 17 mutations not addressed by regorafenib.

In addition to the use of the compounds described herein as single agents in the refractory GIST setting, the use of combinations of imatinib, sunitinib and/or regorafenib with the compounds disclosed herein may allow for the prevention of emergence of resistance to exon 17 mutations.

There is a subset of GIST patients with a D842V mutation in PDGFRα; this subgroup of GIST patients can be stratified by identifying this mutation. This subset of patients is refractory to all tyrosine kinase inhibitors currently available. The compounds described herein, due to their activity against PDGFRα D842V, can be useful in treating these patients.

The compounds described herein may also be useful in treating AML. AML patients harbor KIT mutations as well, with the majority of these mutations at the D816 position.

In addition, mutations in KIT have been linked to Ewing's sarcoma, DLBCL (diffuse large B cell lymphoma), dysgerminoma, MDS (myelodysplastic syndrome), NKTCL (nasal NK/T-cell lymphoma), CMML (chronic myelomonocytic leukemia), and brain cancers.

The compounds disclosed herein may be used to treat conditions associated with the KIT mutations in Exon 9, Exon 11, Exon 13, Exon 14, Exon 17 and/or Exon 18. They may also be used to treat conditions associated with wild-type KIT. The compounds described herein may be used as single agents to treat the conditions described herein, or they may be used in combination with other therapeutic agents, including, without limitation, imatinib, sunitinib and regorafenib. Other agents include the compounds described in WO 2014/039714 and WO 2014/100620.

Compounds described herein can be active against one or more KIT mutations in Exon 17 (e.g., D816V, D816Y, D816F, D816K, D816H, D816A, D816G, D820A, D820E, D820G, N822K, N822H, Y823D, and A829P), and much less active against wild-type KIT. These compounds can be administered in combination with an agent that is (a) active against other activating mutations of KIT, such as Exon 9 and 11 mutations, but (b) not active against the Exon 17 mutations. Such agents include imatinib, sunitinib, and regorafenib. The combination of the compound and the agent will thus inhibit Exon 17 mutant KIT, as well as inhibiting Exon 9/11 mutant KIT. The compound and agent can be co-administered, or administered in an alternating regimen. That is, the Exon 17 mutant KIT inhibitor can be administered alone for a period of time; then the Exon 9/11 mutant KIT inhibitor can be administered alone for a period of time following. This cycle may then be repeated. It is believed that such a regimen could slow the development of resistance to the Exon 17 mutant KIT inhibitor and/or the Exon 9/11 mutant KIT inhibitor.

In addition, compounds described herein that can be selective for Exon 17 KIT mutations can be administered with agents that are active against Exon 9/11 mutations, in combination with a third agent that covers mutations that are missed with the two-way combo. The combination of the three agents could inhibit a spectrum of KIT mutations, as well as wild-type KIT in some instances. The agents could be administered simultaneously, or in an alternating regimen. They can be administered one at a time, or two agents can be administered together for a period of time; then the third agent can be administered alone for a following period of time. It is believed that such a regimen could slow the development of resistance to the mutant KIT inhibitors.

Pharmaceutical Compositions

While it is possible for a compound disclosed herein to be administered alone, it is preferable to administer the compound as a pharmaceutical formulation, where the compound is combined with one or more pharmaceutically acceptable excipients or carriers. The compounds disclosed herein may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Examples of pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) cyclodextrins such as Captisol®; and (22) other non-toxic compatible substances employed in pharmaceutical formulations.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Solid dosage forms (e.g., capsules, tablets, pills, dragees, powders, granules and the like) can include one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or *acacia*; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents.

Liquid dosage forms can include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

When the compounds disclosed herein are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The formulations can be administered topically, orally, transdermally, rectally, vaginally, parentally, intranasally, intrapulmonary, intraocularly, intravenously, intramuscularly, intraarterially, intrathecally, intracapsularly, intradermally, intraperitoneally, subcutaneously, subcuticularly, or by inhalation.

Dosages

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound disclosed herein employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day. If desired, the effective daily dose of the active compound may be administered as two, three, four, five, six or more sub-doses administered separately at appropriate intervals throughout the day, optionally, in unit dosage forms. In some embodiments, the dose for humans will be 100-1000 mg, or 400-800 mg, administered twice daily; or 400-1000 mg, administered once daily.

EXAMPLES

The following examples are intended to be illustrative, and are not meant in any way to be limiting.

The below Schemes are meant to provide general guidance in connection with preparing the compounds of the invention. One skilled in the art would understand that the preparations shown in the Schemes can be modified or optimized using general knowledge of organic chemistry to prepare various compounds of the invention.

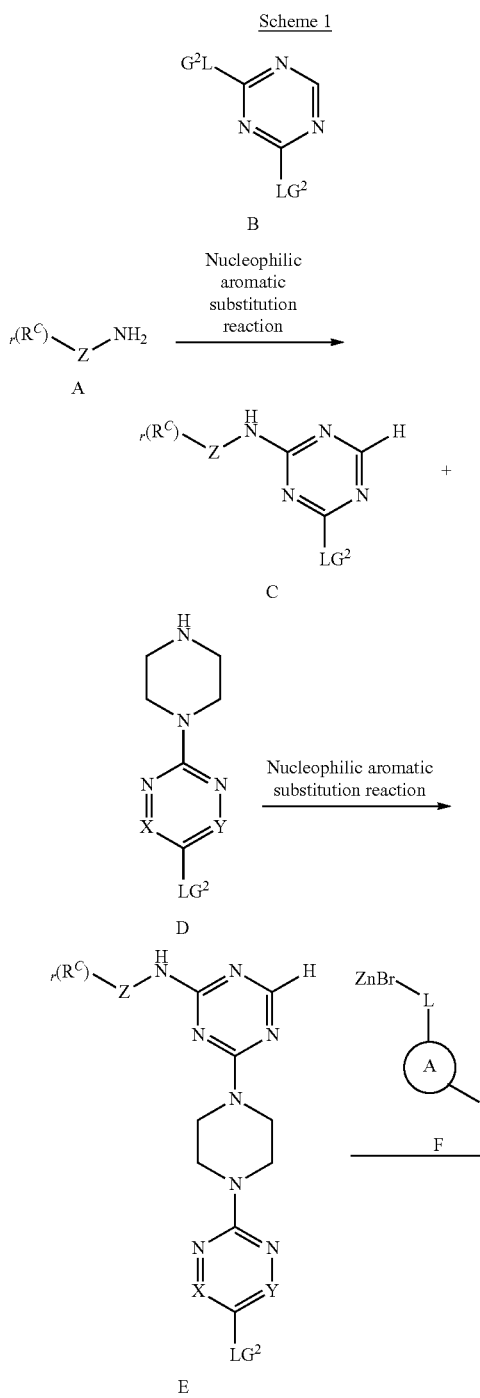

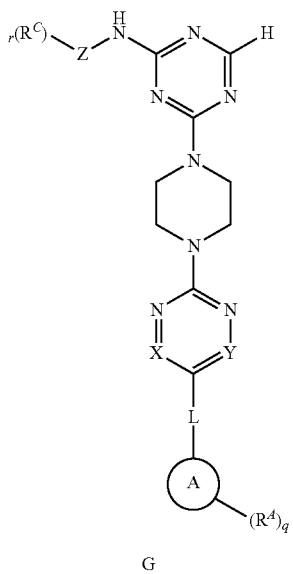

LG² = halogen (e.g., bromo or chloro)

Scheme 1 schematically depicts synthetic protocol 1. Triazine (B) can be reacted with amine (A, Z is aryl or heteroaryl) under nucleophilic aromatic substitution reaction conditions using an amine base such as diisopropylethylamine (DIPEA) or triethylamine (TEA) in a polar solvent such as dioxane to provide the amine-substituted triazine (C). The amine-substituted triazine (C) can be substituted with piperazine (D, X and Y are —CH—) under nucleophilic aromatic substitution reaction conditions using an amine base such as diisopropylethylamine (DIPEA) or triethylamine (TEA) in a polar solvent such as dioxane to provide the piperazine-substituted triazine (E). Piperazine-substituted heteroaryl (E) can be coupled to the organozinc bromide (F) using Negishi coupling conditions to provide the substituted triazine (G). As shown below, Compound 186 was prepared using synthetic protocol 1.

Synthesis of N-(1-((S)-morpholin-2-ylmethyl)-1H-pyrazol-4-yl)-4-(4-(5-((R)-1-phenylethyl)pyrimidin-2-yl)piperazin-1-yl)-1,3,5-triazin-2-amine (Compound 186)

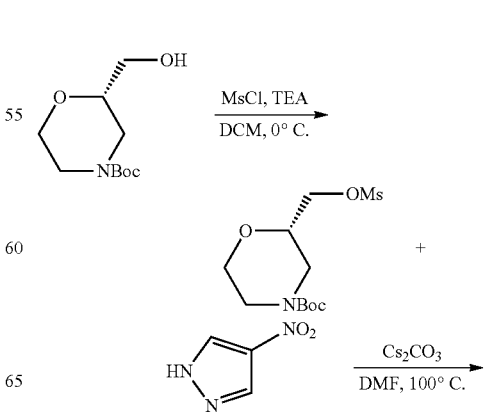

199
-continued
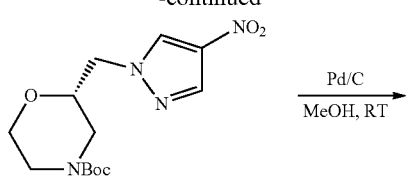
→ Pd/C, MeOH, RT
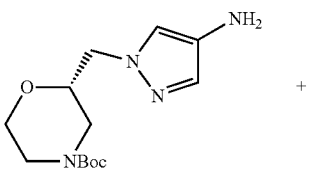
+
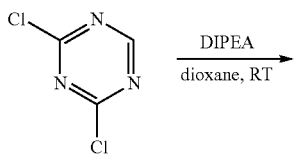
→ DIPEA, dioxane, RT
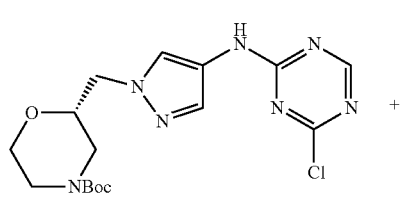
+
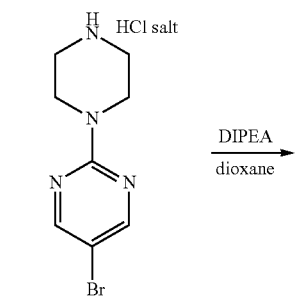
→ DIPEA, dioxane
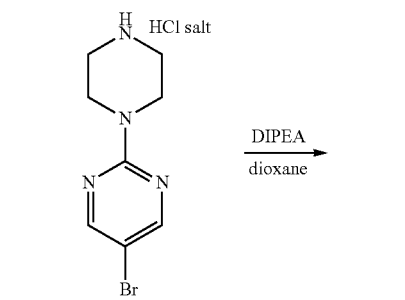
+
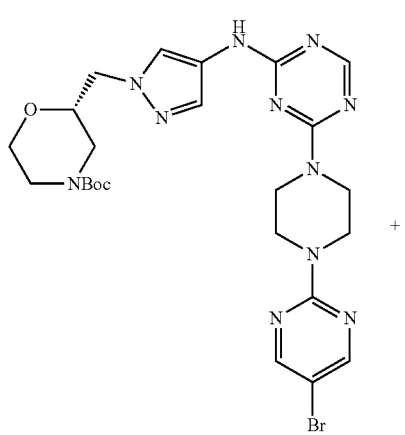
200
-continued
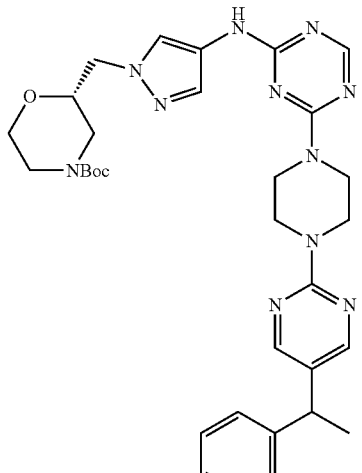
→ Pd(Amphos)Cl₂, THF, 70° C.
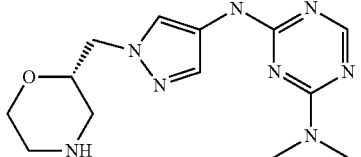
→ TFA / DCM
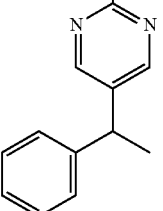
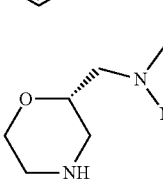
chiral separation →
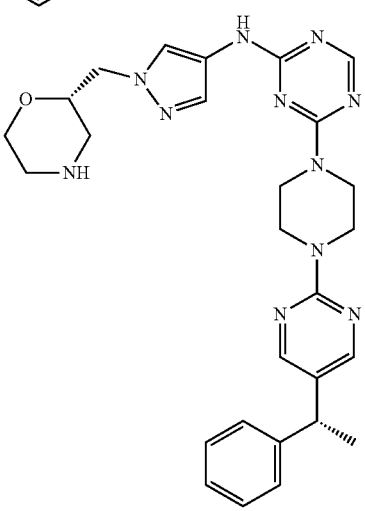

Step 1: Synthesis of (S)-tert-butyl 2-((methylsulfonyloxy)methyl)morpholine-4-carboxylate

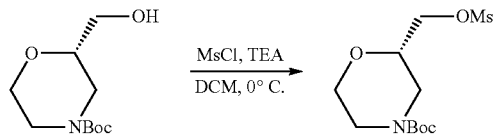 [SMILES: CC(C)(C)OC(=O)N1CCO[C@H](CO)C1 ; CC(C)(C)OC(=O)N1CCO[C@H](COS(C)(=O)=O)C1]

To a solution of (S)-tert-butyl 2-(hydroxymethyl)morpholine-4-carboxylate (3.0 g, 13.8 mmol) and triethylamine (4.2 g, 41.4 mmol) in dichloromethane (80 mL) at 0° C. was dropwise added mesyl chloride (1.9 g, 16.5 mmol). The reaction mixture was stirred at 0° C. for 2 hour, and then diluted with dichloromethane (100 mL). The organic layers were washed with water (100 mL) and brine (100 mL), dried over sodium sulfate, filtered and concentrated to afford (S)-tert-butyl 2-((methylsulfonyloxy)methyl)morpholine-4-carboxylate as a purple oil (4.0 g, 98%), which was directly used in the next step without further purification. MS (ES+) $C_{11}H_{21}NO_6S$ requires: 295, found: 240 $[M+H-56]^+$.

Step 2: Synthesis of (S)-tert-butyl 2-((4-nitro-1H-pyrazol-1-yl)methyl)morpholine-4-carboxylate

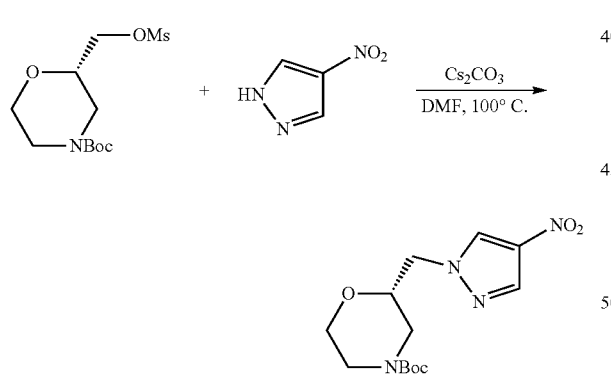

To a solution of (S)-tert-butyl 2-((methylsulfonyloxy)methyl)morpholine-4-carboxylate (2.8 g, 9.5 mmol) and 4-nitro-1H-pyrazole (715 mg, 6.3 mmol) in acetonitrile (100 mL) was added cesium carbonate (6.2 g, 19.0 mmol). The reaction mixture was stirred at 55° C. overnight and then concentrated. The residue was dissolved in ethyl acetate (100 mL), washed with water (50 mL), dried over sodium sulfate, filtered and concentrated. The crude sample was purified by silica gel chromatography, eluting with petroleum ether:ethyl acetate=8:1, to afford (S)-tert-butyl 2-((4-nitro-1H-pyrazol-1-yl)methyl)morpholine-4-carboxylate as a yellow oil (2.12 g, 71%). MS (ES+) $C_{13}H_{20}N_4O_5$ requires: 312, found: 257 $[M+H-56]^+$.

Step 3: Synthesis of (S)-tert-butyl 2-((4-amino-1H-pyrazol-1-yl)methyl)morpholine-4-carboxylate

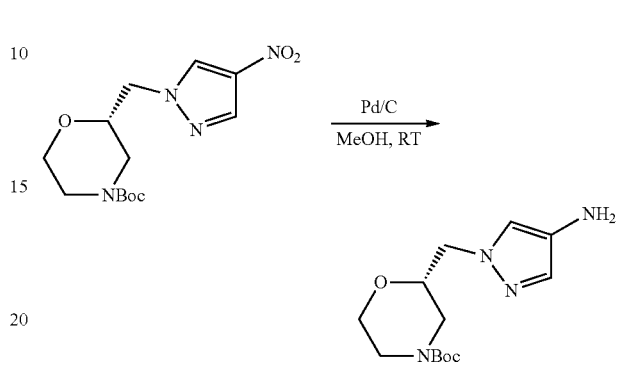

To a solution of (s)-tert-butyl 2-((4-nitro-1H-pyrazol-1-yl)methyl)morpholine-4-carboxylate (3.2 g, 10.2 mmol) in methanol (100 mL) was added Pd/C (600 mg). The mixture was stirred under 1 atm $H_2$ at room temperature overnight, and then filtrated through a pad of celite. The filtrate was concentrated to afford (S)-tert-butyl 2-((4-amino-1H-pyrazol-1-yl)methyl)morpholine-4-carboxylate. MS (ES+) $C_{13}H_{22}N_4O_3$ requires: 282, found: 283 $[M+H]^+$.

Step 4: Synthesis of (S)-tert-butyl 2-((4-(4-chloro-1,3,5-triazin-2-ylamino)-1H-pyrazol-1-yl)methyl)morpholine-4-carboxylate

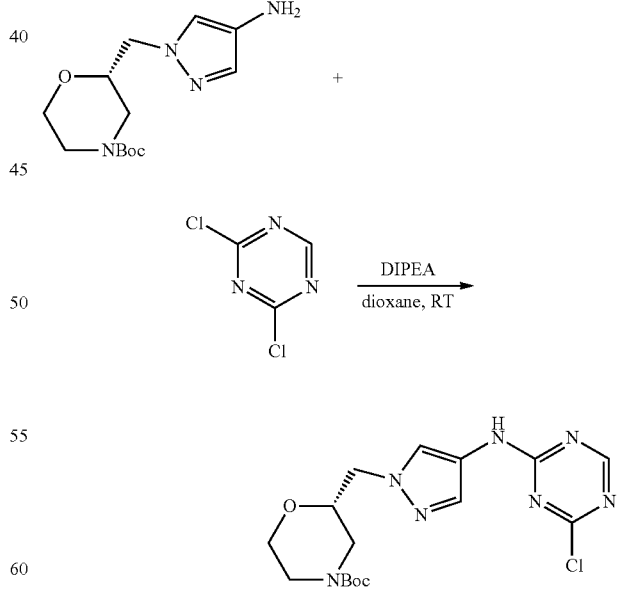

To a solution of 2,4-dichloro-1,3,5-triazine (1.8 g, 6.4 mmol) in dioxane (20 mL) was added diisopropylethylamine (4 mL), followed by the addition of (S)-tert-butyl 2-((4-amino-1H-pyrazol-1-yl)methyl)morpholine-4-carboxylate (1.2 g, 7.2 mmol). The reaction mixture was stirred at 110° C. for 1 hour, and LCMS (liquid chromatography-mass spectrometry) showed the reaction was completed. The solvents were removed under reduced pressure, and the residue was purified by silica gel chromatography, eluting with petroleum ether:ethyl acetate=5:1, to afford (S)-tert-butyl 2-((4-(4-chloro-1,3,5-triazin-2-ylamino)-1H-pyrazol-1-yl)methyl) morpholine-4-carboxylate as a yellow solid (1.8 g, 70%). MS (ES+) $C_{16}H_{22}ClN_7O_3$ requires: 395, 396, found: 396, 397 $[M+H]^+$.

Step 5: Synthesis of 5-bromo-2-(piperazin-1-yl)pyrimidine HCl Salt

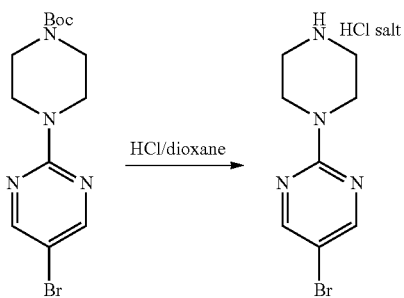 [SMILES: CC(C)(C)OC(=O)N1CCN(c2ncc(Br)cn2)CC1 ; Brc1cnc(N2CCNCC2)nc1]

A solution of tert-butyl 4-(5-bromopyrimidin-2-yl)piperazine-1-carboxylate (5 g, 14.6 mmol) in 4 M HCl-dioxane (50 mL) was stirred at room temperature for 1 hour. The reaction mixture was concentrated to give 5-bromo-2-(piperazin-1-yl) pyrimidine HCl salt (crude, 3.3 g, 94%) as a white solid. MS (ES+) $C_8H_{11}BrN_4$ requires: 242, 244, found: 243, 245 $[M+H]^+$.

Step 6: Synthesis of (S)-tert-butyl 2-((4-(4-(4-(5-bromopyrimidin-2-yl)piperazin-1-yl)-1,3,5-triazin-2-ylamino)-1H-pyrazol-1-yl)methyl)morpholine-4-carboxylate

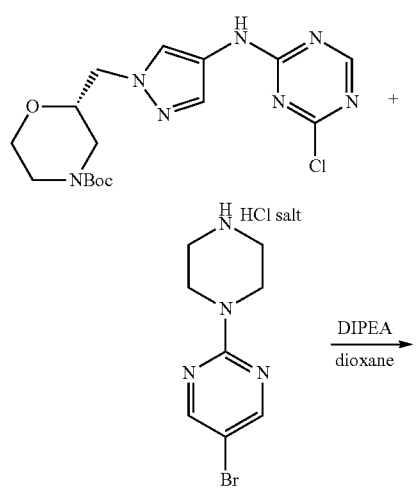

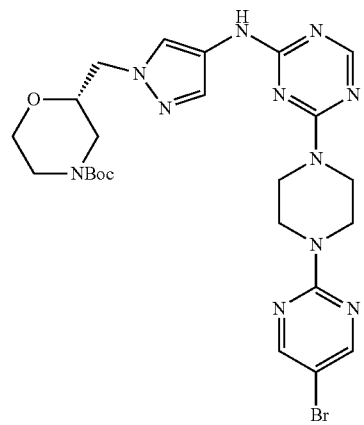

To a solution of (S)-tert-butyl 2-((4-(4-chloro-1,3,5-triazin-2-ylamino)-1H-pyrazol-1-yl)methyl)morpholine-4-carboxylate (1.8 g, 4.5 mmol) in dioxane (50 mL) was added diisopropylethylamine (4 mL) and 5-bromo-2-(piperazin-1-yl)pyrimidine (1.3 g, 5.5 mmol). The reaction mixture was stirred at room temperature for 2 hours. The solvents were removed, and the residue was washed with methanol (10 mL) to afford (S)-tert-butyl 2-((4-(4-(4-(5-bromopyrimidin-2-yl) piperazin-1-yl)-1,3,5-triazin-2-ylamino)-1H-pyrazol-1-yl) methyl)-morpholine-4-carboxylate as a white solid (2.4 g, 89%), which was directly used in the next step without further purification. MS (ES+) $C_{24}H_{32}BrN_{11}O_3$ requires: 601, 603, found: 602, 604 $[M+H]^+$.

Step 7: Synthesis of (2S)-tert-butyl 2-((4-(4-(4-(5-(1-phenylethyl)pyrimidin-2-yl)piperazin-1-yl)-1,3,5-triazin-2-ylamino)-1H-pyrazol-1-yl)methyl)morpholine-4-carboxylate

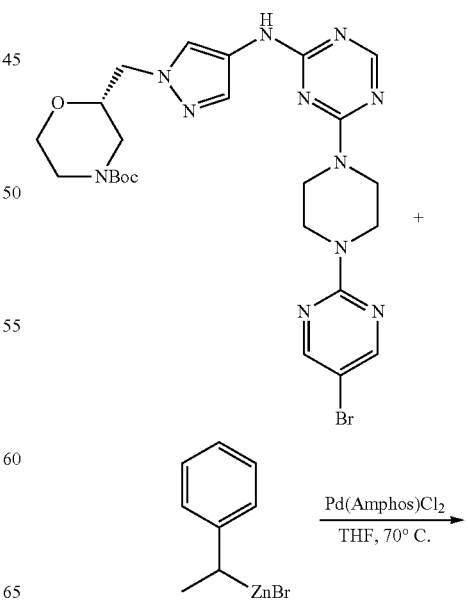

205
-continued

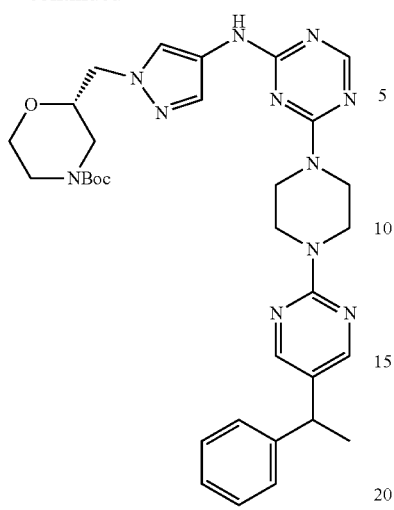

206
-continued

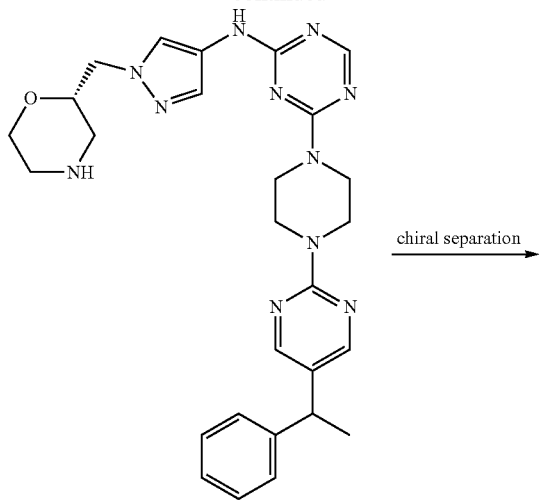

→ chiral separation

To a solution of (S)-tert-butyl 2-((4-(4-(4-(5-bromopyrimidin-2-yl)piperazin-1-yl)-1,3,5-triazin-2-ylamino)-1H-pyrazol-1-yl)methyl)morpholine-4-carboxylate (100 mg, 0.17 mmol) and Pd(Amphos)Cl$_2$ (11.7 mg, 0.17 mmol) in THF (2 mL, dried) was dropwise added a solution of (1-phenylethyl)zinc(II) bromide in THF (7.0 mL, 0.5 M, 3.4 mmol). The reaction mixture was stirred at 70° C. for 1 hour under N$_2$, then cooled to room temperature and diluted with ethyl acetate (50 mL). After filtration, the filtrate was concentrated to afford (2S)-tert-butyl 2-((4-(4-(4-(5-(1-phenylethyl)pyrimidin-2-yl)piperazin-1-yl)-1,3,5-triazin-2-ylamino)-1H-pyrazol-1-yl)methyl)morpholine-4-carboxylate as a white solid (130 mg, crude), which was directly used in the next step without further purification. MS (ES+) C$_{32}$H$_{41}$N$_{11}$O$_3$ requires: 627, found: 628 [M+H]$^+$.

Step 8: Synthesis of N-(1-((S)-morpholin-2-ylmethyl)-1H-pyrazol-4-yl)-4-(4-(5-((R)-1-phenylethyl)pyrimidin-2-yl)piperazin-1-yl)-1,3,5-triazin-2-amine

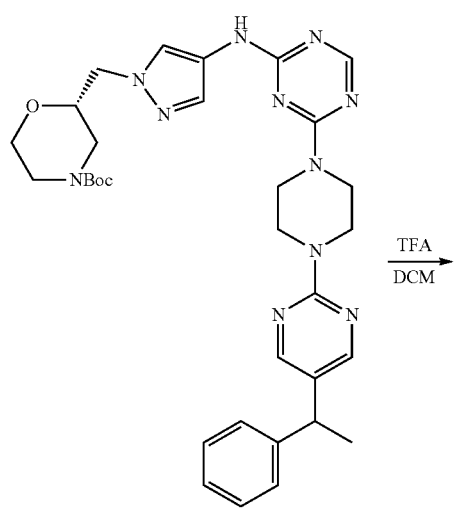

→ TFA / DCM

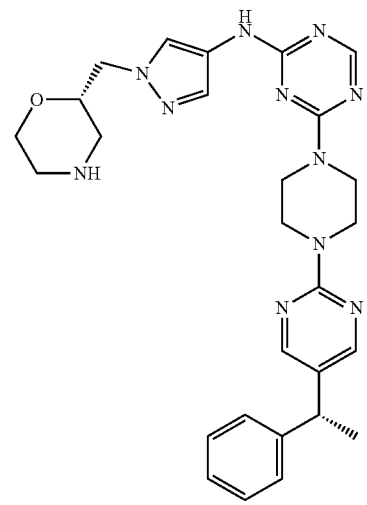

To a solution of (2S)-tert-butyl 2-((4-(4-(4-(5-(1-phenylethyl)pyrimidin-2-yl)piperazin-1-yl)-1,3,5-triazin-2-ylamino)-1H-pyrazol-1-yl)methyl)morpholine-4-carboxylate (130 mg, crude) in dichloromethane (6 mL) was dropwise added trifluoroacetic acid (2 mL). The reaction mixture was stirred at room temperature for 0.5 hour and then concentrated. The residue was purified by Prep-HPLC to provide N-(1-((S)-morpholin-2-ylmethyl)-1H-pyrazol-4-yl)-4-(4-(5-(1-phenylethyl)pyrimidin-2-yl)piperazin-1-yl)-1,3,5-triazin-2-amine as a white solid, which was then separated by Chiral-HPLC to afford N-(1-((S)-morpholin-2-ylmethyl)-1H-pyrazol-4-yl)-4-(4-(5-((R)-1-phenylethyl)pyrimidin-2-yl)piperazin-1-yl)-1,3,5-triazin-2-amine as a white solid (15.4 mg, 17%).

Scheme 2

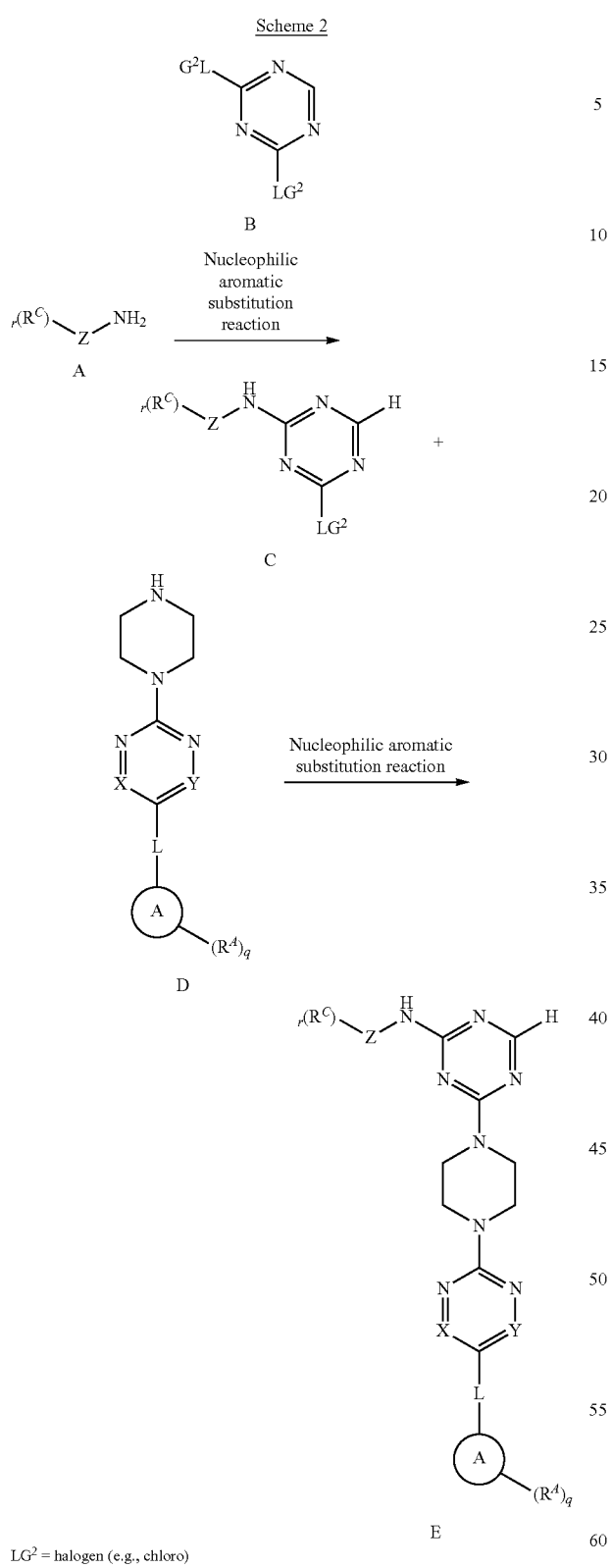

LG² = halogen (e.g., chloro)

Scheme 2 schematically depicts synthetic protocol 2. Triazine (B) can be reacted with amine (A, Z is aryl or heteroaryl) under nucleophilic aromatic substitution reaction conditions using an amine base such as diisopropylethylamine (DIPEA) or triethylamine (TEA) in a polar solvent such as dioxane to provide the amine-substituted triazine (C). The amine-substituted triazine (C) can be substituted with piperazine (D, X and Y are —CH—, A is aryl, and L is $C_{1-6}$ alkyl, cycloalkyl, $C_{1-6}$ haloalkyl, or sulfur) under nucleophilic aromatic substitution reaction conditions using an amine base such as diisopropylethylamine (DIPEA) or triethylamine (TEA) in a polar solvent such as dioxane to provide the piperazine-substituted triazine (E). As shown below, Compound 165 was prepared using synthetic protocol 2.

Synthesis of (R)-1-(4-((4-(4-(5-benzylpyrimidin-2-yl)piperazin-1-yl)-1,3,5-triazin-2-yl)amino)benzyl)piperidin-3-ol (Compound 165)

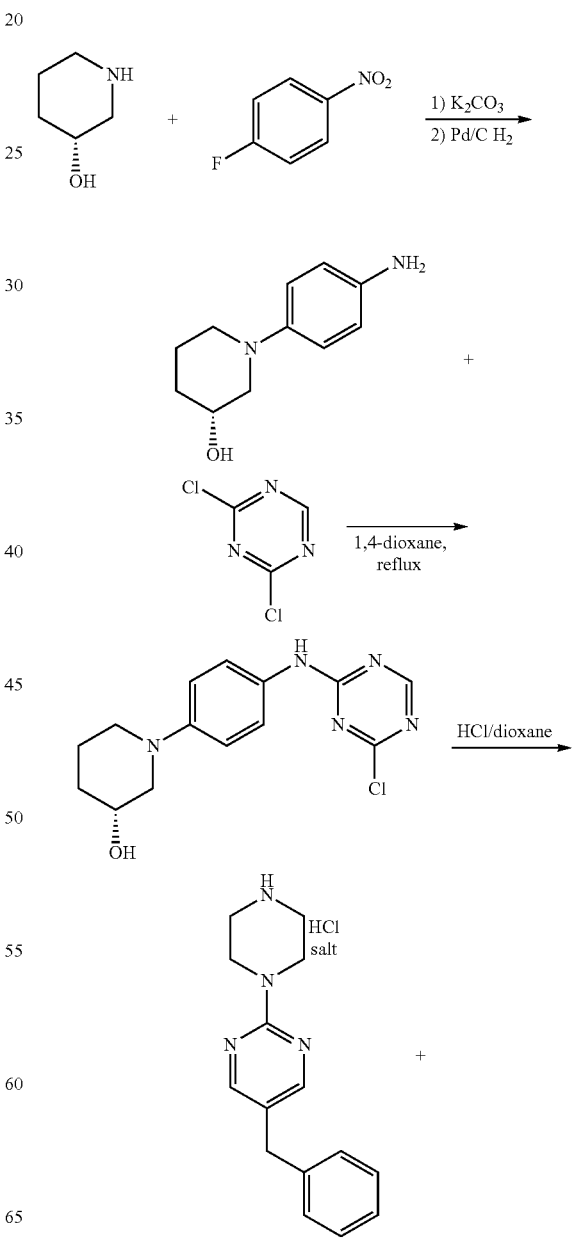

-continued

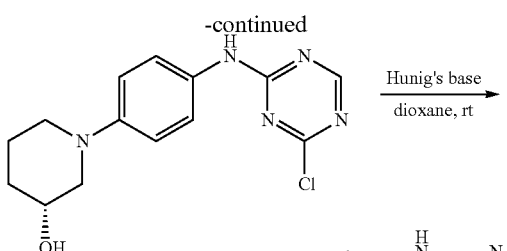

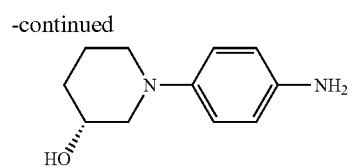

To a solution of (R)-1-(4-nitrophenyl)piperidin-3-ol was added Pd/C. The mixture was stirred under 1 atm H$_2$ at room temperature overnight, and then filtrated through a pad of Celite. The filtrate was concentrated to afford (R)-1-(4-aminophenyl)piperidin-3-ol.

Step 3: Synthesis of (R)-1-(4-((4-chloro-1,3,5-triazin-2-yl)amino)phenyl)piperidin-3-ol

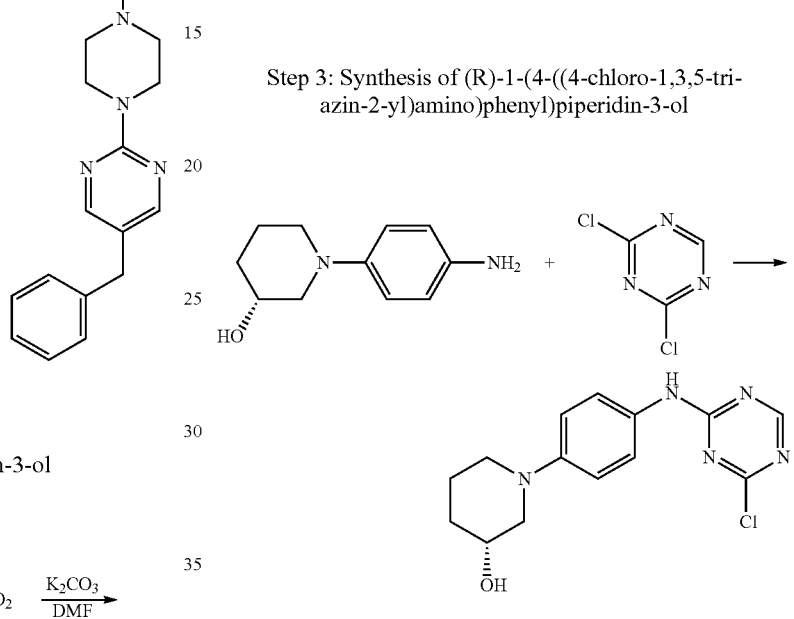

Step 1: Synthesis of (R)-1-(4-nitrophenyl)piperidin-3-ol

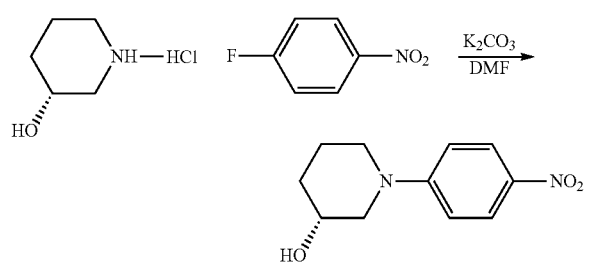

4-Fluoronitrobenze (1.5 g, 10.6 mmole), (R)-piperidin-3-ol HCl (1.76 g, 12.8 mmole) and potassium carbonate (4.41 g, 31.9 mmole) were combined in 10 mL DMF and heated to 60° C. overnight. The reaction mixture was cooled to room temperature and poured into ~75 mL water; the suspension was stirred at room temperature for 30 minutes. The mixture was then filtered, washed with water and suction dried to give 2.25 g (95%) of (R)-1-(4-nitrophenyl)piperidin-3-ol as a yellow solid.

To a solution of 2,4-dichloro-1,3,5-triazine in dioxane was added diisopropylethylamine, followed by the addition of (R)-1-(4-aminophenyl)piperidin-3-ol. The reaction mixture was stirred at 110° C. for 1 hour, and LCMS (liquid chromatography-mass spectrometry) showed the reaction was completed. The solvents were removed under reduced pressure, and the residue was purified by silica gel chromatography, eluting with petroleum ether:ethyl acetate=5:1, to afford (R)-1-(4-((4-chloro-1,3,5-triazin-2-yl)amino)phenyl)piperidin-3-ol.

Step 4: Synthesis of (R)-1-(4-((4-(4-(5-benzylpyrimidin-2-yl)piperazin-1-yl)-1,3,5-triazin-2-yl)amino)benzyl)piperidin-3-ol

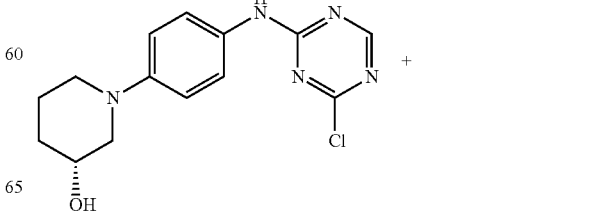

Step 2: Synthesis of (R)-1-(4-aminophenyl)piperidin-3-ol

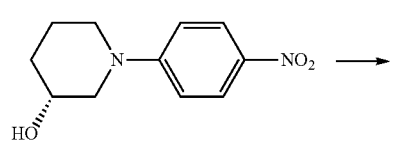

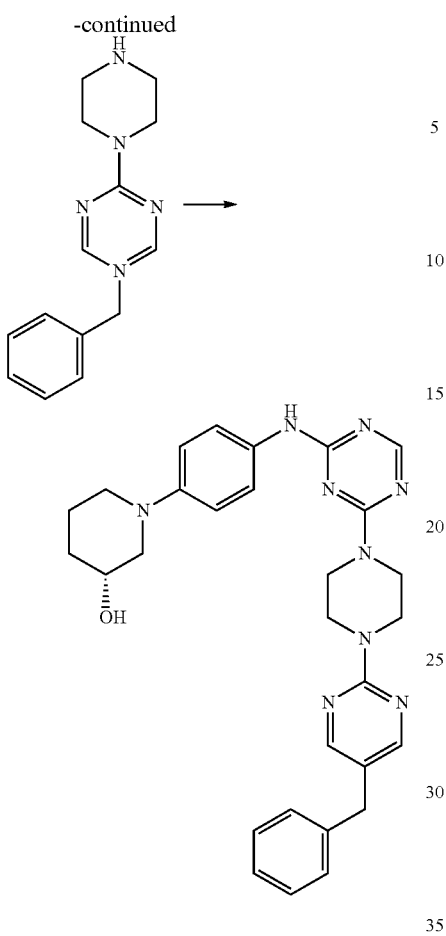

To a solution of (R)-1-(4-((4-chloro-1,3,5-triazin-2-yl)amino)phenyl)piperidin-3-ol in dioxane was added diisopropylethylamine 5-benzyl-2-(piperazin-1-yl)pyrimidine. The reaction mixture was stirred at room temperature for 2 hours. The solvents were removed, and the residue was washed with methanol (10 mL) to afford (R)-1-(4-((4-(4-(5-benzylpyrimidin-2-yl)piperazin-1-yl)-1,3,5-triazin-2-yl)amino)benzyl)piperidin-3-ol (Compound 165).

Scheme 3

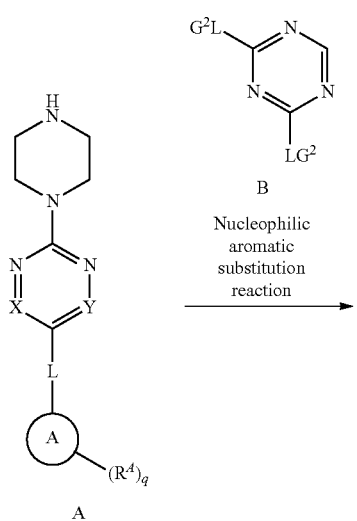

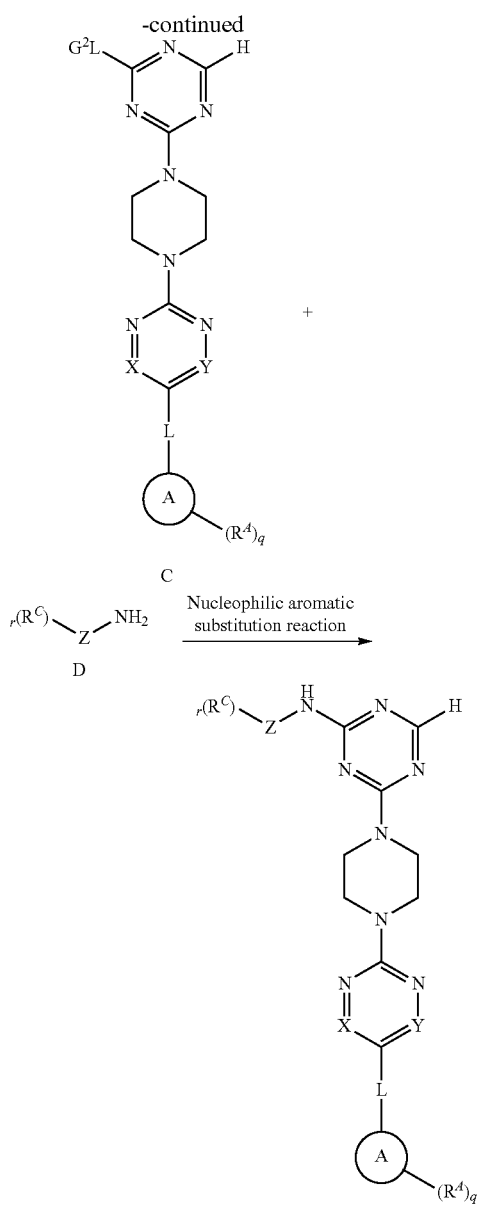

LG² = halogen (e.g., chloro)

Scheme 3 schematically depicts synthetic protocol 3. Triazine (B) can be reacted with piperizine (A, X and Y are —CH—, A is aryl, and L is $C_{1-6}$ alkyl, cycloalkyl, $C_{1-6}$ haloalkyl, or sulfur) under nucleophilic aromatic substitution reaction conditions using an amine base such as diisopropylethylamine (DIPEA) or triethylamine (TEA) in a polar solvent such as dioxane to provide the piperizine-substituted triazine (C). The piperizine-substituted triazine (C) can be substituted with amine (D, Z is aryl or heteroaryl) under nucleophilic aromatic substitution reaction conditions using an amine base such as diisopropylethylamine (DIPEA) or triethylamine (TEA) in a polar solvent such as dioxane to provide the piperazine-substituted triazine (E). As shown below, Compound 64 was prepared using synthetic protocol 3.

Synthesis of 1-(4-(4-(4-(5-benzylpyrimidin-2-yl)piperazin-1-yl)-1,3,5-triazin-2-ylamino)-1H-pyrazol-1-yl)ethane-1,2-diol
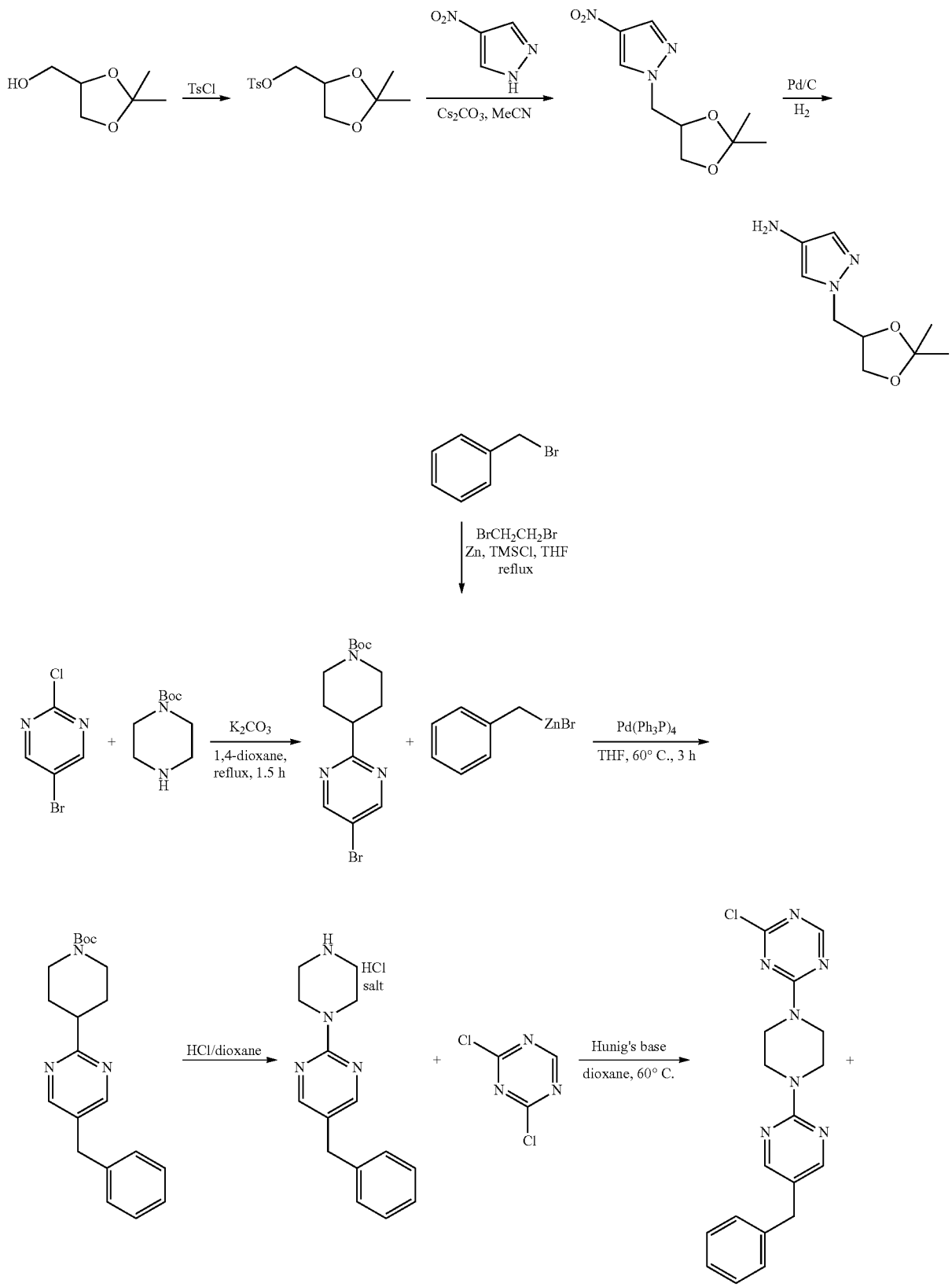

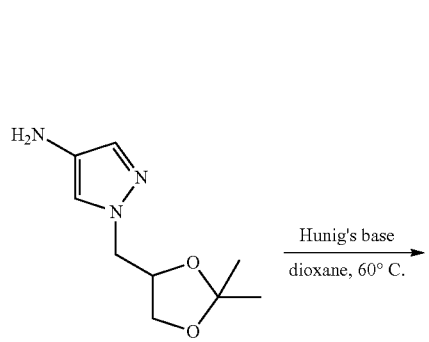
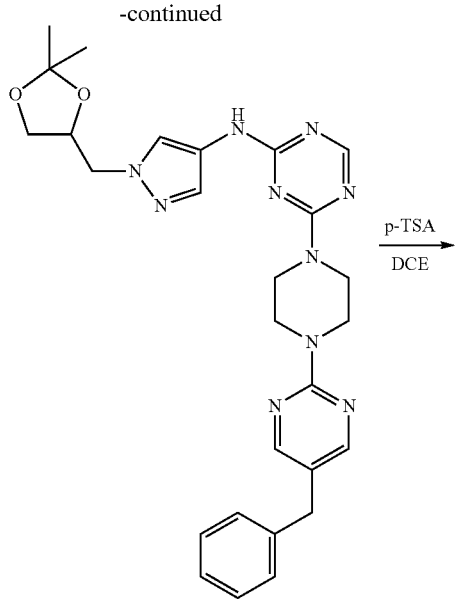
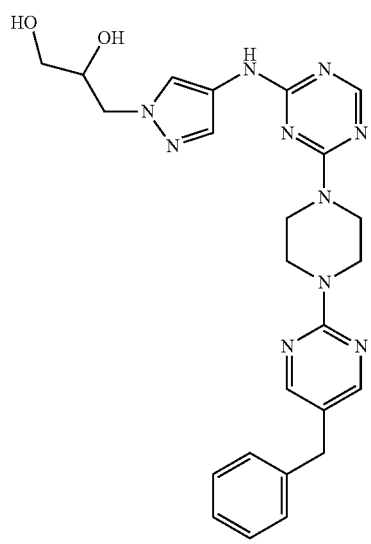

Step 1: Synthesis of (2,2-dimethyl-1,3-dioxolan-4-yl)methyl 4-methylbenzenesulfonate

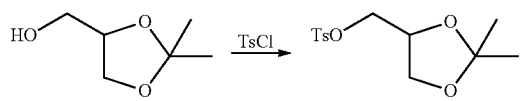

To a solution of (2,2-dimethyl-1,3-dioxolan-4-yl)methanol (5.28 g, 40.0 mmol), triethyl amine (12.12 g, 120.0 mmol) and 4-dimethylaminopyridine (500 mg, 4.0 mmol) in dichloromethane (200 mL) was added tosyl chloride (15.2 g, 80.0 mmol). The reaction mixture was stirred at RT overnight, then quenched with water (200 mL) and extracted with ethyl acetate. The organic layers were separated, combined, washed with water (200 mL) and brine (200 mL), dried over sodium sulfate, filtered, and concentrated. The residue was purified by silica gel chromatography, eluting with ethyl acetate/petroleum ether=1/8, to afford (2,2-dimethyl-1,3-dioxolan-4-yl)methyl 4-methylbenzenesulfonate (6.1 g, yield 53%), MS (ES+) $C_{13}H_{18}O_5S$ requires: 286, found: 287 $[M+H]^+$.

Step 2: Synthesis of 1((2,2-dimethyl-1,3-dioxolan-4-yl)methyl)-4-nitro-1H-pyrazole

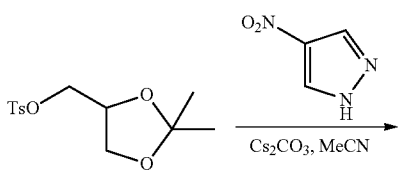

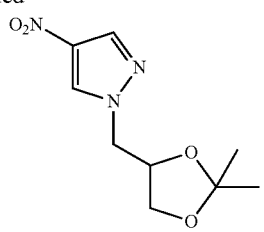

A solution of (2,2-dimethyl-1,3-dioxolan-4-yl)methyl 4-methylbenzenesulfonate (1.57 g, 5.5 mmol), 4-nitro-1H-pyrazole (0.57 g, 5.0 mmol) and cesium carbonate (4.89 g, 15.0 mmol) in acetonitrile (30 mL) was stirred at 70° C. under N₂ overnight. The reaction mixture was filtered, and the resulting filtrate was concentrated. The residue was diluted with ethyl acetate (50 mL), washed with water (50 mL×2) and brine (50 mL), dried over sodium sulfate, filtered, and concentrated to afford 1-((2,2-dimethyl-1,3-dioxolan-4-yl)methyl)-4-nitro-1H-pyrazole (1.01 g, crude), which was directly used in the next step without further purification. MS (ES+) C₉H₁₃N₃O₄ requires: 227, found: 228 [M+H]⁺.

Step 3: Synthesis of 1((2,2-dimethyl-1,3-dioxolan-4-yl)methyl)-1H-pyrazol-4-amine

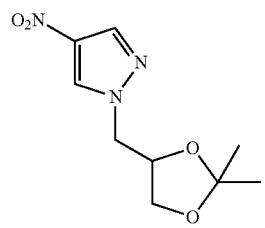

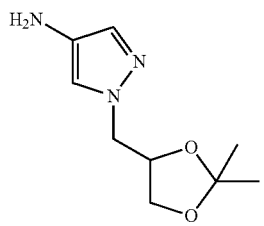

A mixture of 1-((2,2-dimethyl-1,3-dioxolan-4-yl)methyl)-4-nitro-1H-pyrazole (2.0 g, 9.5 mmol) and Pd/C (400 mg) in methanol (40 mL) was stirred at RT under H₂ overnight. LCMS showed the reaction was completed. The reaction mixture was filtered through a pad of celite, and the filtrate was concentrated to give 1-((2,2-dimethyl-1,3-dioxolan-4-yl)methyl)-1H-pyrazol-4-amine (1.7 g, crude) as a purple oil, which was directly used in the next step without further purification. MS (ES+) C₉H₁₅N₃O₂ requires: 197, found: 198 [M+H]⁺.

Step 4: Synthesis of tert-butyl 4-(5-bromopyrimidin-2-yl) piperazine-1-carboxylate

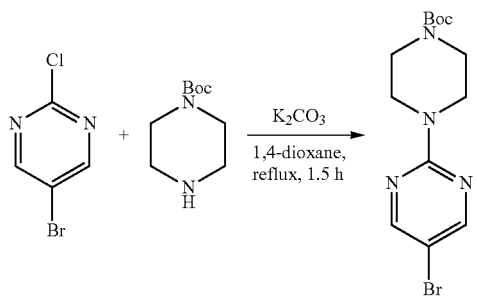

To a solution of 5-bromo-2-chloropyrimidine (50.0 g, 258 mmol) and 1-tert-butoxycarbonylpiperazine (72.2 g, 387 mmol) in 1,4-dioxane (500 mL) was added potassium carbonate (67.8 g, 491 mmol), and the mixture was stirred under reflux for 1.5 h. The mixture was diluted with water (500 mL) and extracted with diethyl ether (1000 mL*2). The combined organic layers were dried over sodium sulfate, filtered and concentrated. The residue was purified with silica gel chromatography (elute: hexane:ethyl acetate=8:1 to 4:1) to give tert-butyl 4-(5-bromopyrimidin-2-yl) piperazine-1-carboxylate (70.5 g, 80%) as a white solid. MS (ES+) C₁₃H₁₉BrN₄O₂ requires: 342, found: 243 [M+H-100]⁺.

Step 5: Synthesis of benzylzinc(II) bromide

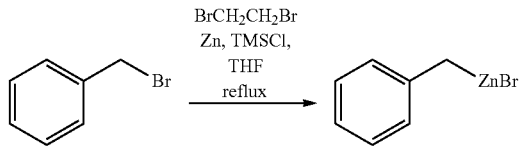

To a suspension mixture of zinc powder (active, 65 g, 1.0 mol) in dry THF (200 mL) was dropwise added 1,2-dibromoethane (3.5 mL, 40 mmol) at 65° C. under nitrogen atmosphere, followed by the addition of chlorotrimethylsilane (87 mg, 80 mmol). The mixture was then stirred at 60° C. for another 1 h. Subsequently, (bromomethyl)benzene (60 mL, 500 mmol) was dropwise added, and the suspension was stirred at 60° C. for another 1 h. The reaction mixture was directly used in the next step.

Step 6: Synthesis of tert-butyl 4-(5-benzylpyrimidin-2-yl)piperazine-1-carboxylate

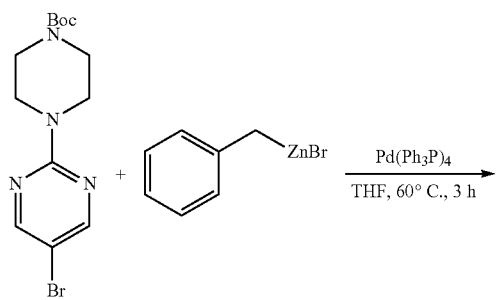

-continued

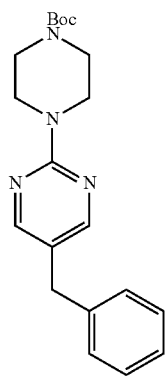

To a solution of tert-butyl 4-(5-bromopyrimidin-2-yl)piperazine-1-carboxylate (12.0 g, 35.0 mmol) and tetrakis(triphenylphosphine)palladium (2.0 g, 1.7 mmol) in THF (200 mL, dry) was added dropwise a solution of benzylzinc(II) bromide in THF (140 mL, 0.5 M, 70 mmol). The reaction mixture was stirred at 70° C. for 4 h under $N_2$, cooled to RT, then diluted with ethyl acetate (300 mL), filtered and concentrated. The residue was purified by silica gel chromatography, eluting with ethyl acetate/petroleum ether=1/20~1/10, to give -butyl 4-(5-benzylpyrimidin-2-yl)piperazine-1-carboxylate (7.5 g, yield 60%) as a white solid, MS (ES+) $C_{20}H_{26}N_4O_2$ requires: 354, found: 355 $[M+H]^+$.

Step 7: Synthesis of 5-benzyl-2-(piperazin-1-yl)pyrimidine hydrogen chloride salt

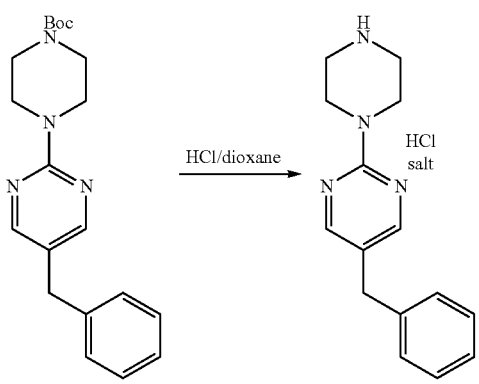 [SMILES: CC(C)(C)OC(=O)N1CCN(c2ncc(Cc3ccccc3)cn2)CC1 ; c1ccc(Cc2cnc(N3CCNCC3)nc2)cc1]

To a solution of tert-butyl 4-(5-benzylpyrimidin-2-yl)piperazine-1-carboxylate (8.0 g, 23.0 mmol) in 1,4-dioxane (30 mL) was dropwise added a solution of 4 M HCl-dioxane (20 mL, 80 mmol). The reaction mixture was stirred at RT overnight, and then concentrated to give 5-benzyl-2-(piperazin-1-yl)pyrimidine HCl salt (10.2 g, crude) as a yellow solid, MS (ES+) $C_{15}H_{18}N_4$ requires: 254, found: 255 $[M+H-100]^+$.

Step 8: Synthesis of 2-(4-(5-benzylpyrimidin-2-yl) piperazin-1-yl)-4-chloro-1,3,5-triazine

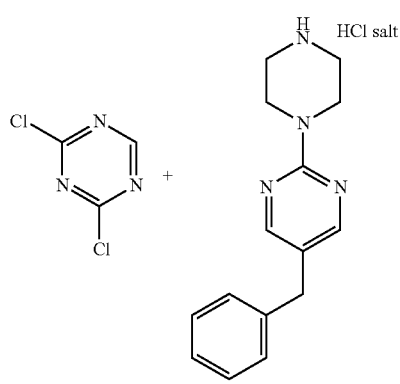

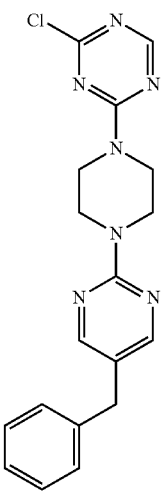

A solution of 2,4-dichloro-1,3,5-triazine (315 mg, 2.1 mmol), 5-benzyl-2-(piperazin-1-yl)pyrimidine (510 mg, 2.0 mmol) and Hunig's base (540 mg, 4.2 mmol) in 1,4-dioxane (6 mL) was stirred at 60° C. for 1 h. LCMS showed the reaction was completed. The reaction mixture was cooled to RT, diluted by water (60 mL), and extracted with ethyl acetate (40 mL×3). The organic layers were combined, washed with water and brine, dried over sodium sulfate, filtered and concentrated to give 1-(2,2-dimethyl-1,3-dioxolan-4-yl)-1H-pyrazol-4-amine (280 mg, crude) as a yellow solid, which was directly used in the next step without further purification. MS (ES+) $C_{18}H_{18}ClN_7$ requires: 367, found: 368 $[M+H]^+$.

Step 9: Synthesis of 4-(4-(5-benzylpyrimidin-2-yl)piperazin-1-yl)-N-(1-((2,2-dimethyl-1,3-dioxolan-4-yl)methyl)-1H-pyrazol-4-yl)-1,3,5-triazin-2-amine

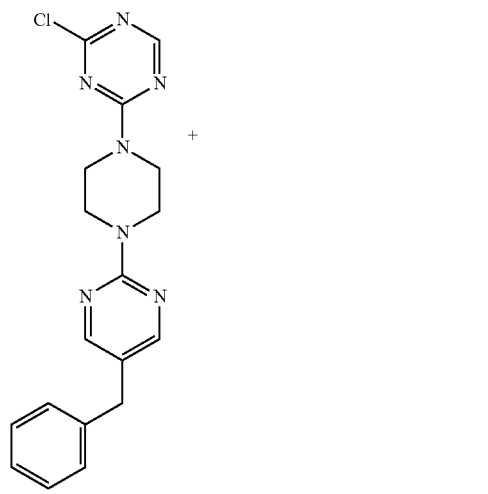

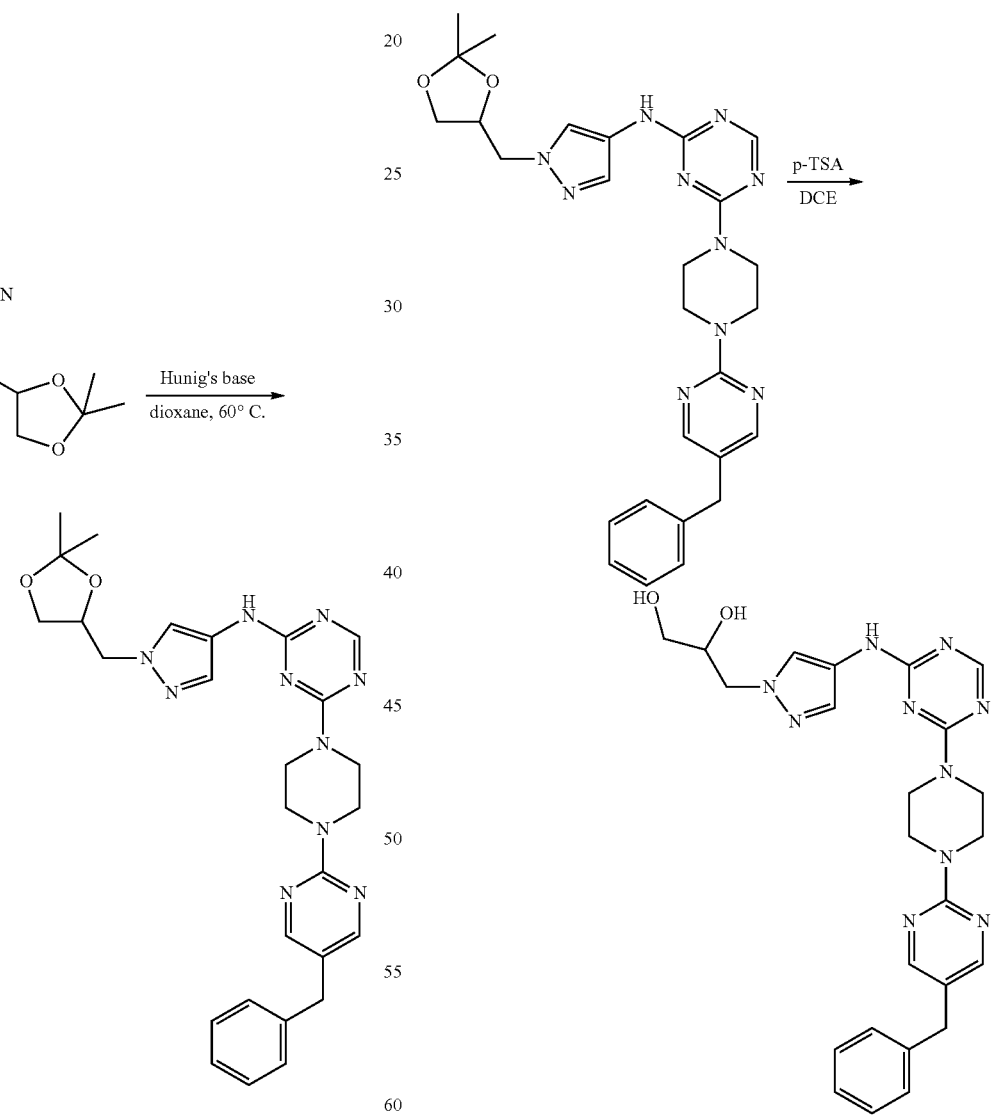

A solution of 2-(4-(5-benzylpyrimidin-2-yl)piperazin-1-yl)-4-chloro-1,3,5-triazine (110 mg, 0.3 mmol), 1((2,2-dimethyl-1,3-dioxolan-4-yl)methyl)-1H-pyrazol-4-amine (90 mg, 0.45 mmol) and Hunig's base (80 mg, 0.6 mmol) in 1,4-dioxane (4 mL) was stirred at 60° C. for 5 h. LCMS showed the reaction was completed. The reaction mixture was cooled to RT and diluted with ethyl acetate (40 mL). The organic phase was washed with water (40 mL) and brine (20 mL), dried over sodium sulfate, filtered and concentrated to give 4-(4-(5-benzylpyrimidin-2-yl)piperazin-1-yl)-N-(1-((2,2-dimethyl-1,3-dioxolan-4-yl)methyl)-1H-pyrazol-4-yl)-1,3,5-triazin-2-amine (200 mg, crude) as a yellow solid, which was directly used in the next step without further purification. MS (ES+) $C_{26}H_{30}N_{10}O_2$ requires: 528, found: 529 [M+H]$^+$.

Step 10: Synthesis of 3-(4-(4-(4-(5-benzylpyrimidin-2-yl)piperazin-1-yl)-1,3,5-triazin-2-ylamino)-1H-pyrazol-1-yl)propane-1,2-diol A solution of 4-(4-(5-benzylpyrimidin-2-yl)piperazin-1-yl)-N-(1-((2,2-dimethyl-1,3-dioxolan-4-yl)methyl)-1H-pyrazol-4-yl)-1,3,5-triazin-2-amine (200 mg, 0.3 mmol), and p-TSA (40 mg, 0.2 mmol) in dichloroethane (2.5 mL) was-stirred at 80° C. under $N_2$ overnight. LCMS showed the reaction was completed. The reaction mixture was cooled to RT and diluted with ethyl acetate (40 mL). The organic phase was washed with water (30 mL) and brine (30 mL), dried over sodium sulfate, filtered and concentrated. The residue was purified by Prep-HPLC to give 3-(4-(4-(4-(5-benzylpyrimidin-2-yl)piperazin-1-yl)-1,3,5-triazin-2-ylamino)-1H-pyrazol-1-yl)propane-1,2-diol (13.8 mg, yield 7%) as a white solid. MS (ES+) $C_{24}H_{28}N_{10}O_2$ requires: 488, found: 489 $[M+H]^+$.

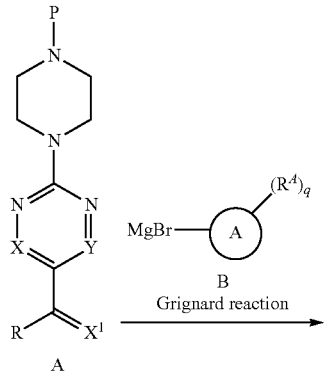

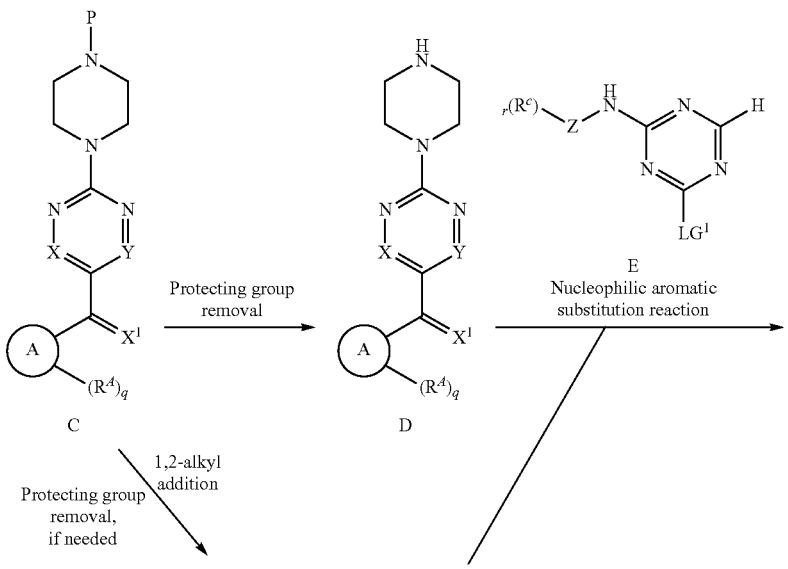

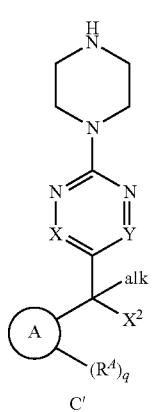

-continued

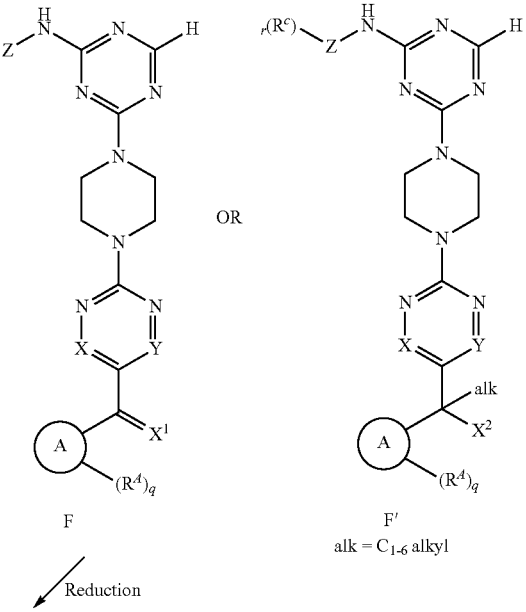

F

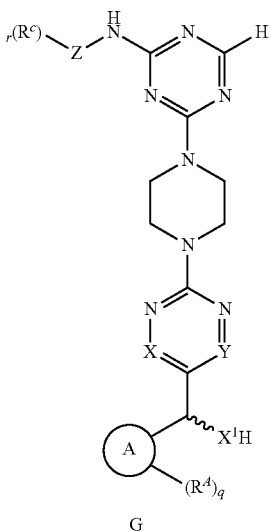

F' alk = C₁₋₆ alkyl

Reduction

G

R = leaving group
LG¹ = halogen
P = protecting group (e.g., Boc)
X¹ = C, O, CH₂, S, N—S(O)tBu
X² = CR¹₃, OH, NHR¹, SH
X³ = OR¹, NR¹₂, SR¹

Scheme 4 schematically depicts synthetic protocol 4. The piperazine carbonyl derivative, e.g., carbamoyl, (A, X and Y are each —CH—) can be coupled to the Grignard bromide (2, Ring A is aryl), to provide the protected di-substituted carbonyl (C, X¹ is CH₂, S, NH, or O). When X¹ is O, i.e., a carbonyl, the carbonyl can be further reacted with an organometallic reagent such as trialkylaluminum, e.g., trimethylaluminum, which can also deprotect the piperazine nitrogen to provide the dialkyl compound (C', alkyl is C₁₋₆ alkyl). Removal of the protecting group (P) from the piperazine ring of (C) can be carried out using strong acids such as 4M hydrochloric acid (HCl) in dioxane or trifluoroacetic acid (TFA) in a polar solvent such as methanol or dichloromethane (DCM) to afford amine (D). Triazine (E) can be substituted with amine (C') or (D) under nucleophilic aromatic substitution reaction conditions using an amine base such as diisopropylethylamine (DIPEA) or triethylamine (TEA) in a polar solvent such as dioxane to provide the piperazine-substituted triazine (F) or (F'). Reduction of —C(=X¹)—, wherein X¹ is CH₂, S, NH, or O, e.g., carbonyl, of (F) can be performed using a reducing agent such as sodium borohydride to provide —C—(XH)—, e.g., the alcohol (G). As shown below, Compound 189 was prepared using synthetic protocol 4.
Synthesis of (S) (2 (4 (4 (1 (morpholin-2-ylmethyl)-1H-pyrazol-4-ylamino)-1,3,5-triazin-2-yl)piperazin-1-yl)pyrimidin-5-yl)(phenyl)methanol (Compound 189)
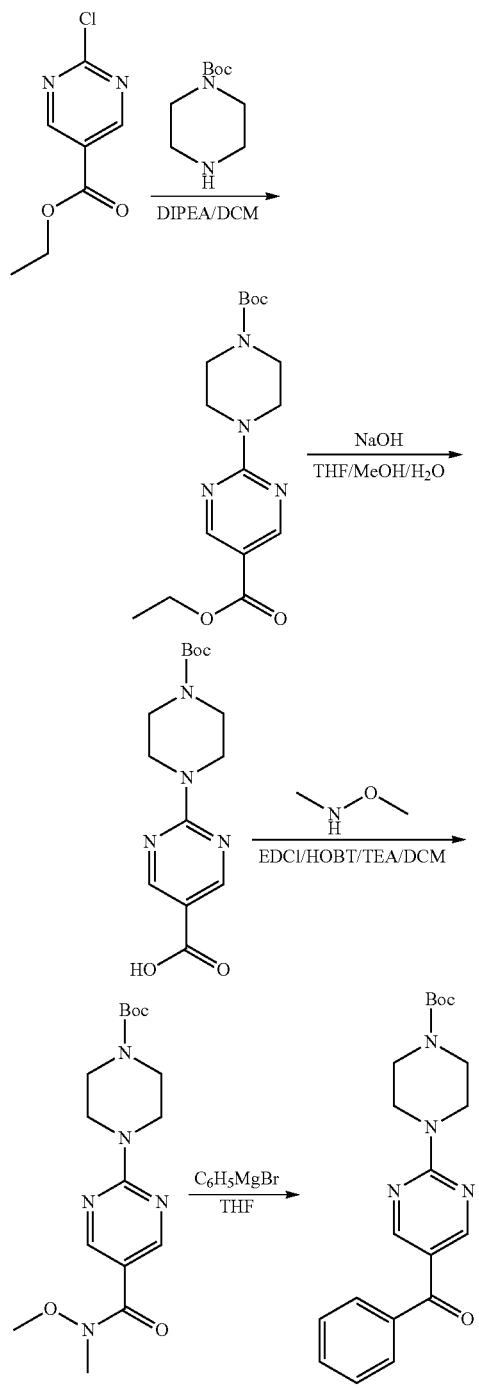
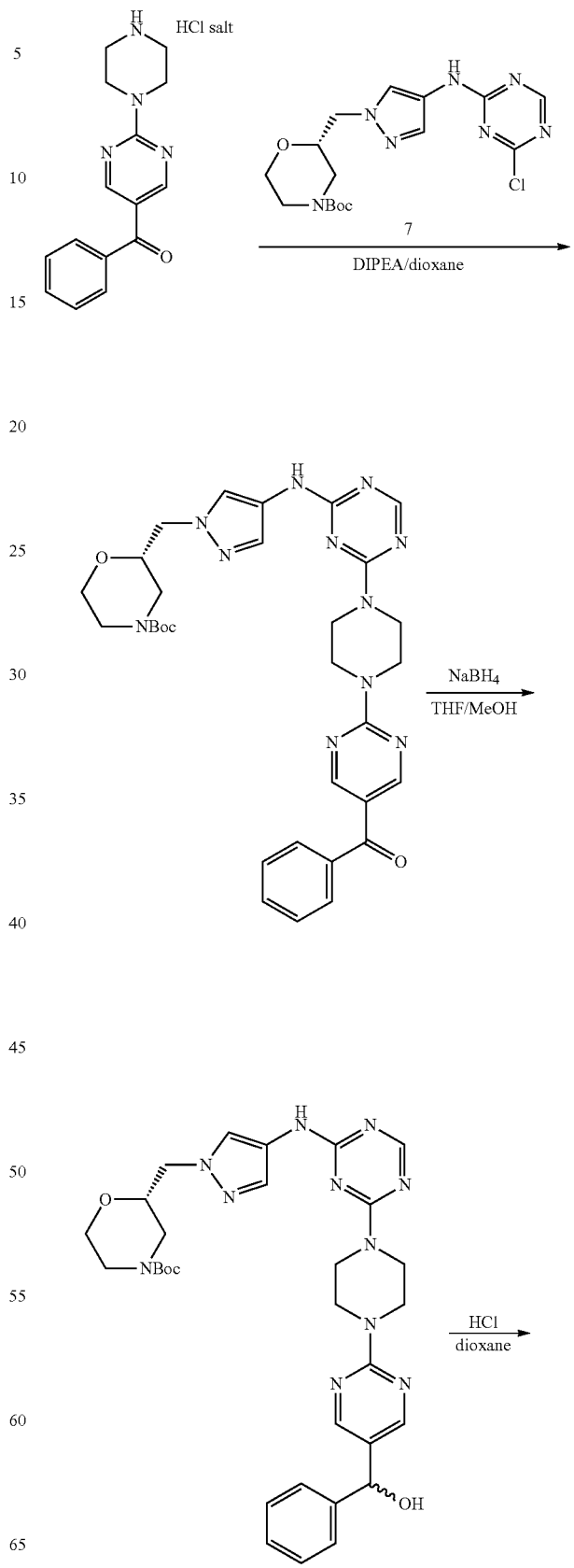

-continued

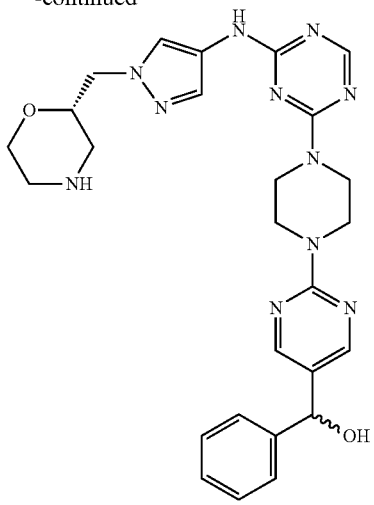

Step 1: Synthesis of ethyl 2-(4-(tert-butoxycarbonyl) piperazin-1-yl)pyrimidine-5-carboxylate

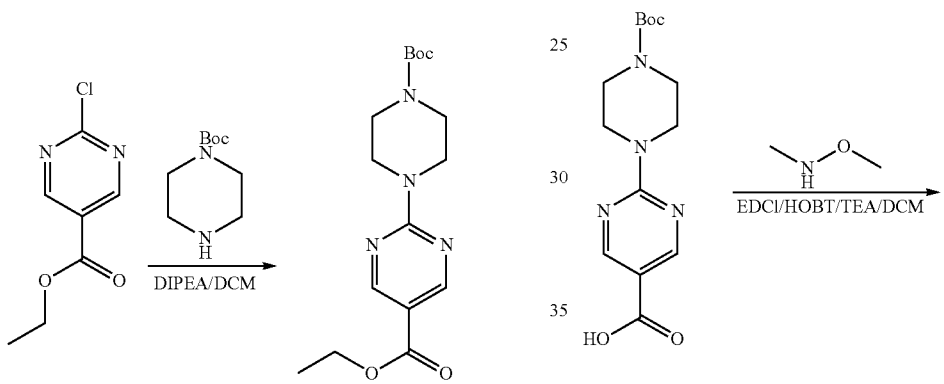

To a solution of tert-butyl piperazine-1-carboxylate (7.9 g, 42.5 mmol) and diisopropylethylamine (13.69 g, 106.1 mmol) in dichloromethane (80 mL) was added ethyl 2-chloropyrimidine-5-carboxylate (7.9 g, 42.5 mmoL), and the reaction mixture was stirred at room temperature for 3 hours. LCMS showed the reaction was completed. The reaction mixture was directly concentrated to afford ethyl 2-(4-(tert-butoxycarbonyl)piperazin-1-yl)pyrimidine-5-carboxylate (17 g, crude), which was directly used in the next step without further purification. MS (ES+) $C_{16}H_{24}N_4O_4$ requires: 336, found: 237, 281 [M-56+H]$^+$.

Step 2: Synthesis of 2-(4-(tert-butoxycarbonyl)piperazin-1-yl)pyrimidine-5-carboxylic acid

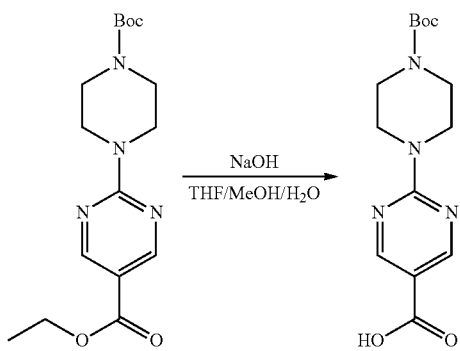 [SMILES: CCOC(=O)c1cnc(N2CCN(C(=O)OC(C)(C)C)CC2)nc1 ; "NaOH" ; CC(C)(C)OC(=O)N1CCN(c2ncc(C(=O)O)cn2)CC1]

To a solution of ethyl 2-(4-(tert-butoxycarbonyl)piperazin-1-yl)pyrimidine-5-carboxylate (17 g, crude) in THF/methanol/H$_2$O (300 mL) was added sodium hydroxide (4.3 g, 107.5 mmol), and the reaction mixture was stirred at 70 0° C. for 2 hours. LCMS showed the reaction was completed. The reaction mixture was brought to pH≈5-6 with 1 M HCl, and then filtered. The solid was collected and dried to give 2-(4-(tert-butoxycarbonyl)piperazin-1-yl)pyrimidine-5-carboxylic acid as a white solid (16 g, 96%), which was directly used in the next step without further purification. MS (ES+) $C_{14}H_{20}N_4O_4$ requires: 308, found: 253 [M-56+H]$^+$.

Step 3: Synthesis of tert-butyl 4-(5-(methoxy(methyl)carbamoyl)pyrimidin-2-yl)piperazine-1-carboxylate

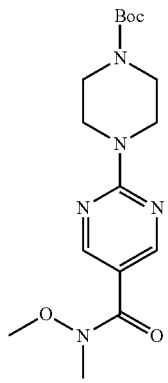

To a suspension of 2-(4-(tert-butoxycarbonyl)piperazin-1-yl)pyrimidine-5-carboxylic acid (13.8 g, 44.8 mmol), 1-ethyl-3-(3-dimethylaminopropyl)carbodiimide (12.8 g, 67.2 mmol) and hydroxybenzotriazole (7.2 g, 53.7 mmol) in dichloromethane (200 mL) was added triethylamine (25 mL, 179.2 mmol). The mixture was stirred at room temperature for 1 hour, and then N,O-dimethylhydroxylamine (5 g, 53.7 mmol) was added. The reaction mixture was stirred for another 3 hours. LCMS showed the reaction was completed. The reaction mixture was directly washed with water (100 mL), and the organic layer was dried over sodium sulfate, filtered and concentrated. The residue was purified by silica gel chromatography (petroleum ether:ethyl acetate=1:1) to give tert-butyl 4-(5-(methoxy(methyl)carbamoyl)pyrimidin-2-yl)piperazine-1-carboxylate (11.2 g, 67%) as a white solid. MS (ES+) C$_{16}$H$_{25}$N$_5$O$_4$ requires: 351, found: 296 [M-56+H]$^+$.

Step 4: Synthesis of tert-butyl 4-(5-benzoylpyrimidin-2-yl)piperazine-1-carboxylate

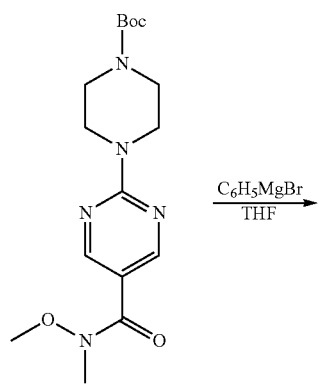

To a solution of tert-butyl 4-(5-(methoxy(methyl)carbamoyl)pyrimidin-2-yl)piperazine-1-carboxylate (2.6 g, 7.4 mmol) in dry THF (30 mL) was added benzylmagnesium bromide (1 M in THF, 29.6 mL) at 0° C. under N$_2$, and the mixture was stirred at room temperature for 3 hours. LCMS showed the reaction was completed. The reaction mixture was quenched with 1 M HCl and extracted with ethyl acetate. The organic layer was washed with water and brine, dried over sodium sulfate, filtered and concentrated. The residue was purified by silica gel chromatography (petroleum ether:ethyl acetate=5:1) to get tert-butyl 4-(5-benzoylpyrimidin-2-yl)piperazine-1-carboxylate (2 g, 73%) as a yellow solid. MS (ES+) C$_{20}$H$_{24}$N$_4$O$_3$ requires: 368, found: 313 [M-56+H]$^+$.

Step 5: Synthesis of phenyl(2-(piperazin-1-yl)pyrimidin-5-yl)methanone HCl salt

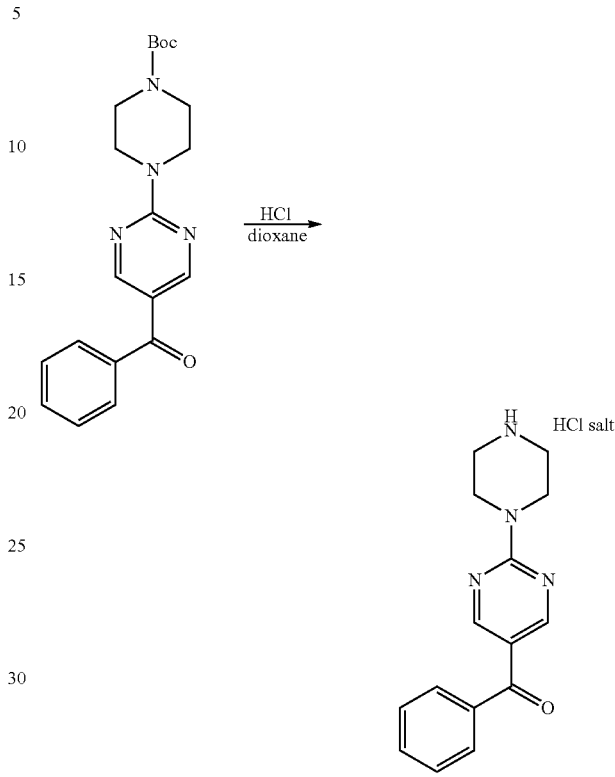

To a solution of tert-butyl 4-(5-benzoylpyrimidin-2-yl)piperazine-1-carboxylate (1 g, 2.7 mmol) in dioxane (20 mL) was added 4 M HCl-dioxane (20 mL), and the reaction mixture was stirred at room temperature overnight. LCMS showed the reaction was completed. The mixture was directly concentrated to give phenyl(2-(piperazin-1-yl)pyrimidin-5-yl)methanone HCl salt as a yellowish solid (0.95 g, 90%). MS (ES+) C$_{15}$H$_{16}$N$_4$O requires: 268, found: 269 [M+H]$^+$.

Step 6: Synthesis of (S)-tert-butyl 2-((4-(4-(4-(5-benzoylpyrimidin-2-yl)piperazin-1-yl)-1,3,5-triazin-2-ylamino)-1H-pyrazol-1-yl)methyl)morpholine-4-carboxylate

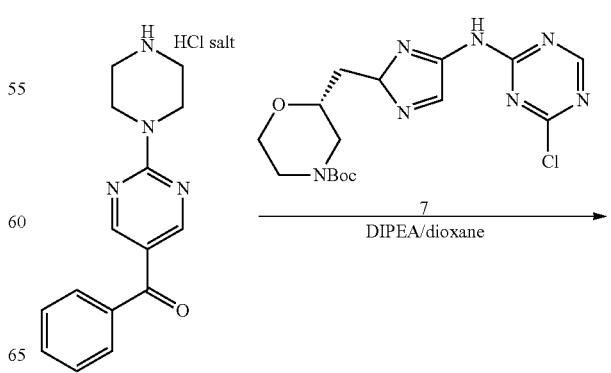

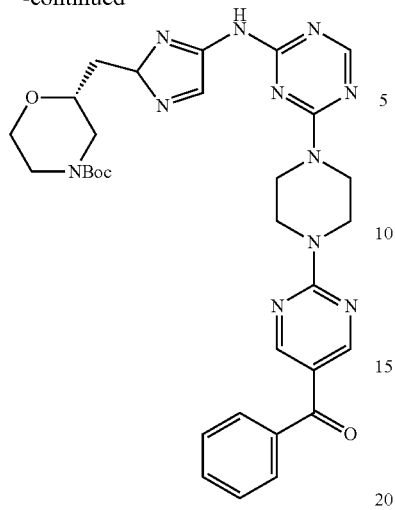
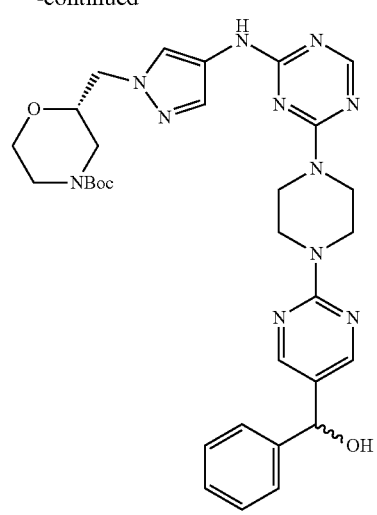

The synthesis of (S)-tert-butyl 2-((4-(4-chloro-1,3,5-triazin-2-ylamino)-1H-pyrazol-1-yl)methyl)morpholine-4-carboxylate (7) was carried out following the synthetic procedure of Example 1.)

To a mixture of phenyl(2-(piperazin-1-yl)pyrimidin-5-yl)methanone HCl salt (141.6 mg, 0.38 mmol) and (S)-tert-butyl 2-((4-(4-chloro-1,3,5-triazin-2-ylamino)-1H-pyrazol-1-yl)methyl)morpholine-4-carboxylate (150 mg, 0.38 mmol) in dioxane (10 mL) was added diisopropylethylamine (1 mL), and the reaction was stirred at room temperature overnight. LCMS showed the reaction was completed. The solvents were removed under reduced pressure, and the residue was purified by silica gel chromatography (petroleum ether:ethyl acetate=1:1) to give (S)-tert-butyl 2-((4-(4-(4-(5-benzoylpyrimidin-2-yl)piperazin-1-yl)-1,3,5-triazin-2-ylamino)-1H-pyrazol-1-yl)methyl)morpholine-4-carboxylate (230 mg, 95%) as a yellowish solid. (MS (ES+) $C_{31}H_{37}N_{11}O_4$ requires: 627, found: 573 [M-56+H]$^+$.

Step 7: Synthesis of (S)-tert-butyl 2-((4-(4-(4-(5-(hydroxy(phenyl)methyl)pyrimidin-2-yl)piperazin-1-yl)-1,3,5-triazin-2-ylamino)-1H-pyrazol-1-yl)methyl)morpholine-4-carboxylate To a solution of (S)-tert-butyl 2-((4-(4-(4-(5-benzoylpyrimidin-2-yl)piperazin-1-yl)-1,3,5-triazin-2-ylamino)-1H-pyrazol-1-yl)methyl)morpholine-4-carboxylate (80 mg, 0.127 mmol) in THF/methanol was added sodium borohydride (20 mg, 0.51 mmol). The mixture was stirred at room temperature for 1 hour, and LCMS showed the reaction was completed. The solvents were removed to give (S)-tert-butyl 2-((4-(4-(4-(5-(hydroxy(phenyl)methyl)pyrimidin-2-yl)piperazin-1-yl)-1,3,5-triazin-2-ylamino)-1H-pyrazol-1-yl)methyl)morpholine-4-carboxylate (80 mg, crude) as a yellowish solid. (MS (ES+) $C_{31}H_{39}N_{11}O_4$ requires: 629, found: 630 [M+H]$^+$.

Step 8: Synthesis of (S)-(2-(4-(4-(1-(morpholin-2-ylmethyl)-1H-pyrazol-4-ylamino)-1,3,5-triazin-2-yl)piperazin-1-yl)pyrimidin-5-yl)(phenyl)methanol

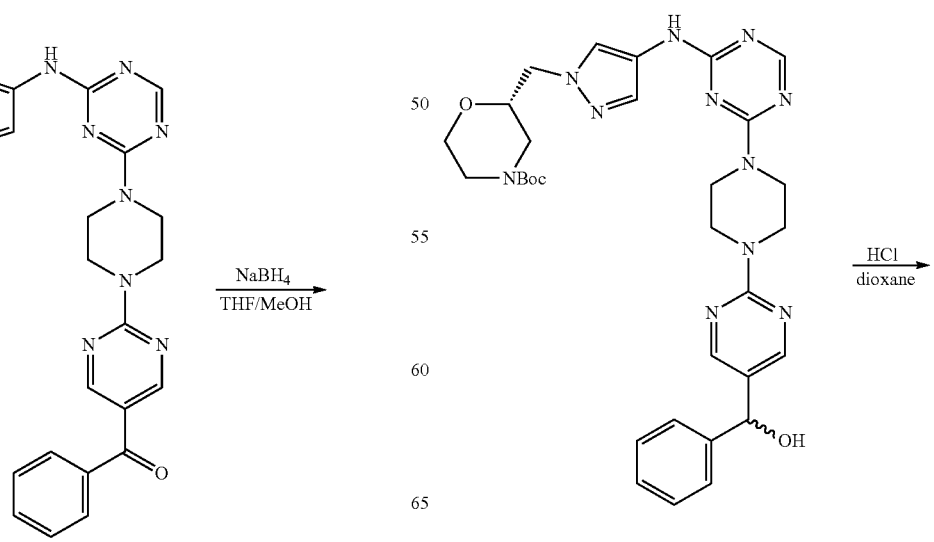

235
-continued

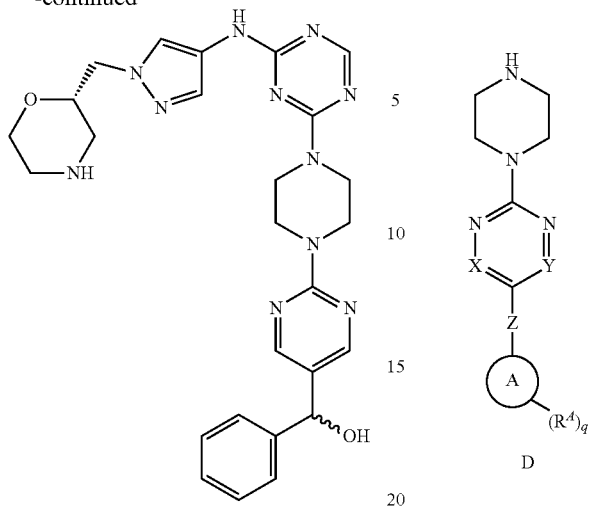

To a solution of (S)-tert-butyl 2-((4-(4-(4-(5-benzoylpyrimidin-2-yl)piperazin-1-yl)-1,3,5-triazin-2-ylamino)-1H-pyrazol-1-yl)methyl)morpholine-4-carboxylate (80 mg, 0.127 mmol, crude) in dioxane (4 mL) was added 4 M HCl-dioxane (4 mL), and the reaction was stirred at room temperature overnight. LCMS showed the reaction was completed. The solvent was removed, and the residue was purified by Prep-HPLC to provide the title compound (S)-(2-(4-(4-(1-(morpholin-2-ylmethyl)-1H-pyrazol-4-ylamino)-1,3,5-triazin-2-yl)piperazin-1-yl)pyrimidin-5-yl)(phenyl)methanol (Compound 189) (24.0 mg, 18%) as a yellowish solid.

Scheme 5

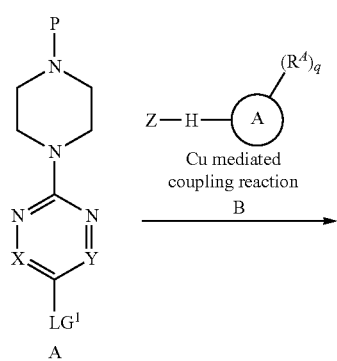

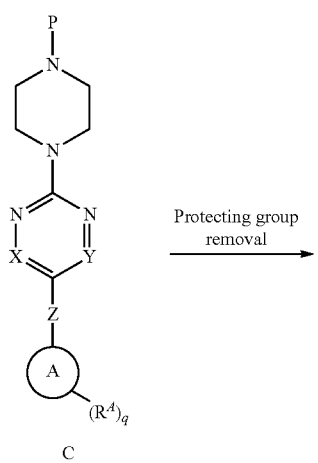

236
-continued

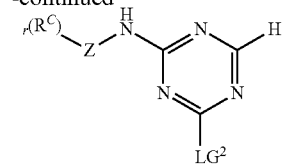

Nucleophilic aromatic substitution reaction
⟶

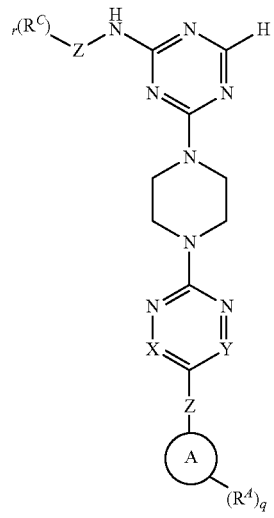

LG¹ = bromide, iodide, triflate
LG² = halogen
P = protecting group (e.g., Boc)
Z = O, S, NH Scheme 5 schematically depicts synthetic protocol 5. The N-protected heteroaryl-substituted piperazine (A, X and Y are each —CH—) can be coupled to an alcohol, thiol, or amine, (B, —Z—H is —OH, —SH, or —NH$_2$; Ring A is aryl) via a copper-mediated coupling reaction, e.g., such as the Ullman reaction, to provide the protected heteroaryl-ether (C). Removal of the protecting group (P) from the piperazine ring can be carried out using strong acids such as 4M hydrochloric acid (HCl) in dioxane or trifluoroacetic acid (TFA) in a polar solvent such as methanol or dichloromethane (DCM) to afford amine (D). Triazine (E) can be substituted with amine (D) under nucleophilic aromatic substitution reaction conditions using an amine base such as diisopropylethylamine (DIPEA) or triethylamine (TEA) in a polar solvent such as dioxane to provide the piperazine-substituted triazine (F). As shown below, Compound 203 was prepared using synthetic protocol 5.

237

Synthesis of (S)-4-(4-(5-(2-fluorophenoxyl)pyrimidin-2-yl)piperazin-1-yl)-N-(1-(morpholin-2-ylmethyl)-1H-pyrazol-4-yl)-1,3,5-triazin-2-amine (Compound 203)

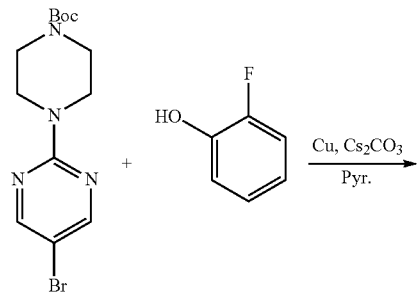

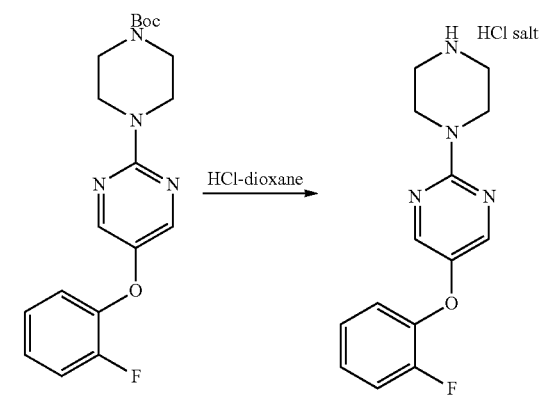

238

-continued

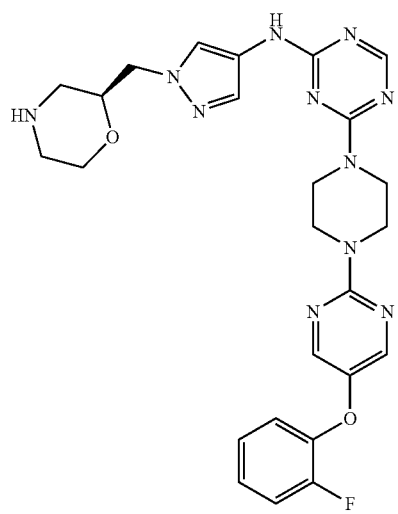

Step 1: Synthesis of tert-butyl 4-(5-(2-fluorophenoxyl)pyrimidin-2-yl)piperazine-1-carboxylate

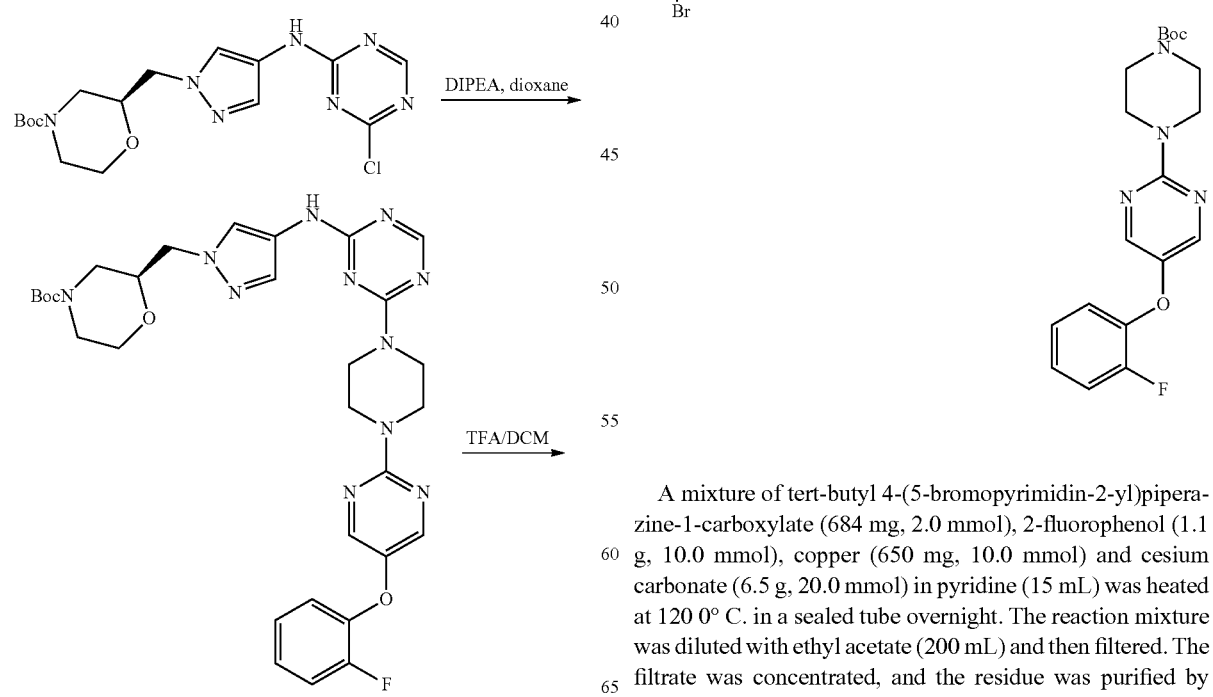

A mixture of tert-butyl 4-(5-bromopyrimidin-2-yl)piperazine-1-carboxylate (684 mg, 2.0 mmol), 2-fluorophenol (1.1 g, 10.0 mmol), copper (650 mg, 10.0 mmol) and cesium carbonate (6.5 g, 20.0 mmol) in pyridine (15 mL) was heated at 120 0° C. in a sealed tube overnight. The reaction mixture was diluted with ethyl acetate (200 mL) and then filtered. The filtrate was concentrated, and the residue was purified by silica gel chromatography (petroleum ether:ethyl acetate 20:1) to give tert-butyl 4-(5-(2-fluorophenoxyl)pyrimidin-2- yl)piperazine-1-carboxylate (50 mg, 6%) as a yellow solid. MS (ES+) $C_{19}H_{23}FN_4O_3$ requires: 374, found: 397 [M+Na]+.

Step 2: Synthesis of 5-(2-fluorophenoxy)-2-(piperazin-1-yl)pyrimidine HCl Salt

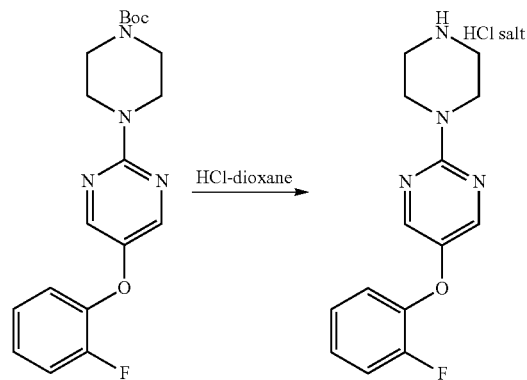 [SMILES: CC(C)(C)OC(=O)N1CCN(c2ncc(Oc3ccccc3F)cn2)CC1 ; Fc1ccccc1Oc1cnc(N2CCNCC2)nc1]

To a solution of tert-butyl 4-(5-(2-fluorophenoxyl)pyrimidin-2-yl)piperazine-1-carboxylate (50 mg, 0.13 mmol) in dioxane (3 mL) was added 4 M HCl/dioxane (3 mL). The reaction mixture was stirred at room temperature overnight and then concentrated to dryness. The residue (50 mg, yellow solid) was directly used in the next reaction.

Step 3: Synthesis of (S)-tert-butyl 2-((4-(4-(4-(5-(2-fluorophenoxyl)pyrimidin-2-yl)piperazin-1-yl)-1,3,5-triazin-2-ylamino)-1H-pyrazol-1-yl)methyl)morpholine-4-carboxylate

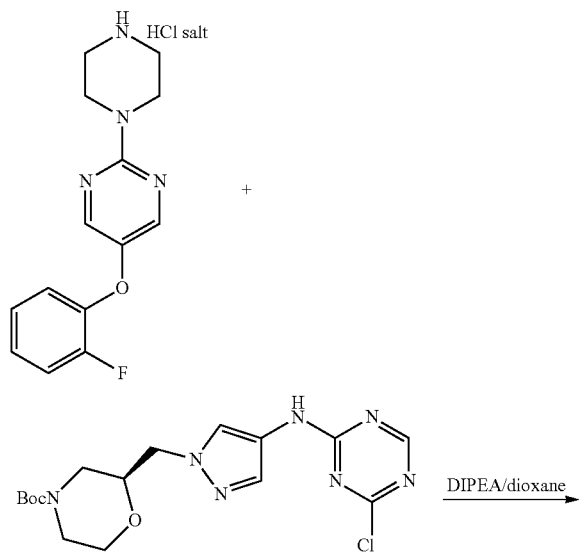

The synthesis of (S)-tert-butyl 2-((4-(4-chloro-1,3,5-triazin-2-ylamino)-1H-pyrazol-1-yl)methyl)morpholine-4-carboxylate (5) was carried out following the synthetic procedure of Example 1.

A mixture of 5-(2-fluorophenoxy)-2-(piperazin-1-yl)pyrimidine HCl salt (27 mg, 0.1 mmol), (S)-tert-butyl 2-((4-(4-chloro-1,3,5-triazin-2-ylamino)-1H-pyrazol-1-yl)methyl)-morpholine-4-carboxylate (40 mg, 0.1 mmol) and diisopropylethylamine (25 mg, 2.0 mmol) in dioxane (2 mL) was stirred at room temperature for 2 hours. The reaction mixture was directly evaporated and used in the next step.

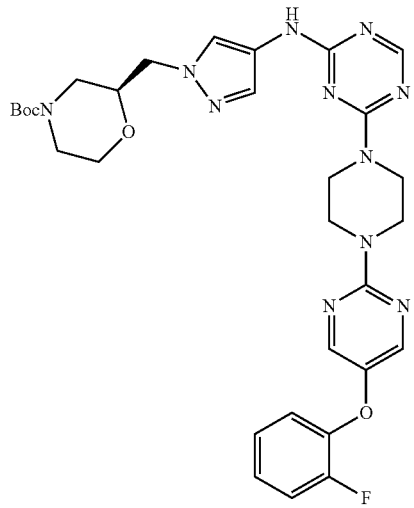

Step 4: Synthesis of (S)-4-(4-(5-(2-fluorophenoxyl)pyrimidin-2-yl)piperazin-1-yl)-N-(1-(morpholin-2-ylmethyl)-1H-pyrazol-4-yl)-1,3,5-triazin-2-amine

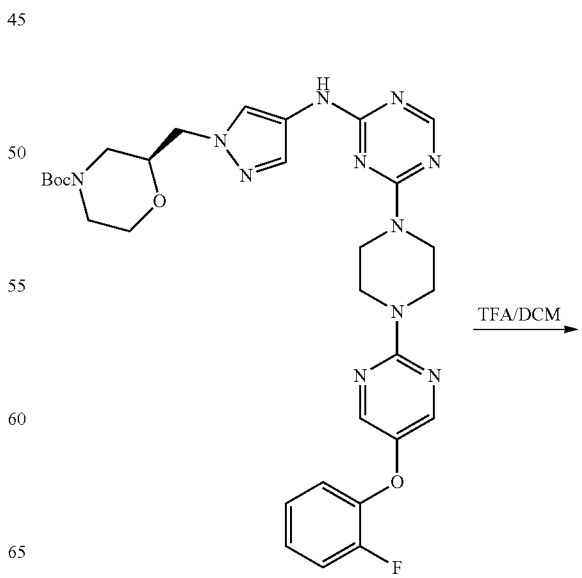

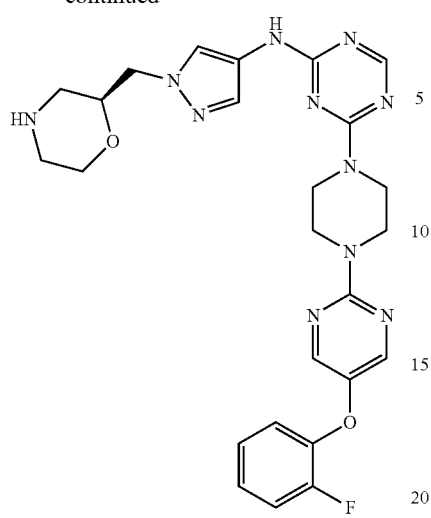

The above crude sample was dissolved in dichloromethane (10 mL), followed by the addition of trifluoroacetic acid (4 mL). The mixture was stirred at room temperature overnight. The solvent was removed, and the residue was purified by Prep-HPLC to (S)-4-(4-(5-(2-fluorophenoxy)-pyrimidin-2-yl)piperazin-1-yl)-N-(1-(morpholin-2-ylmethyl)-1H-pyrazol-4-yl)-1,3,5-triazin-2-amine (4.3 mg) as a white solid.

Scheme 6

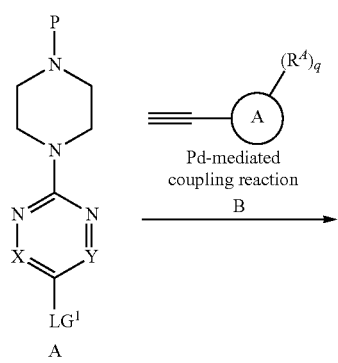

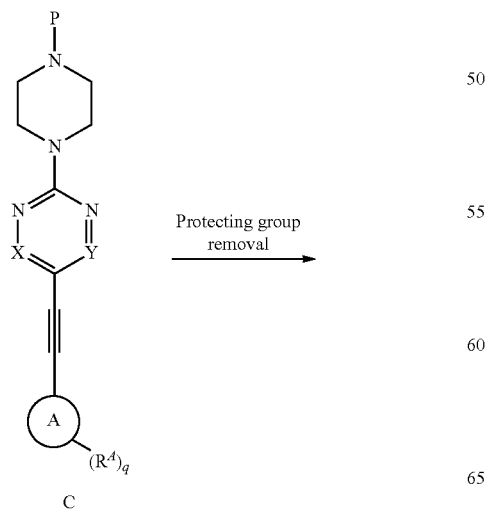

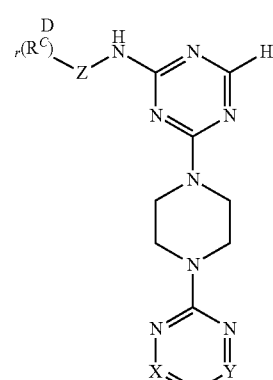

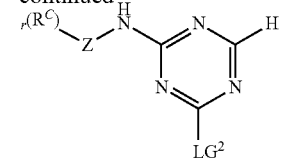

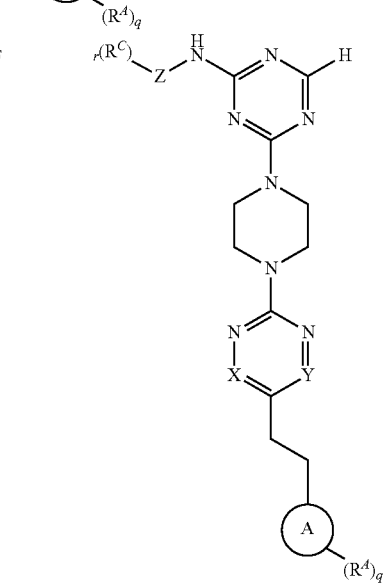

$LG^1$ = bromide, iodide, triflate
$LG^2$ = halogen
P = protecting group (e.g., Boc)

Scheme 6 schematically depicts synthetic protocol 6. The N-protected heteroaryl-substituted piperazine (A, X and Y are each —CH—) can be coupled to alkyne (B, Ring A is cycloalkyl) via a palladium-mediated coupling reaction, e.g., Sonogashira coupling, to provide the protected heteroaryl-alkyne (C). Removal of the protecting group (P) from the piperazine ring can be carried out using strong acids such as 4M hydrochloric acid (HCl) in dioxane or trifluoroacetic acid (TFA) in a polar solvent such as methanol or dichloromethane (DCM) to afford amine (D). Triazine (E) can be substituted with amine (D) under nucleophilic aromatic substitution reaction conditions using an amine base such as diisopropylethylamine (DIPEA) or triethylamine (TEA) in a polar solvent such as dioxane to provide the piperazine-substituted triazine (F). As shown below, Compound 63 was prepared using synthetic protocol 6.

Synthesis of (S)-4-(4-(5-(cyclopropylethynyl)pyrimidin-2-yl)piperazin-1-yl)-N-(1-(morpholin-2-ylmethyl)-1H-pyrazol-4-yl)-1,3,5-triazin-2-amine (Compound 63)

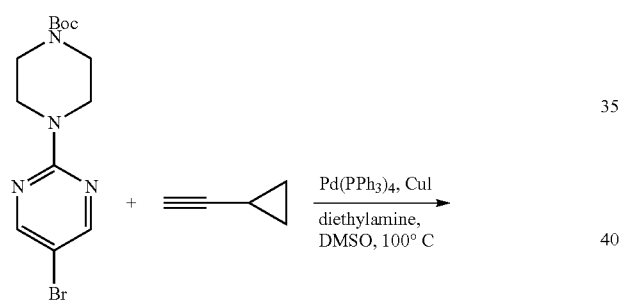

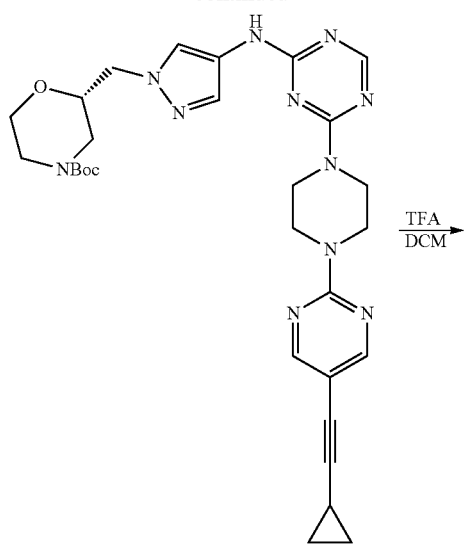

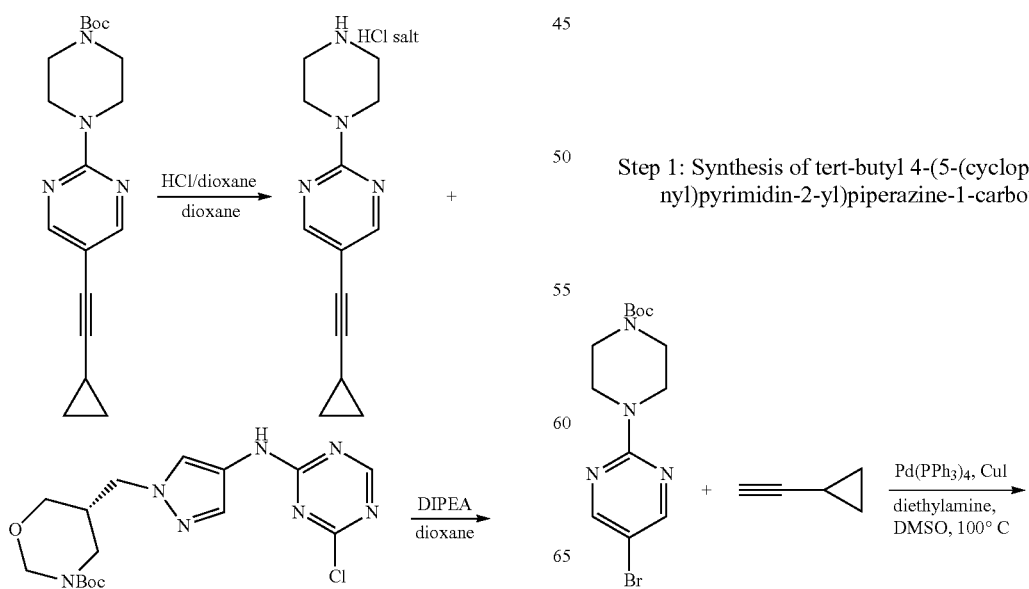

Step 1: Synthesis of tert-butyl 4-(5-(cyclopropylethynyl)pyrimidin-2-yl)piperazine-1-carboxylate -continued

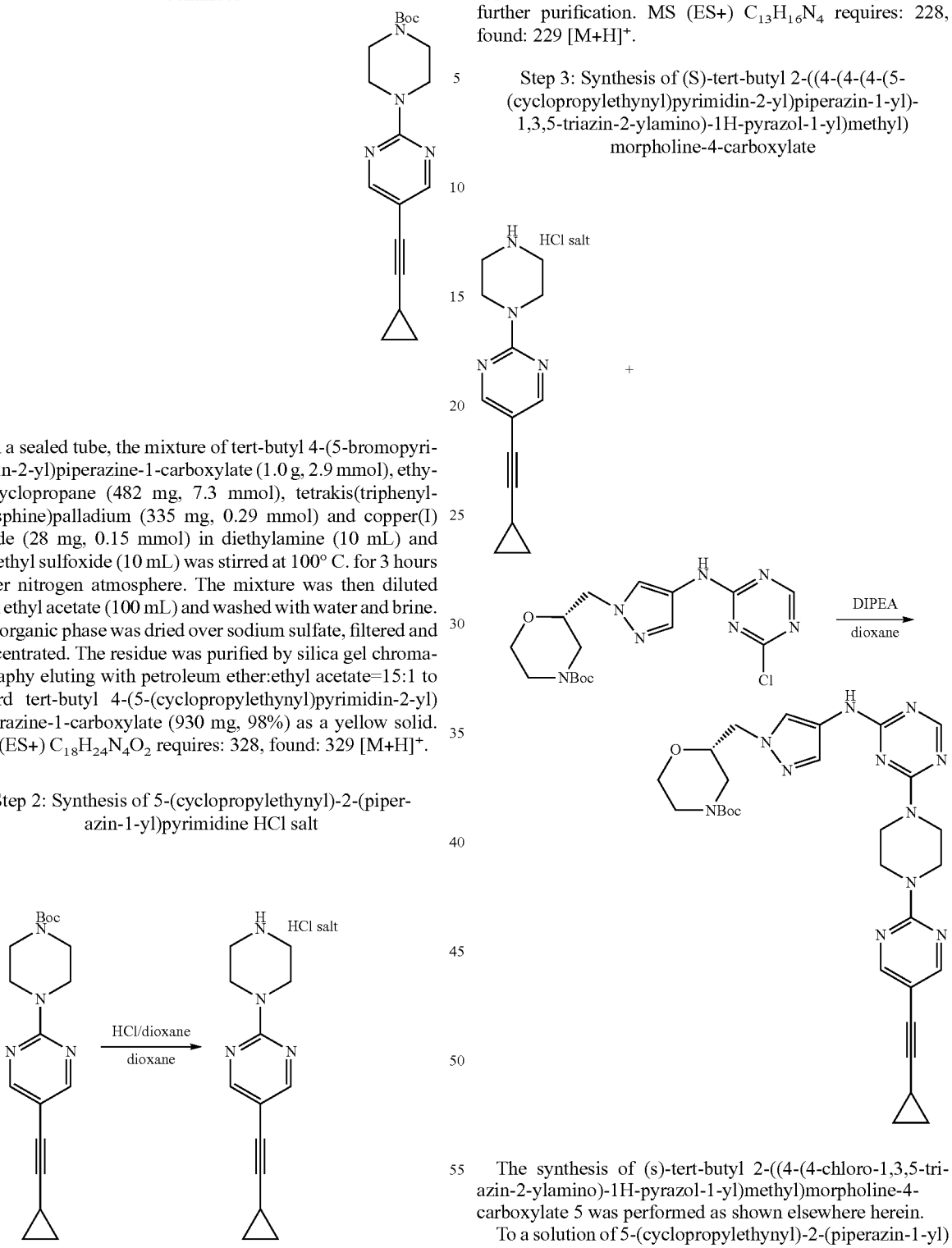

In a sealed tube, the mixture of tert-butyl 4-(5-bromopyrimidin-2-yl)piperazine-1-carboxylate (1.0 g, 2.9 mmol), ethynylcyclopropane (482 mg, 7.3 mmol), tetrakis(triphenylphosphine)palladium (335 mg, 0.29 mmol) and copper(I) iodide (28 mg, 0.15 mmol) in diethylamine (10 mL) and dimethyl sulfoxide (10 mL) was stirred at 100° C. for 3 hours under nitrogen atmosphere. The mixture was then diluted with ethyl acetate (100 mL) and washed with water and brine. The organic phase was dried over sodium sulfate, filtered and concentrated. The residue was purified by silica gel chromatography eluting with petroleum ether:ethyl acetate=15:1 to afford tert-butyl 4-(5-(cyclopropylethynyl)pyrimidin-2-yl)piperazine-1-carboxylate (930 mg, 98%) as a yellow solid. MS (ES+) $C_{18}H_{24}N_4O_2$ requires: 328, found: 329 [M+H]$^+$.

Step 2: Synthesis of 5-(cyclopropylethynyl)-2-(piperazin-1-yl)pyrimidine HCl salt To a solution of tert-butyl 4-(5-(cyclopropylethynyl)pyrimidin-2-yl)piperazine-1-carboxylate (150 mg, 0.46 mmol) in dioxane (3 mL) was added 4 M HCl-dioxane (3 mL), and the reaction mixture was stirred room temperature for 1 hour. LCMS showed the reaction was completed. The reaction mixture was concentrated to afford 5-(cyclopropylethynyl)-2-(piperazin-1-yl)pyrimidine HCl salt as a white solid (100 mg, crude), which was directly used in the next step without further purification. MS (ES+) $C_{13}H_{16}N_4$ requires: 228, found: 229 [M+H]$^+$.

Step 3: Synthesis of (S)-tert-butyl 2-((4-(4-(4-(5-(cyclopropylethynyl)pyrimidin-2-yl)piperazin-1-yl)-1,3,5-triazin-2-ylamino)-1H-pyrazol-1-yl)methyl)morpholine-4-carboxylate The synthesis of (s)-tert-butyl 2-((4-(4-chloro-1,3,5-triazin-2-ylamino)-1H-pyrazol-1-yl)methyl)morpholine-4-carboxylate 5 was performed as shown elsewhere herein.

To a solution of 5-(cyclopropylethynyl)-2-(piperazin-1-yl)pyrimidine HCl salt (172 mg, 0.44 mmol) and (s)-tert-butyl 2-((4-(4-chloro-1,3,5-triazin-2-ylamino)-1H-pyrazol-1-yl)methyl)morpholine-4-carboxylate was added diisopropylethylamine (169 mg, 1.311 mmol), and the reaction mixture was stirred at room temperature. LCMS showed the reaction was completed. The mixture was concentrated, and the residue was purified by silica gel chromatography, eluting with petroleum ether:ethyl acetate=1:2, to afford (S)-tert-butyl 2-((4-(4-(4-(5-(cyclopropylethynyl)pyrimidin-2-yl)piperazin-1-yl)-1,3,5-triazin-2-ylamino)-1H-pyrazol-1-yl)methyl)morpholine-4-carboxylate (240 mg, 94%) as a yellowish solid. MS (ES+): $C_{29}H_{37}N_{11}O_3$ requires: 587, found: 588 $[M+H]^+$.

Step 4: Synthesis of (S)-4-(4-(5-(cyclopropylethynyl)pyrimidin-2-yl)piperazin-1-yl)-N-(1-(morpholin-2-ylmethyl)-1H-pyrazol-4-yl)-1,3,5-triazin-2-amine

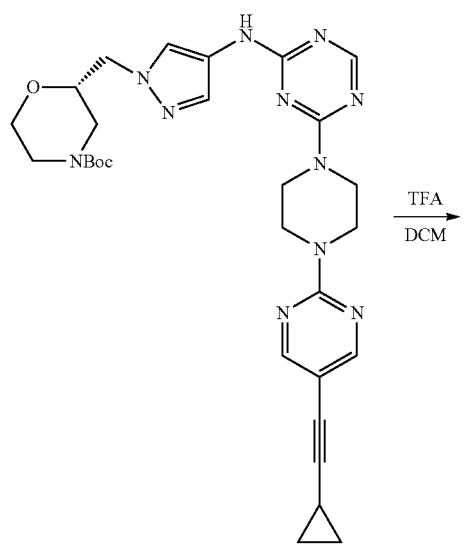

To a solution of (S)-tert-butyl 2-((4-(4-(4-(5-(cyclopropylethynyl)pyrimidin-2-yl)piperazin-1-yl)-1,3,5-triazin-2-ylamino)-1H-pyrazol-1-yl)methyl)morpholine-4-carboxylate (30 mg, 0.05 mmol) in dichloromethane (2 mL) was dropwise added trifluoroacetic acid (1 mL). The reaction mixture was stirred at room temperature for 0.5 hour and concentrated. The residue was purified by Prep-HPLC to afford (S)-4-(4-(5-(cyclopropylethynyl)pyrimidin-2-yl)piperazin-1-yl)-N-(1-(morpholin-2-ylmethyl)-1H-pyrazol-4-yl)-1,3,5-triazin-2-amine (14 mg, 57%) as a white solid.

Preparation of Common Intermediates

Synthesis of 5-(2-phenylpropan-2-yl)-2-(piperazin-1-yl)pyrimidine

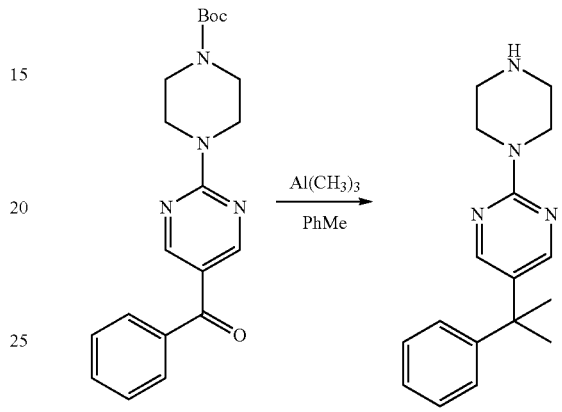

In a sealed tube, the mixture of tert-butyl 4-(5-benzoylpyrimidin-2-yl) piperazine-1-carboxylate (500 mg, 1.36 mmol) and trimethylaluminum (2 M in toluene, 2.7 mL) in dry toluene (10 mL) was stirred at 100 0° C. overnight. LCMS showed the reaction was completed. The reaction mixture was cooled to RT, quenched with ice-water and extracted with ethyl acetate. The organic layer was washed with water and brine, dried over sodium sulfate, filtered and concentrated. The residue was purified by Prep-HPLC to get 5-(2-phenylpropan-2-yl)-2-(piperazin-1-yl)pyrimidine (40 mg, 7%) as a yellowish solid. MS (ES+) $C_{17}H_{22}N_4$ requires: 282, found: 283 $[M+H]^+$.

Synthesis of 2-methyl-1-(4-nitro-1H-pyrazol-1-yl)propan-2-ol

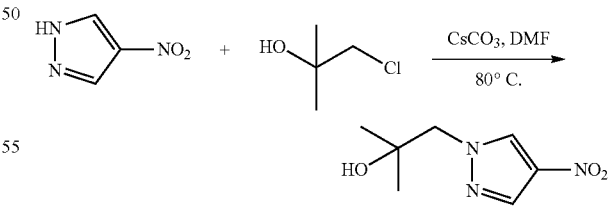

A mixture of 4-nitro-1H-pyrazole (1.6 g, 13.9 mmol), 1-chloro-2-methylpropan-2-ol (1.5 g, 13.9 mmol) and $Cs_2CO_3$ (9.1 g, 27.8 mmol) in DMF (20 mL) was stirred at 80° C. for 5 h. The reaction mixture was cooled to RT and diluted with EA (200 ml). The organic phase was washed by water (50 mL) and brine (50 mL), dried over anhydrous sodium sulfate and concentrated under reduced pressure to give 2-methyl-1-(4-nitro-1H-pyrazol-1-yl)propan-2-ol as a yel-

Synthesis of 1-(4-amino-1H-pyrazol-1-yl)-2-methyl-propan-2-ol

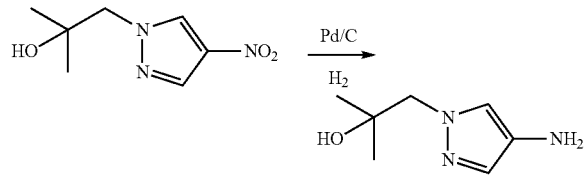

A stirred suspension mixture of 2-methyl-1-(4-nitro-1H-pyrazol-1-yl)propan-2-ol (2.0 g, 10.8 mmol) and 10% Pd/C (0.2 g, 0.1 w/w) in MeOH (20 mL) was exposed to 1 atm $H_2$ at RT overnight. The reaction mixture was filtered through a pad of celite. The filtrate was concentrated under reduced pressure to give 1-(4-amino-1H-pyrazol-1-yl)-2-methylpropan-2-ol as a yellow oil (1.9 g, 99%), which was used for the next step without further purification. MS (ES+) $C_7H_{13}N_3O$ requires: 155, found: 156 $[M+H]^+$.

Synthesis of 1-((4-bromophenyl)diazenyl)pyrrolidine

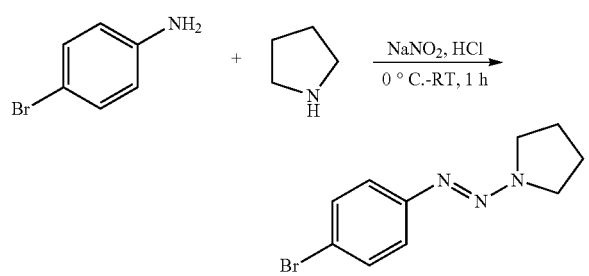

To a solution of 4-bromoaniline (1.7 g, 9.88 mmol) in conc. HCl (2 mL) was added a solution of $NaNO_2$ (682 mg, 9.88 mmol) in water (3 mL) at 0° C. The solution was stirred at 0° C. for 10 minutes, followed by the addition of pyrrolidine (844 mg, 11.86 mmol) in KOH solution (1 mL, 1 N). The resultant mixture was stirred at 0° C. for 0.5 h. The formed precipitate was collected by filtration, washed with 1 mL of ethanol and dried to give the title compound as a yellow solid (1.5 g, yield 60%). MS (ES+) $C_{10}H_{12}BrN_3$ requires: 253, 255, found 254, 256 $[M+H]^+$, purity: 93%.

Synthesis of 3-(4-(pyrrolidin-1-yldiazenyl)phenyl)oxetan-3-ol

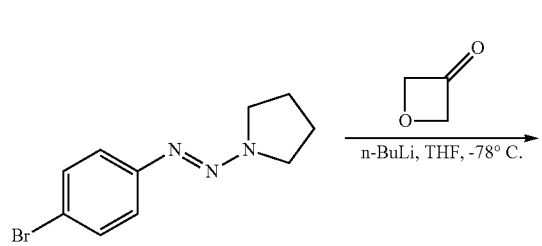

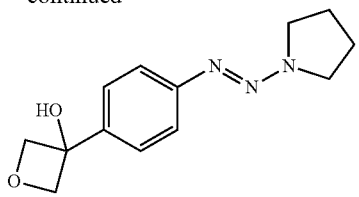

To a solution of 1-((4-bromophenyl)diazenyl)pyrrolidine (500 mg, 1.97 mmol) in anhydrous THF (20 mL) was added n-BuLi (1.8 mL, 4.33 mmol) dropwise at −78° C. under $N_2$. The solution was stirred at −78° C. for 1 h, followed by the addition of oxetan-3-one (326 mg, 4.53 mmol). The resultant mixture was stirred at RT for 18 h. The reaction was quenched by saturated aqueous $NH_4Cl$ aq. (20 mL) and extracted with ethyl acetate (20 mL*3). The combined organic layers were concentrated under reduced pressure to give a residue, which was purified by silica gel chromatography (DCM:MeOH=20:1) to afford the title compound (500 mg, yield 97%) as a light yellow solid. MS (ES+) $C_{13}H_{17}N_3O_2$ requires: 247, found 248 $[M+H]^+$, purity: 90%.

Synthesis of 3-(4-aminophenyl)oxetan-3-ol

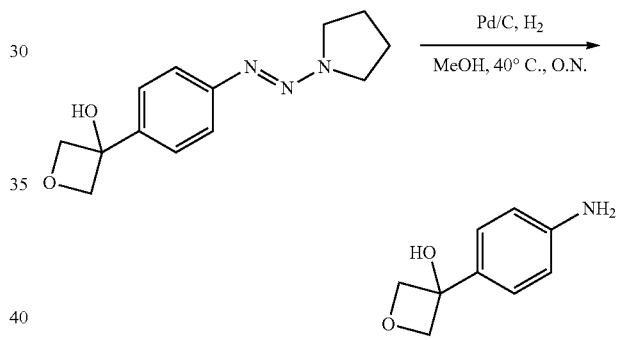

To a solution of 3-(4-(pyrrolidin-1-yldiazenyl)phenyl)oxetan-3-ol (500 mg, 2.02 mmol) in methanol (15 mL) was added Pd/C (10%, 250 mg) at RT. The reaction mixture was stirred under 1 atm $H_2$ atmosphere (balloon) at 40° C. for 18 h. The mixture was filtered through a pad of Celite. The filtrate was concentrated to give a residue, which was purified by Prep-HPLC to afford the title compound (200 mg, yield 60%) as a white solid. MS (ES+) $C_9H_{11}NO_2$ requires: 165, found 166 $[M+H]^+$, purity: 96%.

Synthesis of tert-butyl 1-(2-methylprop-1-enyl)-4-nitrobenzene

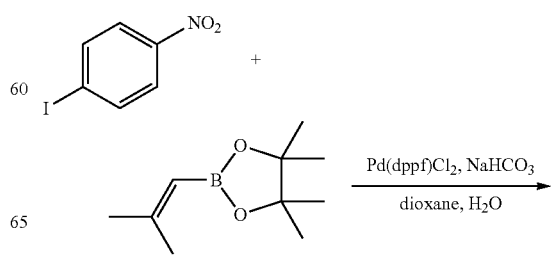

-continued

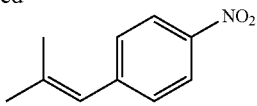

A mixture of 1-iodo-4-nitrobenzene (2.49 g, 10.0 mmol), 4,4,5,5-tetramethyl-2-(2-methylprop-1-enyl)-1,3,2-dioxaborolane (1.82 g, 10.0 mmol), sodium bicarbonate (2.52 g, 30.0 mmol) and [1,1-bis(diphenylphosphino)ferrocene]dichloropalladium(II) complex with dichloromethane (816 mg, 1.0 mmol) in dioxane/water (5:1, 60 mL) was stirred at 90° C. for 20 h under $N_2$. LCMS and TLC monitored the reaction was completed. The reaction mixture was cooled to RT and concentrated. The residue was dissolved in 100 mL of EtOAc, washed with water (150 mL×3) and brine, dried over $Na_2SO_4$, filtered and concentrated under vacuo. The crude product was purified by silica gel column, eluting with PE:EA (6:1), to obtain the desired product (1.9 g, 100% yield) as a yellow oil, $^1$H-NMR (400 MHz, $CDCl_3$) δ ppm 8.17 (d, 2H, J=8.8 Hz), 7.35 (d, 2H, J=8.8 Hz), 6.36 (s, 1H), 1.96 (d, 3H, J=0.4 Hz), 1.90 (d, 3H, J=0.4 Hz).

Synthesis of 2-methyl-1-(4-nitrophenyl)propane-1,2-diol

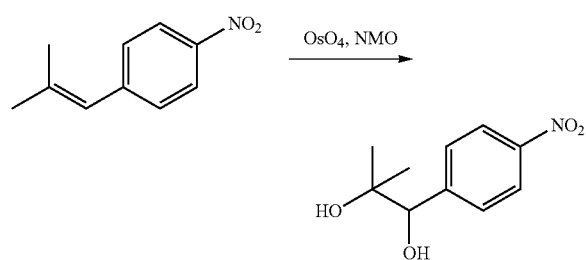

To a solution of N-methyl morpholine-N-oxide (1.5 g, 12.8 mmol) in 4.5 mL of water was added a solution of tert-butyl 1-(2-methylprop-1-enyl)-4-nitrobenzene (1.5 g, 8.5 mmol) in acetone/water (5:1, 36 mL), followed by the addition of a solution of osmium tetraoxide in water (2 mL, 4%). This mixture was allowed to RT and stirred for 16 h. The reaction was quenched by sat. $Na_2SO_3$. aq (100 mL) and extracted with EtOAc (50 mL x 3). The combined organic layers were washed with water and brine, dried over $Na_2SO_4$, filtered and concentrated under vacuo. The crude product (1.7 g, yield 100%) was obtained as a yellow foam, which was directly used into the next step without further purification. $^1$H-NMR (400 MHz, $CDCl_3$) δ ppm 8.20 (d, 2H, J=9.2 Hz), 7.57 (d, 2H, J=9.2 Hz), 4.63 (d, 1H, J=2.4 Hz), 2.69 (d, 1H, J=3.2 Hz), 2.03 (d, 1H, J=3.2 Hz), 1.19 (s, 3H), 1.08 (s, 3H).

Synthesis of 2,2,4,4-tetramethyl-5-(4-nitrophenyl)-1,3-dioxolane

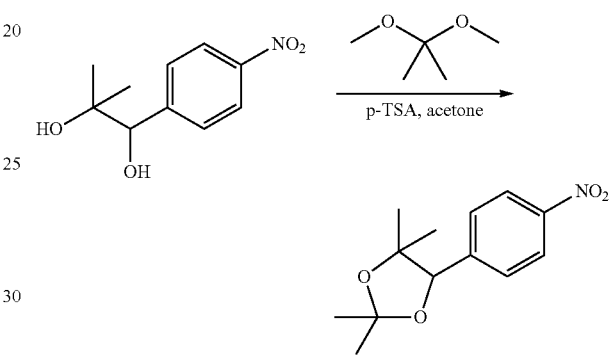

A solution of 2-methyl-1-(4-nitrophenyl)propane-1,2-diol (1.5 g, 7.1 mmol), 2,2-dimethoxypropane (1.45 g, 14.2 mmol) and TsOH (cat., 260 mg, 1.5 mmol) in acetone (40 mL) was stirred at 30° C. for 16 h. The reaction mixture was concentrated. The residue was purified by silica gel chromatography, eluting with PE:EA (8:1), to obtain the desired product (1.5 g, 85% yield) as a white solid. $^1$H-NMR (500 MHz, $CDCl_3$) δ ppm 8.23 (d, 2H, J=9.0 Hz), 7.57 (d, 2H, J=9.0 Hz), 4.93 (s, 1H), 1.59 (s, 3H), 1.48 (s, 3H), 1.46 (s, 3H), 0.78 (s, 3H).

Synthesis of (R) and (S)-2,2,4,4-tetramethyl-5-(4-nitrophenyl)-1,3-dioxolane

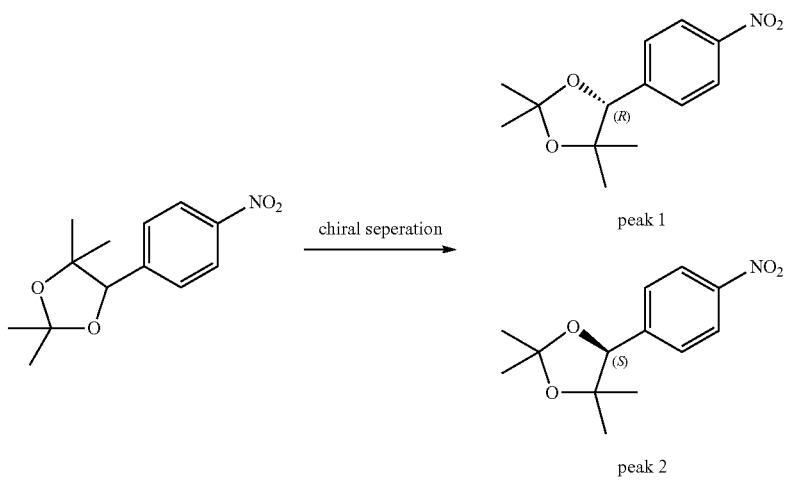

The racemic material 2,2,4,4-tetramethyl-5-(4-nitrophenyl)-1,3-dioxolane (1.3 g) was separated by chiral HPLC to obtain peak 1 (630 mg, 100% ee) and peak 2 (610 mg, 99.6% ee).

Synthesis of (R)-4-(2,2,5,5-tetramethyl-1,3-dioxolan-4-yl)aniline

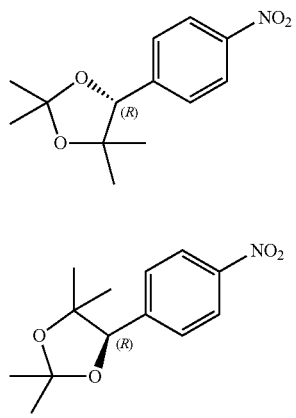

A mixture of (R)-2,2,4,4-tetramethyl-5-(4-nitrophenyl)-1,3-dioxolane (200 mg, 0.797 mmol) and Pd/C (10%, 60 mg) in EtOAc/IPA (10 mL/10 mL) was stirred under 1 atm H$_2$ atmosphere (balloon) at RT for 16 h. The mixture was filtered through a pad of Celite. The filtrate was concentrated under reduced pressure to afford the desired product (180 mg, 100%), which was directly used into the next step without further purification.

Synthesis of 1-(4-nitrophenyl)ethane-1,2-diol

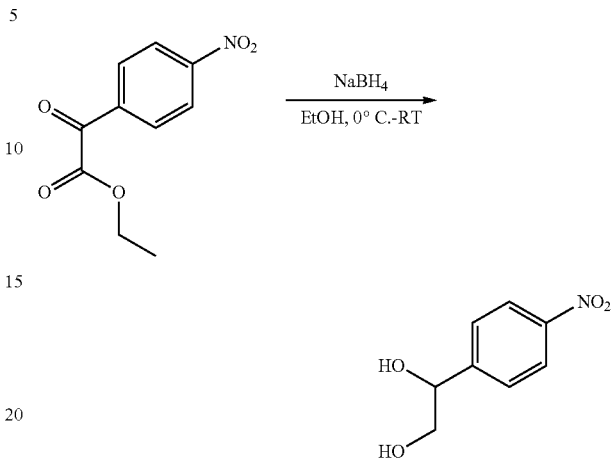

To a stirred solution of ethyl 2-(4-nitrophenyl)-2-oxoacetate (10.0 g, 47.8 mmol) in ethanol (100 mL) was slowly added sodium borohydride (4.54 g, 119.5 mmol) at 0° C. After the addition was completed, the reaction mixture was allowed to warm to RT and stirred for 12 h. The reaction was quenched by acetone (10 mL) and concentrated. The residue was purified by silica gel column chromatography (dichloromethane/methanol=5/1) to afford the title compound (8.0 g, 87%) as a brown solid. MS (ES+) C$_8$H$_9$NO$_4$ requires: 183, found: 184 [M+H]$^+$.

Synthesis of 2,2-dimethyl-4-(4-nitrophenyl)-1,3-dioxolane

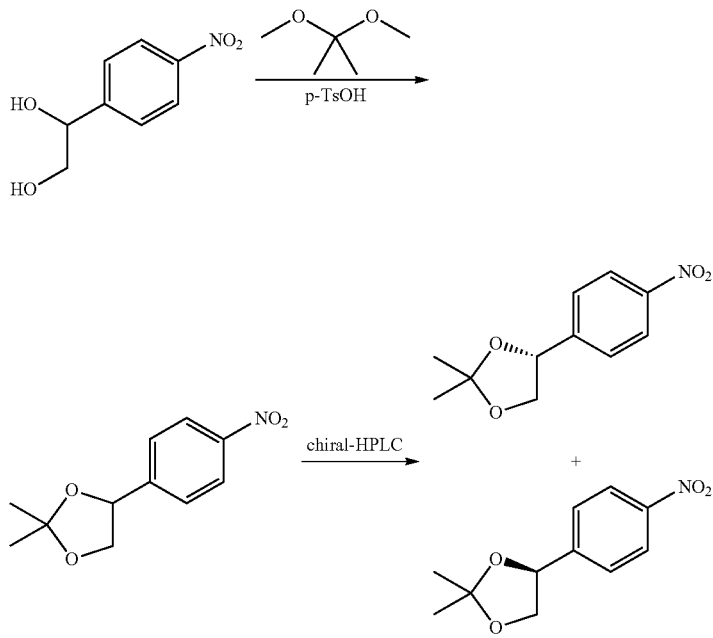

A mixture of 1-(4-nitrophenyl)ethane-1,2-diol (7.0 g, 38.3 mmol), 2,2-dimethoxypropane (16 g, 153.2 mmol) and 4-methylbenzenesulfonic acid (2.6 g, 15.32 mmol) in acetone (100 mL) was stirred at 25° C. for 12 h. The reaction mixture was concentrated and then dissolved in ethyl acetate (300 mL). The organic layer was separated, washed by water (100 mL) and brine (100 mL), dried over sodium sulfate, filtered and concentrated. The residue was purified by silica gel column chromatography (petroleum ether/ethyl acetate=5/1) to afford the title compound (4.0 g, 40%) as a yellow oil.

The racemic material was separated by chiral-HPLC to afford the desired isomer (shown on the bottom, above) (1.8 g, 45%).

Synthesis of (S)-4-(2,2-dimethyl-1,3-dioxolan-4-yl)benzenamine

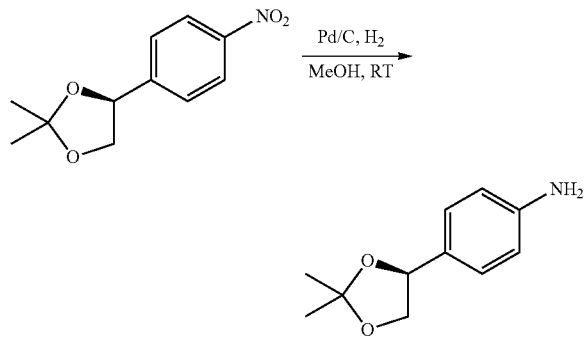

A mixture of (S)-2,2-dimethyl-4-(4-nitrophenyl)-1,3-dioxolane (3.6 g, 16.1 mmol) and 5% palladium on carbon (50% wet, 700 mg) in methanol (30 mL) was stirred under 1 atm hydrogen atmosphere ($H_2$ balloon) at RT for 16 h. After the reaction mixture was filtered through a pad of Celite, the filtrate was concentrated to afford the title compound (3.1 g, 100%) as a yellow solid. MS (ES+) $C_{11}H_{15}NO_2$ requires: 193, found: 194 [M+H]$^+$.

Synthesis of tert-butyl 4-(5-acetylpyrimidin-2-yl)piperazine-1-carboxylate

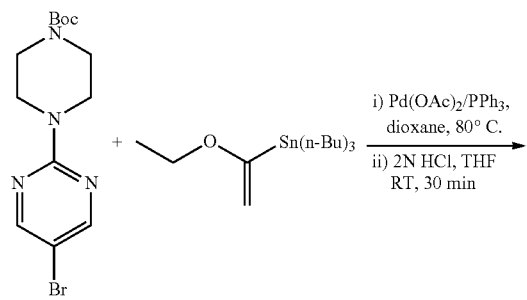

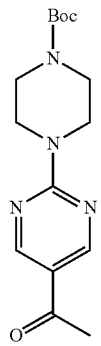

To a mixture of tert-butyl 4-(5-bromopyrimidin-2-yl)piperazine-1-carboxylate (5.0 g, 14.6 mmol), palladium diacetate (240 mg, 1.46 mmol) and triphenylphosphine (376 mg, 2.92 mmol) in dioxane (100 mL) was added tributyl(1-ethoxyvinyl)stannane (5.3 mL, 16.1 mL) under $N_2$, and the reaction mixture was stirred at 80° C. overnight. The reaction was cooled to RT and diluted with THF (100 mL), followed by the addition of 2 N HCl (100 mL). The mixture was stirred at RT for 30 mins, and LCMS showed the reaction was completed. The reaction mixture was diluted with ethyl acetate (200 mL). The organic phase was separated, washed with water (3×100 mL), dried over sodium sulfate, filtered and concentrated. The residue was purified by silica gel column chromatography to afford the title compound (3.0 g, 67%). MS (ES+) $C_{15}H_{22}N_4O_3$ requires: 306, found: 251 [M-56+H]$^+$.

Synthesis of 1-(2-(piperazin-1-yl)pyrimidin-5-yl)ethanone

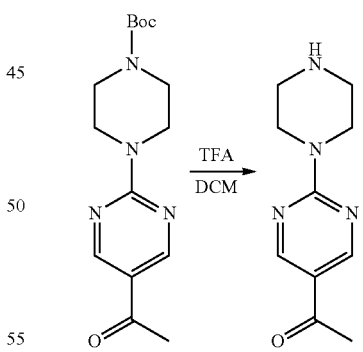

To a solution of -butyl 4-(5-acetylpyrimidin-2-yl)piperazine-1-carboxylate (4.5 g, 14.7 mmol) in dichloromethane (80 mL) was added trifluoroethyl acetate (20 mL), and the mixture was stirred at RT for 3 h. LCMS showed the reaction was completed. The reaction mixture was neutralized with sodium carbonate solution and extracted with dichloromethane. The organic layer was dried over sodium sulfate, filtered and concentrated to afford the title compound as a light yellow solid (2.6 g, 86%), which was directly used in the next step without further purification. MS (ES+) $C_{10}H_{14}N_4O$ requires: 206, found: 207 $[M+H]^+$.

Synthesis of 1-(4-fluorophenyl)-1-(2-(piperazin-1-yl)pyrimidin-5-yl)ethanol

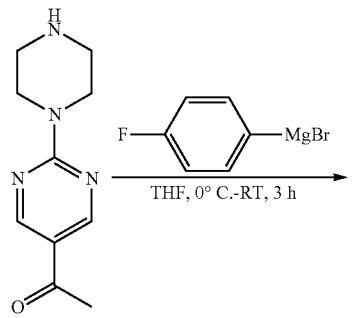

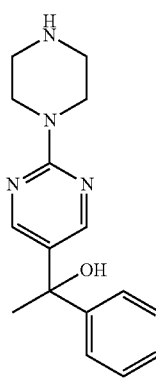

To a solution of 1-(2-(piperazin-1-yl)pyrimidin-5-yl)ethanone (1.8 g, 8.73 mmol) in dry THF (100 mL) was added (4-fluorophenyl)magnesium bromide (1 M in THF, 87.3 mL) at 0° C. under $N_2$. The mixture was stirred at RT for 3 h, then quenched with ammonium chloride solution and extracted with dichloromethane (300 mL). The organic layer was dried over sodium sulfate, filtered and concentrated. The residue was purified by Combi-flash (dicholomethane:methanol=10:1) to give the title compound (1.02 g, 38%) as a yellow solid.

Chiral separation of 1-(4-fluorophenyl)-1-(2-(piperazin-1-yl)pyrimidin-5-yl)ethanol

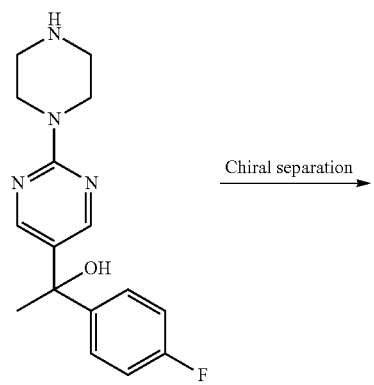

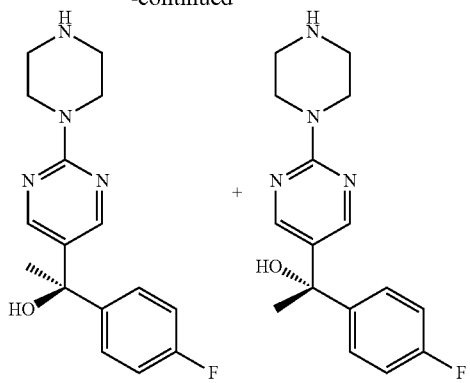

The racemate compound (1.02 g) was separated by chiral HPLC to afford enantiomer 1 (320 mg) and enantiomer 2 (220 mg). MS (ES+) $C_{16}H_{19}FN_4O$ requires: 302, found: 303 $[M+H]^+$. The absolute configuration was assigned randomly.

Chiral separation conditions: Chiral column: OZ—H (4.6*250 mm, 5um); Mobile phase: co-solvent EtOH (0.1% DEA)

Synthesis of (4-nitrophenyl)methanesulfonamide

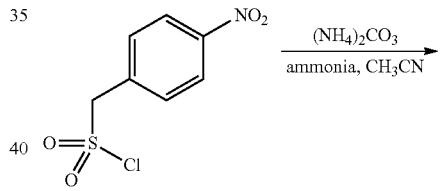

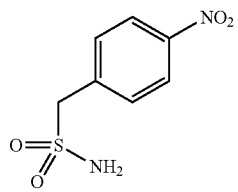

To a solution of (4-nitrophenyl)methanesulfonyl chloride (4 g, 17 mmol) in acetonitrile (100 mL) was added a solution of ammonium carbonate (3 g, 31.3 mmol) in ammonia (50 mL). The reaction mixture was stirred for 1 h, and TLC indicated the starting material consumed completely. The organic solvent was removed under reduced pressure. Addition of water (10 mL) led to precipitate formation. The solid was collected, washed with water (2×5 mL), and dried to give (4-nitrophenyl)methanesulfonamide (3.4 g, 93%) as a white solid. MS (ES+) $C_7H_8N_2O_4S$ requires: 216, found: 217 $[M+H]^+$.

Synthesis of 6-nitro-3,4-dihydro-1H-benzo[d][1,2]thiazine 2,2-dioxide

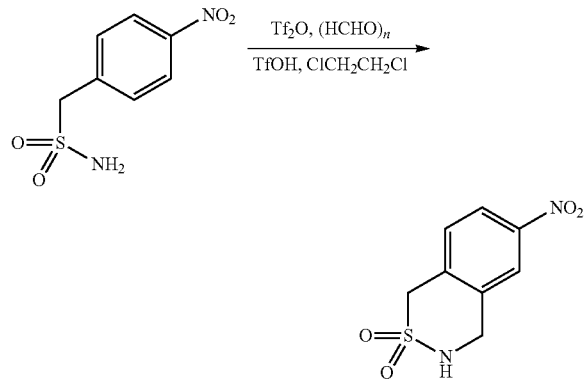

To a mixture of (4-nitrophenyl)methanesulfonamide (864 mg, 4.0 mmol) and s-trioxane (120 mg, 4.0 mmol) in 1,2-dichoroethane (10 mL) was added trifluoromethanesulfonic acid (1.5 mL), followed by the addition of trifluoromethanesulfonic anhydride (1.5 mL, 4.0 mmol). The reaction mixture was stirred at 35° C. for 2 hours and refluxed overnight. The mixture was then diluted with dichloromethane (100 mL) and washed with water (100 mL) and brine (50 mL). The solvents were evaporated and the residue was purified by Prep-HPLC to give 6-nitro-3,4-dihydro-1H-benzo[d][1,2]thiazine 2,2-dioxide (210 mg, 23%) as a gray solid. MS (ES+) $C_8H_8N_2O_4S$ requires: 228, found: 229 $[M+H]^+$.

Synthesis of tert-butyl 6-nitro-1,4-dihydro-3H-benzo[d][1,2]thiazine-3-carboxylate 2,2-dioxide

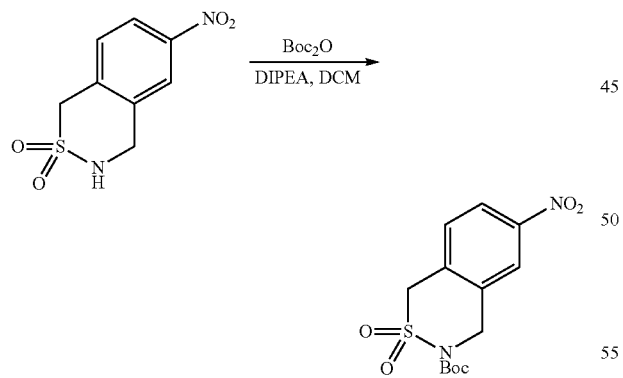

To a solution of compound 3 (40 mg, 0.17 mmol) and diisopropylethylamine (44 mg, 0.34 mmol) in dichloromethane (5 mL) was added di-tert-butyl dicarbonate (57 mg, 0.26 mmol). The mixture was then stirred at RT for 1 h, and then diluted with dichloromethane (100 mL). The organic layer was washed with water (100 mL) and brine (50 mL), concentrated and dried to give tert-butyl 6-nitro-1,4-dihydro-3H-benzo[d][1,2]thiazine-3-carboxylate 2,2-dioxide (crude, 60 mg) as a yellow solid. MS (ES+) $C_{13}H_{16}N_2O_6S$ requires: 328, found: 351 $[M+Na]^+$.

Synthesis of tert-butyl 6-Amino-1,4-dihydro-3H-benzo[d][1,2]thiazine-3-carboxylate 2,2-dioxide

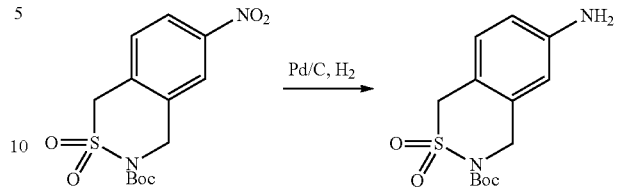

A suspension of compound 4 (220 mg, 0.738 mmol) and Pd/C (50 mg) in methanol (30 mL) was stirred at 80° C. under 1 atm hydrogen overnight. The reaction mixture was cooled to RT, and filtered through a pad of celite. The filtrate was concentrated to afford the tert-butyl 6-Amino-1,4-dihydro-3H-benzo[d][1,2]thiazine-3-carboxylate 2,2-dioxide (160 mg, 79.2%) as a white solid. MS (ES+) $C_{26}H_{34}N_4O_{10}S_2$ requires: 626, found: 627 $[M+H]^+$.

Synthesis of 5-bromo-2-chloropyrimidin-4-ol

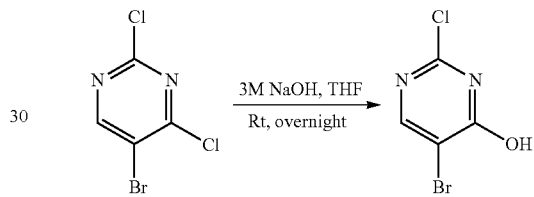

To a solution of 5-bromo-2,4-dichloropyrimidine (10 g, 44.2 mmol) in THF (135 mL) was added sodium hydroxide solution (3 M, 45 mL), and the mixture was stirred overnight at RT. The solvent was evaporated, and the residue was diluted with water (100 mL). The aqueous solution was cooled to 0° C., brought to pH 2-3 with 1 N HCl and then extracted with methanol/dichloromethane (5%, 5×100 mL). The organic layers were separated, combined, dried over sodium sulfate, filtered and concentrated to give 5-bromo-2-chloropyrimidin-4-ol (6.5 g, 71%) as a yellow solid. MS (ES+) $C_4H_2BrClN_2O$ requires: 208, 210, found: 209, 211 $[M+H]^+$.

Synthesis of tert-butyl 4-(5-bromo-4-hydroxypyrimidin-2-yl)piperazine-1-carboxylate

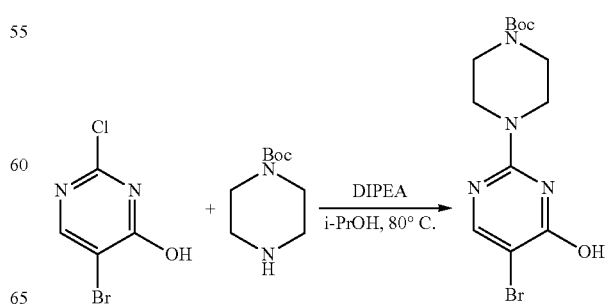

A solution of 5-bromo-2-chloropyrimidin-4-ol (6.5 g, 31 mmol), tert-butyl piperazine-1-carboxylate (6.5 g, 35 mmol) in propan-2-ol (200 mL) and diisopropylethylamine (10 mL) was stirred at 80° C. overnight. The mixture was cooled to RT and then concentrated. The residue was purified by silica gel chromatography eluting with ethyl acetate:petroleum ether (100:1) to give tert-butyl 4-(5-bromo-4-hydroxypyrimidin-2-yl)piperazine-1-carboxylate (9 g, 80%) as a yellow solid. MS (ES+) $C_{13}H_{19}BrN_4O_3$ requires: 358, 360, found: 303, 305 [M+H-56]$^+$.

Synthesis of 5-benzyl-2-(piperazin-1-yl)pyrimidin-4-ol

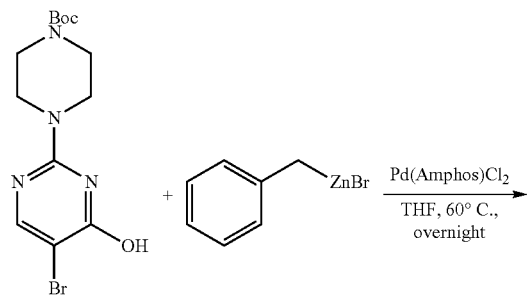

To a solution of tert-butyl 4-(5-bromo-4-hydroxypyrimidin-2-yl)piperazine-1-carboxylate (20 g, 56 mmol) and Pd(Amphos)Cl$_2$ (4.0 g 5.6 mmol) in THF (200 mL, dry) was added benzylzinc(II) bromide (168 mL, 168 mmol) under argon and the mixture was stirred at 60° C. overnight. The reaction mixture was diluted with ethyl acetate (1.5 L), filtered and the filtrate was concentrated under reduced pressure. The residue was purified by silica gel chromatography (petroleum ether/ethyl acetate=1:1 to 100% ethyl acetate) to give 5-benzyl-2-(piperazin-1-yl)pyrimidin-4-ol (8.2 g, 54%) as a pale yellow solid. MS (ES+) $C_{15}H_{18}N_4O$ requires: 270, found: 271 [M+H]$^+$.

Synthesis of tert-butyl 4-(5-benzyl-4-hydroxypyrimidin-2-yl)piperazine-1-carboxylate

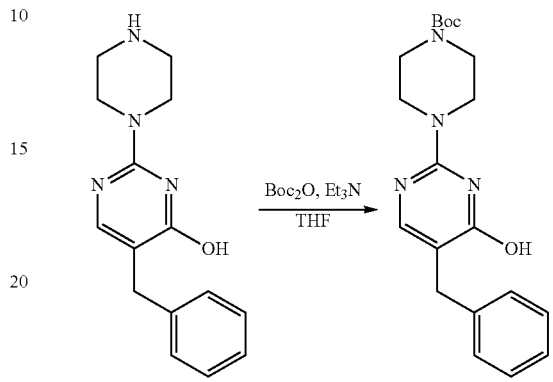

To a solution of 5-benzyl-2-(piperazin-1-yl)pyrimidin-4-ol (8.0 g, 29.5 mmol) and triethylamine (8.9 g, 88.5 mmol) in THF (90 mL) was added di-tert-butyl dicarbonate (7.7 g, 35.4 mmol). The mixture was stirred at RT overnight, and then diluted with ethyl acetate (300 mL). The organic phase was washed with water (300 mL) and brine (150 mL), dried over sodium sulfate, and evaporated under reduced pressure. The residue was purified by silica gel chromatography (petroleum ether/ethyl acetate=2:1 to 1:2) to give tert-butyl 4-(5-benzyl-4-hydroxypyrimidin-2-yl)piperazine-1-carboxylate (4.5 g, 41%) as a pale yellow solid. MS (ES+) $C_{20}H_{26}N_4O_3$ requires: 370, found: 371 [M+H]$^+$.

Synthesis of tert-butyl 4-(5-benzyl-4-(trifluoromethylsulfonyloxy)pyrimidin-2-yl)piperazine-1-carboxylate

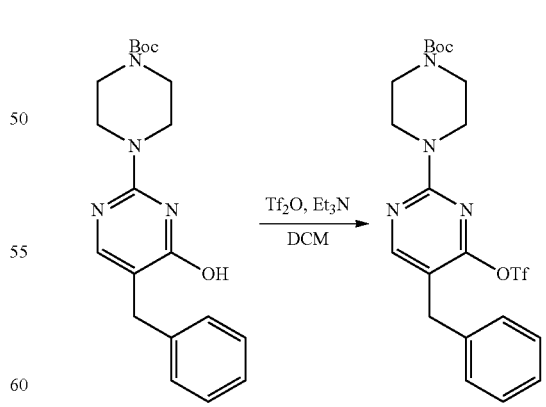

To a solution of tert-butyl 4-(5-benzyl-4-hydroxypyrimidin-2-yl)piperazine-1-carboxylate (4.3 g, 11.5 mmol), triethylamine (3.2 mL, 23 mmol) and N,N-dimethylpyridin-4-amine (183 mg, 1.15 mmol) in dichloromethane (40 mL) was added trifluoromethanesulfonic anhydride (2.3 mL, 13.9 mmol). The reaction mixture was stirred at RT for 1 h, and diluted with dichloromethane (200 mL). The organic phase was washed with water (200 mL) and brine (100 mL), dried over sodium sulfate, filtered and concentrated. The residue was purified by silica gel chromatography (petroleum ether/ ethyl acetate=10:1 to 5:1) to give tert-butyl 4-(5-benzyl-4-(trifluoromethylsulfonyloxy)pyrimidin-2-yl)piperazine-1-carboxylate (2.4 g, 41%) as a yellow oil. MS (ES+) $C_{21}H_{25}F_3N_4O_5S$ requires: 502, found: 525 [M+Na]$^+$ Synthesis of tert-butyl 4-(5-benzyl-4-methylpyrimidin-2-yl)piperazine-1-carboxylate

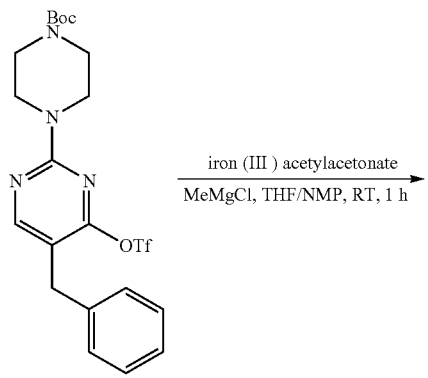

To a mixture of tert-butyl 4-(5-benzyl-4-(trifluoromethylsulfonyloxy)pyrimidin-2-yl)piperazine-1-carboxylate (280 mg, 0.56 mmol) and iron (III) acetylacetonate (21 mg, 0.06 mmol) in THF (5 mL, dry) and 1-methyl-2-pyrrolidinone (1 mL) was added methylmagnesium chloride (1.68 mL, 1.68 mmol). The reaction mixture was stirred at RT for 1 h, and diluted with ethyl acetate (100 mL) and sat. aq. NH$_4$Cl (100 mL). The organic layer was washed with brine (100 mL), dried over sodium sulfate, filtered and evaporated to give tert-butyl 4-(5-benzyl-4-methylpyrimidin-2-yl)piperazine-1- carboxylate (crude, 250 mg) as a yellow solid. MS (ES+) $C_{21}H_{28}N_4O_2$ requires: 368, found: 369 [M+H]$^+$.

Synthesis of 5-benzyl-4-methyl-2-(piperazin-1-yl)pyrimidine

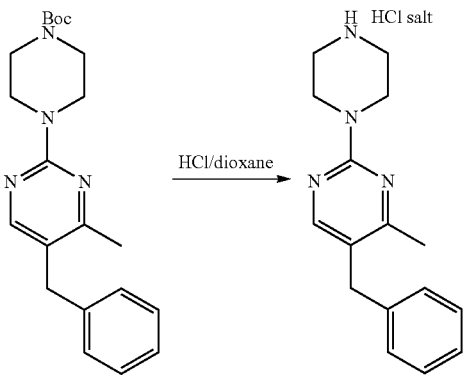 [SMILES: Cc1nc(N2CCN(C(=O)OC(C)(C)C)CC2)ncc1Cc1ccccc1 ; Cc1nc(N2CCNCC2)ncc1Cc1ccccc1]

To a solution of tert-butyl 4-(5-benzyl-4-methylpyrimidin-2-yl)piperazine-1-carboxylate (250 mg, 0.68 mmol) in dioxane (2 mL) was added 4 M HCl-dioxane (2 mL). The reaction mixture was stirred at RT for 2 h and then concentrated to afford crude 5-benzyl-4-methyl-2-(piperazin-1-yl)pyrimidine. MS (ES+) $C_{16}H_{20}N_4$ requires: 268, found: 269 [M+H]$^+$.

Synthesis of tert-butyl 4-(5-benzylpyrimidin-2-yl)-3-(hydroxymethyl)piperazine-1-carboxylate

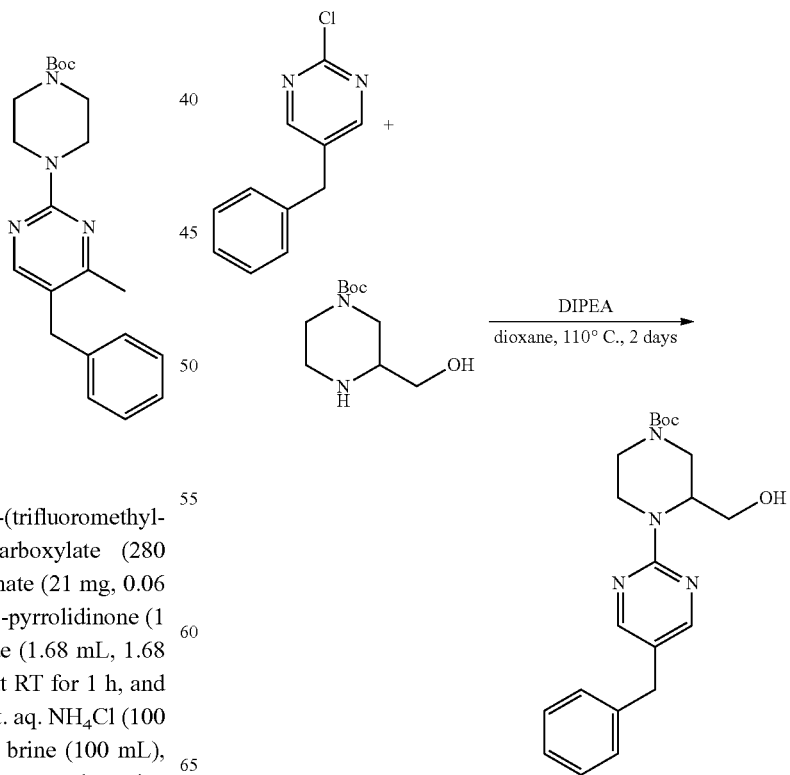

A solution of 5-benzyl-2-chloropyrimidine (944 mg, 4.626 mmol), tert-butyl 3-(hydroxymethyl)piperazine-1-carboxylate (1.0 g, 6.939 mmol) and diisopropylethylamine (1.8 g, 13.878 mmol) in dioxane (100 mL) was stirred at 110° C. for two days. The reaction mixture was cooled to room temperature, concentrated and directly purified by silica gel chromatography eluting with petroleum ether:ethyl acetate=1:1, to afford tert-butyl 4-(5-benzylpyrimidin-2-yl)-3-(hydroxymethyl)piperazine-1-carboxylate (400 mg, 15%) as a white solid. MS (ES+) $C_{21}H_{28}N_4O_3$ requires: 384, found: 385 $[M+H]^+$.

Synthesis of (1-(5-benzylpyrimidin-2-yl)piperazin-2-yl)methanol

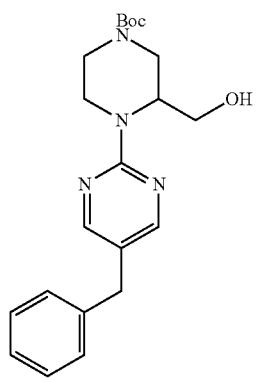

A solution of tert-butyl 4-(5-benzylpyrimidin-2-yl)-3-(hydroxymethyl)piperazine-1-carboxylate (400 mg, 1.042 mmol) in 4 M HCl/dioxane (20 mL) was stirred at room temperature for 2 h. The reaction mixture was concentrated under reduced pressure to afford (1-(5-benzylpyrimidin-2-yl) piperazin-2-yl)methanol HCl salt (294 mg, 100%). MS (ES+) $C_{16}H_{20}N_4O$ requires: 284, found: 285 $[M+H]^+$.

Synthesis of benzyl 4-(5-benzoylpyrimidin-2-yl) piperazine-1-carboxylate

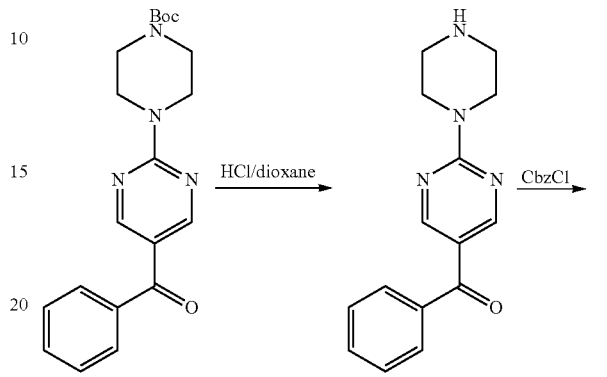

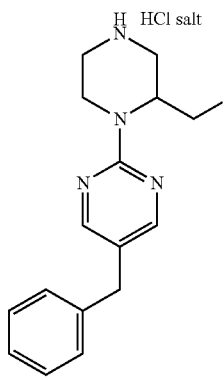

To a solution of tert-butyl 4-(5-benzoylpyrimidin-2-yl) piperazine-1-carboxylate (957 mg, 2.6 mmol) in dioxane (20 mL) was added 4 M HCl-dioxane (20 mL). The reaction mixture was stirred at room temperature overnight and concentrated to afford crude phenyl(2-(piperazin-1-yl)pyrimidin-5-yl)methanone which was used in the next step directly.

To a solution of phenyl(2-(piperazin-1-yl)pyrimidin-5-yl) methanone (crude, 2.6 mmol assumed) and triethylamine (780 mg, 7.8 mmol) in dichloromethane (10 mL) was added benzyl chloroformate (663 mg, 3.9 mmol). The reaction mixture was stirred at room temperature for 2 hours, and diluted with dichloromethane (100 mL). The organic phase was washed with water (100 mL) and brine (50 mL), dried over sodium sulfate, filtered and concentrated. The residue was purified by silica gel chromatography (etroleum ether/ ethyl acetate=4:1~2:1) to give benzyl 4-(5-benzoylpyrimidin-2-yl)piperazine-1-carboxylate (600 mg, 57%) as a yellow solid. MS (ES+) $C_{23}H_{22}N_4O_3$ requires: 402, found: 403 $[M+H]^+$.

Synthesis of benzyl 4-(5-(difluoro(phenyl)methyl)pyrimidin-2-yl)piperazine-1-carboxylate

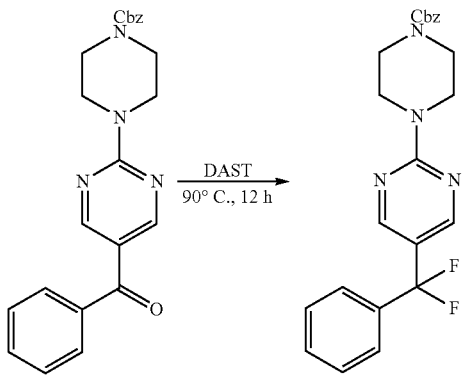

Benzyl 4-(5-benzoylpyrimidin-2-yl)piperazine-1-carboxylate (360 mg, 0.37 mmol) in diethylaminosulfur trifluoride (2 mL) was stirred at 90° C. overnight. The reaction mixture was diluted with ethyl acetate (100 mL), washed with sat. aq. sodium bicarbonate (100 mL) and brine (100 mL), and evaporated in vacuum. The residue was purified by silica gel chromatography (petroleum ether/ethyl acetate=10:1) to give benzyl 4-(5-(difluoro(phenyl)methyl)pyrimidin-2-yl)piperazine-1-carboxylate (180 mg, 47%) as a brown solid. MS (ES+) $C_{23}H_{22}F_2N_4O_2$ requires: 424, found: 425 [M+H]$^+$.

Synthesis of 5-(difluoro(phenyl)methyl)-2-(piperazin-1-yl)pyrimidine

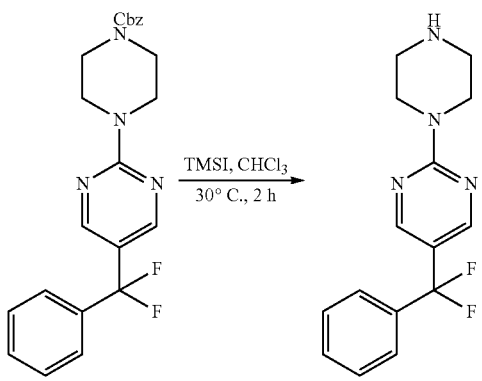 [SMILES: O=C(OCc1ccccc1)N1CCN(c2ncc(C(F)(F)c3ccccc3)cn2)CC1 ; FC(F)(c1ccccc1)c1cnc(N2CCNCC2)nc1]

To a solution of 4-(5-(difluoro(phenyl)methyl)pyrimidin-2-yl)piperazine-1-carboxylate (180 mg, 0.42 mmol) in chloroform (5.0 mL) was added iodotrimethylsilane (0.8 mL) and the mixture was stirred at room temperature for 0.5 h. The reaction was quenched by methanol (1.0 mL), followed by the addition of 2 N HCl/dioxane (2.0 mL) and evaporated to dryness. The residue was dissolved in methanol (1.5 mL) and dropwise added into acetone (100 mL). The solid was collected by filtration and washed with acetone (10 mL) to afford crude 5-(difluoro(phenyl)methyl)-2-(piperazin-1-yl)pyrimidine (88 mg) as a yellow solid. MS (ES+) $C_{15}H_{16}F_2N_4$ requires: 290, found: 291 [M+H]$^+$.

Synthesis of (S)-1-(5-methyl-4-nitro-1H-pyrazol-1-yl)propan-2-ol

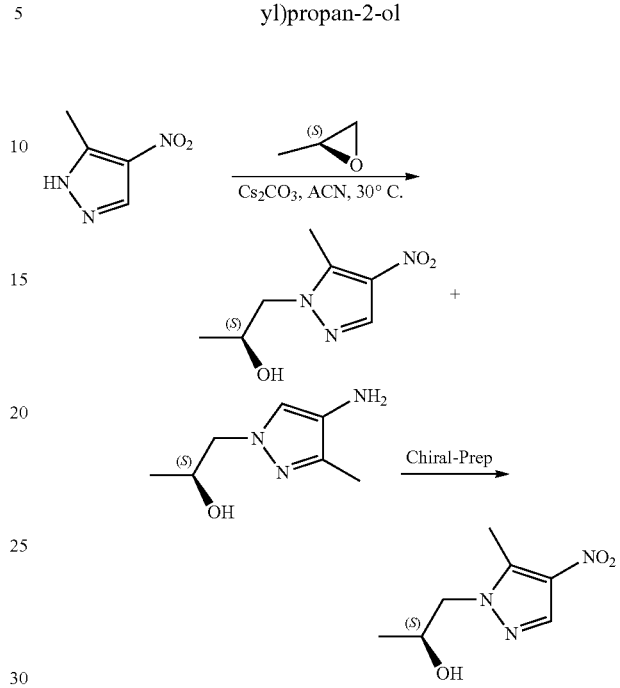

To a solution of 5-methyl-4-nitro-1H-pyrazole (2.5 g, 19.7 mmol) in acetonitrile (100 mL) was added (S)-2-methyloxirane (1.37 g, 23.6 mmol) and cesium carbonate (19.3 g, 59.1 mmol). The mixture was stirred at 30° C. for 7 days, then cooled to room temperature and filtered. The filtrate was concentrated under reduced pressure, and the residue was purified by Prep-HPLC and then chiral-HPLC to give (S)-1-(5-methyl-4-nitro-1H-pyrazol-1-yl)propan-2-ol (0.33 g) as a yellowish solid. MS (ES+) $C_7H_{11}N_3O_3$ requires: 185, found: 186 [M+H]$^+$.

Synthesis of (S)-1-(4-amino-5-methyl-1H-pyrazol-1-yl)propan-2-ol

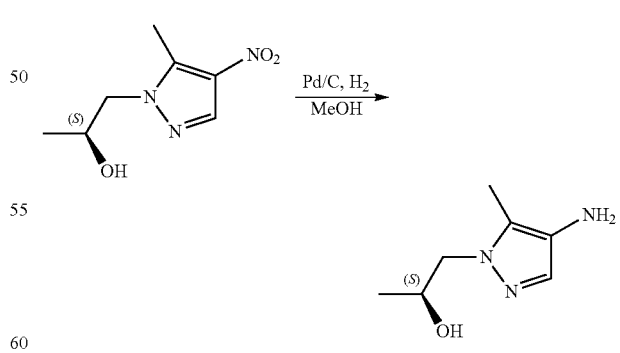

To a solution of (S)-1-(5-methyl-4-nitro-1H-pyrazol-1-yl)propan-2-ol (100 mg, 0.54 mmol) in methanol (20 mL) was added 10% Pd/C (20 mg). The reaction mixture was stirred under 1 atm H$_2$ atmosphere at room temperature overnight, and filtered through a pad of Celite. The filtrate was concentrated to give (S)-1-(4-amino-5-methyl-1H-pyrazol-1-yl)propan-2-ol (96 mg, crude) as a yellowish oil. MS (ES+) $C_7H_{13}N_3O$ requires: 155, found: 156 [M+H]⁺.

Synthesis of tert-butyl 4-(5-(1-phenylvinyl)pyrimidin-2-yl)piperazine-1-carboxylate

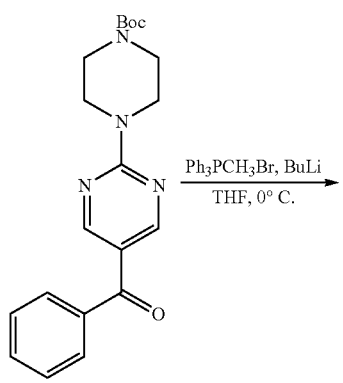

To a solution of Ph₃PCH₃Br (1.69 g, 5.45 mmol) in dry THF (20 mL) was added n-butyl lithium (2.06 mL, 2.5 M in hexane) at room temperature. The mixture was stirred for 1.5 h, and the yellow solution was directly used in the next reaction.

The above solution was added to a solution of tert-butyl 4-(5-benzoylpyrimidin-2-yl)piperazine-1-carboxylate (1 g, 2.7 mmol) in dry THF (20 mL) at 0° C., and the reaction solution was stirred at room temperature for 2 h. The reaction was quenched by water (20 mL) and extracted with ethyl acetate (200 mL). The organic layer was separated, dried over sodium sulfate, filtered and concentrated. The residue was purified by silica gel chromatography eluting with petroleum ether:ethyl acetate 10:1 to give tert-butyl 4-(5-(1-phenylvinyl)pyrimidin-2-yl)piperazine-1-carboxylate (890 mg, 89%) as a white solid. MS (ES+) $C_{21}H_{26}N_4O_2$ requires: 366, found: 367 [M+H]⁺.

Synthesis of tert-butyl 4-(5-(1-phenylcyclopropyl)pyrimidin-2-yl)piperazine-1-carboxylate

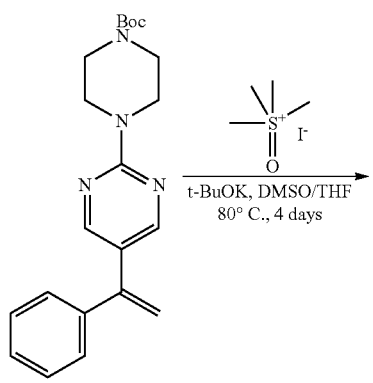

To a solution of tert-butyl 4-(5-(1-phenylvinyl)pyrimidin-2-yl)piperazine-1-carboxylate (366 mg, 1.0 mmol) in THF (20 mL) was added trimethylsulfoxonium iodide (1.1 g 5.0 mmol) in dimethyl sulfoxide (7 mL). The reaction mixture was stirred at 80° C. for 4 days, and diluted with ethyl acetate (200 mL). The organic phase was washed with water (200 mL) and brine (100 mL), dried over sodium sulfate, and concentrated. The residue was purified by silica gel chromatography (petroleum ether:ethyl acetate=20:1) to give tert-butyl 4-(5-(1-phenylcyclopropyl)pyrimidin-2-yl)piperazine-1-carboxylate (40 mg, 10%) as a yellow solid. MS (ES+) $C_{22}H_{28}N_4O_2$ requires: 380, found: 381 [M+H]⁺.

Synthesis of 5-(1-phenylcyclopropyl)-2-(piperazin-1-yl)pyrimidine

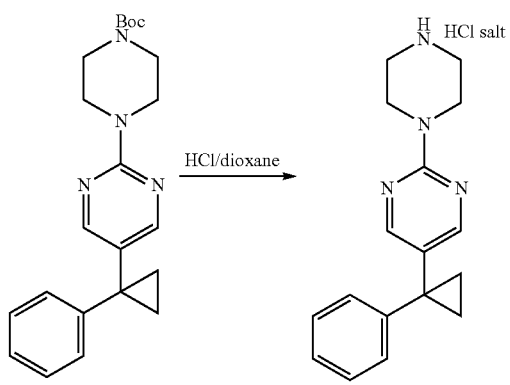 [SMILES: CC(C)(C)OC(=O)N1CCN(c2ncc(C3(c4ccccc4)CC3)cn2)CC1 ; c1ccc(C2(c3cnc(N4CCNCC4)nc3)CC2)cc1]

To a solution of tert-butyl 4-(5-(1-phenylcyclopropyl)pyrimidin-2-yl)piperazine-1-carboxylate (30 mg, 0.08 mmol) in dioxane (2 mL) was added 4 M HCl-dioxane (2 mL). The reaction mixture was stirred at room temperature overnight and then concentrated to afford crude 5-(1-phenylcyclopropyl)-2-(piperazin-1-yl)pyrimidin. MS (ES+) $C_{17}H_{20}N_4$ requires: 280, found: 281 [M+H]⁺.

Synthesis of (S,Z)-tert-butyl 4-(5-((tert-butylsulfinylimino)(4-fluorophenyl)methyl)pyrimidin-2-yl)piperazine-1-carboxylate

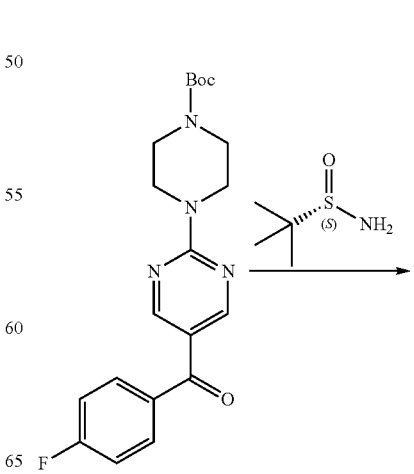

-continued

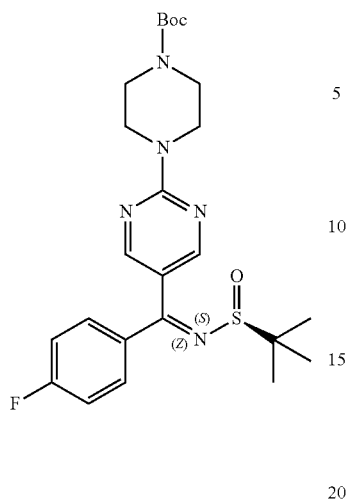

To a solution of tert-butyl 4-(5-(4-fluorobenzoyl)pyrimidin-2-yl)piperazine-1-carboxylate (4.0 g, 10.4 mmol), (S)-2-methylpropane-2-sulfinamide (2.5 g, 20.7 mmol) in THF (60 mL) was added titanium ethoxide (20 mL) at room temperature. The resultant solution was heated at 70° C. overnight. After that, the reaction was cooled to room temperature, diluted with ethyl acetate (200 mL) and saturated aqueous sodium bicarbonate (500 mL). The mixture was filtered through Celite. The filtrate was separated. Aqueous layer was extracted with ethyl acetate (200 mL×3). Then organic layers were combined, dried over sodium sulfate, filtered and concentrated in vacuo. The residue was purified by silica gel column (petroleum ether:ethyl acetate 2:1) to afford the title compound (3.3 g, yield 66%) as a yellow solid. MS (ES+) requires: 489, found 490 [M+H]$^+$; purity: 95% (UV at 254 nm).

Synthesis of tert-butyl 4-(5-(1-((S)-1,1-dimethylethylsulfinamido)-1-(4-fluorophenyl)ethyl)pyrimidin-2-yl)piperazine-1-carboxylate

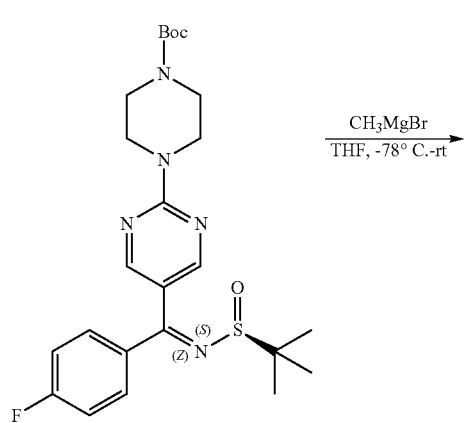

-continued

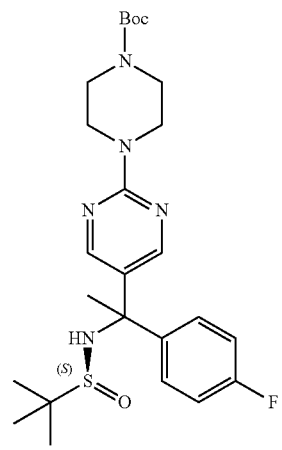

To a solution of (S,Z)-tert-butyl 4-(5-((tert-butylsulfinylimino)(4-fluorophenyl)methyl)pyrimidin-2-yl)piperazine-1-carboxylate (3.0 g, 6.1 mmol) in THF (20 mL) was dropwise added methyl magnesium bromide (2.1 mL, 6.1 mmol, 3 M in ethyl ether) slowly at −60° C. under nitrogen. After addition, the mixture was allowed to warm to room temperature and stirred for 2 h. Then, the reaction was quenched by methanol (20 mL) and saturated aqueous ammonium chloride (50 mL), and extracted with ethyl acetate (50 mL×3). The combined organic layers were dried over sodium sulfate, filtered and concentrated in vacuo. The residue was purified by silica gel column (dichloromethane:methanol=40:1) to give the title compound 3 (2.5 g, yield 77%) as a yellow solid. MS (ES+) requires: 505, found 506 [M+Na]$^+$; purity: 100% (UV at 254 nm).

Preparation of (S)-1-(4-fluorophenyl)-1-(2-(piperazin-1-yl)pyrimidin-5-yl)ethanamine

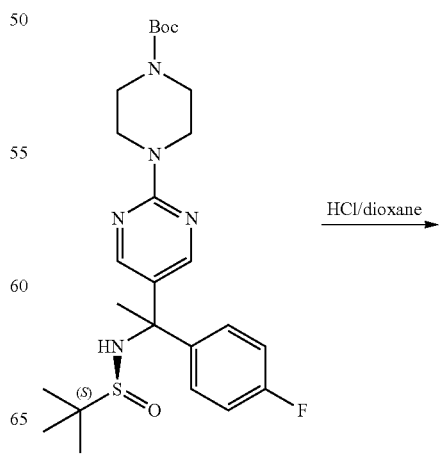

-continued

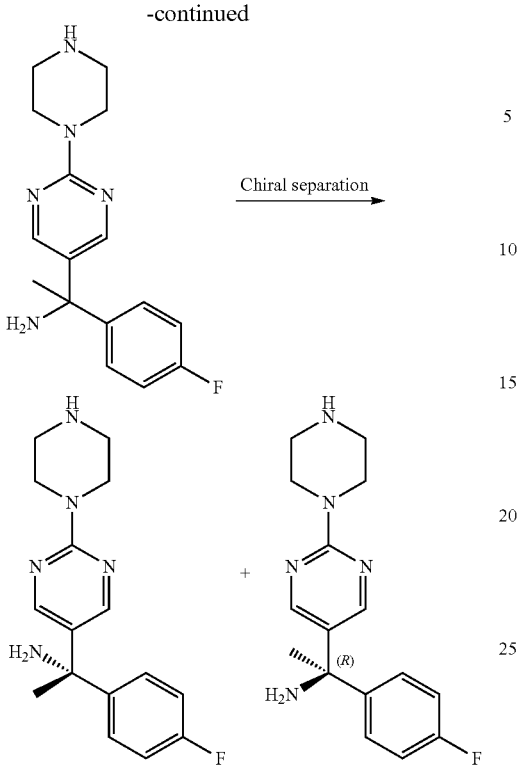

To a solution of tert-butyl 4-(5-(1-((S)-1,1-dimethylethyl-sulfinamido)-1-(4-fluorophenyl)ethyl)pyrimidin-2-yl)piperazine-1-carboxylate (2.5 g, 5.0 mmol) in dioxane (5.0 mL) was dropwise added HCl (4M in dioxane, 10 mL). The reaction solution was stirred at room temperature overnight. Then the solution was concentrated under vacuo to give the title compound (1.5 g, crude yield 100%) as a yellow solid. MS (ES+) $C_{16}H_{20}FN_5$ requires: 301, found 302 $[M+H]^+$; purity: 100% (UV at 254 nm). The above racemate (1.5 g) was separated by Chiral-HPLC to afford the desired single enantiomer (600 mg, 40%) as a yellow solid. MS (ES+) $C_{16}H_{20}FN_5$ requires: 301, found: 302 $[M+H]^+$.

The synthetic protocol that can be used to prepare the compounds disclosed herein is shown below. The NMR and LC MS data obtained for compounds disclosed herein are also shown below.

| Compound Number | Synthetic Protocol | $^1$H NMR | LC/MS M + 1 |
|---|---|---|---|
| 4 | 3 | This spectrum contains some rotamers in the aromatic region - 1H NMR (400 MHz, DMSO-d6) δ 12.54 (s, 1H), 9.52 (d, J = 61.6 Hz, 2H), 8.30 (s, 2H), 8.14 (s, 1H), 7.82 (s, 1H), 7.55 (d, J = 21.1 Hz, 1H), 7.34-7.11 (m, 5H), 3.80 (q, J = 9.2, 7.5 Hz, 10H). | 416 |
| 5 | 3 | | 416 |
| 6 | 2 | $^1$H-NMR (500 MHz, DMSO-d$_6$) δ ppm 9.66, 9.53 (s, s, 1H), 8.40 (d, 2H, J = 4.5 Hz), 8.31, 8.17 (s, s, 1H), 7.84 (s, 1H), 7.51, 7.50 (s, s, 1H), 6.68 (t, 1H, J = 5.0 Hz), 4.11-4.07 (m, 2H), 3.86-3.66 (m, 10H), 3.39-3.34 (m, 1H), 2.67-2.64 (m, 3H), 2.38-2.34 (br, 1H). | |
| 7 | 3 | 1H NMR (400 MHz, DMSO-d6) δ 9.75-9.62 (m, 1H), 8.31 (s, 2H), 8.26 (s, 1H), 7.75-7.66 (m, 2H), 7.37-7.13 (m, 7H), 7.04-6.93 (m, 1H), 3.93-3.68 (m, 10H). | 426 |
| 9 | 5 | | 426 |
| 10 | 3 | This spectrum contains some rotamers in the aromatic region: 1H NMR (400 MHz, DMSO-d6) δ 9.62, 9.48 (s, 1H), 8.31, 8.26 (s, 2H), 8.14 (s, 1H), 7.82, 7.78 (s, 1H), 7.47, 7.42 (s, 1H), 7.34-7.11 (m, 5H), 3.87-3.71 (m, 10H). | 429 |
| 11 | 3 | $^1$H NMR (400 MHz, DMSO-d6) δ 10.42 (s, 1H), 8.31 (m, 3H), 7.34-7.15 (m, 5H), 6.71 (s, 1H), 3.81 (m, 10H), 3.41-3.22 (m, 2H), 2.40 (m, 3H). | 430 |
| 12 | 3 | $^1$H NMR (400 MHz, DMSO-d6) δ 9.38 (s, 1H), 8.31 (d, J = 1.0 Hz, 2H), 8.22 (s, 1H), 7.34-7.14 (m, 5H), 7.06 (s, 1H), 6.91 (t, J = 7.9 Hz, 1H), 6.82-6.76 (m, 1H), 6.27-6.19 (m, 1H), 5.12 (s, 2H), 3.89-3.72 (m, 10H). | 440 |
| 13 | 3 | $^1$H NMR (400 MHz, DMSO-d6) δ 9.60 (s, 1H), 8.31 (s, 2H), 8.25 (s, 1H), 7.99 (d, J = 2.1 Hz, 1H), 7.58 (d, J = 2.4 Hz, 1H), 7.44 (t, J = 2.4 Hz, 1H), 7.33-7.14 (m, 5H), 5.37 (s, 2H), 3.80 (m, 10H). | 441 |
| 14 | 3 | $^1$H NMR (400 MHz, DMSO-d6) δ 9.62 (s, 1H), 8.31 (s, 2H), 8.25 (s, 1H), 7.78 (s, 1H), 7.45 (d, J = 8.1 Hz, 1H), 7.35-7.14 (m, 6H), 6.96 (d, J = 7.6 Hz, 1H), 3.87-3.74 (m, 10H), 3.70 (s, 2H). | 454 |
| 15 | 3 | $^1$H NMR (400 MHz, DMSO-d6) δ 9.66 (s, 1H), 8.31 (s, 2H), 8.25 (s, 1H), 7.83 (s, 1H), 7.47 (d, J = 8.1 Hz, 1H), 7.34-7.13 (m, 6H), 6.92 (d, J = 7.5 Hz, 1H), 5.17 (t, J = 5.7 Hz, 1H), 4.47 (d, J = 5.7 Hz, 2H), 3.91-3.70 (m, 10H). | 455 |
| 16 | 3 | $^1$H NMR (400 MHz, DMSO-d6) δ 9.64 (s, 1H), 8.31 (s, 2H), 8.25 (s, 1H), 7.64 (dd, J = 8.6, 2.4 Hz, 2H), 7.35-7.14 (m, 7H), 4.43 (s, 2H), 3.90-3.72 (m, 10H). | 455 |

-continued

| Compound Number | Synthetic Protocol | ¹H NMR | LC/MS M + 1 |
|---|---|---|---|
| 17 | 3 | ¹H-NMR (400 MHz, DMSO-d₆) δ ppm 10.05 (s, 1H), 8.36 (s, 1H), 8.32 (s, 2H), 7.98 (d, 1H, J = 5.6 Hz), 7.31-7.18 (m, 7H), 3.86-3.76 (m, 13H). | |
| 19 | 1 | ¹H-NMR (400 MHz, DMSO-d₆) δ ppm 9.67, 9.53 (s, s, 1H), 8.29-8.16 (m, 3H), 7.83 (s, 1H), 7.51-7.48 (m, 1H), 4.21-4.05 (m, 2H), 3.83-3.68 (m, 11H), 3.51-3.42 (m, 1H), 2.82-2.63 (m, 3H), 2.45-2.39 (m, 1H), 1.80-1.76 (m, 1H), 0.89-0.86 (m, 2H), 0.66-0.63 (m, 2H). | |
| 22 | 3 | ¹H NMR (400 MHz, DMSO-d6) δ 9.90 (s, 1H), 8.53 (br. s, 1H), 8.31 (s, 2H), 8.29 (s, 1H), 7.82 (d, J = 8.0 Hz, 1H), 7.61 (dd, J = 7.8, 1.7 Hz, 1H), 7.45 (t, J = 7.9 Hz, 1H), 7.29 (t, J = 7.4 Hz, 2H), 7.25-7.14 (m, 3H), 3.94-3.72 (m, 14H), 2.57 (s, 3H). | 467 |
| 23 | 3 | ¹H NMR (400 MHz, DMSO-d6) δ 9.99 (s, 1H), 8.39 (s, 1H), 8.32 (d, J = 1.4 Hz, 2H), 7.91 (s, 1H), 7.70 (dd, J = 8.0, 2.2 Hz, 1H), 7.56-7.48 (m, 1H), 7.44-7.12 (m, 6H), 3.94-3.69 (m, 10H). | 468 |
| 24 | 3 | ¹H NMR (400 MHz, DMSO-d6) δ 9.91 (s, 1H), 8.31 (s, 3H), 7.88-7.72 (m, 5H), 7.35-7.12 (m, 6H), 3.91-3.73 (m, 10H). | 468 |
| 25 | 3 | | 468 |
| 26 | 3 | ¹H NMR (400 MHz, DMSO-d6) δ 9.64 (s, 1H), 8.31 (s, 2H), 8.25 (s, 1H), 7.90 (s, 1H), 7.41 (s, 1H), 7.32-7.25 (m, 2H), 7.25-7.15 (m, 4H), 6.95 (d, J = 7.5 Hz, 1H), 5.14 (d, J = 4.0 Hz, 1H), 4.73-4.64 (m, 1H), 3.82 (d, J = 21.7 Hz, 10H), 1.31 (d, J = 6.4 Hz, 3H). | 469 |
| 27 | 3 | ¹H-NMR (500 MHz, DMSO-d₆) δ 9.72, 9.59 (br. s., br. s., 1H), 8.32-8.30 (m, 2H), 8.17 (s, 1H), 7.99-7.96 (m, 1H), 7.61-7.55 (m, 1H), 7.31-7.18 (m, 5H), 5.22-5.13 (m, 1H), 4.34-3.69 (m, 15H). | |
| 28 | 3 | ¹H-NMR (500 MHz, DMSO-d₆) δ 9.72, 9.58 (s, s, 1H), 8.32-8.29 (m, 2H), 8.17 (s, 1H), 8.00, 7.94 (s, s, 1H), 7.67, 7.61 (s, s, 1H), 7.35-7.15 (m, 5H), 5.66-5.44 (m, 1H), 4.96-4.79 (m, 4H), 3.84-3.78 (m, 10H). | |
| 29 | 4 | ¹H-NMR (400 MHz, DMSO-d6) δ ppm 9.70 (s, 1H), 8.39 (s, 2H), 8.27 (s, 1H), 7.72-7.70 (m, 2H), 7.48-7.44 (m, 2H), 7.32-7.29 (m, 2H), 7.13-7.08 (m, 2H), 7.00 (t, 1H, J = 7.6 Hz), 3.85-3.72 (m, 8H), 2.55 (br, 2H), 1.72 (s, 3H). | 472 |
| 30 | 3 | This spectrum contains some rotamers in the aromatic region: 1H NMR (400 MHz, DMSO-d6) δ 9.61 , 9.48 (s, 1H), 8.30, 8.23 (s, 2H), 8.14 (s, 1H), 7.87, 7.85 (s, 1H), 7.47, 7.45 (s, 1H), 7.32-7.13 (m, 5H), 4.13 (t, J = 6.1 Hz, 2H), 3.79 (m, 10H), 2.82 (t, J = 6.0 Hz, 2H), 2.27 (s, 3H). | 472 |
| 31 | 3 | ¹H-NMR (500 MHz, DMSO-d₆) δ ppm 9.63, 9.48 (s, s, 1H), 8.32 (s, 2H), 8.16 (s, 1H), 7.86 (s, 1H), 7.49 (s, 1H), 7.29-7.19 (m, 5H), 4.25-4.19 (m, 2H), 3.94-3.79 (m, 10H), 3.66 (s, 2H), 3.25 (s, 3H). | |
| 32 | 3 | ¹H-NMR (500 MHz, DMSO-d₆) δ ppm 8.33-8.27 (m, 3H), 8.15, 8.05 (s, s, 1H), 7.90, 7.88 (s, s, 1H), 7.49 (s, 1H), 7.32-7.20 (m, 5H), 4.03-3.90 (m, 3H), 3.80 (m, 11H), 1.04 (d, 3H, J = 6.0 Hz). | |
| 33 | 3 | ¹H-NMR (500 MHz, DMSO-d₆) δ ppm 8.34-8.26 (m, 3H), 8.15 (s, 1H), 7.90, 7.87 (s, s, 1H), 7.49 (s, 1H), 7.31-7.20(m, 5H), 4.01-3.94 (m, 3H), 3.82-3.74 (m, 11H), 1.03 (d, 3H, J = 6.0 Hz). | |
| 36 | 4 | ¹H NMR (400 MHz, DMSO-d6) δ ppm 9.64, 9.50 (s, 1H), 8.38 (s, 2H), 8.27, 8.14 (s, 1H), 7.82, 7.79 (s, 1H), 7.47-7.43 (m, 3H), 7.11-7.07 (m, 2H), 3.82-3.77 (m, 11H), 2.49 (s, 2H), 1.71 (s, 3H). | 477 |
| 37 | 2 | | 476 |
| 38 | 4 | ¹H-NMR (400 MHz, CDCl3) δ ppm 8.35 (s, 2H), 8.21 (br. s., 1H), 7.80, 7.22 (br. s., br. s., 1H), 7.61-7.55 (m, 1H), 7.43-7.38 (m, 2H), 7.04-7.00 (m, 2H), 3.90 (br. s., 11H), 2.30 (br. s., 1H), 1.92 (s, 3H). | 477 |
| 39 | 4 | ¹H-NMR (400 MHz, CDCl3) δ ppm 8.35 (s., 2H), 8.20 (br. s., 1H), 7.77, 7.32 (br. s., br. s., 1H), 7.61-7.56 (m, 1H), 7.42-7.38 (m, 2H), 7.05-7.00 (m, 2H), 3.89 (br. s., 11H), 2.32 (br. s., 1H), 1.92 (s., 3H). | 477 |
| 41 | 3 | ¹H NMR (400 MHz, DMSO-d6) δ 9.55 (s, 1H), 8.31, 8.30 (s, 2H), 8.24 (s, 1H), 7.42 (s, 1H), 7.37 (dd, J = 8.2, 2.3 Hz, 1H), 7.34-7.25 (m, 2H), 7.25-7.15 (m, 3H), 6.99 (d, J = 8.4 Hz, 1H), 3.89-3.71 (m, 12H), 2.96 (t, J = 5.9 Hz, 2H), 2.64 (t, J = 5.9 Hz, 2H). | 480 |
| 42 | 3 | | 480 |
| 43 | 3 | ¹H NMR (400 MHz, DMSO-d6) δ 9.73 (s, 1H), 8.61, 8.56 (s, 1H), 8.32, 8.30 (s, 2H), 8.27 (s, 1H), 7.86-7.73 (m, 1H), 7.35-7.14 (m, 5H), 3.97-3.65 (m, 12H), 3.00 (t, J = 6.0 Hz, 1H), 2.94-2.79 (m, 2H), 2.70 (t, J = 5.8 Hz, 1H). | 481 |
| 44 | 1 | ¹H NMR (400 MHz, DMSO-d6) δ 9.56 (s, 1H), 8.52-8.42 (m, 1H), 8.35 (s, 2H), 8.24 (s, 1H), 7.76-7.67 (m, 2H), 7.48-7.34 (m, 2H), 7.31 (d, J = 7.7 Hz, 1H), 7.21 (dd, J = 7.5, 4.7 Hz, 1H), 7.01 (d, J = 8.3 Hz, 1H), 3.94 (s, 2H), 3.88 (s, 2H), 3.80 (br. s., 8H), 3.00 (t, J = 6.0 Hz, 2H), 2.67 (t, J = 5.9 Hz, 2H). | 481 |
| 45 | 1 | ¹H-NMR (500 MHz, DMSO-d₆) δ ppm 9.55 (br, 1H), 8.52 (s, 1H), 8.42 (d, 1H, J = 4.5 Hz), 8.35 (s, 2H), 8.24 (s, 1H), 7.64 (d, 1H, J = | |

| Compound Number | Synthetic Protocol | ¹H NMR | LC/MS M + 1 |
|---|---|---|---|
| | | 8.0 Hz), 7.41 (s, 1H), 7.37 (d, 1H, J = 8.0 Hz), 7.31 (dd, 1H, J = 8.0, 4.7 Hz), 6.99 (d, 1H, J = 8.0 Hz), 3.83 (br. s., 12H), 2.95 (d, 2H, J = 6.0 Hz), 2.63 (t, 2H, J = 6.0 Hz). | |
| 46 | 5 | ¹H NMR (400 MHz, Methanol-d4) δ 8.22 (s, 3H), 7.61-7.48 (m, 2H), 7.39-7.29 (m, 2H), 7.22 (d, J = 8.4 Hz, 1H), 7.09 (tt, J = 7.3, 1.1 Hz, 1H), 7.00-6.92 (m, 2H), 4.36 (s, 2H), 3.98-3.84 (m, 8H), 3.51 (t, J = 6.4 Hz, 2H), 3.09 (t, J = 6.4 Hz, 2H). | 482 |
| 47 | 3 | ¹H NMR (400 MHz, DMSO-d6) δ 9.87 (s, 1H), 9.65 (s, 1H), 8.31 (s, 2H), 8.24 (s, 1H), 7.38-7.01 (m, 9H), 3.82 (m, 10H), 2.03 (s, 3H). | 482 |
| 48 | 3 | ¹H NMR (400 MHz, DMSO-d6) δ 9.66 (s, 1H), 8.31 (s, 2H), 8.25 (d, J = 2.0 Hz, 2H), 7.85 (s, 1H), 7.43 (s, 1H), 7.34-7.14 (m, 6H), 6.98 (d, J = 7.6 Hz, 1H), 3.87-3.75 (m, 10H), 3.65 (q, J = 6.5 Hz, 1H), 2.18 (s, 3H), 1.28 (d, J = 6.6 Hz, 3H). | 482 |
| 49 | 3 | ¹H NMR (400 MHz, DMSO-d6) δ 9.65 (s, 1H), 8.31 (s, 2H), 8.25 (s, 1H), 7.86 (s, 1H), 7.45 (d, J = 8.4 Hz, 1H), 7.33-7.14 (m, 6H), 6.89 (d, J = 7.5 Hz, 1H), 3.93-3.70 (m, 10H), 3.34 (s, 2H), 2.15 (s, 6H). | 482 |
| 50 | 3 | ¹H NMR (400 MHz, DMSO-d6) δ 9.62 (s, 1H), 8.31 (s, 2H), 8.24 (s, 1H), 7.36 (s, 1H), 7.28 (t, J = 7.4 Hz, 2H), 7.21 (m, 4H), 7.09 (d, J = 7.6 Hz, 1H), 4.97 (s, 1H), 3.82 (m, 10H), 3.65-3.53 (m, 3H), 3.19-3.07 (m, 3H), 1.42 (s, 6H). | 483 |
| 51 | 3 | This spectrum contains some rotamers in the aromatic region: 1H NMR (400 MHz, DMSO-d6) δ 9.61, 9.47 (s, 1H), 8.30, 8.25 (s, 2H), 8.13 (s, 1H), 7.81 (s, 1H), 7.45 (d, J = 11.5 Hz, 1H), 7.32-7.13 (m, 5H), 4.25 (dd, J = 23.2, 7.4 Hz, 2H), 3.88-3.70 (m, 10H), 3.53-3.42 (m, 2H), 3.05-2.85 (m, 2H) - one peak is obscured partially by the water signal. | 484 |
| 52 | 3 | This spectrum contains some rotamers in the aromatic region: 1H NMR (400 MHz, DMSO-d6) δ 9.68-9.45 (m, 1H), 8.35-8.23 (m, 2H), 8.14 (d, J = 4.5 Hz, 1H), 7.89 (s, 1H), 7.48 (d, J = 18.8 Hz, 1H), 7.31-7.14 (m, 5H), 4.91-4.77 (mz, 1H), 3.90-3.67 (m, 10H), 3.20-3.10 (m, 1H), 3.07-2.80 (m, 3H), 2.76-2.58 (m, 0H), 2.40-2.22 (m, 1H), 2.17 (dd, J = 13.8, 7.2 Hz, 1H), 1.98 (s, 1H). | 484 |
| 53 | 3 | This spectrum contains some rotamers in the aromatic region: 1H NMR (400 MHz, DMSO-d6) δ 9.71-9.44 (m, 1H), 8.35-8.22 (m, 2H), 8.13 (d, J = 2.8 Hz, 1H), 7.94-7.82 (m, 1H), 7.57-7.39 (m, 1H), 7.33-7.11 (m, 5H), 4.92-4.75 (m, 1H), 3.89-3.70 (m, 10H), 3.08-2.94 (m, 1H), 2.94-2.76 (m, 2H), 2.76-2.60 (m, 1H), 2.40-2.24 (m, 1H), 2.23-2.07 (m, 1H), 2.07-1.89 (m, 1H). | 484 |
| 54 | 3 | | 485 |
| 55 | 3 | ¹H NMR (400 MHz, DMSO-d6) δ 9.51 (s, 1H), 8.32 (s, 2H), 7.56 (d, J = 8.5 Hz, 2H), 7.37-7.08 (m, 5H), 6.89 (d, J = 8.5 Hz, 2H), 4.92 (d, J = 4.9 Hz, 1H), 4.65 (t, J = 5.6 Hz, 1H), 3.96 (dd, J = 9.5, 4.0 Hz, 1H), 3.80 (m, 10H), 3.44 (t, J = 5.5 Hz, 2H). | 485 |
| 56 | 3 | ¹H-NMR (400 MHz, DMSO-d6) δ ppm 9.64 (s, 1H), 8.31 (s, 2H), 8.25 (s, 1H), 7.63 (d, 2H, J = 8.4 Hz), 7.31-7.17 (m, 7H), 5.15 (d, 1H, J = 4.0 Hz), 4.69 (t, 1H, J = 5.6 Hz), 4.49 (dd, 1H, J = 10 Hz, J = 5.6 Hz), 3.83-3.80 (m, 10H), 3.39 (t, 1H, J = 5.6 Hz). | 485 |
| 57 | 3 | ¹H-NMR (400 MHz, DMSO-d6) δ ppm 9.65 (s, 1H), 8.32 (s, 2H), 8.26 (s, 1H), 7.63 (d, 2H, J = 8.4 Hz), 7.31-7.17 (m, 7H), 5.15 (d, 1H, J = 4.0 Hz), 4.69 (t, 1H, J = 5.6 Hz), 4.49 (dd, 1H, J = 10 Hz, J = 5.6 Hz), 3.83-3.80 (m, 10H), 3.41 (t, 1H, J = 5.6 Hz). | 485 |
| 58 | 3 | ¹H NMR (400 MHz, DMSO-d6) δ 9.33 (s, 1H), 8.31 (s, 2H), 8.17 (s, 1H), 7.62 (s, 1H), 7.29 (mz, 2H), 7.26-7.14 (m, 3H), 6.49 (d, J = 8.9 Hz, 1H), 6.30 (t, J = 5.8 Hz, 1H), 4.70 (t, J = 5.3 Hz, 1H), 3.78 (m, 10H), 3.55-3.46 (m, 2H) - one peak obscured by water signal. | 485 |
| 60 | 3 | ¹H NMR (400 MHz, DMSO-d6) δ 9.61 (s, 1H), 8.31 (s, 2H), 8.13 (d, J = 7.8 Hz, 1H), 7.87 (d, J = 13.9 Hz, 1H), 7.45 (s, 1H), 7.30-7.15 (m, 5H), 4.22-4.13 (m, 2H), 3.81 (d, J = 15.3 Hz, 10H), 2.59 (t, J = 6.3 Hz, 2H), 2.20-2.11 (m, 6H). | 486 |
| 61 | 3 | This spectrum contains some rotamers in the aromatic region: ¹H NMR (400 MHz, DMSO-d6) δ 9.61, 9.48 (s, 1H), 8.30, 8.27 (s, 2H), 8.14 (s, 1H), 7.87, 7.84 (s, 1H), 7.47, 7.45 (s, 1H), 7.31-7.25 (m, 2H), 7.24-7.15 (m, 3H), 4.20-4.02 (m, 3H), 3.79 (t, J = 11.9 Hz, 12H), 2.82 (t, J = 6.0 Hz, 2H), 2.27 (s, 3H). | 486 |
| 62 | 3 | ¹H-NMR (400 MHz, DMSO-d₆) δ ppm 9.64, 9.52 (s, s, 1H), 8.32 (s, 2H), 8.16 (s, 1H), 7.94, 7.90 (s, s, 1H), 7.45 (s, 1H), 7.34-7.26 (m, 2H), 7.25-7.14 (m, 3H), 4.71, 4.69 (s, s, 1H), 3.99, 3.97 (s, s, 2H), 3.82-3.77 (m, 10H), 1.05 (s, 6H). | |
| 63 | 6 | ¹H-NMR (400 MHz, DMSO-d₆) δ ppm 9.67, 9.54 (s, s, 1H), 8.42 (s, 2H), 8.29, 8.16 (s, s, 1H), 7.82 (s, 1H), 7.50, 7.48 (s, s, 1H), 4.13-4.04 (m, 2H), 3.85-3.69 (m, 11H), 3.44-3.39 (m, 1H), 2.77- | |

-continued

| Compound Number | Synthetic Protocol | ¹H NMR | LC/MS M + 1 |
|---|---|---|---|
| | | 2.63 (m, 3H), 2.42-2.37 (m, 1H), 1.56-1.52 (m, 1H), 0.89-0.85 (m, 2H), 0.73-0.69 (m, 2H). | |
| 64 | 3 | ¹H-NMR (500 MHz, DMSO-d₆) δ ppm 9.62, 9.49 (s, s, 1H), 8.32 (s, 2H), 8.28, 8.15 (s, s, 1H), 7.90, 7.86 (s, s, 1H), 7.49 (s, 1H), 7.29 (t, 2H, J = 7.0 Hz), 7.23 (d, 2H, J = 7.0 Hz), 7.19 (t, 1H, J = 7.0 Hz), 5.01-4.84 (m, 1H), 4.74-4.71 (m, 1H), 4.21-4.17 (m, 1H), 4.00-3.95 (m, 1H), 3.83-3.76 (m, 11H). | |
| 65 | 3 | ¹H-NMR (400 MHz, DMSO-d₆) δ ppm 9.63, 9.49 (s, s, 1H), 8.32 (s, 2H), 8.28, 8.15 (s, s, 1H), 7.90, 7.86 (s, s, 1H), 7.46 (s, 1H), 7.31-7.17 (m, 5H), 5.01-4.98 (m, 1H), 4.72 (dd, 1H, J = 11.6, 5.6 Hz), 4.18 (dd, 1H, J = 14.0, 3.6 Hz), 3.97 (dd, 1H, J = 14.4, 7.6 Hz), 3.84-3.72 (m, 11H), 3.33-3.30 (m, 2H). | |
| 66 | 3 | ¹H-NMR (500 MHz, DMSO-d₆) δ ppm 9.65, 9.52 (s, s, 1H), 8.32 (s, 2H), 8.29, 8.16 (s, s, 1H), 7.91, 7.86 (s, s, 1H), 7.48 (s, 1H), 7.31-7.18 (m, 5H), 5.03-4.96 (m, 1H), 4.76-4.72 (m, 1H), 4.19 (dd, 1H, J = 13.5, 3.5 Hz), 3.98 (dd, 1H, J = 14.0, 7.0 Hz), 3.83-3.72 (m, 11H), 3.33-3.30 (m, 2H). | |
| 67 | 6 | ¹H-NMR (400 MHz, DMSO-d₆) δ ppm 9.65, 9.52 (s, s, 1H), 8.29 (s, 2H), 8.16 (s, 1H), 7.83 (s, 1H), 7.50, 7.47-7.47 (s, s, 1H), 4.12-4.03 (m, 2H), 3.84-3.63 (m, 10H), 3.42-3.39 (m, 3H), 2.72-2.57 (m, 3H), 2.33 (t, 1H, J = 10.8 Hz), 1.44-1.39 (m, 2H), 0.67-0.61 (m, 1H), 0.40-0.38 (m, 2H), 0.03-0.00 (m, 2H). | |
| 68 | 3 | ¹H NMR (400 MHz, DMSO-d6) δ 10.20 (s, 1H), 9.63 (s, 1H), 8.32 (d, J = 1.0 Hz, 2H), 8.23 (s, 1H), 7.40 (s, 1H), 7.34-7.15 (m, 5H), 7.07 (s, 2H), 3.81 (m, 10H), 2.80 (t, J = 7.5 Hz, 2H), 2.42 (t, J = 7.6 Hz, 2H). | 494 |
| 69 | 3 | ¹H NMR (400 MHz, DMSO-d6) δ 9.54 (s, 1H), 8.30 (s, 2H), 8.23 (s, 1H), 7.45-7.35 (m, 2H), 7.31-7.25 (m, 2H), 7.24-7.16 (m, 3H), 7.01 (d, J = 8.2 Hz, 1H), 3.79 (d, J = 6.8 Hz, 10H), 3.44 (s, 2H), 2.74 (t, J = 6.0 Hz, 2H), 2.57 (t, J = 5.9 Hz, 2H), 2.33 (s, 3H). | 494 |
| 70 | 3 | ¹H-NMR (500 MHz, DMSO-d₆) δ ppm 9.53 (br. s., 1H), 8.25 (s, 1H), 8.18 (s, 1H), 7.40-7.37 (m, 2H), 7.31-7.28 (m, 2H), 7.21-7.15 (m, 3H), 6.99 (d, 1H, J = 8.5 Hz), 3.84-3.82 (m, 12H), 2.93 (t, 2H, J = 5.5 Hz), 2.64-2.62 (m, 2H), 2.22 (s, 3H). | |
| 72 | 3 | ¹H NMR (400 MHz, DMSO-d6) δ 9.67 (s, 1H), 8.37-8.23 (m, 3H), 7.57-7.44 (m, 2H), 7.32-7.13 (m, 6H), 4.00 (s, 2H), 3.80 (d, J = 11.6 Hz, 10H), 3.17 (t, J = 5.3 Hz, 2H), 2.91-2.83 (m, 2H), 1.75 (q, J = 6.4, 5.3 Hz, 2H). | 494 |
| 73 | 1 | ¹H NMR (400 MHz, DMSO-d6) δ 9.54 (s, 1H), 8.22 (s, 1H), 7.64 (s, 1H), 7.46 (s, 1H), 7.40-7.33 (m, 1H), 7.28-7.20 (m, 4H), 7.19-7.13 (m, 1H), 7.00 (d, J = 8.2 Hz, 1H), 6.30 (s, 2H), 3.89 (s, 2H), 3.81-3.63 (m, 12H), 3.00 (t, J = 5.9 Hz, 2H), 2.67 (t, J = 5.9 Hz, 2H). | 495 |
| 74 | 3 | ¹H NMR (400 MHz, DMSO-d6) δ 9.67 (s, 1H), 8.31 (m, 3H), 8.25 (s, 1H), 7.68 (s, 1H), 7.49 (d, J = 8.0 Hz, 1H), 7.34-7.12 (m, 6H), 6.89 (d, J = 7.6 Hz, 1H), 4.22 (d, J = 5.9 Hz, 2H), 3.80 (d, J = 12.2 Hz, 10H), 1.87 (s, 3H). | 496 |
| 75 | 2 | | 496 |
| 76 | 3 | ¹H NMR (400 MHz, DMSO-d6) δ 9.64 (s, 1H), 8.31 (s, 2H), 8.24 (s, 1H), 7.62 (d, J = 2.7 Hz, 1H), 7.48 (dd, J = 8.6, 2.6 Hz, 1H), 7.33-7.25 (m, 2H), 7.25-7.13 (m, 3H), 6.97 (d, J = 8.6 Hz, 1H), 4.06-3.93 (m, 4H), 3.80 (d, J = 8.9 Hz, 10H), 3.22 (t, J = 4.4 Hz, 3H). | 496 |
| 77 | 2 | ¹H NMR (400 MHz, DMSO-d6) δ 9.51 (s, 1H), 8.30 (s, 2H), 8.20 (s, 1H), 7.61-7.49 (m, 2H), 7.34-7.14 (m, 5H), 6.74 (d, J = 8.7 Hz, 2H), 4.97-4.83 (m, 1H), 3.87-3.69 (m, 12H), 3.54-3.43 (m, 2H). | 496 |
| 78 | 1 | ¹H NMR (400 MHz, DMSO-d6) δ 9.70 (s, 1H), 8.60-8.46 (m, 1H), 8.26 (s, 1H), 7.79 (d, J = 2.4 Hz, 1H), 7.64 (s, 1H), 7.33-7.11 (m, 5H), 6.31 (s, 2H), 3.90-3.57 (m, 12H), 3.00 (t, J = 6.0 Hz, 2H), 2.70 (t, J = 6.0 Hz, 2H). | 496 |
| 79 | 3 | ¹H-NMR (400 MHz, DMSO-d6) δ ppm 9.74 (s, 1H), 8.32 (s, 2H), 8.27 (s, 1H), 7.72 (d, 2H, J = 8.4 Hz), 7.52 (d, 2H, J = 8.4 Hz), 7.32-7.17 (m, 5H), 6.26 (s, 1H), 4.75 (d, 2H, J = 6.0 Hz), 4.69 (d, 2H, J = 6.4 Hz), 3.89-3.74 (m, 10H). | 497 |
| 80 | 1 | ¹H-NMR (400 MHz, DMSO-d6) δ ppm 9.54 (br, 1H), 8.34 (s, 2H), 8.24 (s, 1H), 7.44-7.29 (m, 3H), 7.11-7.08 (m, 2H), 7.04-6.97 (m, 2H), 3.82 (br, 13H), 2.94-2.91 (br, 2H), 2.53-2.48 (m, 2H). | |
| 81 | 2 | ¹H-NMR (500 MHz, DMSO-d₆) δ ppm 9.32, 9.17 (br. s., br. s., 1H), 8.32 (s, 2H), 8.16 (s, 1H), 7.35-7.18 (m, 7H), 6.55 (br, 2H), 5.30-5.26 (m, 1H), 4.68 (br. s., 1H), 3.80-3.77 (m, 11H), 2.93-2.86 (m, 2H), 1.11 (d, 3H, J = 5.5 Hz). | |
| 82 | 2 | ¹H-NMR (500 MHz, DMSO-d₆) δ ppm 9.31, 9.15 (br., s., br. s., 1H), 8.31 (s, 2H), 8.15 (s, 1H), 7.34-7.17 (m, 7H), 6.55 (br. s., 2H), 5.26-5.24 (m, 1H), 4.66 (d, 1H, J = 5.0 Hz), 3.79-3.77 (m, 11H), 2.95-2.88 (m, 2H), 1.10 (d, 3H, J = 6.0 Hz). | |

-continued

| Compound Number | Synthetic Protocol | ¹H NMR | LC/MS M + 1 |
|---|---|---|---|
| 83 | 3 | This spectrum contains some rotamers in the aromatic region: ¹H NMR (400 MHz, DMSO-d6) δ 9.61, 9.49 (s, 1H), 8.30, 8.27 (s, 2H), 8.14 (s, 1H), 7.82 (s, 1H), 7.49 (s, 1H), 7.23 (tt, J = 20.6, 7.2 Hz, 5H), 4.08-3.93 (m, 2H), 3.79 (m 11H), 2.90-2.70 (m, 2H), 1.83-1.69 (m, 1H), 1.40 (dd, J = 16.3, 9.3 Hz, 1H) - one peak is obscured by DMSO. | 498 |
| 84 | 3 | This spectrum contains some rotamers in the aromatic region: ¹H NMR (400 MHz, DMSO-d6) δ 9.61, 9.49 (s, 1H), 8.31, 8.27 (s, 2H), 8.14 (s, 1H), 7.91, 7.87 (s, 1H), 7.47 (s, 1H), 7.35-7.11 (m, 6H), 4.06-3.91 (m, 3H), 3.81 (mz, 10H), 2.85-2.70 (m, 2H), 1.76-1.53 (m, 3H), 1.41-1.27 (m, 1H). | 498 |
| 85 | 3 | This spectrum contains some rotamers in the aromatic region: ¹H NMR (400 MHz, DMSO-d6) δ 9.61, 9.49 (s, 1H), 8.3, 8.27 (s, 2H), 8.14 (s, 1H), 7.91, 7.87 (s, 1H), 7.46 (d, J = 3.8 Hz, 1H), 7.32-7.25 (m, 2H), 7.25-7.15 (m, 3H), 4.05-3.92 (m, 2H), 3.81 (m, 10H), 2.85-2.71 (m, 2H), 1.77-1.50 (m, 3H), 1.41-1.26 (m, 1H) - a peak is partially obscured by water signal. | 498 |
| 86 | 3 | ¹H-NMR (400 MHz, DMSO-d$_6$) δ ppm 9.65, 9.54 (s, s, 1H), 8.32 (s, 2H), 8.29, 8.16 (s, s, 1H), 7.89, 7.86 (s, s, 1H), 7.51, 7.47 (s, s, 1H), 7.31-7.17 (m, 5H), 4.12-4.03 (m, 2H), 3.83-3.73 (m, 10H), 3.66-3.60 (m, 2H), 3.48-3.45 (m, 2H), 2.72-2.63 (m, 1H), 1.93-1.87 (m, 1H), 1.62-1.55 (m, 1H). | |
| 87 | 3 | ¹H-NMR (400 MHz, DMSO-d$_6$) δ ppm 9.65, 9.59 (s, s, 1H), 8.33-8.31 (m, 2H), 8.16 (s, 1H), 7.87 (s, 1H), 7.50 (s, 1H), 7.34-7.18 (m, 5H), 4.59 (d, 2H, J = 5.6 Hz), 4.35-4.22 (m, 4H), 3.85-3.75 (m, 10H), 1.13 (s, 3H). | |
| 88 | 3 | This spectrum contains some rotamers in the aromatic region: 1H NMR (400 MHz, DMSO-d6) δ 9.61, 9.48 (s, 1H), 8.31, 8.27 (s, 2H), 8.14 (s, 1H), 7.83, 7.79 (s, 1H), 7.50, 7.45 (s, 1H), 7.32-7.13 (m, 5H), 4.12-4.02 (m, 2H), 3.80 (d, J = 12.9 Hz, 10H), 2.13 (s, 8H), 1.93-1.80 (m, 2H). | 500 |
| 89 | 3 | ¹H NMR (400 MHz, DMSO-d$_6$) δ 9.94 (s, 1H), 8.31 (d, J = 1.8 Hz, 3H - actually two closely spaced singlets), 7.89-7.81 (m, 2H), 7.68 (dd, J = 11.0, 8.4 Hz, 2H), 7.35-7.14 (m, 5H), 3.88-3.75 (m, 10H), 1.62 (s, 3H), 1.59 (s, 3H). | 501 |
| 91 | 1 | ¹H-NMR (500 MHz, DMSO-d$_6$) δ ppm 9.66, 9.60 (s, s, 1H), 8.52 (s, 2H), 8.24, 8.17 (s, s, 1H), 7.83 (s, 1H), 7.50, 7.49 (s, s, 1H), 4.18-4.01 (m, 2H), 3.92-3.62 (m, 10H), 3.45-3.37 (m, 1H), 2.75-2.56 (m, 3H), 2.39-2.28 (m, 1H). | |
| 92 | 2 | ¹H-NMR (400 MHz, DMSO-d6) δ ppm 9.63 (br. s., 1H), 8.32 (s, 2H), 8.25 (s, 1H), 7.62 (d, 2H, J = 8.8 Hz), 7.29-7.25 (m, 4H), 7.14-7.09 (m, 2H), 5.12 (d, 1H, J = 4.0 Hz), 4.68-4.65 (m, 1H), 4.50-4.46 (m, 1H), 3.83 (s, 5H), 3.79 (s, 5H), 3.42-3.39 (m, 2H). | 503 |
| 93 | 2 | ¹H-NMR (400 MHz, DMSO-d6) δ ppm 9.62 (br. s., 1H), 8.31 (s, 2H), 8.25 (s, 1H), 7.62 (d, 2H, J = 8.8 Hz), 7.29-7.25 (m, 4H), 7.14-7.09 (m, 2H), 5.11 (br. s., 1H), 4.66 (br. s., 1H, J = 6.0 Hz), 4.50-4.46 (m, 1H), 3.84-3.79 (m, 10H), 3.42-3.40 (m, 2H). | 503 |
| 94 | 3 | ¹H NMR (400 MHz, DMSO-d6) δ 10.21 (s, 1H), 8.36 (s, 1H), 8.32 (s, 2H), 8.02-7.93 (m, 2H), 7.89-7.81 (m, 2H), 7.34-7.14 (m, 5H), 3.85 (br. s, 10H), 3.15 (s, 3H). | |
| 95 | 3 | ¹H NMR (400 MHz, DMSO-d6) δ 10.05 (s, 1H), 8.60 (s, 1H), 8.32 (s, 2H), 8.31 (s, 1H), 7.66 (d, J = 7.6 Hz, 1H), 7.51-7.43 (m, 2H), 7.38-7.12 (m, 7H), 3.92-3.73 (m, 14H). | 504 |
| 96 | 3 | ¹H NMR (400 MHz, DMSO-d6) δ 10.03 (s, 1H), 8.32 (s, 1H), 8.31 (s, 2H), 7.91-7.84 (m, 2H), 7.78-7.71 (m, 2H), 7.32-7.14 (m, 7H), 3.92-3.68 (m, 10H). | 504 |
| 98 | 3 | | 508 |
| 99 | 3 | ¹H NMR (400 MHz, DMSO-d6) δ 10.31 (s, 1H), 9.62 (s, 2H), 8.37 (d, J = 12.4 Hz, 3H), 7.57-7.41 (m, 3H), 7.33-7.14 (m, 5H), 4.23 (d, J = 4.5 Hz, 2H), 3.81 (m, 10H), 3.17 (dd, J = 6.8, 2.8 Hz, 2H), 1.34 (s, 6H). | 508 |
| 100 | 5 | ¹H-NMR (500 MHz, CDCl$_3$) δ ppm 8.46 (s, 2H), 8.32, 8.22 (br. s., br. s., 1H), 7.87-7.50 (m, 2H), 7.30, 6.60 (br. s., br. s., 1H), 7.21-7.16 (m, 1H), 7.09-7.01 (m, 3H), 4.24-4.14 (m, 2H), 4.00-3.94 (m, 9H), 1.25 (d, 3H, J = 6.5 Hz). | |
| 102 | 3 | ¹H NMR (400 MHz, DMSO-d6) δ 9.44 (s, 1H), 8.30 (s, 2H), 8.19 (s, 1H), 7.50 (d, J = 8.5 Hz, 2H), 7.33-7.24 (m, 2H), 7.25-7.15 (m, 3H), 6.87 (d, J = 8.8 Hz, 2H), 3.79 (br. s, 10H), 2.99 (dd, J = 6.5, 3.5 Hz, 4H), 2.85 (dd, J = 6.3, 3.6 Hz, 4H). | 509 |
| 103 | 3 | ¹H NMR (400 MHz, DMSO-d6) δ 9.45 (s, 1H), 8.30 (s, 2H), 8.19 (s, 1H), 7.52 (d, J = 8.4 Hz, 2H), 7.33-7.12 (m, 5H), 6.90 (d, J = 8.6 Hz, 2H), 3.94-3.66 (m, 14H), 3.03 (t, J = 4.7 Hz, 4H). | 510 |
| 105 | 2 | | 510 |

| Compound Number | Synthetic Protocol | ¹H NMR | LC/MS M + 1 |
|---|---|---|---|
| 101 | 5 | ¹H-NMR (500 MHz, CDCl₃) δ ppm 8.42 (s, 2H), 8.33, 8.22 (br. s., br. s., 1H), 7.86-7.50 (m, 2H), 7.35, 6.62 (br. s., br. s., 1H), 7.21-7.18 (m, 2H), 6.98-6.95 (m, 2H), 4.24-4.13 (m, 2H), 4.00-3.93 (m, 9H), 1.25 (d, 3H, J = 6.0 Hz). | |
| 104 | 3 | ¹H NMR (400 MHz, DMSO-d6) δ 9.53 (s, 1H), 8.31 (s, 2H), 8.24 (s, 1H), 7.44 (s, 1H), 7.32-7.05 (m, 7H), 6.61 (d, J = 7.2 Hz, 1H), 3.86-3.71 (m, 14H), 3.07 (t, J = 4.8 Hz, 4H). | 510 |
| 106 | 2 | | 510 |
| 107 | 2 | ¹H NMR (400 MHz, DMSO-d6) δ 9.52 (s, 1H), 8.30 (s, 2H), 8.21 (s, 1H), 7.57 (d, J = 8.5 Hz, 2H), 7.35-7.12 (m, 5H), 6.87 (d, J = 8.7 Hz, 2H), 4.87 (t, J = 5.6 Hz, 1H), 3.79 (m, 10H), 3.20-3.11 (m, 2H), 3.07-2.89 (m, 3H), 2.12-1.97 (m, 1H), 1.91-1.80 (m, 1H). | 510 |
| 108 | 2 | ¹H NMR (400 MHz, DMSO-d6) δ 9.50 (s, 1H), 8.30 (s, 2H), 8.20 (s, 1H), 7.55 (d, J = 8.6 Hz, 2H), 7.34-7.12 (m, 5H), 6.84 (d, J = 8.5 Hz, 2H), 4.85-4.68 (m, 1H), 3.79 (d, J = 5.8 Hz, 10H), 3.08-2.95 (m, 1H), 2.94-2.69 (m, 3H), 2.04-1.91 (m, 1H), 1.79-1.67 (m, 1H). | 510 |
| 109 | 1 | ¹H-NMR (500 MHz, DMSO-d₆) δ ppm 9.52 (br. s., 1H), 8.26-8.25 (m, 3H), 7.41-7.36 (m, 3H), 7.24-7.19 (m, 2H), 7.13-7.11 (m, 1H), 6.99 (d, 1H, J = 8.0 Hz), 5.14 (t, 1H, J = 5.5 Hz), 4.54 (d, 2H, J = 5.5 Hz), 3.85-3.78 (m, 12H), 2.93 (t, 2H, J = 5.5 Hz), 2.62 (t, 2H, J = 5.5 Hz). | |
| 110 | 2 | ¹H-NMR (500 MHz, CDCl₃) δ ppm 8.27 (s, 1H), 8.12 (s, 1H), 7.30-7.21 (m, 4H), 7.11 (d, 2H, J = 7.5 Hz), 7.08 (d, 1H, J = 8.5 Hz), 6.93 (br. s., 1H), 4.50 (s, 2H), 4.02 (s, 2H), 3.92 (br. s., 8H), 3.75 (s, 2H), 3.15 (t, 2H, J = 6.0 Hz), 2.78 (t, 2H, J = 5.5 Hz). | |
| 111 | 2 | ¹H NMR (400 MHz, DMSO-d6) δ 9.33 (s, 1H), 8.31 (s, 2H), 8.17 (s, 1H), 7.44 (s, 2H), 7.29 (t, J = 7.5 Hz, 2H), 7.26-7.16 (m, 3H), 6.48 (d, J = 8.3 Hz, 2H), 4.92 (d, J = 3.9 Hz, 1H), 4.45-4.31 (m, 1H), 3.79 (d, J = 10.2 Hz, 10H), 3.39 (dd, J = 10.0, 5.0 Hz, 1H), 3.23 (td, J = 8.6, 3.9 Hz, 1H), 3.04 (d, J = 9.7 Hz, 1H), 2.03 (ddd, J = 13.2, 8.7, 5.0 Hz, 1H), 1.87 (ddt, J = 11.3, 7.0, 3.6 Hz, 1H) - appears to be one peak under water signal. | 510 |
| 112 | 2 | ¹H NMR (400 MHz, DMSO-d6) δ 9.34 (s, 1H), 8.31 (s, 2H), 8.17 (s, 1H), 7.44 (s, 2H), 7.33-7.26 (m, 2H), 7.26-7.15 (m, 3H), 6.48 (d, J = 8.5 Hz, 2H), 4.92 (d, J = 3.8 Hz, 1H), 3.79 (d, J = 7.9 Hz, 10H), 3.39 (dd, J = 10.0, 5.0 Hz, 1H), 3.26-3.18 (m, 1H), 3.04 (d, J = 10.0 Hz, 1H), 2.11-1.97 (m, 1H), 1.87 (ddt, J = 11.4, 7.0, 3.7 Hz, 1H) - appears to be one peak under the water signal. | 510 |
| 113 | 1 | ¹H-NMR (400 MHz, DMSO-d₆) δ ppm 9.53 (br, 1H), 8.27, 8.24 (s, s, 3H), 7.40 (s, 1H), 7.36 (d, 1H, J = 8.4 Hz), 7.22-7.16 (m, 2H), 6.97 (t, 2H, J = 7.2 Hz), 6.88 (t, 1H, J = 7.2 Hz), 3.79-3.72 (m, 16H), 2.92 (t, 2H, J = 5.6 Hz), 2.61 (t, 2H, J = 5.6 Hz). | |
| 114 | 5 | | 511 |
| 115 | 1 | ¹H-NMR (400 MHz, DMSO-d₆) δ ppm 9.80 (br. s., 1H), 9.50-9.46 (br, 1H), 9.06 (s, 2H), 8.28 (s, 3H), 7.61 (s, 1H), 7.48 (dd, 1H, J = 8.4, 2.0 Hz), 7.16 (d, 1H, J = 8.4 Hz), 7.08-7.00 (m, 2H), 6.78 (d, 1H, J = 7.2 Hz), 6.73-6.69 (m, 1H), 4.27 (br. s., 2H), 3.89-3.37 (m, 10H), 3.39-3.35 (m, 2H), 2.93 (t, 2H, J = 2.0 Hz). | |
| 16 | 3 | This spectrum contains some rotomers in the aromatic region: ¹H NMR (400 MHz, DMSO-d6) δ 9.60, 9.49 (s, 1H), 8.30, 8.28 (s, 2H), 8.12, 8.14 (s, 1H), 7.81, 7.77 (s, 1H), 7.48, 7.44 (s, 1H), 7.34-7.10 (m, 5H), 3.95 (d, J = 7.2 Hz, 2H), 3.79 (t, J = 10.2 Hz, 10H), 2.76 (m, 2H), 2.23 (t, J = 10.6 Hz, 1H), 2.03-1.76 (m, 2H), 1.56 (br. s, 2H), 1.30 (m, 1H), 1.06 (m, 1H). | 512 |
| 117 | 3 | This spectrum contains some rotamers in the aromatic region: ¹H NMR (400 MHz, DMSO-d6) δ 9.61, 9.48 (s, 1H), 8.30, 8.26 (s, 2H), 8.14, 8.12 (s, 1H), 7.79, 7.78 (s, 1H), 7.49, 7.44 (s, 1H), 7.34-7.09 (m, 5H), 4.17-3.98 (m, 2H), 3.79 (t, J = 12.4 Hz, 10H), 2.40 (t, J = 6.9 Hz, 2H), 2.24, 2.15 (s, 3H), 1.85 (t, J = 6.7 Hz, 2H). | 512 |
| 118 | 3 | ¹H-NMR (500 MHz, DMSO-d₆) δ ppm 9.61, 9.50 (s, s, 1H), 8.32, 8.28 (s, s, 2H), 8.15 (s, 1H), 7.85, 7.82 (s, s, 1H), 7.50, 7.47 (s, s, 1H), 7.29 (t, 2H, J = 7.5 Hz), 7.23 (d, 2H, J = 7.5 Hz), 7.19 (t, 1H, J = 7.5 Hz), 4.01-3.93 (m, 2H), 3.83-3.77 (m, 12H), 3.24 (t, 2H, J = 11.5 Hz), 2.01 (br. s., 1H), 1.41-1.37 (m, 2H), 1.28-1.20 (m, 2H). | |
| 119 | 4 | ¹H-NMR (400 MHz, DMSO-d6) δ ppm 9.62 (br. s., 1H), 8.26-8.25 (m, 3H), 7.63 (d, 2H, J = 8.8 Hz), 7.31-7.25 (m, 6H), 7.21-7.17 (m, 1H), 5.12 (d, 1H, J = 4.0 Hz), 4.67-4.64 (m, 1H), 4.49-4.46 (m, 1H), 3.84 (br. s., 4H), 3.80 (br. s., 4H), 3.42-3.39 (m, 2H), 1.64 (s, 6H). | 513 |
| 120 | 4 | ¹H-NMR (400 MHz, DMSO-d6) δ ppm 9.62 (br. s., 1H), 8.26, 8.25 (s, s, 3H), 7.63 (d, 2H, J = 8.4 Hz), 7.33-7.17 (m, 7H), 5.11 (d, 1H, J = 4.4 Hz), 4.68-4.65 (m, 1H), 4.49-4.48 (m, 1H), 3.85-3.80 (m, 8H), 3.43-3.40 (m, 2H), 1.64 (s, 6H). | 513 |

-continued

| Compound Number | Synthetic Protocol | ¹H NMR | LC/MS M + 1 |
|---|---|---|---|
| 121 | 3 | ¹H-NMR (400 MHz, DMSO-d6) δ ppm 10.02-9.96 (br, 1H), 8.34, 8.33 (s, s, 3H), 7.57 (d, 2H, J = 8.4 Hz), 7.31-7.17 (m, 7H), 4.76-4.41 (m, 4H), 4.28 (s, 1H), 3.86-3.80 (m, 8 H), 1.06 (s, 3H), 0.96 (s, 3H). | 513 |
| 122 | 3 | ¹H-NMR (400 MHz, DMSO-d6) δ ppm 9.65 (br. s., 1H), 8.32 (s, 2H), 8.26 (s, 1H), 7.59 (d, 2H, J = 8.4 Hz), 7.31-7.17 (m, 7H), 5.10 (d, 1H, J = 3.6 Hz), 4.26 (d, 1H, J = 3.6 Hz), 4.21 (s, 1H), 3.85-3.75 (m, 10H), 1.05 (s, 3H), 0.96 (s, 3H). | 513 |
| 123 | 3 | This spectrum contains some rotamers in the aromatic region: ¹H NMR (400 MHz, DMSO-d6) δ 9.62, 9.48 (s, 1H), 8.31, 8.27 (s, 2H), 8.14 (s, 1H), 7.81 (s, 1H), 7.48, 7.45 (s, 1H), 7.33-7.12 (m, 4H), 4.21-3.98 (m, 2H), 3.80 (d, J = 12.7 Hz, 10H), 2.84-2.57 (m, 3H), 2.41-2.26 (m, 1H) There is a peak partially obscured by water signal. | 514 |
| 124 | 3 | ¹H NMR (400 MHz, DMSO-d6) δ 9.63, 9.49 (s, 1H), 8.32, 8.28 (s, 2H), 8.15 (s, 1H), 7.82 (s, 1H), 7.49, 7.47 (s, 1H), 7.34-7.26 (m, 2H), 7.26-7.15 (m, 3H), 4.13-4.01 (m, 2H), 3.87-3.64 (m, 13H), 2.74-2.58 (m, 3H), 2.40-2.29 (m, 1H). | 514 |
| 125 | 3 | This spectrum contains some rotamers in the aromatic region: 1H NMR (400 MHz, DMSO-d6) δ 9.64, 9.51 (s, 1H), 8.31, 8.27 (s, 2H), 8.15 (s, 1H), 7.84 (s, 1H), 7.51, 7.47 (s, 1H), 7.35-7.13 (m, 5H), 4.10-3.95 (m, 2H), 3.81 (m, 10H), 3.68-3.55 (m, 2H), 3.17-3.00 (m, 2H), 2.81 (d, J = 12.3 Hz, 1H), 2.70 (t, J = 11.7 Hz, 1H), 2.34 (d, J = 16.8 Hz, 1H). | 514 |
| 126 | 3 | This spectrum contains some rotamers in the aromatic region: 1H NMR (400 MHz, DMSO-d6) δ 9.63, 9.51 (s, 1H), 8.31, 8.27 (s, 2H), 8.15 (s, 1H), 7.84 (s, 1H), 7.50, 7.47 (s, 1H), 7.35-7.12 (m, 5H), 4.02 (d, J = 6.2 Hz, 2H), 3.81 (d, J = 13.9 Hz, 10H), 3.65-3.51 (m, 2H), 3.09 (t, J = 9.8 Hz, 1H), 3.00 (d, J = 8.4 Hz, 1H), 2.77 (d, J = 12.3 Hz, 1H), 2.68 (d, J = 11.3 Hz, 1H), 2.34 (d, J = 16.8 Hz, 1H). | 514 |
| 127 | 1 | ¹H-NMR (400 MHz, DMSO-d$_6$) δ ppm 9.79 (br. s., 1H), 9.04 (br. s., 2H), 8.30 (s, 2H), 8.28 (s, 1H), 7.61 (s, 1H), 7.48 (d, 1H, J = 9.6 Hz), 7.33-7.24 (m, 2H), 7.18-7.12 (m, 3H), 4.27 (br. s., 2H), 3.82-3.80 (m, 10H), 3.39-3.35 (m, 2H), 2.93 (t, 2H, J = 1.6 Hz). | |
| 128 | 3 | ¹H NMR (400 MHz, DMSO-d6) δ 9.93 (s, 1H), 8.30 (d, J = 2.9 Hz, 2H), 7.90-7.81 (m, 2H), 7.68 (dd, J = 11.1, 8.3 Hz, 2H), 7.33-7.14 (m, 5H), 4.98-4.82 (m, 1H), 4.69-4.38 (m, 4H), 3.78 (s, 2H), 3.15 (s, 2H), 1.62, 1.59 (2 close singlets, 6H), 1.08 (d, J = 6.9 Hz, 3H). | 515 |
| 129 | 2 | ¹H NMR (400 MHz, DMSO-d6) δ 9.51 (s, 1H), 8.32 (s, 2H), 8.22 (s, 1H), 7.56 (d, J = 8.5 Hz, 2H), 7.37-7.08 (m, 5H), 6.89 (d, J = 8.5 Hz, 2H), 4.92 (d, J = 4.9 Hz, 1H), 4.65 (t, J = 5.6 Hz, 1H), 3.96 (dd, J = 9.5, 4.0 Hz, 1H), 3.80 (h, J = 5.6 Hz, 12H), 3.44 (t, J = 5.5 Hz, 2H). | 515 |
| 130 | 2 | ¹H NMR (400 MHz, DMSO-d6) δ 9.66 (s, 1H), 8.30 (s, 3H), 7.48 (s, 1H), 7.40-7.04 (m, 8H), 3.89-3.88 (m, 0H), 6.58 (d J = 7.9, 1H), 4.96 (s, 1H), 4.67 (s, 1H), 3.97 (dd, J = 9.1, 3.7 Hz, 1H), 3.92-3.67 (m, 14H). | 515 |
| 131 | 2 | ¹H NMR (400 MHz, DMSO-d6) δ 9.51 (s, 1H), 8.32 (s, 2H), 8.22 (s, 1H), 7.56 (d, J = 8.5 Hz, 2H), 7.37-7.08 (m, 5H), 6.89 (d, J = 8.5 Hz, 2H), 4.92 (d, J = 4.9 Hz, 1H), 4.65 (t, J = 5.6 Hz, 1H), 3.96 (dd, J = 9.5, 4.0 Hz, 1H), 3.80 (h, J = 5.6 Hz, 12H), 3.44 (t, J = 5.5 Hz, 2H). | 515 |
| 132 | 2 | ¹H NMR (400 MHz, DMSO-d6) δ 9.66 (s, 1H), 8.30 (s, 3H), 7.48 (s, 1H), 7.40-7.04 (m, 8H), 3.89-3.88 (m, 0H), 6.58 (d J = 7.9, 1H), 4.96 (s, 1H), 4.67 (s, 1H), 3.97 (dd, J = 9.1, 3.7 Hz, 1H), 3.92-3.67 (m, 14H). | 515 |
| 133 | 3 | ¹H-NMR (400 MHz, CDCl$_3$) δ ppm 8.21 (s, 3H), 7.76 (s, 1H), 7.57 (s, 1H), 7.32-7.28 (m, 2H), 7.23-7.16 (m, 4H), 4.14-4.11 (m, 2H), 3.88 (br. s., 9H), 3.80 (br. s., 4H), 3.72-3.69 (m, 2H), 3.62-3.55 (m, 1H), 3.33-3.28 (m, 1H). | |
| 134 | 3 | ¹H-NMR (400 MHz, CDCl$_3$) δ ppm 8.21 (s, 3H), 7.75 (s, 1H), 7.59 (s, 1H), 7.35-7.28 (m, 3H), 7.23-7.16 (m, 3H), 4.14-4.11 (m, 2H), 3.93-3.89 (m, 9H), 3.81-3.69 (m, 6H), 3.61-3.55 (m, 1H), 3.33-3.27 (m, 1H). | |
| 135 | 5 | ¹H NMR (400 MHz, DMSO-d$_6$) δ 9.64, 9.50 (s, 1H, rotamer), 8.31, 8.17 (s, 3H, rotamer), 7.83 (s, 1H), 7.72 (s, 1H), 7.49 (s, 1H), 7.15 (t, J = 7.8 Hz, 2H), 6.79 (d, J = 8.0 Hz, 2H), 6.71 (t, J = 7.5 Hz, 1H), 4.14-4.00 (m, 2H), 3.87-3.64 (m, 10H), 3.47-3.35 (m, 1H), 2.75-2.66 (m, 1H), 2.62 (d, J = 12.4 Hz, 1H), 2.41-2.30 (m, 1H). | 515 |
| 136 | 1 | ¹H-NMR (400 MHz, DMSO-d$_6$ + 1d D$_2$O) δ ppm 8.26 (s, 2H), 8.25 (s, 1H), 7.63 (s, 1H), 7.49 (s, 1H), 7.45 (d, 1H, J = 8.4 Hz), 7.41-7.31 (m, 1H), 7.13-7.09 (m, 3H), 4.07 (s, 2H), 3.85-3.72 (m, 10H), 3.18 (d, 2H, J = 6.0 Hz), 2.83 (t, 2H, J = 5.2 Hz). | |

| Compound Number | Synthetic Protocol | ¹H NMR | LC/MS M + 1 |
|---|---|---|---|
| 137 | 1 | ¹H-NMR (400 MHz, DMSO-d₆) δ ppm 9.58 (br, 1H), 8.32 (s, 2H), 8.25 (s, 1H), 7.43 (s, 1H), 7.38 (d, 1H, J = 8.0 Hz), 7.33-7.26 (m, 1H), 7.21-7.09 (m, 2H), 7.01 (d, 1H, J = 8.4 Hz), 3.92-3.77 (m, 13H), 2.97 (t, 2H, J = 6.0 Hz), 2.66 (t, 2H, J = 5.6 Hz). | |
| 138 | 1 | ¹H-NMR (400 MHz, DMSO-d₆) δ ppm 9.55 (br, 1H), 8.30 (s, 2H), 8.24 (s, 1H), 7.40-7.35 (m, 3H), 7.21 (t, 1H, J = 10.4 Hz), 7.04 (t, 1H, J = 9.2 Hz), 6.98 (d, 1H, J = 8.0 Hz), 3.80 (br, 12H), 2.92 (t, 2H, J = 5.6 Hz), 2.67-2.61 (m, 2H). | |
| 139 | 1 | ¹H-NMR (400 MHz, DMSO-d₆) δ ppm 9.54 (br, 1H), 8.33 (s, 2H), 8.23 (s, 1H), 7.42-7.29 (m, 4H), 7.10-7.07 (m, 1H), 6.97 (d, 1H, J = 8.4 Hz), 3.80 (br, 13H), 2.91 (t, 2H, J = 5.6 Hz), 2.61 (t, 2H, J = 5.2 Hz). | |
| 140 | 4 | ¹H-NMR (400 MHz, DMSO-d6) δ ppm 9.65 (br. s., 1H), 8.39 (s, 2H), 8.26 (s, 1H), 7.63 (d, 2H, J = 8.4 Hz), 7.46 (dd, 2H, J = 8.4, 5.6 Hz), 7.27 (d, 2H, J = 8.4 Hz), 7.13-7.08 (m, 2H), 5.06 (d, 1H, J = 4.0 Hz), 4.70-4.64 (m, 1H), 3.85-3.70 (m, 8H), 3.45-3.25 (m, 2H), 1.73 (s, 3H), 1.31 (d, 3H, J = 6.4 Hz). | 516 |
| 141 | 1 | ¹H-NMR (500 MHz, DMSO-d₆) δ ppm 9.66, 9.52 (s, s, 1H), 8.33 (s, 2H), 8.29, 8.16 (s, s, 1H), 7.83 (s, 1H), 7.50, 7.48 (s, s, 1H), 7.31-7.18 (m, 5H), 4.12-4.03 (m, 2H), 3.84-3.66 (m, 11H), 2.72-2.60 (m, 3H), 2.38-2.33 (m, 1H). | |
| 142 | 1 | ¹H-NMR (500 MHz, DMSO-d₆) δ ppm 9.01, 8.77 (s, s, 1H), 8.50 (s, 2H), 8.16, 8.14 (s, s, 1H), 7.55, 7.41 (s, s, 1H), 4.02-3.96 (m, 2H), 3.82-3.64 (m, 10H), 3.34 (br, 2H), 2.73-2.71 (m, 1H), 2.63-2.59 (m, 2H), 2.41-2.36 (m, 1H), 2.17, 2.12 (s, s, 3H). | |
| 143 | 1 | 1H NMR (400 MHz, DMSO-d6) δ 10.17 (s, 1H), 8.35 (s, 1H), 7.99-7.92 (m, 2H), 7.88-7.81 (m, 2H), 7.63 (s, 1H), 7.28-7.18 (m, 4H), 7.18-7.11 (m, 1H), 3.83 (s, 4H), 3.68 (s, 4H), 3.56 (s, 2H), 3.15 (s, 3H). | 519 |
| 145 | 3 | ¹H-NMR (500 MHz, DMSO-d₆) δ ppm 9.56 (br. s., 1H), 8.32 (s, 2H), 8.24 (s, 1H), 7.42-7.40 (m, 2H), 7.29 (t, 2H, J = 7.5 Hz), 7.23 (d, 2H, J = 7.0 Hz), 7.20 (t, 1H, J = 7.5 Hz), 7.01 (d, 1H, J = 8.0 Hz), 3.82-3.80 (m, 10H), 3.67 (s, 2H), 2.82 (t, 2H, J = 5.5 Hz), 2.71 (t, 2H, J = 5.5 Hz), 1.88-1.77 (m, 1H), 0.51-0.47 (m, 2H), 0.41-0.38 (m, 2H). | |
| 148 | 3 | ¹H NMR (400 MHz, DMSO-d6) δ 9.54, 9.49 (s, 1H), 8.31, 8.27 (s, 2H), 8.24 (s, 1H), 7.40 (d, J = 8.2 Hz, 2H), 7.33-7.26 (m, 2H), 7.25-7.16 (m, 3H), 7.01 (d, J = 8.3 Hz, 1H), 3.85-3.76 (m, 10H), 3.59 (s, 2H), 2.90-2.82 (m, 1H), 2.69 (d, J = 16.3 Hz, 4H), 1.05 (d, J = 6.4 Hz, 6H). | 522 |
| 149 | 5 | ¹H-NMR (500 MHz, DMSO-d₆) δ ppm 9.68, 9.55 (s, s, 1H), 8.54 (s, 2H), 8.30, 8.17 (s, s, 1H), 7.96, 7.88 (s, s, 1H), 7.47-7.46 (m, 1H), 7.27-7.25 (m, 2H), 7.19-7.16 (m, 2H), 4.73, 4.67 (s, s, 1H), 3.95-3.88 (m, 10H), 1.06-1.05 (m, 6H). | |
| 150 | 5 | ¹H-NMR (500 MHz, DMSO-d₆) δ ppm 9.70, 9.58 (s, s, 1H), 8.56 (s, 2H), 8.31, 8.18 (s, s, 1H), 7.96, 7.88 (s, s, 1H), 7.48-7.46 (m, 1H), 7.28-7.26 (m, 2H), 7.17-7.14 (m, 1H), 7.04-7.01 (m, 1H), 4.75, 4.68 (s, s, 1H), 4.00-3.89 (m, 10H), 1.06-1.05 (m, 6H). | |
| 155 | 2 | ¹H-NMR (400 MHz, CDCl₃) δ ppm 8.28 (s, 1H), 8.20 (s, 2H), 7.53 (d, 2H, J = 8.4 Hz), 7.48 (d, 2H, J = 8.4 Hz), 7.32-7.26 (m, 2H), 7.23-7.16 (m, 3H), 3.91-3.88 (m, 8H), 3.81 (s, 2H), 1.88-1.71 (m, 8H), 1.65-1.62 (m, 1H), 1.34-1.25 (m, 1H). | |
| 156 | 2 | ¹H NMR (400 MHz, DMSO-d6) δ 9.44 (s, 1H), 8.30 (s, 2H), 8.19 (s, 1H), 7.50 (d, J = 8.4 Hz, 2H), 7.34-7.13 (m, 5H), 6.89 (d, J = 8.6 Hz, 2H), 3.89-3.66 (m, 10H), 3.07 (t, J = 4.9 Hz, 4H), 2.23 (s, 3H) - one peak is obscured by water signal. | 523 |
| 157 | 2 | ¹H NMR (400 MHz, DMSO-d6) δ 9.51 (s, 1H), 8.31 (s, 2H), 8.24 (s, 1H), 7.43 (s, 1H), 7.31-7.03 (m, 7H), 6.64-6.56 (m, 1H), 3.98-3.65 (m, 12H), 3.11 (t, J = 4.9 Hz, 4H), 2.24 (s, 3H). | 523 |
| 158 | 3 | ¹H NMR (400 MHz, DMSO-d6) δ 8.77 (s, 1H), 8.29 (s, 2H), 8.10 (s, 1H), 7.28 (t, J = 7.5 Hz, 2H), 7.25-7.12 (m, 4H), 6.81-6.69 (m, 2H), 3.75 (m, 10H), 3.03 (dd, J = 6.6, 3.5 Hz, 4H), 2.85 (dd, J = 6.2, 3.6 Hz, 4H), 2.12 (s, 3H). | 523 |
| 159 | 3 | ¹H NMR (400 MHz, DMSO-d6) δ 9.62 (s, 1H), 8.31 (s, 2H), 8.23 (s, 1H), 7.53 (d, J = 8.2 Hz, 2H), 7.35-7.11 (m, 5H), 6.95 (d, J = 8.5 Hz, 2H), 4.87 (br. s, 1H), 4.58 (br. s, 1H), 4.46 (t, J = 15.2 Hz, 4H), 3.78 (s, 2H), 3.77-3.69 (m, 4H), 3.26 (m, 1H), 3.11-3.03 (m, 4H), 1.05 (d, J = 6.4 Hz, 3H). | 524 |
| 160 | 3 | ¹H NMR (400 MHz, DMSO-d6) δ 9.66 (s, 1H), 8.31 (d, J = 1.3 Hz, 2H), 8.25 (s, 1H), 7.79 (s, 1H), 7.50 (d, J = 8.1 Hz, 1H), 7.36-7.13 (m, 6H), 6.98-6.87 (m, 1H), 3.89-3.73 (m, 10H), 3.64-3.52 (m, 4H), 3.42 (s, 2H), 2.42-2.28 (m, 9H). | 524 |
| 161 | 2 | ¹H NMR (400 MHz, DMSO-d6) δ 9.51 (s, 1H), 8.30 (s, 2H), 8.21 (s, 1H), 7.55 (d, J = 8.5 Hz, 2H), 7.33-7.24 (m, 2H), 7.24-7.15 (m, 3H), 6.90 (d, J = 9.0 Hz, 2H), 4.25-4.18 (m, 1H), 3.78 (br. s, J = 6.9 Hz, 10H), 3.15-3.05 (m, 1H), 2.86-2.74 (m, 1H), 2.62- | 524 |

| Compound Number | Synthetic Protocol | ¹H NMR | LC/MS M + 1 |
|---|---|---|---|
| | | 2.54 (m, 1H), 2.05-1.91 (m, 2H), 1.72-1.65 (m, 1H), 1.56-1.36 (m, 2H). This spectra has slight evidence of rotamers in the aromatic region. | |
| 162 | 2 | ¹H NMR (400 MHz, DMSO-d6) δ 9.51 (s, 1H), 8.30 (s, 2H), 8.21 (s, 1H), 7.55 (d, J = 8.5 Hz, 2H), 7.33-7.24 (m, 2H), 7.24-7.15 (m, 3H), 6.90 (d, J = 9.0 Hz, 2H), 4.25-4.18 (m, 1H), 3.78 (br. s, J = 6.9 Hz, 10H), 3.15-3.05 (m, 1H), 2.86-2.74 (m, 1H), 2.62-2.54 (m, 1H), 2.05-1.91 (m, 2H), 1.72-1.65 (m, 1H), 1.56-1.36 (m, 2H). This spectra has slight evidence of rotamers in the aromatic region. | 524 |
| 163 | 3 | ¹H NMR (400 MHz, DMSO-d6) δ 9.90 (s, 1H), 9.74 (s, 1H), 8.31 (s, 2H), 8.27 (s, 1H), 7.58 (s, 1H), 7.56-7.50 (m, 1H), 7.32-7.25 (m, 2H), 7.25-7.11 (m, 4H), 5.42-5.28 (m, 1H), 4.59-4.25 (m, 4H), 3.92-3.71 (m, 12H), 3.09-2.94 (m, 2H). | 524 |
| 164 | 3 | ¹H NMR (400 MHz, DMSO-d6) δ 9.62 (s, 1H), 8.39-8.06 (m, 3H), 7.62-6.91 (m, 7H), 4.93 (d, J = 23.8 Hz, 2H), 4.58 (dd, J = 29.9, 13.0 Hz, 4H), 4.02 (s, 2H), 3.78 (s, 2H), 3.57-2.85 (m, 3H), 2.76 (t, J = 5.8 Hz, 2H), 1.64 (bs, 2H). | 524 |
| 165 | 2 | ¹H NMR (400 MHz, DMSO-d6) δ 9.43 (s, 1H), 8.30 (s, 2H), 8.19 (s, 1H), 7.49 (d, J = 8.2 Hz, 2H), 6.87 (d, J = 8.4 Hz, 2H), 4.78 (s, 1H), 3.79 (p, J = 7.1 Hz, 10H), 3.62-3.54 (m, 1H), 3.51 (dd, J = 11.7, 4.0 Hz, 1H), 2.64-2.54 (m, 2H), 2.48-2.37 (m, 1H), 1.86 (dt, J = 12.1, 4.1 Hz, 1H), 1.73 (dt, J = 13.5, 3.8 Hz, 1H), 1.60-1.44 (m, 2H), 1.30-1.16 (m, 2H); one signal is partially obscured by water peak. | 524 |
| 166 | 2 | ¹H NMR (400 MHz, DMSO-d6) δ 9.43 (s, 1H), 8.30 (s, 2H), 8.19 (s, 1H), 7.49 (d, J = 8.4 Hz, 2H), 6.87 (d, J = 8.4 Hz, 2H), 4.77 (s, 1H), 3.65-3.43 (m, 2H), 2.57 (t, J = 10.7 Hz, 1H), 2.42 (t, J = 10.2 Hz, 1H), 1.87 (dq, J = 12.6, 4.3 Hz, 1H), 1.73 (dt, J = 13.2, 3.8 Hz, 1H), 1.62-1.44 (m, 1H), 1.31-1.15 (m, 2H). | 524 |
| 167 | 2 | ¹H NMR (400 MHz, DMSO-d6) δ 9.32 (s, 1H), 8.30 (s, 2H), 8.15 (s, 1H), 7.43 (s, 2H), 7.34-7.12 (m, 5H), 6.55 (d, J = 8.5 Hz, 2H), 4.70 (dd, J = 6.3, 5.1 Hz, 1H), 3.78 (m, 10H), 3.60 (dt, J = 8.4, 4.5 Hz, 1H), 3.48 (dt, J = 9.3, 4.4 Hz, 1H), 3.15 (ddd, J = 10.7, 8.6, 6.5 Hz, 1H), 3.04-2.92 (m, 1H), 2.04-1.77 (m, 4H) - one peak is obscured by water signal. | 524 |
| 168 | 2 | ¹H NMR (400 MHz, DMSO-d6) δ 9.32 (s, 1H), 8.30 (s, 2H), 8.15 (s, 1H), 7.43 (s, 2H), 7.35-7.13 (m, 5H), 6.55 (d, J = 8.5 Hz, 2H), 4.70 (dd, J = 6.4, 5.1 Hz, 1H), 3.78 (m, 10H), 3.66-3.56 (m, 2H), 3.48 (dt, J = 9.5, 4.4 Hz, 1H), 3.20-3.09 (m, 1H), 3.04-2.91 (m, 2H), 2.04-1.81 (m, 4H) one peak is obscured by water signal. | 524 |
| 169 | 2 | ¹H NMR (400 MHz, DMSO-d6) δ 9.50 (s, 1H), 8.30 (s, 2H), 8.21 (s, 1H), 7.61-7.50 (m, 2H), 7.34-7.12 (m, 5H), 6.87 (d, J = 8.7 Hz, 2H), 3.87-3.69 (m, 10H), 2.86-2.72 (m, 2H), 1.88-1.76 (m, 1H), 1.74-1.55 (m, 2H), 1.49-1.35 (m, 1H) - one peak obscured by water signal. | 524 |
| 170 | 2 | ¹H NMR (400 MHz, DMSO-d6) δ 9.50 (s, 1H), 8.30 (s, 2H), 8.21 (s, 1H), 7.55 (d, J = 8.0 Hz, 2H), 7.34-7.12 (m, 4H), 6.87 (d, J = 8.7 Hz, 2H), 3.87-3.69 (m, 10H), 2.86-2.73 (m, 2H), 1.89-1.75 (m, 1H), 1.74-1.55 (m, 2H), 1.49-1.35 (m, 1H) - one peak obscured by water signal. | 524 |
| 171 | 2 | ¹H NMR (400 MHz, DMSO-d6) δ 9.60 (s, 1H), 8.35 (s, 1H), 8.32 (s, 2H), 8.24 (s, 1H), 7.94 (dd, J = 8.9, 2.7 Hz, 1H), 7.36-7.15 (m, 5H), 6.75 (d, J = 8.9 Hz, 1H), 4.84 (dt, J = 8.9, 4.7 Hz, 1H), 3.79 (d, J = 5.4 Hz, 10H), 3.11 (dd, J = 12.0, 3.9 Hz, 1H), 2.77 (dt, J = 12.2, 4.0 Hz, 1H), 2.04 (d, J = 11.0 Hz, 1H), 1.66 (dt, J = 12.5, 4.3 Hz, 1H), 1.57-1.37 (m, 2H) - one peak obscured by DMSO signal. | 525 |
| 172 | 3 | ¹H-NMR (400 MHz, DMSO-d6) δ ppm 9.67 (s, 1H), 8.32 (s, 2H), 8.26 (s, 1H), 7.65 (s, 1H), 7.63 (d, 1H, J = 8.4 Hz), 7.33-7.15 (m, 7H), 5.48 (d, 1H, J = 3.6 Hz), 4.77-4.65 (m, 3H), 4.10 (d, 1H, J = 5.2 Hz), 4.01 (d, 1H, J = 5.2 Hz), 3.88-3.70 (m, 10H), 1.11 (s, 3H). | 525 |
| 173 | 4 | ¹H-NMR (500 MHz, DMSO-d₆) δ ppm 9.67, 9.54 (s, s, 1H), 8.34 (s, 2H), 8.30, 8.17 (s, s, 1H), 7.83 (s, 1H), 7.50, 7.47 (s, s, 1H), 7.41-7.34 (m, 5H), 5.51 (s, 1H), 5.43 (s, 1H), 4.12-4.03 (m, 2H), 3.91-3.87 (m, 8H), 3.72-3.66 (m, 2H), 3.41-3.37 (m, 1H), 2.72-2.59 (m, 3H), 2.37-2.33 (m, 2H). | |
| 174 | 3 | rotamers in aromatic region: 1H NMR (400 MHz, DMSO-d6) δ 9.60 (s, 1H), 8.31 (s, 2H), 8.14 (s, 1H), 7.82, 7.80 (s, 1H), 7.47, 7.45 (s, 1H), 7.33-7.13 (m, 5H), 4.04-3.89 (m, 2H), 3.80 (m, 8H), 2.76 (m, 2H), 2.16 (s, 3H), 1.85 (m, 2H), 1.75 (m, 1H), 1.43 (m, 2H), 1.21 (m, 2H). | 526 |
| 175 | 3 | | 527 |
| 176 | 3 | ¹H-NMR (400 MHz, DMSO-d₆) δ ppm 9.66, 9.53 (s, s, 1H), 8.32 (s, 2H), 8.29, 8.15 (s, s, 1H), 7.87, 7.85 (s, s, 1H), 7.46 (s, 1H), 7.31-7.17 (m, 5H), 4.31-4.12 (m, 2H), 3.99-3.79 (m, 11H), 2.69-2.55 (m, 3H), 2.29-2.22 (m, 5H), 2.10-2.05 (m, 1H). | |

-continued

| Compound Number | Synthetic Protocol | ¹H NMR | LC/MS M + 1 |
|---|---|---|---|
| 177 | 3 | ¹H-NMR (400 MHz, DMSO-d$_6$) δ ppm 9.67, 9.54 (s, s, 1H), 8.31-8.28 (m, 2H), 8.15 (s, 1H), 7.88 (s, 1H), 7.47 (s, 1H), 7.30-7.17 (m, 5H), 4.32-4.22 (m, 2H), 3.83-3.79 (m, 11H), 2.84-2.64 (m, 4H), 2.44-2.28 (m, 5H), 2.18-2.13 (m, 1H). | |
| 178 | 4 | ¹H-NMR (500 MHz, DMSO-d$_6$) δ ppm 9.70, 9.57 (s, s, 1H), 8.77 (s, 2H), 8.32, 8.19 (s, s, 1H), 7.84 (s, 1H), 7.75 (d, 2H, J = 7.5 Hz), 7.69 (t, 1H, J = 7.5 Hz), 7.58 (t, 2H, J = 8.0 Hz), 7.51, 7.48 (s, s, 1H), 4.16-3.95 (m, 6H), 3.93-3.87 (m, 4H), 3.73-3.64 (m, 2H), 3.39-3.31 (m, 1H), 2.72-2.55 (m, 3H), 2.38-2.34 (m, 2H). | |
| 179 | 1 | | 528 |
| 180 | 3 | This spectrum contains some rotamers in the aromatic region: ¹H NMR (400 MHz, DMSO-d6) δ 9.63, 9.51 (s, 1H), 8.31, 8.27 (s, 2H), 8.15 (s, 1H), 7.83 (s, 1H), 7.49 (s, 1H), 7.34-7.14 (m, 5H), 4.20-4.08 (m, 2H), 3.79 (s, 10H), 3.58-3.41 (m, 2H), 2.29-2.09 (m, 3H) - some peaks are partially obscured by water signal. | 528 |
| 181 | 3 | This spectrum contains some rotamers in the aromatic region: ¹H NMR (300 MHz, DMSO-d6) δ 9.65, 9.51 (s, 1H), 8.32, 8.28 (s, 2H), 8.16 (s, 1H), 7.84 (s, 1H), 7.50 (s, 1H), 7.35-7.13 (m, 5H), 4.22-4.04 (m, 2H), 3.81 (d, J = 9.4 Hz, 10H), 3.46 (m, 1H), 2.58 (t, J = 11.8 Hz, 2H), 2.15 (s, 3H), 2.03-1.87 (m, 2H), 1.72 (t, J = 10.6 Hz, 2H). | 528 |
| 182 | 3 | ¹H NMR (400 MHz, DMSO-d6) δ 9.65, 9.63 (s, 1H), 8.30, 8.31 (s, 2H), 8.14 (d, J = 2.9 Hz, 1H), 7.91 (s, 1H), 7.46, 7.43 (s, 1H), 7.34-7.10 (m, 5H), 4.09-3.93 (m, 2H), 3.90-3.67 (m, 10H), 2.90-2.69 (m, 2H), 2.33-2.23 (m, 2H), 1.52-1.24 (m, 4H). | 528 |
| 183 | 3 | This spectrum contains some rotamers in the aromatic region: ¹H NMR (400 MHz, DMSO-d6) δ 9.62, 9.46 (s, 1H), 8.30, 8.26 (s, 2H), 8.14 (s, 1H), 7.82 (d, J = 2.7 Hz, 1H), 7.46 (s, 1H), 7.35-7.12 (m, 4H), 5.01-4.38 (m, 5H), 4.16-3.96 (m, 2H), 3.78 (s, 2H), 3.75-3.60 (m, 2H), 3.38 (dd, J = 11.6, 8.3 Hz, 1H), 3.21-2.99 (m, 2H), 2.76-2.56 (m, 3H), 2.40-2.27 (m, 1H), 1.05 (d, J = 6.4 Hz, 3H). | 528 |
| 184 | 3 | ¹H-NMR (400 MHz, DMSO-d$_6$) δ ppm 9.06, 8.79 (s, s, 1H), 8.32 (s, 2H), 8.18, 8.16 (s, s, 1H), 7.79, 7.70 (s, s, 1H), 7.29 (t, 2H, J = 9.0 Hz), 7.24-7.17 (m, 3H), 4.03-3.94 (m, 2H), 3.79-3.63 (m, 7H), 3.43-3.38 (m, 1H), 2.83-2.56 (m, 3H), 2.38-2.32 (m, 1H), 2.12, 2.07 (s, s, 3H). | |
| 185 | 3 | ¹H-NMR (400 MHz, DMSO-d$_6$) δ ppm 8.97, 8.73 (s, s, 2H), 8.30, 8.14 (s, s, 3H), 7.54, 7.40 (s, s, 1H), 7.31-7.17(m, 4H), 4.02-3.98 (m, 2H), 3.79-3.64 (m, 10H), 3.78-3.35 (m, 1H), 2.74-2.59 (m, 4H), 2.49-2.36 (m, 2H), 2.16-2.12 (m, 3H). | |
| 186 | 1 | ¹H-NMR (400 MHz, DMSO-d$_6$) δ ppm 9.62, 9.50 (s, s, 1H), 8.32-8.14 (m, 3H), 7.83-7.81 (m, 1H), 7.48-7.46 (m, 1H), 7.29-7.16 (m, 5H), 4.10-4.02(m, 3H), 3.82-3.64 (m, 11H), 2.71-2.58 (m, 3H), 2.49-2.33 (m, 1H), 1.56 (d, 3H, J = 7.2 Hz). | |
| 187 | 5 | | 511 |
| 188 | 3 | ¹H NMR (400 MHz, DMSO-d6) δ 9.67 (s, 1H), 8.31 (s, 2H), 8.26 (s, 1H), 7.76 (s, 1H), 7.54 (d, J = 8.0 Hz, 1H), 7.35-7.12 (m, 6H), 6.92 (d, J = 7.5 Hz, 1H), 3.94-3.51 (m, 16H). | 530 |
| 189 | 4 | ¹H-NMR (500 MHz, DMSO-d$_6$) δ ppm 9.66, 9.52 (s, s, 1H), 8.33 (s, 2H), 8.28, 8.16 (s, s, 1H), 7.83 (s, 1H), 7.49, 7.47 (s, s, 1H), 7.39 (d, 2H, J = 7.5 Hz), 7.34 (t, 2H, J = 7.5 Hz), 7.24 (t, 1H, J = 7.0 Hz), 5.96 (d, 1H, J = 4.5 Hz), 5.66 (d, 1H, J = 4.0 Hz), 4.14-4.02 (m, 2H), 3.85-3.75 (m, 8H), 3.73-3.62 (m, 2H), 3.41-3.39 (m, 1H), 2.71-2.55 (m, 3H), 2.35-2.31 (m, 2H). | |
| 190 | 2 | ¹H NMR (400 MHz, DMSO-d6) δ 9.64, 9.51 (s, 1H, rotamer), 8.51 (s, 2H), 7.83 (s, 1H), 8.17 (s, 1H) 7.49 (s, 1H), 7.35-7.26 (m, 2H), 7.05-6.91 (m, 3H), 4.96 (s, 2H), 4.10-4.03 (m, 2H), 3.86 (m, 8H), 3.76-3.64 (m, 2H), 3.45-3.27 (m, 1H), 2.70-2.62 (m, 3H), 2.41-2.30 (m, 2H). | 530 |
| 191 | 3 | This spectrum contains some rotamers in the aromatic region: ¹H NMR (400 MHz, DMSO-d6) δ 9.65, 9.53 (s, 1H), 8.31, 8.28 (s, 2H), 8.15 (s, 1H), 7.84 (s, 1H), 7.50, 7.48 (s, 1H), 7.32-7.13 (m, 5H), 4.32 (d, J = 21.6 Hz, 2H), 3.79 (m, 10H), 2.84-2.60 (m, 4H), 1.67-1.43 (m, 4H). | 530 |
| 192 | 3 | ¹H-NMR (500 MHz, DMSO-d$_6$) δ ppm 9.75 (br. s., 1H), 8.33 (s, 2H), 8.29 (s, 1H), 7.63 (s, 1H), 7.54 (dd, 1H, J = 8.0, 1.5 Hz), 7.37 (br. s., 1H), 7.30 (t, 2H, J = 7.5 Hz), 7.24 (d, 2H, J = 7.5 Hz), 7.20 (t, 1H, J = 7.0 Hz), 7.08 (d, 1H, J = 8.5 Hz), 4.42 (s., 2H), 4.31 (s, 2H), 3.88-3.75 (m, 10H). | |
| 193 | 4 | ¹H-NMR (400 MHz, DMSO-d6) δ ppm 9.63 (br. s., 1H), 8.39 (s, 2H), 8.25 (s, 1H), 7.61 (d, 2H, J = 8.4 Hz), 7.46 (dd, 2H, J = 8.4, 5.6 Hz), 7.39 (d, 2H, J = 8.8 Hz), 7.13-7.08 (m, 2H), 4.93 (s, 1H), 3.85-3.70 (m, 8H), 2.67-2.64 (m, 2H), 1.73 (s, 3H), 1.41 (s, 6H). | 530 |
| 194 | 1 | ¹H-NMR (400 MHz, DMSO-d$_6$) δ ppm 9.64, 9.49 (s, br. s., 1H), 8.28, 8.14 (s, s, 1H), 7.96 (s, 1H), 7.83 (br. s., 1H), 7.48 (br. s., 1H), | |

| Compound Number | Synthetic Protocol | ¹H NMR | LC/MS M + 1 |
|---|---|---|---|
| | | 6.80-6.75 (br, 1H), 4.91-4.80 (m, 1H), 4.76-4.45 (m, 3H), 4.09-3.99 (m, 2H), 3.75-3.63 (m, 2H), 3.26-2.99 (m, 4H), 2.72-2.62 (m, 3H), 2.42-2.33 (m, 2H), 1.04 (br. s., 3H). | |
| 195 | 4 | ¹H-NMR (400 MHz, DMSO-d6) δ ppm 9.67 (s, 1H), 8.39 (s, 2H), 8.26 (s, 1H), 7.63 (d, 2H, J = 8.0 Hz), 7.48-7.44 (m, 2H), 7.26 (d, 2H, J = 8.0 Hz), 7.13-7.09 (m, 2H), 5.16 (d, 1H, J = 4.0 Hz), 4.71 (t, 1H, J = 5.6 Hz), 4.50-4.46 (m, 1H), 3.83-3.82 (m, 8H), 3.42-7.39 (m, 2H), 2.50 (s, 3H), 1.72 (s, 3H). | 532 |
| 196 | 1 | ¹H-NMR (400 MHz, DMSO-d6) δ ppm 9.63, 9.50 (s, s, 1H), 8.32-8.16 (m, 3H), 7.82 (s, 1H), 7.49-7.47 (m, 1H), 7.29-7.26 (m, 2H), 7.14-7.09 (m, 2H), 4.11-4.02 (m, 2H), 3.83-3.65 (m, 12H), 3.42-3.39 (m, 1H), 2.71-2.59 (m, 3H), 2.38-2.32 (m, 1H). | |
| 197 | 1 | ¹H-NMR (400 MHz, DMSO-d6) δ ppm 9.64, 9.50 (s, s, 1H), 8.34-8.16 (m, 3H), 7.83 (s, 1H), 7.50-7.47 (m, 1H), 7.36-7.30 (m, 1H), 7.11-7.00 (m, 3H), 4.10-4.03 (m, 2H), 3.83-3.65 (m, 12H), 3.39-3.33 (m, 1H), 2.71-2.60 (m, 3H), 2.38-2.33 (m, 1H). | |
| 198 | 1 | ¹H-NMR (400 MHz, DMSO-d6) δ ppm 9.64, 9.50 (s, s, 1H), 8.30 (s, 2H), 8.16 (s, 1H), 7.83 (s, 1H), 7.49-7.47(m, 1H), 7.34-7.26 (m, 2H), 7.19-7.13 (m, 2H), 4.11-4.03 (m, 2H), 3.83-3.66 (m, 12H), 3.42-3.34 (m, 1H), 2.71-2.50 (m, 3H), 2.38-2.32 (m, 1H). | |
| 199 | 5 | ¹H-NMR (500 MHz, DMSO-d6) δ ppm 9.67, 9.54 (s, s, 1H), 8.54 (s, 2H), 8.30, 8.17 (s, s, 1H), 7.83 (s, 1H), 7.50, 7.47 (s, s, 1H), 7.33-7.30 (m, 2H), 7.21-7.16 (m, 3H), 4.14-4.03 (m, 2H), 3.94-3.88 (m, 8H), 3.72-3.64 (m, 2H), 3.41-3.36 (m, 1H), 2.71-2.58 (m, 3H), 2.37-2.31 (m, 1H). | |
| 200 | 5 | 1H NMR (400 MHz, DMSO-d6) δ 9.50, 9.64 (s, 1H, rotamer), 8.29, 8.17 (s, 2H, rotamer), 7.83 (s, 1H), 7.68 (s, 1H), 7.48, 7.51 (s, 1H, rotamer), 7.00 (t, J = 8.8 Hz, 2H), 6.80 (dd, J = 8.9, 4.6 Hz, 2H), 4.23-3.50 (m, 12H), 3.49-3.37 (m, 2H), 2.82-2.55 (m, 3H), 2.42-2.17 (m, 2H). | 533 |
| 201 | 4 | ¹H-NMR (400 MHz, CD3OD) δ ppm 8.23 (s, 2H), 8.13 (s, 1H), 8.05 (s, 1H), 7.56 (s, 1H), 7.32-7.29 (m, 2H), 7.06-7.01 (m, 2H), 4.09-4.06 (m, 2H), 3.93-3.87 (m, 8H), 1.68 (3, 3H), 1.19 (s, 3H). | 533 |
| 202 | 5 | ¹H-NMR (400 MHz, DMSO-d6) δ ppm 9.64, 9.50 (s, s, 1H), 8.34 (s, 2H), 8.29, 8.16 (s, s, 1H), 7.82 (s, 1H), 7.50, 7.49 (s, s, 1H), 7.20-7.16 (m, 2H), 7.05-7.01 (m, 2H), 4.10-4.00 (m, 2H), 3.86-3.78 (m, 8H), 3.75-3.61 (m, 2H), 3.47-3.36 (m, 1H), 2.71-2.62 (m, 3H), 2.40-2.30 (m, 1H). | |
| 203 | 5 | ¹H-NMR (400 MHz, DMSO-d6) δ ppm 9.65, 9.52 (s, s, 1H), 8.37 (s, 2H), 8.28, 8.16 (s, s, 1H), 7.82 (s, 1H), 7.50, 7.46 (s, s, 1H), 7.39-7.33 (m, 1H), 7.16-7.11 (m, 2H), 7.06-7.02 (m, 1H), 4.18-4.01 (m, 2H), 3.86-3.80 (m, 8H), 3.71-3.65 (m, 2H), 3.39-3.37 (m, 2H), 2.71-2.56 (m, 3H), 2.34-2.30 (m, 1H). | |
| 204 | 5 | ¹H-NMR (400 MHz, DMSO-d6) δ ppm 9.64, 9.52 (br. s., br. s., 1H), 8.38 (s, 2H), 8.32, 8.16 (s, s, 1H), 7.82 (s, 1H), 7.50, 7.48 (s, 1H), 7.39-7.35 (m, 1H), 6.95-6.85 (m, 2H), 6.81 (dd, 1H, J = 8.0, 2.0 Hz), 4.10-4.06 (m, 2H), 3.87-3.82 (m, 8H), 3.76-3.61 (m, 2H), 3.45-3.35 (m, 1H), 2.66-2.62 (m, 3H), 2.41-2.29 (m, 1H). | |
| 205 | 5 | ¹H-NMR (400 MHz, DMSO-d6) δ ppm 10.14 (br. s., 1H), 8.56 (s, 2H), 8.36 (s, 1H), 7.77-7.75 (m, 2H), 7.42-7.40 (m, 2H), 7.28-7.25 (m, 2H), 7.18-7.14 (m, 1H), 7.07-7.03 (m, 1H), 3.91 (br. s., 10H), 3.25-3.23 (m, 1H), 3.12-3.06 (m, 1H), 1.13 (d, 3H, J = 6.0 Hz). | |
| 206 | 5 | ¹H-NMR (400 MHz, DMSO-d6) δ ppm 10.08 (br. s., 1H), 8.56 (s, 2H), 8.35 (s, 1H), 7.77-7.75 (m, 2H), 7.36-7.25 (m, 4H), 7.18-7.14 (m, 1H), 7.06-7.03 (m, 1H), 3.91 (br. s., 10H), 3.25-3.22 (m, 1H), 3.11-3.06 (m, 1H), 1.13 (d, 3H, J = 6.0 Hz). | |
| 207 | 4 | ¹H-NMR (400 MHz, DMSO-d6) δ ppm 9.66, 9.53 (s, s, 1H), 8.39 (s, 2H), 8.30, 8.16 (s, s, 1H), 7.94, 7.87 (s, s, 1H), 7.48-7.44 (m, 3H), 7.15-7.10 (m, 2H), 5.89 (s, 1H), 4.73, 4.67 (s, s, 1H), 4.00, 3.94 (s, s, 2H), 3.83-3.79 (m, 8H), 1.81 (s, 3H), 1.06 (s, 6H). | 535 |
| 208 | 4 | ¹H-NMR (400 MHz, DMSO-d6) δ ppm 9.66, 9.52 (s, s, 1H), 8.39 (s, 2H), 8.28, 8.15 (s, s, 1H), 7.93, 7.86 (s, s, 1H), 7.47-7.43 (m, 3H), 7.15-7.01 (m, 2H), 5.89 (s, 1H), 4.73, 4.67 (s, s, 1H), 4.00, 3.94 (s, s, 2H), 3.82-3.78 (m, 8H), 1.81 (s, 3H), 1.06 (s, 6H). | 535 |
| 211 | 3 | | 537 |
| 212 | 3 | ¹H NMR (400 MHz, DMSO-d6) δ 8.77 (s, 1H), 8.29 (s, 2H), 8.09 (s, 1H), 7.32-7.24 (m, 2H), 7.24-7.12 (m, 4H), 6.80-6.68 (m, 2H), 3.75 (m, 10H), 3.13-3.03 (m, 4H), 2.43 (t, J = 5.0 Hz, 4H), 2.21 (s, 3H), 2.12 (s, 3H). | 537 |
| 215 | 3 | ¹H NMR (400 MHz, DMSO-d6) δ 9.55 (s, 1H), 8.30 (s, 2H), 8.23 (s, 1H), 7.39 (d, J = 9.4 Hz, 1H), 7.33-7.13 (m, 6H), 7.00 (d, J = 8.1 Hz, 1H), 3.80 (d, J = 8.1 Hz, 10H), 3.60-3.47 (m, 4H), 3.29 (s, 4H), 3.26 (s, 3H), 2.76-2.59 (m, 4H). | 538 |
| 216 | 2 | ¹H NMR (400 MHz, DMSO-d6) δ 9.51 (s, 1H), 8.30 (s, 2H), 8.21 (s, 1H), 7.55 (d, J = 8.6 Hz, 2H), 7.34-7.13 (m, 5H), 6.90 (d, J = 8.5 Hz, 2H), 4.34-4.27 (m, 1H), 3.79 (m, 10H), 2.91-2.83 (m, | 538 |

| Compound Number | Synthetic Protocol | ¹H NMR | LC/MS M + 1 |
|---|---|---|---|
| | | 1H), 2.61-2.52 (m, 1H), 2.20 (s, 3H), 2.08-1.87 (m, 3H), 1.75-1.67 (m, 1H), 1.58-1.49 (m, 1H), 1.37-1.28 (m, 1H). | |
| 217 | 2 | ¹H NMR (400 MHz, DMSO-d6) δ 9.51 (s, 1H), 8.30 (s, 2H), 8.21 (s, 1H), 7.55 (d, J = 8.6 Hz, 2H), 7.34-7.13 (m, 5H), 6.90 (d, J = 8.5 Hz, 2H), 4.34-4.27 (m, 1H), 3.79 (m, 10H), 2.91-2.83 (m, 1H), 2.61-2.52 (m, 1H), 2.20 (s, 3H), 2.08-1.87 (m, 3H), 1.75-1.67 (m, 1H), 1.58-1.49 (m, 1H), 1.37-1.28 (m, 1H). | 538 |
| 218 | 2 | ¹H NMR (400 MHz, DMSO-d6) δ 9.50 (s, 1H), 8.30 (s, 2H), 8.21 (s, 1H), 7.55 (d, J = 8.7 Hz, 2H), 7.34-7.14 (m, 5H), 6.89 (d, J = 8.5 Hz, 2H), 3.94 (dd, J = 9.6, 5.4 Hz, 1H), 3.79 (d, J = 3.9 Hz, 10H), 2.97 (br. s, 1H), 2.37 (s, 3H), 2.21 (br. s, 1H), 2.03-1.88 (m, 1H), 1.76-1.63 (m, 2H), 1.64-1.51 (m, 1H) - a peak is obscured by the water signal. | 538 |
| 219 | 2 | ¹H NMR (400 MHz, DMSO-d6) δ 9.50 (s, 1H), 8.30 (s, 2H), 8.21 (s, 1H), 7.56 (d, J = 8.6 Hz, 2H), 7.35-7.12 (m, 5H), 6.89 (d, J = 8.5 Hz, 2H), 3.94 (dd, J = 9.6, 5.4 Hz, 1H), 3.79 (d, J = 6.6 Hz, 10H), 2.98 (br. s, 1H), 2.38 (br. s, 3H), 2.22 (s, 1H), 2.03-1.89 (m, 1H), 1.77-1.64 (m, 2H), 1.64-1.53 (m, 1H) a peak is obscured by the water signal. | 538 |
| 220 | 3 | ¹H-NMR (500 MHz, CD₃OD) δ ppm 8.25 (s, 2H), 8.19 (s, 1H), 7.38 (d, 1H, J = 8.0 Hz), 7.37 (s, 1H), 7.32 (d, 1H, J = 8.0 Hz), 7.31 (d, 1H, J = 8.0 Hz), 7.24-7.20 (m, 3H), 7.10 (d, 1H, J = 8.0 Hz), 4.64 (s, 2H), 4.11-4.06 (m, 1H), 3.93-3.90 (m, 4H), 3.87-3.84 (m, 6H), 3.78-3.76 (m, 2H), 2.93-2.87 (m, 4H), 2.62-2.54 (m, 2H), 1.22 (d, 3H, J = 6.0 Hz). | |
| 223 | 1 | ¹H NMR (400 MHz, DMSO-d6) δ 9.42 (s, 1H), 8.31 (s, 2H), 8.19 (s, 1H), 7.49 (d, J = 8.4 Hz, 2H), 7.35-7.22 (m, 4H), 7.17 (tt, J = 5.5, 2.5 Hz, 1H), 6.86 (d, J = 8.6 Hz, 2H), 4.77 (d, J = 4.7 Hz, 1H), 4.05 (q, J = 7.3 Hz, 1H), 3.78 (q, J = 7.0, 6.4 Hz, 8H), 3.62-3.47 (m, 2H), 3.43-3.35 (m, 1H), 2.62-2.52 (m, 1H), 2.42 (dd, J = 11.4, 9.0 Hz, 1H), 1.86 (dt, J = 12.5, 4.1 Hz, 1H), 1.73 (dt, J = 13.0, 3.8 Hz, 1H), 1.56 (d, J = 7.3 Hz, 4H), 1.29-1.17 (m, 1H). | 538 |
| 224 | 1 | ¹H NMR (400 MHz, DMSO-d6) δ 9.43 (s, 1H), 8.31 (s, 2H), 8.19 (s, 1H), 7.49 (d, J = 8.3 Hz, 2H), 7.36-7.23 (m, 4H), 7.23-7.13 (m, 1H), 6.86 (d, J = 8.6 Hz, 2H), 4.77 (d, J = 4.7 Hz, 1H), 4.05 (q, J = 7.2 Hz, 1H), 3.78 (m, 8H), 3.64-3.46 (m, 2H), 2.56 (td, J = 11.7, 3.0 Hz, 1H), 2.42 (dd, J = 11.4, 9.0 Hz, 1H), 1.87 (m, 1H), 1.73 (m, 1H), 1.63-1.45 (m, 4H), 1.22 (tdd, J = 12.1, 9.5, 4.1 Hz, 1H). | 538 |
| 225 | 2 | ¹H NMR (400 MHz, DMSO-d6) δ 9.42 (s, 1H), 8.30 (s, 2H), 8.18 (s, 1H), 7.48 (d, J = 8.6 Hz, 2H), 7.24 (tt, J = 19.9, 7.5 Hz, 5H), 6.85 (d, J = 9.3 Hz, 2H), 4.38 (s, 1H), 3.98-3.65 (m, 10H), 2.97 (d, J = 6.1 Hz, 2H), 2.89-2.80 (m, 2H), 1.78 (m, 1H), 1.57-1.40 (m, 3H), 1.16 (s, 3H). | 538 |
| 226 | 3 | ¹H NMR (400 MHz, DMSO-d6) δ 9.42 (s, 1H), 8.31 (s, 2H), 8.19 (s, 1H), 7.48 (d, J = 8.4 Hz, 2H), 7.34-7.14 (m, 5H), 6.86 (d, J = 8.5 Hz, 2H), 4.38 (s, 1H), 3.79 (s, 10H), 2.98 (d, J = 6.5 Hz, 2H), 2.90-2.79 (m, 2H), 1.79 (dt, J = 11.4, 6.1 Hz, 1H), 1.59-1.52 (m, 1H), 1.47 (t, J = 6.1 Hz, 2H), 1.16 (s, 3H). | 539 |
| 227 | 3 | ¹H NMR (400 MHz, DMSO-d6) δ 9.42 (s, 1H), 8.31 (s, 2H), 8.19 (s, 1H), 7.48 (d, J = 8.4 Hz, 2H), 7.33-7.15 (m, 5H), 6.86 (d, J = 8.3 Hz, 2H), 4.38 (s, 1H), 3.79 (br. s, 10H), 2.97 (dt, J = 7.4, 3.9 Hz, 2H), 2.89-2.80 (m, 2H), 1.79 (dt, J = 11.4, 5.9 Hz, 1H), 1.54 (dt, J = 13.5, 6.6 Hz, 1H), 1.47 (t, J = 6.0 Hz, 2H), 1.16 (s, 3H). | 538 |
| 228 | 1 | ¹H NMR (400 MHz, DMSO-d6) δ 8.74 (s, 1H), 8.09 (s, 1H), 7.63 (s, 1H), 7.30-7.11 (m, 6H), 6.81-6.67 (m, 2H), 6.29 (s, 2H), 3.68 (m, 10H), 3.01 (dd, J = 6.6, 3.5 Hz, 4H), 2.84 (dd, J = 6.3, 3.6 Hz, 4H), 2.12 (s, 3H). | 538 |
| 229 | 1 | ¹H NMR (400 MHz, DMSO-d6) δ 9.53 (s, 1H), 8.22 (s, 1H), 7.64 (s, 1H), 7.40 (d, J = 7.2 Hz, 2H), 7.31-7.13 (m, 5H), 7.01 (d, J = 8.4 Hz, 1H), 6.31 (s, 2H), 4.47 (br. s, 1H), 3.83-3.53 (m, 14H), 2.73 (br. s, 4H), 2.57 (br. s, 2H). | 539 |
| 221 | 3 | ¹H-NMR (500 MHz, DMSO-d₆) δ ppm 9.58 (br. s., 1H), 8.32 (s, 2H), 8.24 (s, 1H), 7.41 (d, 1H, J = 7.5 Hz), 7.40 (s, 1H), 7.29 (d, 2H, J = 7.5 Hz), 7.23 (d, 2H, J = 7.5 Hz), 7.19 (d, 1H, J = 7.5 Hz), 7.01 (d, 1H, J = 7.5 Hz), 4.39 (d, 1H, J = 4.0 Hz), 3.89-3.79 (m, 11H), 3.56 (s, 2H), 2.74-2.67 (m, 4H), 2.44-2.31 (m, 2H), 1.07 (d, 3H, J = 5.5 Hz). | |
| 222 | 2 | ¹H NMR (400 MHz, DMSO-d6) δ 9.44 (s, 1H), 8.31 (s, 2H), 8.19 (s, 1H), 7.51 (s, 2H), 7.34-7.27 (m, 2H), 7.27-7.16 (m, 3H), 6.88 (d, J = 8.5 Hz, 2H), 4.95-4.73 (m, 2H), 4.47 (dd, J = 24.2, 13.2 Hz, 2H), 4.34 (d, J = 4.2 Hz, 2H), 3.78 (d, J = 10.8 Hz, 3H), 3.66-3.47 (m, 2H), 3.40 (d, J = 12.1 Hz, 1H), 3.27-3.09 (m, 2H), 2.59 (d, J = 10.0 Hz, 1H), 2.43 (t, J = 10.2 Hz, 1H), 1.88 (d, J = 12.4 Hz, 1H), 1.73 (dd, J = 11.1, 7.2 Hz, 1H), 1.53 (d, J = 12.8 Hz, 1H), 1.31-1.17 (m, 2H), 1.04 (d, J = 6.3 Hz, 10H). | 538 |

-continued

| Compound Number | Synthetic Protocol | ¹H NMR | LC/MS M + 1 |
|---|---|---|---|
| 231 | 1 | ¹H NMR (400 MHz, DMSO-d6) δ 9.41 (s, 1H), 8.19 (s, 1H), 7.65 (s, 1H), 7.50 (d, J = 8.4 Hz, 2H), 7.35-7.11 (m, 4H), 6.87 (d, J = 8.5 Hz, 2H), 6.31 (s, 2H), 4.78 (d, J = 4.7 Hz, 1H), 3.93-3.46 (m, 12H), 3.40 (d, J = 11.8 Hz, 1H), 1.88 (d, J = 12.8 Hz, 1H), 1.79-1.68 (m, 1H), 1.60-1.45 (m, 1H), 1.31-1.16 (m, 1H) - two peaks are obscured on either side of DMSO signal. | 539 |
| 232 | 2 | ¹H NMR (400 MHz, DMSO-d6) δ 9.43 (s, 2H), 8.32 (s, 3H), 7.49 (d, J = 8.5 Hz, 2H), 7.38-7.07 (m, 5H), 6.88 (d, J = 8.7 Hz, 2H), 4.63-4.26 (m, 2H), 3.78 (m, 10H), 3.61 (m, 1H), 3.21-2.91 (m, 3H), 1.88-1.49 (m, 2H), 1.04 (d, J = 6.1 Hz, 1H). | 540 |
| 234 | 4 | ¹H-NMR (400 MHz, DMSO-d6) δ ppm 9.46 (br. s., 1H), 8.38 (s, 2H), 8.20 (s, 1H), 7.53 (d, 2H, J = 8.0 Hz), 7.44 (d, 2H, J = 8.0 Hz), 7.33-7.29 (m, 2H), 7.22-7.18 (m, 1H), 6.91 (d, 2H, J = 8.0 Hz), 5.80 (s, 1H), 3.81 (br. s., 8H), 3.73 (t, 4H, J = 4.8 Hz), 3.04 (t, 4H, J = 4.8 Hz), 1.82 (s, 3H). | 540 |
| 235 | 4 | ¹H-NMR (400 MHz, DMSO-d6) δ ppm 9.47 (br. s., 1H), 8.38 (s, 2H), 8.21 (s, 1H), 7.53 (d, 2H, J = 8.0 Hz), 7.45-7.43 (m, 2H), 7.33-7.29 (m, 2H), 7.22-7.19 (m, 1H), 6.91 (d, 2H, J = 8.0 Hz), 5.80 (s, 1H), 3.81 (br. s., 8H), 3.73 (t, 4H, J = 4.8 Hz), 3.04 (t, 4H, J = 4.8 Hz), 1.82 (s, 3H). | 540 |
| 236 | 3 | ¹H-NMR (400 MHz, CDCl₃) δ ppm 8.53 (br. s., 1H), 8.26 (s, 1H), 8.19 (s, 2H), 7.53-7.51 (m, 2H), 7.41-7.40 (m, 2H), 7.30-7.29 (m, 2H), 7.24-7.15 (m, 3H), 3.86-3.73 (m, 11H), 3.39-3.30 (m, 3H), 3.07-3.05 (m, 1H), 2.81-2.79 (m, 1H), 2.32-2.22 (m, 1H), 1.96-1.75 (m, 3H). | |
| 237 | 3 | ¹H NMR (400 MHz, DMSO-d6) δ 9.67 (s, 1H), 8.31 (s, 2H), 8.25 (s, 1H), 7.55 (d, J = 15.1 Hz, 1H), 7.40 (s, 1H), 7.32-7.14 (m, 5H), 6.99 (t, J = 9.4 Hz, 1H), 3.88-3.71 (m, 17H), 2.96 (t, J = 4.7 Hz, 4H), 2.25 (s, 3H) - one peak is partially obscured by water. | 541 |
| 238 | 2 | ¹H NMR (400 MHz, DMSO-d6) δ 9.05 (s, 1H), 8.29 (s, 2H), 8.15 (s, 1H), 7.43-7.11 (m, 6H), 6.87 (dd, J = 12.5, 2.7 Hz, 1H), 6.75 (dd, J = 9.1, 2.7 Hz, 1H), 4.28-4.17 (m, 1H), 3.76 (m, 10H), 3.07 (d, J = 11.4 Hz, 1H), 2.75 (dt, J = 12.4, 4.0 Hz, 1H), 2.01 (s, 1H), 1.71-1.59 (m, 1H), 1.54-1.37 (m, 2H) - one peak obscured by DMSO signal. | 542 |
| 239 | 2 | ¹H-NMR (500 MHz, CDCl₃) δ ppm 8.25 (s, m), 8.17 (s, 2H), 7.41 (d, 2H, J = 8.5 Hz), 7.13-7.10 (m, 2H), 7.00-6.93 (m, 4H), 3.96-3.86 (m, 9H), 3.78 (s, 2H), 3.28-3.24 (m, 1H), 3.08-3.03 (m, 3H), 2.48-2.27 (br, 1H), 1.95-1.91 (m, 1H), 1.84-1.76 (m, 2H), 1.72-1.60 (m, 2H). | 542 |
| 240 | 3 | ¹H NMR (400 MHz, DMSO-d6) δ 9.43 (s, 1H), 8.31 (s, 2H), 8.20 (s, 1H), 7.50 (d, J = 8.4 Hz, 2H), 7.32-7.23 (m, 2H), 7.16-7.07 (m, 2H), 6.87 (d, J = 8.5 Hz, 2H), 4.78 (d, J = 4.7 Hz, 1H), 3.80 (m, 10H), 3.57 (m, 2H), 2.57 (td, J = 11.8, 3.2 Hz, 1H), 2.43 (dd, J = 11.3, 9.0 Hz, 1H), 1.87 (dt, J = 12.6, 4.3 Hz, 1H), 1.73 (ddd, J = 11.6, 7.9, 4.0 Hz, 1H), 1.60-1.45 (m, 1H), 1.29-1.17 (m, 1H). | 542 |
| 241 | 3 | This spectrum contains some rotomers in the aromatic region: ¹H NMR (400 MHz, DMSO-d6) δ 9.62, 9.48 (s, 1H), 8.31, 8.27 (s, 2H), 8.15 (s, 1H), 7.82 (s, 1H), 7.48, 7.47 (s, 1H), 7.36-7.12 (m, 5H), 4.22-4.05 (m, 2H), 3.79 (m, 10H), 3.54-3.39 (m, 2H), 2.75-2.58 (m, 2H), 2.28 (q, J = 7.2 Hz, 2H), 2.02-1.89 (m, 1H), 1.72 (t, J = 10.3 Hz, 1H), 0.96 (t, J = 7.1 Hz, 3H). | 542 |
| 242 | 3 | ¹H-NMR (500 MHz, DMSO-d₆) δ ppm 9.00-8.74 (m, 1H), 8.31 (s, 2H), 8.14 (s, 1H), 7.58-7.41 (m, 1H), 7.30-7.27 (m, 2H), 7.24-7.17 (m, 3H), 4.83 (br. s., 1H), 4.60-4.31 (m, 3H), 4.02-3.96 (m, 2H), 3.78 (s, 2H), 3.69-3.64 (m, 2H), 3.37-3.34 (m, 2H), 3.21-3.13 (m, 2H), 3.02-2.96 (m, 1H), 2.73-2.59 (m, 3H), 2.41-2.37 (m, 1H), 2.17, 2.12 (m, 3H), 1.15-1.01 (br, 3H). | |
| 243 | 1 | ¹H-NMR (400 MHz, DMSO-d₆) δ ppm 8.98, 8.73 (s, s, 1H), 8.31 (s, 2H), 8.14 (s, 1H), 7.53, 7.39 (s, s, 1H), 7.27 (br. s., 4H), 7.19-7.17 (m, 1H), 4.05-3.97 (m, 3H), 3.78-3.66 (m, 10H), 2.73-2.56 (m, 4H), 2.40-2.35 (m, 1H), 2.14-2.07 (m, 3H), 1.55 (d, 3H, J = 6.8 Hz). | |
| 244 | 4 | ¹H-NMR (500 MHz, CDCl₃) δ ppm 8.33, 8.23 (br. s., s, 3H), 7.85, 7.76 (s, s, 1H), 7.58, 7.51 (s, s, 1H), 7.30-7.26 (m, 2H), 7.26-7.24 (m, 1H), 7.20-7.18 (m, 2H), 7.71, 6.60 (br. s., br. s., 1H), 4.16-4.15 (m, 2H), 3.92-3.88 (m, 10H), 3.67-3.65 (m, 1H), 3.00-2.98 (m, 1H), 2.88-2.87 (m, 2H), 2.61-2.55 (m, 1H), 1.67 (s, 6H). | |
| 245 | 1 | ¹H-NMR (500 MHz, DMSO-d₆) δ ppm 8.97, 8.71 (s, s, 1H), 8.13 (d, 1H, J = 6.5 Hz), 7.64 (s, 1H), 7.54, 7.40 (s, s, 1H), 7.28-7.17 (m, 5H), 6.31 (s, 2H), 4.01-3.98 (m, 2H), 3.76-3.65 (m, 13H), 2.74-2.60 (m, 3H), 2.41-2.36 (m, 1H), 2.16, 2.12 (m, 3H). | |
| 246 | 1 | ¹H-NMR (500 MHz, DMSO-d₆) δ ppm 9.62, 9.47 (s, s, 1H), 8.28, 8.18 (s, s, 1H), 8.02 (s, 1H), 7.83 (s, 1H), 7.50, 7.47 (s, s, 1H), 7.26 (t, 2H, J = 7.5 Hz), 7.19-7.15 (m, 3H), 4.13-4.01 (m, 2H), 3.87 (s, | |

| Compound Number | Synthetic Protocol | ¹H NMR | LC/MS M + 1 |
|---|---|---|---|
| | | 3H), 3.87-3.65 (m, 12H), 3.42-3.36 (m, 1H), 2.72-2.57 (m, 3H), 2.37-2.33 (m, 1H). | |
| 247 | 1 | ¹H-NMR (500 MHz, DMSO-$d_6$) δ ppm 9.66-9.52 (m, 1H), 8.32 (d, 2H, J = 7.5 Hz), 8.29, 8.16 (s, s, 1H), 8.02-7.83 (m, 1H), 7.54-7.48 (m, 1H), 7.30 (t, 2H, J = 7.5 Hz), 7.24 (d, 2H, J = 7.0 Hz), 7.20 (t, 1H, J = 7.5 Hz), 4.98-4.28 (m, 5H), 4.09-4.04 (m, 2H), 3.80 (s, 2H), 3.72-3.67 (m, 2H), 3.34-3.07 (m, 4H), 2.70-2.56 (m, 3H), 2.38-2.32 (m, 2H). | |
| 248 | 2 | ¹H-NMR (500 MHz, DMSO-$d_6$) δ ppm 9.64-9.49 (m, 1H), 8.31 (d, 2H, J = 7.0 Hz), 8.28, 8.15 (s, s, 1H), 8.00, 7.83 (s, s, 1H), 7.53, 7.49, 7.47 (s, s, s, 1H), 7.30 (t, 2H, J = 7.5 Hz), 7.24 (d, 2H, J = 7.0 Hz), 7.19 (t, 1H, J = 7.5 Hz), 4.95-3.99 (m, 7H), 3.80 (s, 2H), 3.72-3.65 (m, 2H), 3.46-3.36 (m, 2H), 3.28-3.03 (m, 2H), 2.70-2.54 (m, 3H), 2.38-2.32 (m, 2H). | |
| 249 | 1 | ¹H-NMR (400 MHz, DMSO-$d_6$) δ ppm 9.64, 9.51 (s, s, 1H), 8.33 (s, 2H), 8.28, 8.16 (s, s, 1H), 7.83 (s, 1H), 7.49, 7.47 (s, s, 1H), 7.22-7.18 (m, 1H), 6.82-6.75 (m, 3H), 4.11-4.03 (m, 2H), 3.83-3.65 (m, 11H), 3.43-3.32 (m, 6H), 2.72-2.57 (m, 3H), 2.38-2.32 (m, 1H). | |
| 250 | 4 | ¹H-NMR (500 MHz, DMSO-$d_6$) δ ppm 9.65, 9.52 (s, s, 1H), 8.38 (s, 2H), 8.28, 8.15 (s, s, 1H), 7.82 (s, 1H), 7.49-7.43 (m, 3H), 7.32-7.29 (m, 2H), 7.22-7.19 (m, 1H), 5.83 (s, 1H), 4.11-4.02 (m, 2H), 3.83-3.78 (m, 8H), 3.71-3.64 (m, 2H), 3.40-3.36 (m, 1H), 2.70-2.56 (m, 3H), 2.36-2.32 (m, 2H), 1.81 (s, 3H). | |
| 251 | 5 | ¹H-NMR (500 MHz, DMSO-$d_6$) δ ppm 9.80-9.66 (m, 2H), 8.55 (s, 2H), 8.35 (s, 1H), 7.73, 7.72 (s, s, 2H), 7.35, 7.34 (s, s, 2H), 7.29-7.23 (m, 2H), 7.17-7.14 (m, 1H), 7.06-7.02 (m, 1H), 4.77-7.73 (m, 1H), 4.09 (dd, 1H, J = 12.0, 3.0 Hz), 3.97-3.90 (m, 9H), 3.35 (d, 1H, J = 11.5 Hz), 3.23 (d, 1H, J = 13.0 Hz), 3.12-2.95 (m, 2H). | |
| 252 | 3 | ¹H-NMR (500 MHz, DMSO-$d_6$) δ ppm 9.78 (br. s., 1H), 8.33 (s, 2H), 8.29 (s, 1H), 7.73 (d, 2H, J = 8.5 Hz), 7.35 (d, 2H, J = 8.5 Hz), 7.30 (t, 2H, J = 7.5 Hz), 7.24 (d, 2H, J = 7.0 Hz), 7.20 (t, 1H, J = 7.0 Hz), 4.35 (s, 2H), 3.85-3.81 (m, 10H), 2.72 (s, 6H). | |
| 253 | 2 | ¹H NMR (400 MHz, DMSO-d6) δ 9.64, 9.51 (s, 1H, rotamer), 8.50 (s, 2H), 8.17 (s, 1H), 7.83 (s, 1H), 7.49 (s, 1H), 7.24-6.82 (m, 4H), 4.93 (s, 2H), 4.18-3.97 (m, 2H), 3.96-3.55 (m, 11H), 2.78-2.57 (m, 4H), 2.43-2.21 (m, 1H). | 548 |
| 254 | 4 | ¹H-NMR (500 MHz, CDCl₃) δ ppm 8.82, 8.39 (s, s, 2H), 8.32, 8.22 (br. s., br. s., 1H), 7.83-7.74 (m, 1H), 7.61-7.59 (m, 1H), 7.52-7.45 (m, 5H), 7.30-7.27 (br, 1H), 4.14-4.13 (m, 2H), 3.95-3.82 (m, 11H), 3.62-3.58 (m, 1H), 2.94-2.81 (m, 3H), 2.58-2.54 (m, 1H). | |
| 255 | 5 | ¹H-NMR (500 MHz, DMSO-$d_6$) δ ppm 9.68, 9.55 (s, s, 1H), 8.55 (s, 2H), 8.30, 8.18 (s, s, 1H), 7.83 (s, 1H), 7.50, 7.47 (s, s, 1H), 7.29-7.25 (m, 2H), 7.15 (td, 1H, J = 8.5, 2.0 Hz), 7.04 (t, J = 8.0 Hz, 1H), 4.14-4.03 (m, 2H), 3.94-3.82 (m, 8H), 3.72-3.65 (m, 2H), 3.39 (td, J = 11.0 Hz, J = 3.0 Hz 1H), 2.71-2.58 (m, 3H), 2.37-2.31 (m, 2H). | 550 |
| 256 | 5 | ¹H-NMR (500 MHz, DMSO-$d_6$) δ ppm 9.67, 9.53 (s, s, 1H), 8.54 (s, 2H), 8.30, 8.17 (s, s, 1H), 7.83 (s, 1H), 7.50, 7.47 (s, s, 1H), 7.28-7.25 (m, 2H), 7.17 (t, 2H, J = 8.0 Hz), 4.11-4.03 (m, 2H), 3.94-3.88 (m, 8H), 3.72-3.64 (m, 2H), 3.41-3.36 (m, 1H), 2.71-2.60 (m, 3H), 2.37-2.33 (m, 2H). | 550 |
| 257 | 5 | ¹H-NMR (500 MHz, DMSO-$d_6$) δ ppm 9.67, 9.54 (s, s, 1H), 8.56 (s, 2H), 8.30, 8.18 (s, s, 1H), 7.83 (s, 1H), 7.51, 7.47 (s, s, 1H), 7.38-7.33 (m, 1H), 7.04-6.96 (m, 3H), 4.14-4.03 (m, 2H), 3.95-3.90 (m, 8H), 3.72-3.65 (m, 2H), 3.42-3.37 (m, 1H), 2.71-2.60 (m, 3H), 2.37-2.31 (m, 2H). | |
| 258 | 5 | ¹H NMR (400 MHz, DMSO-d6) δ 9.66 (s, 1H), 8.40 (s, 1H), 8.18 (s, 1H), 7.82 (s, 1H), 7.57-7.45 (m, 3H), 7.31-7.20 (m, 2H), 4.07 (m, 2H), 3.90 (m, 8H), 3.75-3.63 (m, 3H), 3.47-3.24 (m, 3H), 2.74-2.54 (m, 3H), 2.40-2.28 (m, 1H). | 551 |
| 259 | 3 | ¹H NMR (400 MHz, DMSO-d6) δ 9.65 (s, 1H), 8.30 (s, 2H), 8.25 (s, 1H), 8.20 (s, 1H), 7.82 (s, 2H), 7.46 (d, J = 8.1 Hz, 1H), 7.33-7.12 (m, 6H), 6.90 (d, J = 7.5 Hz, 1H), 3.87-3.75 (m, 16H), 2.75-2.63 (m, 3H), 2.65-2.54 (m, 1H), 2.45-2.35 (m, 2H), 2.29-2.20 (m, 2H), 2.08 (s, 6H), 1.89-1.81 (m, 1H), 1.66-1.55 (m, 1H). One peak is obscured by water peak and cannot be accurately integrated | 551 |
| 260 | 3 | ¹H NMR (400 MHz, DMSO-d6) δ 9.64 (s, 1H), 8.30 (s, 2H), 8.24 (s, 1H), 7.82 (s, 1H), 7.45 (s, 1H), 7.31-7.25 (m, 3H), 7.25-7.13 (m, 4H), 6.90 (d, J = 7.5 Hz, 1H), 3.92-3.67 (m, 10H), 3.57 (d, J = 13.1 Hz, 1H), 3.43 (d, J = 13.0 Hz, 1H), 2.74-2.54 (m, 3H), 2.44-2.32 (m, 1H), 2.28-2.16 (m, 1H), 2.05 (s, 6H), 1.90-1.78 (m, 1H), 1.66-1.52 (m, 1H). | 551 |
| 261 | 3 | ¹H NMR (400 MHz, DMSO-d6) δ 9.64 (s, 1H), 8.30 (s, 2H), 8.24 (s, 1H), 7.81 (s, 1H), 7.45 (s, 1H), 7.32-7.23 (m, 3H), 7.26-7.13 (m, 4H), 6.90 (d, J = 7.6 Hz, 1H), 3.91-3.70 (m, 10H), 3.57 (d, J = | 551 |

| Compound Number | Synthetic Protocol | ¹H NMR | LC/MS M + 1 |
|---|---|---|---|
| | | 13.0 Hz, 1H), 3.44 (d, J = 13.0 Hz, 1H), 2.77-2.54 (m, 3H), 2.46-2.34 (m, 1H), 2.30-2.17 (m, 1H), 2.08 (s, 6H), 1.92-1.78 (m, 1H), 1.68-1.53 (m, 1H). | |
| 262 | 3 | ¹H-NMR (500 MHz, CDCl$_3$) δ ppm 8.27 (s, 1H), 8.21 (s, 2H), 7.31-7.28 (m, 3H), 7.25-7.08 (m, 5H), 3.91-3.88 (m, 8H), 3.82-3.80 (m, 4H), 2.94-2.88 (m, 4H), 2.52 (s, 2H), 1.22 (s, 6H). | |
| 263 | 4 | ¹H NMR (400 MHz, DMSO-d6) δ 9.43 (s, 1H), 8.25 (s, 2H), 8.19 (s, 1H), 7.49 (d, J = 8.3 Hz, 2H), 7.35-7.23 (m, 4H), 7.23-7.13 (m, 1H), 6.86 (d, J = 8.6 Hz, 2H), 4.77 (s, 1H), 3.88-3.70 (m, 8H), 3.65-3.46 (m, 3H), 2.62-2.53 (m, 1H), 2.46-2.37 (m, 1H), 1.92-1.82 (m, 1H), 1.72 (dd, J = 10.4, 6.6 Hz, 1H), 1.63 (s, 6H), 1.52 (m, 1H), 1.24 (dt, J = 13.2, 6.2 Hz, 2H). | 552 |
| 265 | 1 | ¹H NMR (400 MHz, DMSO-d6) δ 9.48 (s, 1H), 8.20 (s, 1H), 7.64 (s, 1H), 7.55 (d, J = 8.6 Hz, 2H), 7.31-7.11 (m, 5H), 6.89 (d, J = 8.5 Hz, 2H), 6.30 (s, 2H), 3.94 (dd, J = 9.6, 5.4 Hz, 1H), 3.85-3.58 (m, 10H), 2.97 (br. s, 1H), 2.37 (s, 3H), 2.21 (br. s, 1H), 1.96 (t, J = 10.3 Hz, 1H), 1.76-1.52 (m, 3H) one peak obscured by DMSO signal. | 553 |
| 266 | 1 | ¹H NMR (400 MHz, DMSO-d6) δ 9.48 (s, 1H), 8.20 (s, 1H), 7.64 (s, 1H), 7.56 (dd, J = 9.1, 3.0 Hz, 2H), 7.34-7.10 (m, 5H), 6.88 (d, J = 8.5 Hz, 2H), 6.30 (s, 2H), 3.93 (dd, J = 9.6, 5.3 Hz, 1H), 3.72 (dd, J = 41.7, 13.4 Hz, 10H), 2.96 (s, 1H), 2.36 (s, 3H), 2.19 (s, 1H), 1.95 (dq, J = 12.4, 8.2 Hz, 1H), 1.74-1.62 (m, 2H), 1.63-1.50 (m, 1H) one peak obscured by DMSO signal. | 553 |
| 267 | 4 | ¹H-NMR (400 MHz, DMSO-d6) δ ppm 9.65, 9.50 (s, s, 1H), 8.27 (s, 2H), 8.16 (s, 1H), 7.83 (s, 1H), 7.50, 7.47 (s, s, 1H), 7.30 (dd, 2H, J = 8.8, 6.0 Hz), 7.14-7.09 (m, 2H), 4.11-4.03 (m, 2H), 3.84-3.66 (m, 10H), 2.72-2.57 (m, 4H), 2.35-2.32 (m, 2H), 1.63 (s, 6H). | 560 |
| 268 | 3 | ¹H NMR (400 MHz, DMSO-d6) δ 9.58 (s, 1H), 8.31 (s, 2H), 8.25 (s, 1H), 7.42 (d, J = 6.3 Hz, 2H), 7.33-7.15 (m, 5H), 7.04 (d, J = 8.7 Hz, 1H), 3.89-3.71 (m, 12H), 2.90 (t, J = 5.9 Hz, 2H), 2.75 (t, J = 5.7 Hz, 2H) - one peak is obscured by water signal. | 562 |
| 269 | 4 | ¹H-NMR (400 MHz, CDCl3) δ ppm 8.36 (s, 2H), 8.20 (br. s., 1H), 7.75 (br. s., 1H), 7.57 (br. s., 1H), 7.42-7.38 (m, 2H), 7.05-7.00 (m, 2H), 4.15-4.11 (m, 2H), 3.90-3.84 (m, 11H), 3.62-3.56 (m, 1H), 2.93-2.79 (m, 2H), 2.58-2.53 (m, 1H), 1.93 (s, 3H). | 562 |
| 270 | 4 | ¹H-NMR (400 MHz, DMSO-d6) δ ppm 9.64, 9.50 (s, s, 1H), 8.38 (s, 2H), 8.29, 8.16 (s, s, 1H), 7.83 (s, 1H), 7.49-7.44 (m, 3H), 7.14-7.10 (m, 2H), 5.89 (s, 1H), 4.11-4.02 (m, 2H), 3.84-3.66 (m, 10H), 2.71-2.57 (m, 3H), 2.38-2.32 (m, 1H), 1.81 (s, 3H). | 562 |
| 271 | 1 | ¹H-NMR (500 mhz, DMSO-d$_6$) δ ppm 9.00, 8.75 (s, s, m), 8.30 (s, 2H), 8.25 (s, 1H), 8.15, 8.13 (s, s, 1H), 7.55, 7.41 (s, s, 1H), 7.28-7.25 (m, 2H), 7.13-7.10 (m, 2H), 4.07-3.98 (m, 3H), 3.78-3.70 (m, 13H), 3.41-3.37 (m, 1H), 2.80-2.62 (m, 3H), 2.44-2.42 (m, 1H), 2.16, 2.11 (s, s, 3H). | |
| 272 | 1 | ¹H-NMR (500 MHz, DMSO-d$_6$) δ ppm 8.99, 8.75 (s, s, 1H), 8.29 (s, 2H), 8.20 (s, 1H), 8.15, 8.13 (s, s, 1H), 7.54, 7.40 (s, s, 1H), 7.33-7.25 (m, 2H), 7.17-7.12 (m, 2H), 4.03-3.96 (m, 2H), 3.81-3.69 (m, 12H), 3.45-3.33 (m, 1H), 2.78-2.62 (m, 3H), 2.45-2.36 (m, 2H), 2.15, 2.11 (s, s, 3H). | |
| 273 | 5 | ¹H-NMR (500 MHz, DMSO-d$_6$) δ ppm 9.03, 8.78 (s, s, 1H), 8.53 (s, 2H), 8.16-8.15 (m, 1H), 7.29, 7.24 (s, s, 1H), 7.27-7.24 (m, 2H), 7.19-7.15 (m, 2H), 4.02-3.96 (m, 2H), 3.86-3.64 (m, 10H), 3.37-3.35 (br. s., 2H), 2.74-2.56 (m, 3H), 2.41-2.37 (m, 1H), 2.17, 2.12 (s, s, 3H). | |
| 275 | 4 | ¹H-NMR (400 MHz, CDCl3) δ ppm 8.35 (s, 2H), 8.25 (s, 1H), 7.43-7.35 (m, 4H), 7.00 (t, 2H, J = 8.8 Hz), 6.94 (d, 2H, J = 8.8 Hz), 7.00-6.93 (br., 1H), 3.96-3.93 (m, 1H), 3.92-3.80 (m, 8H), 3.28-3.24 (m, 1H), 3.09-3.03 (m, 3H), 2.35-2.15 (br., 1H), 1.95-1.91 (m, 1H), 1.83 (s, 3H), 1.82-1.70 (m, 3H). | 571 |
| 276 | 4 | ¹H-NMR (400 MHz, CDCl3) δ ppm 8.34 (s, 2H), 8.20 (br. s., 1H), 7.71 (br. s., 0.5H), 7.41-7.38 (m, 2H), 7.04-6.99 (m, 2H), 6.50 (br. s., 0.5H), 4.09-4.08 (m, 2H), 3.87-3.85 (m, 10H), 3.62-3.56 (m, 1H), 2.98-2.83 (m, 3H), 2.65-2.59 (m, 1H), 2.22 (s, 3H), 1.92 (s, 3H). | 576 |
| 277 | 4 | ¹H-NMR (400 MHz, CDCl3) δ ppm 8.34 (s, 2H), 8.20 (br. s., 1H), 7.71 (br. s., 0.5H), 7.41-7.38 (m, 2H), 7.04-6.99 (m, 2H), 6.50 (br. s., 0.5H), 4.09-4.08 (m, 2H), 3.87-3.85 (m, 10H), 3.63-3.57 (m, 1H), 2.99-2.84 (m, 3H), 2.68-2.60 (m, 1H), 2.22 (s, 3H), 1.92 (s, 3H). | 576 |

Biochemical Activity of Compounds

In order to assess the activity of chemical compounds against the relevant kinase of interest, the Caliper Life-Sciences electrophoretic mobility shift technology platform is used. Fluorescently labeled substrate peptide is incubated in the presence of kinase and ATP so that a reflective proportion of the peptide is phosphorylated. At the end of the reaction, the mix of phosphorylated (product) and non-phosphorylated (substrate) peptides are passed through the microfluidic system of the Caliper EZ Reader 2, under an applied potential difference. The presence of the phosphate group on the product peptide provides a difference in mass and charge between those of the substrate peptide, resulting in a separation of the substrate and product pools in the sample. As the pools pass a LEDS within the instrument, these pools are detected and resolved as separate peaks. The ratio between these peaks therefore reflects the activity of the chemical matter at that concentration in that well, under those conditions.

Kit wild type assay at Km: In each well of a 384-well plate, 0.2 ng/ul final (2 nM) of wild type Kit (Carna Bioscience 08-156) was incubated in a total of 12.5 ul of buffer (100 mM HEPES pH 7.5, 0.015% Brij 35, 10 mM MgCl2, 1 mM DTT) with 1 uM Srctide (5-FAM-GEEPLYWSFPAKKK-NH2) and 400 uM ATP at 25 C for 90 minutes in the presence or absence of a dosed concentration series of compound (1% DMSO final concentration). The reaction was stopped by the addition of 70 ul of Stop buffer (100 mM HEPES pH 7.5, 0.015% Brij 35, 35 mM EDTA and 0.2% of Coating Reagent 3 (Caliper Lifesciences)). The plate was then read on a Caliper EZReader 2 (protocol settings: −1.9 psi, upstream voltage −700, downstream voltage −3000, post sample sip 35 s). Data was normalized to 0% and 100% inhibition controls and the IC50 or EC50 calculated using a 4-parameter fit using GraphPad Prism.

Kit D816V assay at Km: In each well of a 384-well plate, 0.04 ng/ul (0.5 nM) of D816V Kit (Carna Bioscience 08-156) was incubated in a total of 12.5 ul of buffer (100 mM HEPES pH 7.5, 0.015% Brij 35, 10 mM MgCl2, 1 mM DTT) with 1 uM Srctide (5-FAM-GEEPLYWSFPAKKK-NH2) and 15 uM ATP at 25 C for 90 minutes in the presence or absence of a dosed concentration series of compound (1% DMSO final concentration). The reaction was stopped by the addition of 70 ul of Stop buffer (100 mM HEPES pH 7.5, 0.015% Brij 35, 35 mM EDTA and 0.2% of Coating Reagent 3 (Caliper Lifesciences)). The plate was then read on a Caliper EZReader 2 (protocol settings: −1.9 psi, upstream voltage −700, downstream voltage −3000, post sample sip 35 s). Data was normalized to 0% and 100% inhibition controls and the IC50 or EC50 calculated using a 4-parameter fit using GraphPad Prism.

PDGFRA D842V assay at Km: In each well of a 384-well plate, 0.7 ng/ul (8 nM) of PDGFRA D842V (ProQinase 0761-0000-1) was incubated in a total of 12.5 ul of buffer (100 mM HEPES pH 7.5, 0.015% Brij 35, 10 mM MgCl2, 1 mM DTT) with 1 uM CSKtide (5-FAM-KKKKEEIYFFF-NH2) and 15 uM ATP at 25 C for 90 minutes in the presence or absence of a dosed concentration series of compound (1% DMSO final concentration). The reaction was stopped by the addition of 70 ul of Stop buffer (100 mM HEPES pH 7.5, 0.015% Brij 35, 35 mM EDTA and 0.2% of Coating Reagent 3 (Caliper Lifesciences)). The plate was then read on a Caliper EZReader 2 (protocol settings: −1.9 psi, upstream voltage −500, downstream voltage −3000, post sample sip 38 s). Data was normalized to 0% and 100% inhibition controls and the $IC_{50}$ or $EC_{50}$ calculated using a 4-parameter fit using GraphPad Prism.

Cellular Activity of Compound

HMC1.2 Autophosphorylation Assay:

10,000 HMC1.2 cells were incubated in 22 ul culture media (phenol-red free IMDM, no serum) in each well of a 384-well plate and serum starved overnight in a tissue culture incubator (5% $CO_2$, 37° C.). A 10-point dose concentration series of compound (25 uM-95.4 pM) were then added to the cells in a volume of 3.1 ul to each well (0.25% DMSO final concentration). After 90 minutes, 6 ul of 5× AlphaLISA Lysis Buffer (Perkin Elmer) supplemented with a protease and phosphatase inhibitor cocktail (Cell Signaling Technologies) was added to each well and shaken at 450 rpm for 15 minutes at 4° C. 10 ul of phospho-Y719 c-Kit and total c-Kit antibodies (15 nM final concentration, Cell Signaling Technologies) and 50 ug/ml AlphaLISA rabbit acceptor beads (Perkin Elmer) were added to each well and shaken at 300 rpm at room temperature for 2 hours. 10 ul of 100 ug/ml streptavidin donor beads (Perkin Elmer) were added to each well, blocked from light with aluminum adhesive and shaken at 300 rpm at room temperature for 2 hours. Fluorescence signal was obtained on Envision (Perkin Elmer) by AlphaScreen 384 well HTS protocol. Data was normalized to 0% and 100% inhibition controls and the IC50 was calculated using Four Parameter Logistic IC50 curve fitting.

The Table below shows the activity of compounds in a Mast cell leukemia cell line, HMC 1.2. This cell line contains Kit mutated at positions V560G and D816V resulting in constitutive activation of the kinase. The following compounds were tested in an assay to measure direct inhibition of Kit D816V kinase activity by assaying Kit autophosphorylation at tyrosine 719 on the Kit protein.

The Table below shows the activity of compounds described herein, against wild-type Kit, mutant Kit (the D816V mutant), and mutan PDFGRA (the D852V mutant). In the Table below, for KIT D816V activity and PDGFRA D842V, the following designations are used: <1.00 nM=A; 1.01-10.0 nM=B; 10.01-100.0 nM=C; >100 nM=D; and ND=not determined. For wild-type Kit activity, the following designations are used: <10 nM=A; 11-100 nM=B; 100-1000 nM=C; >1000 nM=D; and ND=not determined.

In the Table below, for cellular activity, the following designations are used: <10 nM=A; 10.01-100 nM=B; 100.01-1000 nM=C; 1000-10000 nM=D, >10000.01 nM=E; and ND=not determined.

| Compound Numer | D816V KIT | WT KIT | PDFGRA D842V | Cellular Activity |
| --- | --- | --- | --- | --- |
| 1 | D | ND | | |
| 2 | B | ND | | D |
| 3 | D | ND | | |
| 4 | A | A | A | B |
| 5 | B | C | | D |
| 6 | D | ND | | E |
| 7 | B | B | | D |
| 8 | C | ND | | |
| 9 | C | C | | |
| 10 | A | B | B | C |
| 11 | C | ND | | |
| 12 | A | A | A | A |
| 13 | A | A | | B |
| 14 | A | B | | C |
| 15 | A | B | A | B |
| 16 | A | B | | C |
| 17 | B | ND | | D |
| 18 | D | ND | | E |
| 19 | C | ND | | E |
| 20 | A | ND | | B |
| 21 | B | ND | | C |
| 22 | B | C | | C |
| 23 | B | B | | C |
| 24 | B | B | | C |
| 25 | A | B | A | B |
| 26 | B | B | | C |
| 27 | B | ND | | B |
| 28 | A | ND | | B |
| 29 | A | | | B |
| 30 | A | B | A | B |
| 31 | A | A | | B |
| 32 | B | ND | | B |

| Compound Numer | D816V KIT | WT KIT | PDFGRA D842V | Cellular Activity |
|---|---|---|---|---|
| 33 | B | ND | | B |
| 34 | C | ND | | D |
| 35 | D | ND | | E |
| 36 | A | | | A |
| 37 | D | D | | |
| 38 | A | | | B |
| 39 | A | | | B |
| 40 | C | B | | |
| 41 | A | A | | B |
| 42 | B | B | | B |
| 43 | A | B | B | B |
| 44 | B | B | B | B |
| 45 | B | ND | | B |
| 46 | A | A | B | B |
| 47 | A | B | A | B |
| 48 | A | A | A | B |
| 49 | A | B | | B |
| 50 | B | B | | D |
| 51 | A | B | | B |
| 52 | A | A | A | B |
| 53 | A | A | A | B |
| 54 | B | C | | |
| 55 | A | ND | | B |
| 56 | A | | A | B |
| 57 | A | | B | B |
| 58 | B | ND | | C |
| 59 | D | C | | |
| 60 | A | B | | B |
| 61 | A | A | A | B |
| 62 | A | ND | | B |
| 63 | D | ND | | |
| 64 | A | B | | B |
| 65 | A | ND | | B |
| 66 | A | ND | | B |
| 67 | C | ND | | |
| 68 | B | B | A | B |
| 69 | A | A | A | A |
| 70 | B | ND | | C |
| 71 | A | ND | | B |
| 72 | A | ND | | B |
| 73 | A | A | A | A |
| 74 | A | B | | B |
| 75 | A | A | A | B |
| 76 | A | A | | B |
| 77 | B | ND | | B |
| 78 | A | ND | | B |
| 79 | B | | | B |
| 80 | B | ND | | B |
| 81 | A | ND | | B |
| 82 | A | ND | | B |
| 83 | A | A | A | B |
| 84 | A | A | | B |
| 85 | A | B | | B |
| 86 | A | B | | B |
| 87 | B | ND | | B |
| 88 | A | B | A B | |
| 89 | A | B | | C |
| 90 | C | ND | | |
| 91 | B | ND | | D |
| 92 | A | | | B |
| 93 | A | | | B |
| 94 | B | B | | B |
| 95 | A | B | | D |
| 96 | A | B | | C |
| 97 | A | ND | | B |
| 98 | A | A | A | B |
| 99 | B | ND | | A |
| 100 | A | ND | | B |
| 101 | A | ND | A | A |
| 102 | A | A | A | B |
| 103 | B | B | | C |
| 104 | B | B | | C |
| 105 | A | B | | C |
| 106 | A | B | B | C |
| 107 | A | ND | | B |
| 108 | A | ND | | B |
| 109 | A | ND | | A |
| 110 | A | ND | | B |
| 111 | B | ND | | B |
| 112 | B | ND | | C |
| 113 | B | ND | | C |
| 114 | B | C | | C |
| 115 | A | A | | B |
| 116 | A | A | A | B |
| 117 | A | A | A | B |
| 118 | A | A | | B |
| 119 | A | | | A |
| 120 | A | | | B |
| 121 | A | | | B |
| 122 | A | | | B |
| 123 | A | A | A | A |
| 124 | A | A | A | B |
| 125 | A | ND | | B |
| 126 | B | ND | | C |
| 127 | A | A | | B |
| 128 | B | B | | C |
| 129 | B | ND | | B |
| 130 | B | ND | | B |
| 131 | B | ND | | B |
| 132 | A | ND | | B |
| 133 | A | ND | | B |
| 134 | A | ND | | B |
| 135 | B | ND | | B |
| 136 | B | ND | | C |
| 137 | B | ND | | B |
| 138 | A | ND | | B |
| 139 | B | ND | | B |
| 140 | A | | | |
| 141 | B | ND | | B |
| 142 | C | ND | | |
| 143 | B | B | | C |
| 144 | B | B | | C |
| 145 | C | ND | | B |
| 146 | B | ND | | B |
| 147 | B | ND | | C |
| 148 | A | A | A | B |
| 149 | A | ND | B | B |
| 150 | B | ND | | B |
| 151 | B | ND | | B |
| 152 | A | ND | | A |
| 153 | A | ND | | B |
| 154 | B | ND | | B |
| 155 | B | ND | | B |
| 156 | A | A | | B |
| 157 | A | A | B | C |
| 158 | B | B | | C |
| 159 | B | B | | C |
| 160 | B | B | | C |
| 161 | A | A | B | A |
| 162 | A | A | | A |
| 163 | A | A | | B |
| 164 | A | A | | A |
| 165 | B | C | B | B |
| 166 | A | B | B | A |
| 167 | B | C | | B |
| 168 | B | B | | B |
| 169 | A | B | | B |
| 170 | A | B | | B |
| 171 | B | ND | | B |
| 172 | A | | | B |
| 173 | B | ND | | B |
| 174 | A | A | A | A |
| 175 | B | ND | | D |
| 176 | B | ND | | B |
| 177 | B | ND | | B |
| 178 | B | ND | | C |
| 179 | A | A | A | D |
| 180 | A | B | | B |
| 181 | A | A | | B |
| 182 | A | B | | B |
| 183 | B | ND | | B |
| 184 | B | ND | | B |

| Compound Numer | D816V KIT | WT KIT | PDFGRA D842V | Cellular Activity |
|---|---|---|---|---|
| 185 | B | ND | | B |
| 186 | A | ND | | B |
| 187 | B | C | | |
| 188 | B | B | | B |
| 189 | A | ND | | B |
| 190 | B | ND | | B |
| 191 | A | A | | A |
| 192 | A | ND | | A |
| 193 | A | | | A |
| 194 | C | ND | | |
| 195 | A | | | A |
| 196 | A | ND | | B |
| 197 | B | ND | | C |
| 198 | A | ND | | A |
| 199 | B | ND | | B |
| 200 | B | ND | | C |
| 201 | A | | | B |
| 202 | B | ND | | C |
| 203 | B | ND | | B |
| 204 | B | ND | | C |
| 205 | B | ND | | B |
| 206 | B | ND | | B |
| 207 | A | | | B |
| 208 | A | | | A |
| 209 | A | ND | | B |
| 210 | A | ND | | B |
| 211 | A | ND | B | B |
| 212 | B | B | | C |
| 213 | B | ND | | B |
| 214 | A | B | A | B |
| 215 | A | A | | B |
| 216 | A | A | | A |
| 217 | A | A | | A |
| 218 | A | A | | B |
| 219 | A | A | | B |
| 220 | A | ND | | B |
| 221 | A | ND | | A |
| 222 | B | ND | | B |
| 223 | B | | | B |
| 224 | A | | | B |
| 225 | B | | | B |
| 226 | B | | B | B |
| 227 | B | | | B |
| 228 | B | ND | | C |
| 229 | A | ND | | A |
| 230 | B | ND | | D |
| 231 | A | ND | | B |
| 232 | A | ND | | B |
| 233 | B | ND | | B |
| 234 | B | | | B |
| 235 | A | | | A |
| 236 | A | ND | | A |
| 237 | A | B | | B |
| 238 | B | ND | | C |
| 239 | B | | B | B |
| 240 | B | | | A |
| 241 | B | ND | | B |
| 242 | A | ND | | B |
| 243 | B | ND | | B |
| 244 | A | ND | | B |
| 245 | A | ND | | B |
| 246 | B | ND | | D |
| 247 | C | ND | | |
| 248 | A | ND | | B |
| 249 | B | ND | | B |
| 250 | A | ND | | B |
| 251 | B | ND | | C |
| 252 | B | ND | | B |
| 253 | B | ND | | B |
| 254 | B | ND | | |
| 255 | A | ND | | B |
| 256 | A | ND | B | B |
| 257 | B | ND | | C |
| 258 | B | ND | | B |
| 259 | A | A | A | B |
| 260 | A | A | | B |
| 261 | A | A | A | B |
| 262 | A | ND | | B |
| 263 | B | | B | B |
| 264 | B | ND | | C |
| 265 | A | A | | A |
| 266 | A | A | | A |
| 267 | A | | | B |
| 268 | B | C | | C |
| 269 | A | | | B |
| 270 | B | | | |
| 271 | B | ND | B | A |
| 272 | A | ND | | B |
| 273 | B | ND | | B |
| 274 | C | C | | |
| 275 | A | | | B |
| 276 | B | | | B |
| 277 | A | | | B |

Efficacy in an In Vivo Model

Compound 165 and Dasatinib were evaluated in a P815 mastocytoma xenograft model. P815 tumor cells (ATCC, Manassas, Va., cat # ATCC® TIB-64) were maintained in vitro as a suspension and monolayer culture in RPMI1640 medium supplemented with 10% fetal calf serum at 37° C. in an atmosphere of 5% $CO_2$ in air. The tumor cells were sub-cultured twice weekly by trypsin-EDTA treatment. The cells growing in an exponential growth phase were harvested and counted for tumor inoculation.

Female BALB/c nude mice were used for the study. Each mouse was inoculated subcutaneously in the right flank with the P815 tumor cells ($1 \times 10^6$) in 0.1 ml of PBS for tumor development. The treatments were started on day 6 after tumor inoculation when the average tumor size reached approximately 89 $mm^3$. The testing article and vehicle were administrated to the mice according to the regimen shown below.

| Group | n | Treatment | Dose (mg/kg) | Dosing Volume (ml/kg) | Dosing Route | Schedule* |
|---|---|---|---|---|---|---|
| 1 | 13 | Vehicle | 0 | 10 | p.o. | BID x 10 |
| 2 | 10 | Dasatinib | 25 | 10 | p.o. | BID x 10 |
| 3 | 16 | Compound 165 | 3 | 10 | p.o. | BID x 10 |
| 4 | 16 | Compound 165 | 10 | 10 | p.o. | BID x 10 |
| 5 | 16 | Compound 165 | 30 | 10 | p.o. | BID x 10 |
| 6 | 16 | Compound 165 | 100 | 10 | p.o. | BID x 10 |

Note:
*BID = twice per day.

Tumor sizes were measured every other day in two dimensions using a caliper, and the volume was expressed in $mm^3$ using the formula: $V = 0.5 \, a \times b^2$ where a and b were the long and short diameters of the tumor, respectively. The tumor size was then used for calculations of both T-C and T/C values. T-C was calculated with T as the median time (in days) required for the treatment group tumors to reach a predetermined size (e.g., 1000 $mm^3$), and C as the median time (in days) for the control group tumors to reach the same size. The T/C value (in percent) is an indication of antitumor effectiveness; T and C are the mean volumes of the treated and control groups, respectively, on a given day.

TGI was calculated for each group using the formula: TGI (%)=[1−(Ti−T0)/(Vi−V0)]×100; Ti is the average tumor volume of a treatment group on a given day, T0 is the average tumor volume of the treatment group on the day of treatment start, Vi is the average tumor volume of the vehicle control group on the same day with Ti, and V0 is the average tumor volume of the vehicle group on the day of treatment start. Tumor weight was measured at the endpoint.

A statistical analysis of difference in tumor volume and tumor weight among the groups was conducted on the data obtained at the best therapeutic time point after the final dose (the 8$^{th}$ day after the start of treatment). A one-way ANOVA was performed to compare tumor volume and tumor weight among groups. All data were analyzed using Prism 5.0. $p<0.05$ was considered to be statistically significant.

Results. The tumor growth curves of different treatment groups are shown in FIG. 1. Data points represent group mean tumor volume, error bars represent standard error of the mean (SEM). As shown in FIG. 1, Compound 165 was effective in inhibiting tumor growth. Increasing the dose of Compound 165 enhanced the tumor inhibition efficiency.

Thus, Compound 165, as a single agent, produced an observable antitumor activity against the P815 mouse mastocytoma cancer xenograft model in this study.

Incorporation by Reference

All publications and patents mentioned herein are hereby incorporated by reference in their entirety as if each individual publication or patent was specifically and individually indicated to be incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A compound of Formula II:

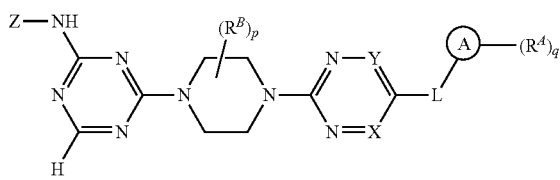

II or a pharmaceutically acceptable salt thereof, wherein:

Ring A is selected from monocyclic or bicyclic aryl, monocyclic or bicyclic heteroaryl, cycloalkyl and heterocyclyl;

each X and Y is independently selected from $CR^1$ and N;

Z is selected from $C_1$-$C_6$ alkyl, cycloalkyl, monocyclic or bicyclic aryl, monocyclic or bicyclic aralkyl, monocyclic or bicyclic heteroaryl, monocyclic or bicyclic heterocyclyl, and monocyclic or bicyclic heterocyclylalkyl; wherein each of $C_1$-$C_6$ alkyl, cycloalkyl, monocyclic or bicyclic aryl, monocyclic or bicyclic aralkyl, monocyclic or bicyclic heteroaryl, monocyclic or bicyclic heterocyclyl, and monocyclic or bicyclic heterocyclylalkyl is substituted with 0-5 independent occurrences of $R^C$;

L is selected from a bond, —$(C(R^2)(R^2))_m$—, —($C_2$-$C_6$ alkynylene)-, —($C_2$-$C_6$ alkenylene)-, —($C_1$-$C_6$ haloalkylene)-, —($C_1$-$C_6$ heteroalkylene)-, —($C_1$-$C_6$ hydroxyalkylene)-, —C(O)—, —O—, —S—, —S(O)—, —$SO_2$—, —$N(R^2)$—, —O—($C_1$-$C_6$ alkylene)-, —($C_1$-$C_6$ alkylene)-O—, —$N(R^2)$—CO—, —CO—$N(R^2)$—, —($C_1$-$C_6$ alkylene)-$N(R^2)$—, —$N(R^2)$—($C_1$-$C_6$ alkylene)-, —$N(R^2)$—CO—($C_1$-$C_6$ alkylene)-, —CO—N($R^2$)—($C_1$-$C_6$ alkylene)-, —$N(R^2)$—$SO_2$—, —$SO_2$—N($R^2$)—, —$N(R^2)$—$SO_2$—($C_1$-$C_6$ alkylene)-, and —$SO_2$—$N(R^2)$—($C_1$-$C_6$ alkylene)-;

each $R^A$ and $R^B$ is independently selected from $C_1$-$C_6$ alkyl, halo, $C_1$-$C_6$ haloalkyl, $C_1$-$C_6$ hydroxyalkyl, $C_1$-$C_6$ heteroalkyl, monocyclic or bicyclic aralkyl, —$N(R^2)(R^2)$, cyano, and —$OR^2$;

each $R^C$ is independently selected from $C_1$-$C_6$ alkyl, $C_1$-$C_6$ alkynyl, halo, $C_1$-$C_6$ heteroalkyl, $C_1$-$C_6$ haloalkyl, $C_1$-$C_6$ haloalkoxy, $C_1$-$C_6$ hydroxyalkyl, cycloalkyl, monocyclic or bicyclic aryl, monocyclic or bicyclic aryloxy, monocyclic or bicyclic aralkyl, monocyclic or bicyclic heterocyclyl, monocyclic or bicyclic heterocyclylalkyl, nitro, cyano, —$C(O)R^2$, —$OC(O)R^2$, —$C(O)OR^2$, —$SR^2$, —$S(O)_2R^2$, —$S(O)_2$—$N(R^2)(R^2)$, —($C_1$-$C_6$ alkylene)-$S(O)_2$—$N(R^2)(R^2)$, —$N(R^2)(R^2)$, —$C(O)$—$N(R^2)(R^2)$, —$N(R^2)(R^2)$—$C(O)R^2$, —($C_1$-$C_6$ alkylene)-$N(R^2)$—$C(O)R^2$, —$NR^2S(O)_2R^2$, —$P(O)(R^2)(R^2)$, and —$OR^2$; wherein each of heteroalkyl, haloalkyl, haloalkoxy, alkyl, alkynyl, cycloalkyl, aryl, aryloxy, aralkyl, heterocyclyl, and heterocyclylalkyl is substituted with 0-5 occurrences of $R^a$; or 2 $R^C$ together with the carbon atom(s) to which they are attached form a cycloalkyl or heterocyclyl ring substituted with 0-5 occurrences of $R^a$;

each $R^1$ is independently selected from hydrogen, $C_1$-$C_6$ alkyl, monocyclic aralkyl, $C_1$-$C_6$ hydroxyalkyl, halo, $C_1$-$C_6$ haloalkyl, —$N(R^2)(R^2)$, and —$OR^2$;

each $R^2$ is independently selected from hydrogen, hydroxyl, halo, $C_1$-$C_6$ alkyl, $C_1$-$C_6$ haloalkyl, $C_1$-$C_6$ hydroxyalkyl, cycloalkyl, cycloalkylalkyl, heterocyclyl, and heterocyclylalkyl; wherein each of $C_1$-$C_6$ alkyl, cycloalkyl and heterocyclyl is substituted with 0-5 occurrences of $R^b$, or 2 $R^2$ together with the carbon or nitrogen atom to which they are attached form a cycloalkyl or heterocyclyl ring;

each $R^a$ and $R^b$ is independently selected from halo, hydroxyl, —C(O)R', $C_1$-$C_6$ alkyl, $C_1$-$C_6$ haloalkyl, $C_1$-$C_6$ heteroalkyl, $C_1$-$C_6$ hydroxyalkyl, —NR'R', and cycloalkyl; wherein cycloalkyl is substituted with 0-5 occurrences of R';

R' is hydrogen, hydroxyl, or $C_1$-$C_6$ alkyl; and m, p, and q are each independently 0, 1, 2, 3, or 4.

2. The compound of claim 1, wherein L is —$(C(R^2)(R^2))_m$—.

3. The compound of claim 2, wherein X and Y are $CR^1$.

4. The compound of claim 2, wherein Z is phenyl.

5. The compound of claim 2, wherein Z is pyridinyl.

6. The compound of claim 2, wherein Z is isoxazolyl.

7. The compound of claim 2, wherein Z is pyrazolyl.

8. The compound of claim 2, wherein Z is dihydroisoquinolinyl.

9. The compound of claim 1, wherein the compound is a compound of Formula II(a):

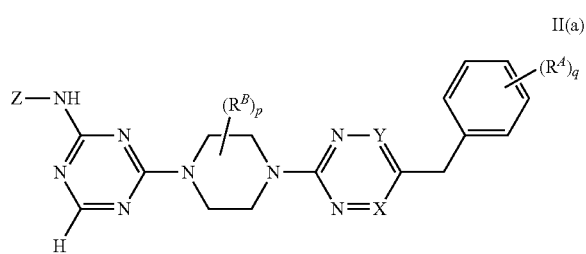

or a pharmaceutically acceptable salt thereof.

10. The compound of claim 9, wherein Z is phenyl.
11. The compound of claim 9, wherein Z is pyridinyl.
12. The compound of claim 9, wherein Z is isoxazolyl.
13. The compound of claim 9, wherein Z is pyrazolyl.
14. The compound of claim 9, wherein Z is dihydroisoquinolinyl.
15. The compound of claim 9, wherein $R^C$ is piperidinyl.
16. A pharmaceutical composition comprising a pharmaceutically acceptable carrier and a compound of claim 1.
17. A method of treating mastocytosis comprising administering to a patient in need thereof a therapeutically effective amount of a compound of claim 1 or a pharmaceutical composition of claim 16.
18. A method of treating gastrointestinal stromal tumor, the method comprising administering to a patient in need thereof a therapeutically effective amount of a compound of claim 1 or a pharmaceutical composition of claim 16.
19. A method of treating acute myeloid leukemia, the method comprising administering to a patient in need thereof a therapeutically effective amount of a compound of claim 1 or a pharmaceutical composition of claim 16.
20. The method of claim 17, wherein the mastocytosis is selected from cutaneous mastocytosis (CM) and systemic mastocytosis (SM).
21. The method of claim 20, wherein the systemic mastocytosis is selected from indolent systemic mastocytosis (ISM), smoldering systemic mastocytosis (SSM), aggressive systemic mastocytosis (ASM), SM with associated hematologic non-mast cell lineage disease (SM-AHNMD), and mast cell leukemia (MCL).

* * * * *